US009970022B2

(12) United States Patent
Avisar et al.

(10) Patent No.: US 9,970,022 B2
(45) Date of Patent: May 15, 2018

(54) GALL WASP CONTROL AGENTS

(75) Inventors: Dror Avisar, Kochav Yair (IL); Hanan Stein, Ness-Ziona (IL); Ziv Shani, Mazkeret Batia (IL); Daniel Siegel, Rehovot (IL)

(73) Assignee: Futuragene Israel Ltd., Peta Tikva (IL)

( * ) Notice: Subject to any disclaimer, the term of this patent is extended or adjusted under 35 U.S.C. 154(b) by 912 days.

(21) Appl. No.: 14/008,914

(22) PCT Filed: Mar. 30, 2012

(86) PCT No.: PCT/US2012/031413
§ 371 (c)(1),
(2), (4) Date: Feb. 14, 2014

(87) PCT Pub. No.: WO2012/135600
PCT Pub. Date: Oct. 4, 2012

(65) Prior Publication Data

US 2014/0157455 A1 Jun. 5, 2014

Related U.S. Application Data

(60) Provisional application No. 61/469,469, filed on Mar. 30, 2011, provisional application No. 61/592,175, filed on Jan. 30, 2012.

(51) Int. Cl.
*C12N 15/82* (2006.01)
*C07K 14/435* (2006.01)
*C12N 15/113* (2010.01)

(52) U.S. Cl.
CPC .... *C12N 15/8286* (2013.01); *C07K 14/43568* (2013.01); *C12N 15/113* (2013.01); *C12N 15/8218* (2013.01); *Y02A 40/162* (2018.01); *Y02A 90/40* (2018.01)

(58) Field of Classification Search
CPC .......... C07K 14/43568; C12N 15/8286; C12N 15/8218; Y02A 90/40
See application file for complete search history.

(56) References Cited

U.S. PATENT DOCUMENTS 6,703,491 B1 * 3/2004 Homburger ........ A01K 67/0333 435/252.3
2007/0244311 A1 * 10/2007 Khvorova ............ C12N 15/111 536/23.1
2009/0010888 A1 * 1/2009 Paine .................... C12N 15/111 424/93.2
2009/0285784 A1 * 11/2009 Raemaekers .......... A01N 57/16 424/93.2

OTHER PUBLICATIONS

Protasov, A., et al. “Biology, revised taxonomy and impact on host plants of*Ophelimus maskelli*, an invasive gall inducer on*Eucalyptus* spp. in the Mediterranean area.” Phytoparasitica 35.1 (2007): 50-76.*

Protasov, A., et al. “Biology, revised taxonomy and impact on host plants of *Ophelimus maskelli*, an invasive gall inducer on *Eucalyptus* spp. in the Mediterranean area.” Phytoparasitica 35.1 (2007): 50-76.*

Werren JH, Richards S, Desjardins CA, Niehuis O, Gadau J, Colbourne JK, Nasonia Genome Working Group. Functional and evolutionary insights from the genomes of three parasitoid *Nasonia* species. Science. Jan. 15, 2010;327(5963):343-8.*

Pei, Yi, and Thomas Tuschl. “On the art of identifying effective and specific siRNAs.” Nature methods 3.9 (2006): 670.*

GenBank Deposition HP526936—“TSA: Apis mellifera isotig 17402.Amelembr mRNA sequence”, <URL: http://www.ncbi.nlm.nih.gov/nuccore/HP526936> (2010).

International Search Report dated Sep. 21, 2012, which issued in corresponding International Application PCT/US2012/031413.

Baulcombe, “RNA silencing in plants,” Nature, 2004, 431:356-363.

Baum et al., “Control of coleopteran insect pests through RNA interference,” Nat Biotechnol, 2007, 25:1322-6.

Chen et al., “New Genes in Drosophila Quickly become essential,” Science, 2010, 330:1682-5.

Cullen, “Enhancing and confirming the specificity of RNAi experiments,” Nature Methods, 2006, 3(9):677-681.

Dietzl et. al., “A Genome Wide Transgenic RNAi Library for Conditional Gene Inactivation in Drosophila,” Nature, 2007, 448:151-7.

Frizzi and Huang, “Tapping RNA silencing pathways for plant biotechnology,” Plant Biotechnol, 2010, 8:655-77.

Gordon et al., “RNAi for insect-proof plants,” Nat Biotechnol, Nov. 2007, 25:1231-2.

Hannon, “RNA interference,” Nature, 2002, 418:244-251.

Huvenne et al., “Mechanisms of dsRNA uptake in insects and potential of RNAi for pest control: a review,” J Insect Physiol, 2010, 56:227-35.

Mao et al., “Silencing a cotton bollworm P450 monooxygenase gene by plant-mediated RNAi impairs larval tolerance of gossypol,” Nat Biotechnol, 2007, 25:1307-13.

Mendel et al., “The taxonomy and natural history of *Leptocybe invasa* (Hymenoptera: Eulophidae) gen & sp. nov., an invasive gall inducer on *Eucalyptus*,”Australian J Entomol, 2004, 43:101-13.

Nunes and Simoes, “A non-invasive method for silencing gene transcription in honeybees maintained under natural conditions,” Insect Biochem Mol Biol, 2009, 39:157-60.

(Continued)

*Primary Examiner* — Lee A Visone
*Assistant Examiner* — Weihua Fan
(74) *Attorney, Agent, or Firm* — Fish & Richardson P.C.

(57) ABSTRACT

The present invention relates to the field of RNA-mediated gene silencing in insect species. The present invention is based, in part, on the inventors' sequencing of genes from *eucalyptus* invasive species gall wasp pests *Leptocybe invasa* (Li) and *Ophelimus maskelli* (Om). In certain aspects, the invention provides Li and Om nucleic acids, derivatives thereof and the use of such nucleic acids and derivatives as gall wasp control agents.

2 Claims, 3 Drawing Sheets

(56) References Cited

OTHER PUBLICATIONS

Price and Gatehouse, "RNAi-mediated crop protection against insects," Trends Biotechnol, 2008, 26:393-400.
Protasov et al., "Biology, revised taxonomy and impact on host plants of *Ophelimus maskelli*, an invasive gall inducer on *Eucalyptus* spp. in the Mediterranean area," Phytoparasitica, 2007, 35:50-76.
Tinoco et al, "In vivo trans-specific gene silencing in fungal cells by in planta expression of a double-stranded RNA," BMC Biol, 2010, 8:27.
Chinese Office Action in Application No. 201280027060.1, dated Dec. 27, 2017 (with Chinese translation).
Israeli Office Action in Application No. IL228,575, dated Nov. 23, 2017, 6 pages.

* cited by examiner

P1 i7 i8 i9 L1 i9 i8 i7 T6 P6 m7 m8 m9 L3 m9 m8 m7 T4 P5 m7 m8 m9 i7 i8 i9 T3

SEQUENCE LISTING

```
<160> NUMBER OF SEQ ID NOS: 245

<210> SEQ ID NO 1
<211> LENGTH: 100
<212> TYPE: DNA
<213> ORGANISM: Leptocybe invasa
<220> FEATURE:
<223> OTHER INFORMATION: i1 100 bp of Alpha COP gene

<400> SEQUENCE: 1

tctcttactt ccaaaaatca aactcaagtt aacgcgtcgt tggccccgca agaaaattat     60

tccatttctg aaggctgggg gagtgacgaa gatggttctg                          100


<210> SEQ ID NO 2
<211> LENGTH: 100
<212> TYPE: DNA
<213> ORGANISM: Leptocybe invasa
<220> FEATURE:
<223> OTHER INFORMATION: i2 100 bp of VCE-F2 gene

<400> SEQUENCE: 2

ggtgccataa gaacggcagg tattttcgga ttgcacggtg gtcagttagc aaaacggttg     60

gatgaagaat ttgaaaaatt gggagctacc actttattgt                          100


<210> SEQ ID NO 3
<211> LENGTH: 100
<212> TYPE: DNA
<213> ORGANISM: Leptocybe invasa
<220> FEATURE:
<223> OTHER INFORMATION: i3 100 bp of Cdh3 gene

<400> SEQUENCE: 3

cgcaaaccgg tagagccggt gaagcccgct gatgcgactg ctgccgctgt accgccagct     60

gctgctgcca acgccacggc cactgcgccg gcgacgaacg                          100


<210> SEQ ID NO 4
```

<211> LENGTH: 100
<212> TYPE: DNA
<213> ORGANISM: Leptocybe invasa
<220> FEATURE:
<223> OTHER INFORMATION: i4 100 bp of Chitin synthase gene

<400> SEQUENCE: 4
ccggtggcgt ggtgccggat ctgttcgaga tactgcccaa cggagagacc gagatcgtca 60
acgctgattt tcacactccg gttcacatgc tgctgttcgc 100

<210> SEQ ID NO 5
<211> LENGTH: 100
<212> TYPE: DNA
<213> ORGANISM: Leptocybe invasa
<220> FEATURE:
<223> OTHER INFORMATION: i5 100 bp of Ferritin gene

<400> SEQUENCE: 5
gccagttgac cagcgacgtt agcaagttgc tcaaattccc gctcaagccg atccgcgagg 60
aatggaacag cggtatcgaa gcacttactg atgctctcaa 100

<210> SEQ ID NO 6
<211> LENGTH: 100
<212> TYPE: DNA
<213> ORGANISM: Leptocybe invasa
<220> FEATURE:
<223> OTHER INFORMATION: i6 100 bp of JHEH gene

<400> SEQUENCE: 6
catggtattg cgaccgtgga cctgggtgaa gacgtacttt tacagctttt ggccgtcgct 60
gttgcctgag gacgaaatcc cgcgtatgtt ccccctgctc 100

<210> SEQ ID NO 7
<211> LENGTH: 100
<212> TYPE: DNA
<213> ORGANISM: Ophelimus maskelli
<220> FEATURE:
<223> OTHER INFORMATION: m1 100 bp of Alpha COP gene with A93C change to eliminate predicted poly A addition site

<400> SEQUENCE: 7
aggctacttg attcaacata ttcataattt aaatacatca gaagatcagt ataactttac 60
ttcagttaaa gctcaagaaa ctattcctgt ttctttatgt 100

<210> SEQ ID NO 8
<211> LENGTH: 101
<212> TYPE: DNA
<213> ORGANISM: Ophelimus maskelli
<220> FEATURE:
<223> OTHER INFORMATION: m2 - 100bp of Cdh3 gene

<400> SEQUENCE: 8
agagccagtg aaaccggctg acggttcagc agttccagtt actccagtac cagcaacggc 60
cacggcaatg gatggaacgg ctacgggatc aacgagtagt a 101

<210> SEQ ID NO 9
<211> LENGTH: 99
<212> TYPE: DNA
<213> ORGANISM: Ophelimus maskelli
<220> FEATURE:
<223> OTHER INFORMATION: m3 - 100bp of VCE-F2 gene

<400> SEQUENCE: 9
ttgagcgata ttcaatggat gactggcgtc acttcagacg aaggtgcttt aaggactcct 60
ggaattttcg gtctcttcga cggtgaatta gcagagcgt 99

<210> SEQ ID NO 10
<211> LENGTH: 100
<212> TYPE: DNA
<213> ORGANISM: Ophelimus maskelli
<220> FEATURE:
<223> OTHER INFORMATION: m4 - 100bp of Chitin synthase gene

<400> SEQUENCE: 10
tctgatgtcg agaaacaaaa acaaggatga gtcgcgtcgt tttgtgctgg tactcgtcga 60
tctagctgca ctggctgcac aaacaacagc tttcgtcgtt 100

<210> SEQ ID NO 11
<211> LENGTH: 101
<212> TYPE: DNA
<213> ORGANISM: Ophelimus maskelli
<220> FEATURE:
<223> OTHER INFORMATION: m5 - 100bp of Ferritin gene

<400> SEQUENCE: 11
gttgactagc gacgttagca aactgctcaa attccctctg aaaccaatcc gtgaagaatg 60
gaacagcggt gttgaggctc tgagcgatgc tctgaatctt t 101

<210> SEQ ID NO 12
<211> LENGTH: 99
<212> TYPE: DNA
<213> ORGANISM: Ophelimus maskelli
<220> FEATURE:
<223> OTHER INFORMATION: m6 - 100bp of JHEH gene

<400> SEQUENCE: 12
tatgtattac tgggtaccca acaaagctac cagtgccttc cggatttact ctgaaacttt 60
gaacaagcac agcatgaagt ataaaatgga taacgtacc 99

<210> SEQ ID NO 13
<211> LENGTH: 106
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: L1 - loop #1 Chitin Synthase intron with XhoI site

<400> SEQUENCE: 13
ggctcgaacg agccgactaa ttgtctttaa acgcgcgata taagcgcaca atgctcgaga 60
aacgataaac tctatcgctc tgtcgcgtgc gtggcatctt cgcgcg 106

<210> SEQ ID NO 14
<211> LENGTH: 108
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: L2 - loop #2 Chitin Synthase intron with AscI site

<400> SEQUENCE: 14
gcgcgcgaaa caacggtaat caaccggcaa ttattaatcg tacatgcgcg gcgcaggcgc 60

```
gcctgcatta tccctcgtca tcaccaaagc gccacattat gcttcttc              108


<210> SEQ ID NO 15
<211> LENGTH: 1563
<212> TYPE: DNA
<213> ORGANISM: Leptocybe invasa
<220> FEATURE:
<223> OTHER INFORMATION: Alpha COP Li- Partial sequence;
      >Coatomer_subunit_alpha_{Alphacoat_protein}_{AlphaCOP}_Li

<400> SEQUENCE: 15

aattttgaga aattagcatt cctatactta ataacaggaa atttagaaaa gcttaaaaaa    60

atgacaaaaa tagctgaaat tagaaaagac ttttctgggc aatatcaggg ttgtctttta   120

cttggcgata tagaagaggt aataaaaatt ttgaagcagt tgagtcaaga agctttagct   180

cacattacaa aaagcataca taaagttgag tgctcgcaat ctgcattgaa tcctgaaagt   240

agtaataaaa acagaaataa ttctaaatta tcatcatttt gtttgcgccc gcccattcct   300

gtatgccaaa cagaaagcaa ttggcctcta ctaacaatat ctcgtggatt ctttgataac   360

tctcttactt ccaaaaatca aactcaagtt aacgcgtcgt tggccccgca agaaaattat   420

tccatttctg aaggctgggg gagtgacgaa gatggttctg aaataaatga gactccaacc   480

tcaaattcca aagcatatag cagttttaat gaagtttcaa acatatcgac aggttgggac   540

gttgaggaag tagatctgcc aatagaatta gtttcaaata attctttaca aatagctgaa   600

aattattttt ccccgccttc taaagggata tcaacttctc agaattggac agttagttcc   660

cagctttcaa tcgaccatgt tttggcggga tcattcgaaa cagctttcca attactaaat   720

gagcaaatag gagtagttaa attcggaaag tacaaaaagt tatttttaaa tattttttca   780

agttcaaaga cgtgcatgac ttcattctca aattcgatta ctttgtacaa ctaccccttta   840

cgaaattgga aagaaaaaca ttcaaaactt tatctaccag ccgcagtatt acaactgtct   900

gatcttgtag acaaactgca agtcagttat caattgacaa cagctgggaa gttcacagag   960

gcaattgaaa agttgcaaac catactactt atgattcctt tgttatattt agattcaaag  1020

caaagtgttg ctgaagcaca gcagcttatt gaaatttgtc gagagtatat cttgggtctc  1080

aaaatggaaa cagcaagaaa aaatcttcca aaaattacgt tgcaagatca acaaagaatt  1140

tgtgaaatga tagcttactt tacacattgt aatttacagc caattcatca aattctaact  1200

ttgagaacag cagtaaatac atttttcaaa tttaaaaact acaaaacagc gcgatcattt  1260

gctagaagac ttctagaact tggaccaaga ccagaaattg ctcaacaaat aagaaaaatt  1320

ttacaggttt gcgataataa tccaagcgat gaaaataaat ttgaatacga tgaacataat  1380

cctttcacac tctgtgcagc atcttacaaa cctatctata aaggcagagc tgaagtgaca  1440

tgcccgtttt gccatgcatc ttaccaggtg cagtttaaag gccaaatttg taacatctgc  1500

gaagtagcaa aaattgataa ggaatgtagt ggattaaaat taactttatt acaaactcgt  1560

tga                                                                1563


<210> SEQ ID NO 16
<211> LENGTH: 6009
<212> TYPE: DNA
<213> ORGANISM: Leptocybe invasa
<220> FEATURE:
<223> OTHER INFORMATION: Cdh3 Li- Full length;
      >chromodomain_helicase_DNA_binding_protein_Li

<400> SEQUENCE: 16
```

```
atggcgtccg acgaagaagt cgacgagagc ttcgccggag aggatgaagt agaagatact     60
agaaatcaag tggcaaatgc cggtcaaaca gtcgaaggct caacagataa tgaagaggct    120
ccaagagtcg aggaagacga cgattatgag cccgaggagc gtaagaaaaa gaagggaaag    180
aagcgaaaag cccgaagtga agacaaaaag ggcaagaaga aaaagaaaaa gaaaaagtcc    240
gactcgggtg atgaaagtga ttttggcggc ggtggagaga acgcagaggt agctggcgag    300
gacagcgact acgcgtcaaa tcgcaaaagt cgcaaatcct cgtcgaggaa gtcgtcgagc    360
catcaagcct cgactcctag cgctgcgtcg gcagcgtcgg cgcaaagcca tcaggaaaca    420
gctgctggca tgccgacgat cgaggaagtc tgcagcactt tcggtctcag cgatgtcgct    480
atcgagtaca cggatgctga cttccagaat ctgacaacgt acaaattgtt ccagcagcac    540
gtcagaccac tcttggccaa ggaaaatccg aaggtaccaa tgtcaaagtt gatgatgttg    600
gtagcagcca agtggagaga tttctccgag atgaatccac acacgcagcc tgaaaacgat    660
gtctcgactc agtcggtcga cgacgatggc agaaatgcta gaaataaccg tagcgcggtg    720
gcacaagacg atgacgagga tgaggaagac gaggatagtg atcgcaaaaa gaaatcgcgt    780
agttctaggg ccaagaaagg caagaaaacc tcaaaagttc cgactcttaa gattaagtta    840
ggcaaacgca agcgaggaag ctcggacgaa gaagcagaag gcagtggacc agcctcggat    900
agggactcag acatggaatt cgaacagatg ctcgctgacg ccgaagaccc gccaccgtct    960
gagaacgcga aagcggagga agttaactcc gagacaacgg ccgagccacc tgtacgcaaa   1020
aaggccaaga ccaaaattgg caataaaagt aaaaagaaaa agaaaacgaa gaccgcgtct   1080
aaattcccag atggagagac tgatcatcaa gactactgtg aagtatgtca gcaaggcgga   1140
gaaattattt tatgtgatac ctgtcctcga gcttaccatc tggtttgttt ggaacctgaa   1200
ttggaagaaa cgccagaagg aaaatggagt tgtccgcatt gtgaaaatga aggcgcggca   1260
gaagacgacg acgagcacat ggagttttgc agagtgtgca aagacggcgg cgagttgttg   1320
tgctgcgata gttgtactag cgcctatcac attcactgtc tgaatccacc gttgacggaa   1380
attcccgacg gcgactggaa gtgtcctcgc tgctcttgcc cagctatctt cggcaaagtg   1440
cagaagattc tcacgtggcg ctggaaagaa gtgagcgagg cttcggaaga gccatcgacg   1500
agcaagtcgt ctggcaaacc gcgcaggatc cgcgaattct tcgtcaagtg ggtggacatg   1560
tcgtattggt actgcgactg ggtgaccgag ctgcagctgg acgtctttca cccactcatg   1620
tacagaaact attcacgcaa atacgatatg gatgagccgc ccaaactcga ggagccactc   1680
gacgacggcg atggccgtgt gaagcggcgc aaggacatgg acaagtcttc taacgacaag   1740
caagagctca atctcgatga gcgtttctac aattacggcg tcagacccga atggctcatt   1800
gttcaccgcg tgatcaatca caggctgcag cgtgacggac gggcattata tttggtcaag   1860
tggagagatt tgggttatga tcaggccacg tgggaggatg aaaacgcaga cattccgggc   1920
ctcaagcagg ccatcgagta ttacctggac ttgcgagcgg ctaattgcgc tgatgggccg   1980
ccttcgagga agggcaaaaa gggcaagggc aagaagtcga agacgaagga aattatcgac   2040
gacgaggaga gagcgccacg aaggtatact ccaccacctg ataagcccac aactgacctc   2100
aaaaggaagt tcgagagaca gccagattat ttggatgtca ctggaatgca gctgcatcct   2160
tatcagttgg agggtttgaa ctggttgaga tactcgtggg gccagggcat tgacacaatc   2220
cttgccgatg agatgggtct cggaaaaact atccagacta ttacattttt atattcgctt   2280
tataaagagg gccactgcaa gggtccattt ttagtatcag taccactttc tactattatt   2340
aattgggaga gagagttcga aacgtgggcg cctgatttct attgcgtcac ttatgttggt   2400
```

-continued

```
gacaaggaca gtcgtatggt gattcgtgaa aacgagttat ccttcgaaga gggtgcagtc   2460
cgaggtggcc gtgcctccaa gattcgctca tcgtcaatca agtttaacgt tcttctgacc   2520
agttatgaac ttatttccat tgactcggct tgcttgggct ctattgactg ggcggttctt   2580
gtggtcgacg aagctcatcg tctcaagtcc aatcagtcca aattcttcag acttcttgcc   2640
tcttacaaca tcgcttacaa gctcttgctt actggtacgc cattacagaa caacctcgag   2700
gaattgttcc acttgttgaa ctttttgtgc cgcgacaagt tcaacgatct ggcagccttc   2760
cagaatgaat tcgctgatat ctcgaaagag gaccaagtga agaagctgca tgagatgttg   2820
ggacctcaca tgctgcgtcg attgaaggct gatgtgctca aaaacatgcc gagcaaatct   2880
gagttcattg tgcgagtaga attgtcgccg atgcagaaga agtactacaa atacattttg   2940
acccgaaact ttgaggcgtt gaacccgaaa ggcggtggcc aacaggtctc acttctaaac   3000
atcatgatgg acctgaagaa atgctgcaat cacccgtacc tgttcccagc agcgtcgcaa   3060
gaggcgccaa ctggacccaa tggcaattac gagacgacgg ctttgatcaa agccgctgga   3120
aagctcgtgt tgctgagtag aatgttgaag aaattgcgcg acgagggcca cagagtgttg   3180
attttctcac agatgacgaa gatgttggat cttctggagg attaccttga aggcgaaggc   3240
tacaagtatg aaagaattga cggcaacatc acgggaactc agcgacagga agccattgac   3300
agattcaatg ctcctggcgc tccgcagttc gtgtttcttc tgtcgaccag agccggtggt   3360
ttaggtatca atctcgccac ggccgacact gtgataatct acgactcgga ctggaatcca   3420
cacaacgaca tccaagcttt cagtcgtgcc catcgtatcg gtcaagccaa caaggtcatg   3480
atctatcgtt tcgtcacgcg taactccgtg gaagagcgcg tcactcaggt tgccaagcgt   3540
aagatgatgt tgactcactt ggttgtgcga ccgggcatgg gtggtaaggg tgccaacttc   3600
agcaagcaag aactcgatga cattcttcga tttggtacgg aagagctgtt caaggaagag   3660
gagggcaaag aagacgaagc tattcactac gatgacaagg ctgtcgccga gttactggac   3720
aggagtaagg aaggtattga gcagaaggag aactgggcta acgagtactt aagctcgttt   3780
aaggtcgcgt cgtacgtcac gaaggagggt gaaatcgaag aggaagccga taccgagatc   3840
atcaagcaag aagctgagaa caccgaccca gcctactgga tcaaactact cagacatcat   3900
tacgagcaac agcaggaaga cattgctagg accctcggta aaggcaagcg cgtgaggaag   3960
caggtatgcc gatatgtgaa ctacaacgac ggtggtgtga ctggtgaaca aggccgcggt   4020
gacgatcagc catggcagga taacatgtcc gactataaca gtgactttag tgcgccgagc   4080
gacgatgaca aagaggacga tgactttgac gaaaagggcg acggcgattt gctttcgagg   4140
cgcagtcgac gcagactcga gcgacgcgac gagaaggatc gacctttgcc gccacttctt   4200
gccagggtca acggcaatat cgaggtcctt ggttttaatg ctcgtcagag aaaggcattc   4260
ctcaatgcta tcatgcgcta tggtatgccg cctcaggacg ctttcaactc gcagtggctc   4320
gttcgtgatt tacgaggcaa atcagaaaag aacttcaagg cctacgtatc cctctttatg   4380
cgtcacttgt gcgaacctgg tgccgacaac gcggaaactt tcgccgacgg tgtaccacgc   4440
gagggtctga gtcgtcagca tgtattgact cgtatcggcg tgatgtcact gatccgaaag   4500
aaggtgcaag agttcgagca cataaacggc tattactcga tgcccgaggt gatccgcaaa   4560
ccggtagagc cggtgaagcc cgctgatgcg actgctgccg ctgtaccgcc agctgctgct   4620
gccaacgcca cggccactgc gccggcgacg aacgatggag ctgccacagg atcgtcgagc   4680
agcaccagtg ccactccggc tacgtcgaat gccccgagcc caagccctgc cgcgacacct   4740
```

```
acgccaactg cttcggcagc tactgctcct gccggcgaga aggacgcgaa agacgaggct   4800

aaagacaagg acgctacaag tgaggagaac aaagagaagg aagcgactga tgctgtcaag   4860

gaggagggca aagaggaaga gaagcccacg ctgaagaccg aggaagaggg taaggacagg   4920

gaagaagtga aggaggagaa agaatctgcc gagggtgaaa aatcatcgga gacgaaggaa   4980

gaaaagtccg atgttaagga gtctgagaag accgaggtca aggatgagaa actcgccaag   5040

gatgagaaat ctgctgacaa cgcggaaact aaagcaaaag ttgacgctga agaagacgtt   5100

gtaattgtga aagacgatga agaagaagct gcgagcggcg aaaagaagga agaaaataag   5160

gaaaaggacg gcaaggagaa ggacagtaaa gacgagaagg aagttgataa gcagaccaag   5220

cgcaagttca tgttcaacat cgccgacggc ggcttcaccg agctccacac attgtggctt   5280

aacgaggaga aggccgccgt tcccggtcgc gaatacgaga tctggcacag gcgacacgac   5340

tactggcttc tggctggtat tgtcactcat ggctacggac gctggcaaga tattcagaat   5400

gacatcaggt tcgccatcat caacgaacca ttcaaaatgg atgtcggcaa aggcaatttc   5460

ctcgaaatca agaacaagtt tttggccagg cgattcaagc tcctcgagca ggctctcgtc   5520

attgaagaac agctgcgcag ggctgcctac cttaatctta ctcaagatcc taatcatcca   5580

gccatgagcc tcaatgctaa attcgccgag gtcgagtgtc tggctgaatc tcatcaacat   5640

ctgagcaagg agagtttggc tggtaacaaa cctgccaacg cagtgttgca taaggtgctt   5700

aatcaattag aagaacttct ttccgacatg aagtccgacg tgagtcggtt gccagccact   5760

ttggctcgca taccaccagt agcgcaaaga ctacaaatgt ccgagcgctc gatcttgagc   5820

agattggcgg cgacgactcc tggtggcaac agcacgcaaa ctggccaagc cgccctattg   5880

gcacagcagt tccctcctgg cttcaccagc ggccagctac cagccacatt cgctggcgct   5940

gctaactttg gaaactttag gccacaatat tccgtacccg gacaaccacc tcaaggtttt   6000

gcagcttga                                                          6009
```

<210> SEQ ID NO 17
<211> LENGTH: 585
<212> TYPE: DNA
<213> ORGANISM: Leptocybe invasa
<220> FEATURE:
<223> OTHER INFORMATION: VCE-F2 Li- Partial sequence;
      > venom carboxylesterase-6 isoform 1(VCE-F2) _Li

<400> SEQUENCE: 17

```
gagcctgatc atccgggagc ctttttaaaa gaagatccag caatttcttt aaagcacgga     60

aggttgaacg atattaattg gatgactggc attacttctg aagagggtgc cataagaacg    120

gcaggtattt tcggattgca cggtggtcag ttagcaaaac ggttggatga agaatttgaa    180

aaattgggag ctaccacttt attgtacgag gatacttgtc cacaagaaaa tcgcgtaaat    240

tcatcgaaat tgattcgtga attttatctt ggaaataagc caataaacga ggccgttaaa    300

accgaattaa ccgacatgta cacggatgct tggttttata ttgctgctga cgaggccgtc    360

cgcgaccatt tagaattgct ttccgcgcca acttactact attactttgc atacagagga    420

agtgcatcat ttagtagtat tttcggcgac gaaaaaagag attacggcgt ttcgcacgct    480

gatgatttgc aatatctctt tccagttggt gagcagcttt tccaagacac gcctttgagc    540

aaagaggata atcgagtaat cgatattatg acaacgcttt ggtac                    585
```

<210> SEQ ID NO 18
<211> LENGTH: 1423
<212> TYPE: DNA

<213> ORGANISM: Leptocybe invasa
<220> FEATURE:
<223> OTHER INFORMATION: Chitin synthase Li- Partial sequence;
      > Chitin_synthase_Li

<400> SEQUENCE: 18

```
atgtcgaaag gccaccaaca gcagcagaat ggctcggtgc ccgggggcgg tggcccggac     60

gacttttccg acgacgacga tagcacgcct ctcactcagg attacggcgg cagtcaacga    120

acggtggtcg agacaaaagg atgggacgtg tttcgcgacc caccgccgaa aatcgactcg    180

ggctcgatgg cagatcagcg ctgcctcgag atcaccacgc agatcaccaa agcggtggtc    240

taccttctag tcttcgtgat cgtcctgacc agcggtgtcg tcgccaaagg gaccatcctc    300

ttcatgacct cgcaactcaa ggccgatcgc accatcgtct attgcaacag gcaattgggt    360

cgcggcagac aattcgtcgt tcagttacca gaggaggagc gcatcgcgtg gatctggtgc    420

atagtgatag cgttcgcggt gccggaagtc ggcacgttct tccgtagcgt gcgcatgtgc    480

gtgttcaagt cgtggaagaa gccgctttcg tcgcacttct tgctcgtgtt ctgcatggaa    540

acctttcacg tcatcggctt ggctctgctg ttcttcgccg ttctgccgga gctcgacgtc    600

gtgcgcggcg ccatgctcac caattgcgtg tgcttcgtgc ctggtatgct cggactctta    660

tcgcgcaaca aaaacaaaga cgagcgtcgt ttcctggtgg tcctcgtcga tctggcagcg    720

ctggcagcgc aagcaacggg tttcgtcgtg tggccgctac tcgacagcaa aaccccgtcg    780

ttgtggctga tccccgcggc actgacaatg gtctcgtgtc gatggtggga gaattacgtg    840

tcggtgcaga gtccgatcgg cgtgatcaag acgctgggcc gagtcaagcg cgacatgatt    900

cagacgcgct acttcacgta cgtcttcata tccatctgga agatcgtggc cttcttcatc    960

accatctgca tcgtgcttca cgtgcaaggc caaaccgtcg gccatctgtt cagcatgttc   1020

ggcgcggctt tcggcgagca caagatcgtc attcaggcga tcagaccgac cgccggtggc   1080

gtggtgccgg atctgttcga gatactgccc aacggagaga ccgagatcgt caacgctgat   1140

tttcacactc cggttcacat gctgctgttc gccatcttcg gcgcttactt catgtacatt   1200

ttcggaaagt tcgcttgcaa gatcatgatc caaggcttca gctacgcgtt ccccgtgaat   1260

ctaacgattc ccgtgtcgat atcccttctg atcgccgctt gcggacttcg caataccgat   1320

ccgtgcttct ttcacggcac cataccggac tacttgttct tcgagtcgcc acccttgtac   1380

ttcctcaacg acttcatctc gaagcagtac gcgtgggtat ggc                     1423
```

<210> SEQ ID NO 19
<211> LENGTH: 648
<212> TYPE: DNA
<213> ORGANISM: Leptocybe invasa
<220> FEATURE:
<223> OTHER INFORMATION: Ferritin Li- Full length; > Ferritin_Li

<400> SEQUENCE: 19

```
atgaagctca tcgaagcctt tgtcctcgct gctgtttgca tcggcatcgc ctcgaccgac     60

aacctcaagt gcacaatcaa acctgctgag gttccacagg catggcggga tatggtaaat    120

ccttgtatca ggattatgga aaatcaggtg aaggttgaaa ttgaagctgc catgacttac    180

cttgctatgg gcgcccattt cgcgcgcgac acagtaaacc gtccaggttt cagcaagctt    240

ttcctcgagt cagcgaacga agagcgtgaa cacgcgatca aagtcatcga atatctgttg    300

atgcgtggcc agttgaccag cgacgttagc aagttgctca aattcccgct caagccgatc    360

cgcgaggaat ggaacagcgg tatcgaagca cttactgatg ctctcaacct tgaggctcag    420
```

gtcacccgca acatccgcga aatcatcatg acctgcgaat caccgaagga cattcccttc 480
aatgattatc acttggtaga ctaccttact ggtgactttt tggatgagca gtacaagggc 540
cagcgtgacc ttgccggaaa gatctcaaca ttgggcaaga tgatggcatc gcacggtgct 600
ctgggtgagt tcttgtacga caagaaactc ctcaataatg aattataa 648

<210> SEQ ID NO 20
<211> LENGTH: 1389
<212> TYPE: DNA
<213> ORGANISM: Leptocybe invasa
<220> FEATURE:
<223> OTHER INFORMATION: JHEH LI- Partial sequence;
 > juvenile_hormone_epoxide_hydrolase_Li

<400> SEQUENCE: 20
attctcttgg gtgtcgcgtt gattggcggt gcgacgattt tcatcgttcc atcagcgcag 60
aagccaccaa attacatgac gtctactggg gacctggtga acaaccgaaa aatcgatcaa 120
agcatcaggc ctttcaagat tagcttctcg aaagagatga tcgatgactt gcgctaccga 180
ttgaaaaaca cgcgcaagtt acaatcgtcc ctggaaagcg ttgcttggac ttacggtata 240
agaagcgacg tcgtgctcaa agtgaccgag cactggctca acaattatga cttcaagaag 300
cgcgagacgt atctcaatca gtatccgcag ttcatcacaa acattcaagg tcttgacatc 360
cacttcattc acgcgaagcc gcagctgccg aaagatcgca aggtcaaggt cttaccgttg 420
tacctgcagc acggctggcc aggctcggtg gtggagtttt acaagataat cccgatgctg 480
acgacaccta gacctaatta cgactttgtc ttcgaagtca ttgctcctgc gctgcctggt 540
ttcggttact ccgatgccgc tgctaaagcc ggcttgggtg ccgttgaaat ggctcatctc 600
atgaagaatc tcatgctgag acttggcttc gacaagtggt atacacaggg tggtgactgg 660
ggcgcagttg taagcgctaa tatggcttcc atgtatcctc agcacgtact gggaatgcac 720
tcgaacatgt gcatggtatt gcgaccgtgg acctgggtga agacgtactt ttacagcttt 780
tggccgtcgc tgttgcctga ggacgaaatc ccgcgtatgt tccccctgct cagggagcta 840
cacaaactca tcgaggagac cggttacctg cacgagcagg ctaccaaacc tgacacactt 900
ggtgttggag taagcgactc gccagctgga ttagcagcct acattttgga aaagttttcc 960
atgggaacga attacgtacg caaattaagg gacgacggtg gcctcacaga gaaattcacc 1020
atggatgaat tgatcgataa tttgatgtat tactgggtgc caaataaaat catgagttcc 1080
ttccgtattt acgctgagac ttttaacaag aaatatacga actacagaat ggaaaatgta 1140
ccaatcaccg tgccaagcgc ctgcgcacag tttccccacg aaataatgtt ccaatcggaa 1200
gtattcctgc gggatcgtta cgtcaacttg gtgcacagga agaagatgcc acagggtgga 1260
cactttgctg ccatggaaga gccgcaattg ctgtctgacg atattttcga ggctattaat 1320
aagatgcgag agctcgatgc tgtcagtaag aaagaaagac ttgaaaaaca aaaatcagga 1380
gaattttag 1389

<210> SEQ ID NO 21
<211> LENGTH: 3645
<212> TYPE: DNA
<213> ORGANISM: Ophelimus maskelli
<220> FEATURE:
<223> OTHER INFORMATION: Alpha COP Om- Full length;
 > Coatomer_subunit_alpha_{Alphacoat_protein}_{AlphaCOP}_Om

<400> SEQUENCE: 21
atgttgctgg aatccattat agttgatgta gaagatattt taaaacagtc aaagcgacca 60

```
tggattctcg ctagtttaca taatggtatt atacagctat gggactatcg aatgtgcact    120
ttactagata aatttgacga acacgatggt ccggtaagag gtatttgttt tcataatcag    180
caaccattgt ttgtttctgg aggagatgat tataaaatta aagtttggaa ctataagcag    240
cgaaggtgta tttttacatt acttggtcac ttagattata ttagaacgac ttttttttcat    300
catgaatatc catggatatt aagtgcttcc gatgatcaaa cgataagaat atggaactgg    360
caaagtagag catgtatttg tgtcttaaca ggtcacaatc attatgttat gtgtgcacat    420
tttcaccctt ctgaagatat tatagtttct gcttcccttg accagaccgt aagagtttgg    480
gatatttctg gcctgagaaa aaaaaatgtt gcccctggtc ctagtggatt agacgatcat    540
ttaaaaaatc ctggttcaac cgatttattt ggacaagctg atgctttagt aaaacatgtt    600
ttagaagggc atgatcgtgg agtaaattgg acttgttttc atcctaactt acctttaatt    660
gtttcgggtg cagatgatag acaaattaaa atgtggcgaa tgaatgatgc aaaagcttgg    720
gaagttgata cttgtagagg tcattataac aatgtatctt gtgttttatt ccaccctaga    780
caagatatta ttctttctaa ttcagaggat aaaagtattc gtatatggga tatgacaaag    840
cgaacgtgcc ttcatacatt tagaagagaa catgaaagat tttgggttct ggcagctcac    900
ccagctttaa atttatttgc agctggccat gattcaggaa tgatcatatt taaattggaa    960
agagaaagac cagcatttac tgtctatggt aatctactct actatgtaaa agaaagattt   1020
ttacgcaaac ttgattttaa tacttccaaa gacacaaccg ttatgcagat tcgaggaagt   1080
agcaaggttc ctgcatactg catatcttat aatcaagctg aaaatgctat tctcatttgt   1140
tctagatcct cttcgaatat tgaaaatagt acatatgatt tgtatgtctt atcatctgaa   1200
ggagattaca atacagaacc agaaatcaag cgagcttctg gaattacagc tttttgggta   1260
gctcgaaatc gatttgctgt ttttgataaa catgttagta catactcttt aattataaag   1320
aatttgaaga atgagattgt taaaaaaatt catattccta attgcgatga cattttttac   1380
gctggaactg gtatggtttt actacgggat tcagataaaa ttgtattatt tgatctacag   1440
caaaagaaga ctattgctga agtgaaagtt gcgaaatgta gatatgcagt ttggtccaca   1500
gacatgacct atgtggcact cttatcgaaa cattctcttg ttgtatgcaa ccgaaagttg   1560
gattgtattt gttcagttca agaaaatatt agaataaagt ctggtgcttg ggatgatttt   1620
aatgttttta tttacactac gaataatcat gttaaataca caattattaa tggtgatcat   1680
ggaattattc gcactttaga tcttccaatt tacattacga gaataaaagg agatcaagtt   1740
tactgcttgg accgtgaatg taaaccgcga atattaagaa ttgattcaac tgagtataaa   1800
tttaagcttt cattaataaa ccgaaaatat gaagatgttt tagagatggt ccgatcttct   1860
aatctggttg gccagtcaat tatcggttat ttacaagaaa aaggttatcc agaagtagct   1920
ttacattttg taaaagatgc aaaaacaaga tttacattag cgttagaatg cagcaatata   1980
gaaattgcat tggaaactgc acgtgttata gataaaaaga attgctggga aagtttagcc   2040
aatgcagcgc ttttacaagg aaaccatcaa atcgtcgaaa tgtgttatca aaggacaaaa   2100
aactttgaaa aactagcatt tttatattta ataacaggtc atttagaaaa actaaagaaa   2160
atgactaaaa ttgctgaaat aagaaaagac ttttcaggcc agtaccaagg caatttatta   2220
ttaggagatg tagaagatgt aaccaaaata ttgaagagtt ctggacaaat gatttttaggc  2280
tacttgattc aacatattca taatttaaat acatcagaag atcagtataa ctttacttca   2340
gttaaagctc aagaaactat tcctgtttat ttatgtcctc cagttcctat tgtttatgct   2400
```

```
gaaaataact ggccactttt aacagtatca aaaggctttt ttgattgtgc gatattatct   2460

aaaaacaaaa agcaaattaa tattgccttc tccccacaag aagatatacc agctgcagga   2520

ggttggggaa gtgaagaaga tgaaaatgcc gaagaaatag tgactgggag tgaatctagc   2580

agaaatgctg catatgagca gtttgaatcc actggatggg atgttgacga tgtagatata   2640

tctttagatt tagatgctgg aaatgtttta agaactgatg aaaattactt ttcacccccca  2700

gtgaagggtt tatcagttaa tcataagtgg ataagtaatt ctacactagc agtggatcat   2760

attatatgtg gctctttttc tactgcattt cagttgttac atgatcagat tggagttact   2820

aaatttgata aatataaatc attatttatg aacctctatt catgttcaag aacatcttca   2880

acattatttt ccaacttaag tcctatagag aattatccgt tacggaattg gaaagatagt   2940

agtaataaaa tgtattttcc agcaattaca ttatacctgt cagaacttat acaacaatta   3000

caaattagtt accaattaac gaccgccggt aaatttcatg aagcggtaaa aaagttacaa   3060

aatatacttc tgtcagtctc tcttctagtt ttagattcaa agcaagatat tacggaagca   3120

caacagttaa ttcaaatttg tcgtgaatat attcttggat taaaaatgga aacagaaaga   3180

aaaaatcatc ccaagactac attatcagaa caaaaaagaa tttgtgaaat ggttgcatat   3240

tttacacatt gtaatttaca acctattcat caaatactaa ctttgagaac agctgttaac   3300

actttttata agttcaaaaa ttataaaacg acaagatcat ttgctagacg attattggaa   3360

ttaggcccta aaccagaaat aggacagcaa gttcgaaaaa ttttacaggt ttgcgataac   3420

agtcctaccg atgagcacat tttagattat gatgaacata atccgtttgt actgtgtgca   3480

ttgtcattta cacctatata caaagggaag cctgagtcaa agtgtccatt ttgtcatgcc   3540

agttatcaaa tagaattcaa aaatagtatt tgcaatattt gtgaggtagc acaaattgat   3600

aaagattgta gaggattaaa aataagctca atgcataatc gataa                   3645
```

<210> SEQ ID NO 22
<211> LENGTH: 5697
<212> TYPE: DNA
<213> ORGANISM: Ophelimus maskelli
<220> FEATURE:
<223> OTHER INFORMATION: Cdh3 Om- Partial sequence;
      > chromodomain_helicase_DNA_binding_protein_Om

<400> SEQUENCE: 22

```
gccggtgaaa ataccgagct agcagctggt ggtgacgaca gcgattacgc gtcgaatcgt     60

aaaagtcgca aatcgtcgtc acgaaaatca tcaagtcact cgactcctgc gccaacgaca    120

caagttcagc aggaaccagc cacgggtatg ccaaccatcg aagaagtctg cagtactttt    180

ggccttactg atgtcgcgat cgagtacacc gacgctgact ttcagaacct cactacgtac    240

aaacttttcc agcagcacgt caggccactt ctttctaagg agaatcctaa ggtacctatg    300

tcaaaattga tgatgttagt agcagccaaa tggagagatt tctcggaaat caatccacat    360

acgcaacccg aaattgaaac atcgactcaa aacgtcgacg aggacagaaa ttcccgaaat    420

aatcgaagca ctacagcgca agatgatgat gacgaagatg aggatgaaga cagtgatcgt    480

aaaaagaaat cacgaagttc gagggctaag aagggaaaga aagcatcgaa agttccaact    540

cttaagatta agttaggaaa acgtaaacga ggaagttcgg atgaagaagc cgaaggaagt    600

ggattaggtt cagacaggga ttcagatatg gaattcgagc aaatgttggc tgatgcagag    660

gatgttccac aatcggaaag caatgccaaa tcggacgatg gtaatgtcga gactccagcc    720

gagccaccgg tacgcaaaaa ggcgaaaact aaaattggta ataagtctaa gaagaaaagg    780
```

```
aagtcaaaaa ctgcgtcaaa attcccagat ggtgagaccg atcaccaaga ctattgtgaa    840
gtgtgtcaac aaggtggaga gattatttta tgtgatacct gtcctcgagc ttaccattta    900
gtttgtctgg aacctgaact ggaagagaca ccggaaggca aatggagttg tccacattgt    960
gaaaacgaag gtgccgcgga tgacgatgac gagcacatgg aattctgtag ggtatgcaaa   1020
gacggtggtg aactgctctg ttgtgacagt tgtacaagtg cttatcacac gcattgtttg   1080
aatccaccgt taaccgaaat cccagatggt gactggaagt gtcctcgttg ttcgtgtcca   1140
cctttgttcg gtagaatcgc taaaattcta acttggcgct ggaaggaagt aactgatcca   1200
ccggatgagc cgtcgactag taaagcaagt ggcaaacccc gcaagattcg tgaatttttc   1260
gttaaatggg ttgacaggtc ctactggtac tgtgattggg taaccgaaat tcaacttgat   1320
gtgttccatc cactcatgta cagaaactat tcacgtaagt acgacatgga cgagccacca   1380
aaacttgaag aaccacttga tgaaggtgag ccatgccccg agccgcgtta taagatgaaa   1440
tgcgacaagg aaaatggagc cgacctcgag gaacgtttct atcgctttgg aatacggccc   1500
gattggctca ttgtgcatcg tgttatcaat caccgattgc agcgtgatgg tcgcgctatg   1560
tatttagtta agtggcgtga acttggttac gaccaagcca cctgggagga tgaacacgca   1620
gacattcctg ggcttaaaca ggccgttgag tattacttag acttgagagc ggctaattgt   1680
gcggatgggc cgcccgcgag aaaaggtaaa aagggtaagg gtaagaaatc taagacgaaa   1740
gaactcattg acgacgaaga gagagcaccc aagagatata cacctccgcc tgataaacct   1800
actacggatc ttaagaagaa gtatgagaag caacctgaat acctggatat tactggaatg   1860
cagcttcatc cttatcagtt agaaggtttg aactggttga ggtactcttg gggacagggc   1920
attgacacca ttcttgctga tgagatgggt ctaggaaaaa ctattcaaac tattacattt   1980
ttatattcgc tttataagga aggtcactgt aaaggtccat ttttagtatc agtacctctt   2040
tcaactatta ttaactggga aagagaattt gaaacgtggg cgccagattt ctattgtgtt   2100
acttatgttg gtgacaaaga cagtcgtatg gtgattcgtg aaaacgaatt gtcattcgag   2160
gagggagcag tcagaggtgg tcgagcttct aagattcgtt catctcaaat caaatttaac   2220
gttcttttaa cgagttatga gttggtctcg attgattcag cttgtttggg ttcgatagac   2280
tgggcagttc tcgtcgtcga cgaggctcac cgtcttaagt ctaatcaatc gaagttcttc   2340
aggcttttgg catcttacaa cattgcctac aaattgctac ttacgggtac accgttgcag   2400
aataaccttg aagaattgtt ccatttactg aacttcttgt gccgagataa attcaatgat   2460
ctcgcagctt ttcaaaatga atttgctgat atttcaaagg aagatcaggt taagaaactg   2520
cacgagatgt tgggaccaca tatgctgcgt cgtttgaaag ccgatgtgct taagaatatg   2580
cccagcaaat ccgaattcat tgtgcgtgta gagttgtcac ccatgcaaaa gaaatattac   2640
aagtacatct tgacccgaaa cttcgaagct ttgaacccga agggtggtgg tcaacaagtg   2700
tctcttctca acattatgat ggacttgaaa aagtgttgta atcatccgta tctgtttccg   2760
gctgcatctc aagaagctcc tactggaccc aacggcaatt acgaaacgtc ggctcttatc   2820
aaagccgctg gaaaactggt attgcttagt aaaatgttga aaaaactccg agatgaaggg   2880
catagagtcc ttatattctc acagatgacg aaaatgttgg atctcttaga agattatttg   2940
gaaggtgaag gttacaaata cgagagaatc gacggtaata tcactggaac gcagaggcaa   3000
gaggctatcg atagatttaa cgctcctgga gctcagcaat ttgttttcct gctttctact   3060
agagctggtg gtttaggtat caatttagca acggccgaca ctgtgataat atacgattcc   3120
gactggaatc cacacaacga catccaggct ttcagtcgtg cccatcgtat tggtcaggcc   3180
```

```
aacaaggtca tgatctatcg tttcgtaacg cgtaactccg ttgaggaacg tgtcacacaa   3240
gtagccaaac gtaagatgat gcttacccat ttggtcgtac gaccgggtat gggtggtaag   3300
ggcgcgaatt tcagtaagca agaactcgac gatattttgc gtttcggtac cgaagaattg   3360
ttcaaagaag aggaaggtaa agaagacgaa gctattcact acgacgataa agccgtagct   3420
gaacttctag acaggagtaa agaaggtatc gaacagaagg agaactgggc taatgaatat   3480
cttagctcgt tcaaggtcgc gtcgtatgtg acgaaagaag gtgaaacgga agaggaagct   3540
gatacggaaa ttatcaaaca agaggctgag aatacagacc ctgcttactg gattaaattg   3600
ttgaggcatc attacgaaca gcaacaagag gacattgcca ggacgctagg aaagggaaag   3660
cgcgtcagga agcaggtgaa ctacaacgac ggtggtgtgg ccggcgacca gggcacgcgt   3720
gacgatcagc catggcaaga taatatgtcg gattacaaca gtgacttcag tgcaccgagc   3780
gaagatgaca aggaggatga tgacttcgac gagaaaggtg acggtgatct gttgtcaaga   3840
cgtagtcgac gtaggcttga acgtcgcgat gaaaaagata gacctttacc acctttactt   3900
gctcgtgtca atggcaatat cgaggttctc ggtttcaatg caagacagag aaaggcattc   3960
ctcaatgcta tcatgcgtta cggtatgcca ccccaggacg ccttcaactc acagtggctt   4020
gtacgtgatt tacgaggaaa atctgaaaag aactttaagg catacgtgtc gttgttcatg   4080
cgtcacctgt gtgagccagg cgctgacaat gccgagactt tcgccgacgg tgttccacgt   4140
gaaggtctga gccgtcagca tgtgcttaca cgtatcggtg ttatgtcctt gatacgcaag   4200
aaggtccaag aattcgagca cataaacggt tactactcga tgcccgaagt tatccgcaag   4260
ccagtagagc cagtgaaacc ggctgacggt tcagcagttc cagttactcc agtaccagca   4320
acggccacgg caatggatgg aacggctacg ggatcaacga gtagtactag tgcaacaccc   4380
gcgacctcga acgcgccaag tcccagtcca gcagctacgc ctacaccggc aggaacaaca   4440
ccgtctggcg atgtagcagc gacgactacc aaggaagagg gtaaagagaa agagacgagt   4500
gctgaagagg ctatggataa ggaaactgca agtgctgctg ataaggaaga gacgaaggag   4560
gaagaaaagc ctactaccaa cgccgctgaa gaggatacta aagtaaatga ggaagttaag   4620
aaagaggaga aggaaccggc agcagatgct gaaaagccag ctgaagcgaa tgactccgag   4680
aaaattgaga ctaaggagaa tgaaaatgcg gaaattaagg gggataagtc tgccaaggat   4740
gagaagcctg cagtatcgac agaaaacgga gaaaataagc ctaaggctga aagtgaagaa   4800
gatgtagtta tcgtgaaaga tgatgatgat gaagttgcaa cgaccaacga aaagaaggaa   4860
gaaagcaaag aatcgaaaga caaggaggtg aaggaaaatg ccgatggaga aaaaccgaaa   4920
cgcaaattta tgtttaacat tgccgatggt ggcttcaccg agctccatac actgtggcta   4980
aacgaagaaa aagcagctgt acccggtcgt gaatacgaaa tctggcacag gcgacacgat   5040
tactggctac tcgctggtat tgtaactcat ggctatggtc gttggcaaga cattcaaaac   5100
gacatcagat ttgccgtcat caatgagcca tttaagatgg acgttggcaa gggtaatttc   5160
ttggagatta agaacaaatt cttagccaga cgattcaaac tgctggaaca ggctctggtt   5220
attgaagagc agcttcgaag agccgcttac ttgaacctca ctcaagatcc aaaccatccg   5280
gctatgagtt tgaacgcgag gttcgccgag gttgagtgtc tcgctgaatc acatcagcat   5340
cttagtaaag agagccttgc tggaaataaa ccagctaatg cagtgctgca taaggtgctt   5400
aatcaattag aggaacttct atcagacatg aagtcagatg taagtcgttt gccagccacc   5460
ttggctcgta taccacctgt ggctcagagg ctacaaatgt ccgagcgatc tattctcagt   5520
```

```
cgactggcag cgactgcacc aggtggtaat agtacgcaga caggacaagc tgcattattg   5580

gcacaacaat tccccctgg tttcaacact ggtcagatac cagccacatt tgctggtgca   5640

gcaaacttcg gtaactttag gccacaatat tcagtgccag gacagccacc tcaaggt     5697
```

<210> SEQ ID NO 23
<211> LENGTH: 576
<212> TYPE: DNA
<213> ORGANISM: Ophelimus maskelli
<220> FEATURE:
<223> OTHER INFORMATION: VCE-F2 Om- Partial sequence;
> venom carboxylesterase-6 isoform 1(VCE-F2) _Om

<400> SEQUENCE: 23

```
gaatcacgca ggagcgtttt tgaaggaaga tccagcgata tccttgaaaa atggccgatt     60

gagcgatatt caatggatga ctggcgtcac ttcagacgaa ggtgctttaa ggactcctgg    120

aattttcggt ctcttcgacg gtgaattagc agagcgtttg aacaaagact tcgagaatat    180

cgcaccgata acgttactct ttggagatta ttgcccggaa caaaataagg cgaattcatc    240

gagattaata cgagaatttt acctcgacga caggcctatc gaccaatctg ctagaagtat    300

aaaagaagtc acagacatgt acacggacgc ttggttctac atcgcggcgg acgaggcagt    360

gcgcgaccat ctggcattat cctcctcgcc aatttactac tattacttcg cgtacagagg    420

aagctcgtcg ttcagtcgga ttttcggtga cgaggagagg gactacggag tttcgcatgc    480

agacgagctc cagtatctct tcccggtcgg cgagcaactc ttccaggatg tgcctctgag    540

caaagaagac caccgggtgg ttgatatcgt gacggc                              576
```

<210> SEQ ID NO 24
<211> LENGTH: 736
<212> TYPE: DNA
<213> ORGANISM: Ophelimus maskelli
<220> FEATURE:
<223> OTHER INFORMATION: Chitin synthase Om- Partial sequence;
> Chitin_synthase_Om

<400> SEQUENCE: 24

```
ctcgatggcg aatcagcgat gcctcgagat aaccgtgcaa ataacgaaag ccctcgtcta     60

ccttctagtc tttgtgatag tactcggcag cggtgtcata gccaaaggga cgttactttt    120

catgacgtcc caactcaagg ccggtcgtac catcgtctac tgtaacagac agatcggtcg    180

agatcgacaa ttcgtagtaa cgttacccga agaggagcgg atagcatgga tatggtgtat    240

aataatagca ttcgcagtac ccgaaatcgg cgcactattc cgtagcatac gtatgtgcat    300

atttaaatcg tggaagaaac cgttatcgtc gcactttctg ctggtcttcg tcatggaaac    360

gtttcacgtt atcggtttgt ccatgatgtt tcttgccgta ctgccagatc ttgatgtcgt    420

caagggtgca atgcttacca gttgcgtctg cttcgtgcct ggtttactag gtctgatgtc    480

gagaaacaaa aacaaggatg agtcgcgtcg ttttgtgctg gtactcgtcg atctagctgc    540

actggctgca caaacaacag ctttcgtcgt ttggccattg cttgacagca aaacaccttc    600

cctttggctc ataccaccag ctctcatact cgtatcctgt aggtggtggg agaactacgt    660

atctgtacag agtcctatca gtttcataaa aacactcgcc cgcgtaaaga aggaactcat    720

acaaacgcgc tacttc                                                    736
```

<210> SEQ ID NO 25
<211> LENGTH: 651
<212> TYPE: DNA
<213> ORGANISM: Ophelimus maskelli

```
<220> FEATURE:
<223> OTHER INFORMATION: Fragment of Om Ferritin gene; Ferritin Om- Full
      length; > Ferritin_Om

<400> SEQUENCE: 25

atgaagcttt tctgcgcctt tgtacttgct ttgtcgtgtt tgggcatctg ctcggccgac      60

agtctcaaat gtaccattaa acctgctgaa gttccacaag gatggcgaga catggtaaat     120

ccttgcataa ggattctaga agctcaagtc aaagttgaaa tcgaagcagc tatgacatat     180

ctagctatgg gcgcacactt cgctaaggac acagtcaatc gccctggttt cagcaaattc     240

ttcatcgaaa gcgctagcga agagcgtgag catgctatca aaataattga atacttgctg     300

atgcgaggtc agttgactag cgacgttagc aaactgctca aattccctct gaaaccaatc     360

cgtgaagaat ggaacagcgg tgttgaggct ctgagcgatg ctctgaatct tgagtcgcag     420

gtcacccgaa acattcgtga aattattatg acttgcgagt cgcctaagga cattcctttc     480

aatgattacc acttggtaga ctatttgact gctgacttct tggatgagca gcacaagggc     540

cagcgagatc ttgctggaaa gatttcaacg ttgggtaaga tgatggcatc gcatggacct     600

ctgggagaat tcttgtttga caagaaactt ctgaatggtg aaccattgta a              651


<210> SEQ ID NO 26
<211> LENGTH: 274
<212> TYPE: DNA
<213> ORGANISM: Ophelimus maskelli
<220> FEATURE:
<223> OTHER INFORMATION: JHEH Om Partial Sequence;
      > juvenile_hormone_epoxide_hydrolase_Om

<400> SEQUENCE: 26

caggctacta aaccggacac attaggtgtt ggagtaagtg attctccagc tggattagca      60

gcttatatat tggagaagtt ctcgactgcc acggtgtacg acaacaaatt ccgygacgac     120

ggtggtctac ttgaaaaatt cacgatggac gagcttattg acaatcttat gtattactgg     180

gtacccaaca aagctaccag tgccttccgg atttactctg aaactttgaa caagcacagc     240

atgaagtata aaatggataa cgtaccgata acag                                 274


<210> SEQ ID NO 27
<211> LENGTH: 914
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P1 - CaMV 35S Promoter& Omega UTR

<400> SEQUENCE: 27

agattagcct tttcaatttc agaaagaatg ctaacccaca gatggttaga gaggcttacg      60

cagcaggtct catcaagacg atctacccga gcaataatct ccaggaaatc aaataccttc     120

ccaagaaggt taaagatgca gtcaaaagat tcaggactaa ctgcatcaag aacacagaga     180

aagatatatt tctcaagatc agaagtacta ttccagtatg gacgattcaa ggcttgcttc     240

acaaaccaag gcaagtaata gagattggag tctctaaaaa ggtagttccc actgaatcaa     300

aggccatgga gtcaaagatt caaatagagg acctaacaga actcgccgta aagactggcg     360

aacagttcat acagagtctc ttacgactca atgacaagaa gaaaatcttc gtcaacatgg     420

tggagcacga cacacttgtc tactccaaaa atatcaaaga tacagtctca gaagaccaaa     480

gggcaattga gacttttcaa caaagggtaa tatccggaaa cctcctcgga ttccattgcc     540
```

```
cagctatctg tcactttatt gtgaagatag tggaaaagga aggtggctcc tacaaatgcc    600

atcattgcga taaaggaaag gccatcgttg aagatgcctc tgccgacagt ggtcccaaag    660

atggaccccc acccacgagg agcatcgtgg aaaaagaaga cgttccaacc acgtcttcaa    720

agcaagtgga ttgatgtgat atctccactg acgtaaggga tgacgcacaa tcccactatc    780

cttcgcaaga cccttcctct atataaggaa gttcatttca tttggagaga acacggggga    840

ctctagatat ttttacaaca attaccaaca acaacaaaca acaaacaaca ttacaattac    900

tatttacaat taca                                                      914
```

```
<210> SEQ ID NO 28
<211> LENGTH: 317
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P2 - AtUBQ1 Promoter

<400> SEQUENCE: 28

gaatcatgta gtgtctttgg accttgggaa tgatagaaac gatttgttat agctactcta     60

tgtatcagac cctgaccaag atccaacaat ctcataggtt ttgtgcatat gaaaccttcg    120

actaacgaga agtggtcttt taatgagaga gatatctaaa atgttatctt aaaagcccac    180

tcaaatctca aggcataagg tagaaatgca aatttggaaa gtgggctggg ccttttgtgg    240

taaaggcctg taacctagcc caatattagc aaaaccctag acgcgtacat tgacatatat    300

aaacccgcct cctcctt                                                   317
```

```
<210> SEQ ID NO 29
<211> LENGTH: 1103
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: P3 - AtActin7 Promoter

<400> SEQUENCE: 29

tagataaaca atacacttta cacacattat tttcttagaa ttgggtctca tatagaacac     60

tcacaaaggt gacttataaa aaatgcttca aagatcctag tcttttagtg tgcattcctc    120

aaaatcgtag ttgatatgta tcttgctcct attcgggttt tggtcttaga attttggttt    180

caggaatttt caattaactc attaaaacat ttataacata aaaagatata tcacgaaaac    240

cgatcaatca tttaatatat ttttatttta ttttattttt tgtcacaata aaatcctaga    300

caatagtgtt taaacattta tcaaaaaatt caccttacga ttaatttgtt ttatattttg    360

tgatgatgca atttaatcta tataaattat aaaacatatc gataatctgt gtttttcttt    420

ttctacatat aaaattcata aaaatgagag ttttgaagct cttaaaatgg actagtcaac    480

aattggccaa tctttgttct aaattgctaa taaacgacca tttccgtcaa ttctccttgg    540

ttgcaacagt ctacccgtca aatgtttact aatttataag tgtgaagttt gaattatgaa    600

agacgaaatc gtattaaaaa ttcacaagaa taaacaactc catagatttt caaaaaaaca    660

gtcacgagaa aaaaaccaca gtccgtttgt ctgctcttct agtttttatt atttttctat    720

taatagtttt ttgttatttc gagaataaaa tttgaacgat gtccgaacca caaaagccga    780
```

gccgataaat cctaagccga gcctaacttt agccgtaacc atcagtcacg gctcctcggg 840
ctaattcatt tgaaccgaat cataatcaac ggtttagatc aaactcaaaa caatctaacg 900
gcaacataga cgcgtcggtg agctaaaaag agtgtgaaag ccaggtcacc atagcattgt 960
ctctcccaga tttttatttt gggaaataat agaagaaata gaaaaaaata aaagagtgag 1020
aaaaatcgta gagctatata ttcgcacctg tactcgtttc gctttcctta gtgttagctg 1080
ctgccgctgt tgtttctcct cca 1103

<210> SEQ ID NO 30
<211> LENGTH: 937
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: P4 - AtGammTI P2 Promoter

<400> SEQUENCE: 30
cgttggaagc tgtatatcct ctgacgccgc attaaatgcg tctgatacgt atctccatct 60
ctctttgctc gcgcttttta ttgtcacatc cgggaatttt tctaataatt ttctcttatg 120
ttttctttcc aagttgctcc gatatgatta ttgtgatttt aaaacatcac atgttgtttc 180
cgtagtactt gtgctgttta ccaaatcgta gtacttctgc tggtcataga ttcaaggtaa 240
aagcccattc accttgttga ataatcaatc cagtacaata ctcacccgaa aaagttacca 300
gcccaatatc gtggtatata ctccatttca atactaattt ttttgttttt taatgattat 360
ttttttaaaa aaaaaatgaa ataaatcctt tcatagtaca tgctgctgca gttgtaaatt 420
gcatgtattt tatgaaacgt tcagtacaaa cttagaaagt tgtagtaatg aaagctctaa 480
attgagatct acactcataa atagttcatg ctttatttag tagtaactgc ataagtaatg 540
catgcttttt ttttttgata cgttgtaatc attgccctac aatctctagc tcccctacat 600
ctacaagtct gctgtcggga atatggtttt gccgcccatc cgtagaggct atatcggata 660
tttcgcatgg taaaaaaacg ttatataccc aacttttctg ggagaaggtc attctcttaa 720
taaggatgtc aaatttggtc attcagtaaa ttaaccctta aaaaaatgca aaataatttg 780
tttatgtgac aaagaaatgg attttatcta taactatcaa gaagaagaaa acactcggct 840
atatatatac gtacaacaca taagaaaaac aaaccaatca cttcactctc tctaatcaaa 900
aaggctttta acctcagccg ttaaatcttt ctccgat 937

<210> SEQ ID NO 31
<211> LENGTH: 301
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: P5 - sgFIMV Promoter

<400> SEQUENCE: 31
tttacagtaa gaactgataa caaaaatttt acttatttcc ttagaattaa tcttaaaggt 60
gatagtaaac aaggacgatt agtccgttgg caaaattggt tcagcaagta tcaatttgat 120
gtcgaacatc ttgaaggtgt aaaaaacgtt ttagcagatt gcctcacgag agattttaat 180
gcttaaaaac gtaagcgctg acgtatgatt tcaaaaaacg cagctataaa agaagccctc 240
cagcttcaaa gttttcatca acacaaattc taaaaacaaa attttttaga gagggggagt 300
g 301

<210> SEQ ID NO 32
<211> LENGTH: 610
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: T1 - AtRiboProS40 Terminator

<400> SEQUENCE: 32
gttatttggc ctctcgttgg atctccttat gtagctttct caatgtttca ttttgttttt 60
tcttagtttg aaaagagttt tggaattact atgctttgtt atagtctcaa ctctgaacag 120
ctttggatct ttttctgtat gaccataaga tattcaaaaa ttggtagtca ttttatctca 180
caaaaaaacc ttgaatttgt gctgtatgat tttgtaaagt cttaggtgcc aaatctttga 240
ttggagttga taaaatattt ttatttggtt gtaattttgt aatatcccag gatatttcac 300
aaattgaaca tagactacag aattttagaa aacaaacttt ctctctctta tctcaccttt 360
atcttttaga gagaaaaagt tcgatttccg gttgaccgga atgtatcttt gttttttttg 420
ttttgtaaca tatttcgttt tccgatttag atcggatctc cttttccgtt ttgtcggacc 480
ttcttccggt ttatccggat ctaataatat ccatcttaga cttagctaag tttggatctg 540
ttttttggtt agctcttgtc aatcgcctca tcatcagcaa gaaggtgaaa tttttgacaa 600
ataaatctta 610

<210> SEQ ID NO 33
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: T2 - AtUBQ1 Terminator

<400> SEQUENCE: 33
agagactctt atcaagaatc ccatctcttg cttgcttttt tttgttgtct tccctttgat 60
agggtttgtt tttcttgttt cagtgacttt ctatgttaaa agataatgtc agtaaaagga 120
tttggttttc tattattctg aatcgattac ggaagattct tgcttaattc caatctatac 180
aagtatcgtg aaataatgac cgtttatgtg attaggagac gtgtttcatt aataaaatat 240
aagatcaata cattgttagt agtgataaac tatgtacaaa ttgtattgat tgtaaaagaa 300
acacaatagg ttcctttttt ctacaatata ttgtgacaga ctctctgttt taacgaatga 360
attaaatttg tcaacgaaaa aattaaagaa tgatgtgatc actttgcacc ttggttcatc 420
ttcagaggct tctgcatgtt ccatgcattg aggctctcta cggtcacagg ttgtgagccg 480
ttgttaaaga caaacaaatg agctttttct cctactgctt ttgtcggata cactctaaga 540
tgttatcact gtctttcctt ttgctccaaa gctctccaca accgagtgat caatctgcaa 600
attcactcaa ttatgttacc tatttgcttc tctatacaag agtaatattc agtaaaatga 660

<210> SEQ ID NO 34
<211> LENGTH: 253
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: T3 - NOS Terminator

<400> SEQUENCE: 34
gatcgttcaa acatttggca ataaagtttc ttaagattga atcctgttgc cggtcttgcg 60
atgattatca tataatttct gttgaattac gttaagcatg taataattaa catgtaatgc 120
atgacgttat ttatgagatg ggtttttatg attagagtcc cgcaattata catttaatac 180
gcgatagaaa acaaaatata gcgcgcaaac taggataaat tatcgcgcgc ggtgtcatct 240
atgttactag atc 253

<210> SEQ ID NO 35
<211> LENGTH: 752
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: T4 - AtDelta TIP Terminator

<400> SEQUENCE: 35
ggaaacaagt gatgattctt gattcatgtt tctgtgtttg gttactttgc ctcgatcttt 60
cttgttttgt ttggagtttg gtccggtttc gttgtaattt ttatccaatt tgtatgaata 120
ttatttaatg gatggctgtt ttggttataa attaactaat ggatgtatga atatatagtt 180
tcacctaaat aggtagttgt aatgttgtat agctaattat cgatccatat atataaaaaa 240
tagatcgtta caattttatg atatagtaac aactaacaac aatgacaaat taatggatgg 300
tttcaagtag aagtttcgag atcatcgtca ttaggtatat tcttagggat gttccactca 360
tgagctttcc actctggcaa ttgttgtatg acaacctatg caataattta ttaatatcaa 420
taaatcacat gcatgtatag aaaaaaatga agattatata ttatagacag agaaaaagag 480
aggttatata ttattaccaa tccggtagaa tctggatttc ccacgttggt ttgacaagct 540
agtctccaat tttttggttt ctgtgaaaac attattcgat tttactccca taaccaagat 600
gatacaagat tactaaatac tataggataa tttcttaaat aaaactatac ccttttgagt 660
ttctccttct caatatcagt tcgcggattt agaagctcct ttccatttac aatctgaaaa 720
gaaatatcca tcaatatctc ataaaccatc at 752

<210> SEQ ID NO 36
<211> LENGTH: 829
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: T5 - AtGammTI P2 Terminator

<400> SEQUENCE: 36
agacgtcaaa ttcaacgttg ttaatctgat gaatttttcg tgatttgctt ttttaatttg 60
catcgtaatg ggtttctggc cgttggatca tttttagatg aatctttgtc tattgattga 120
tcatttatgt gtctttgggt ttgttgttgg agttgtaata tctctggaag gcttttgtgc 180
aattgtattg tacggtttaa taactataat tgagaaaacc agggaatgtg aattatgaaa 240
atgaattttt ttgttattgt ttattttact taaagagccc taactaattt agatcataat 300

```
ttacgagaca tggaaatttt aatgaataat aaacattgtg attgatattt ttggttttca    360

tttccgtttt ttatatttta tatcaacaca ctacagtagt acatatttac acatgattta    420

tgtccaggct aaaattgtat attaagcgtt gaaaaatcat cgagtgttac acttaggagg    480

ggttcgactt ccatgtgtaa aaataatact agcaattcgc aaataacttt acaaacacaa    540

gtcatgactc atgagctaag gttcaaatta ctttgggttg caatgtatgc gtttcatttc    600

tatatcgttc caatcacagc attattattt ccttctttgt gagtcttctt ccaacatttc    660

ggcgggaatc tgtagggaga ttttcgtcat tcggatttca ttttgtttgg tttcaaaacg    720

tgaatagcaa tagatggatg ggaatagatt cgctaaaatc tttgtggggt taatggataa    780

taaagttcgt gaaacgtctg gacagtatac gaaccatcta cctctataa               829

<210> SEQ ID NO 37
<211> LENGTH: 5940
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Gall Wasp DNA construct #1

<400> SEQUENCE: 37

agattagcct tttcaatttc agaaagaatg ctaacccaca gatggttaga gaggcttacg     60

cagcaggtct catcaagacg atctacccga gcaataatct ccaggaaatc aaataccttc    120

ccaagaaggt taaagatgca gtcaaaagat tcaggactaa ctgcatcaag aacacagaga    180

aagatatatt tctcaagatc agaagtacta ttccagtatg gacgattcaa ggcttgcttc    240

acaaaccaag gcaagtaata gagattggag tctctaaaaa ggtagttccc actgaatcaa    300

aggccatgga gtcaaagatt caaatagagg acctaacaga actcgccgta aagactggcg    360

aacagttcat acagagtctc ttacgactca atgacaagaa gaaaatcttc gtcaacatgg    420

tggagcacga cacacttgtc tactccaaaa atatcaaaga tacagtctca gaagaccaaa    480

gggcaattga gacttttcaa caaagggtaa tatccggaaa cctcctcgga ttccattgcc    540

cagctatctg tcactttatt gtgaagatag tggaaaagga aggtggctcc tacaaatgcc    600

atcattgcga taaaggaaag gccatcgttg aagatgcctc tgccgacagt ggtcccaaag    660

atggaccccc acccacgagg agcatcgtgg aaaaagaaga cgttccaacc acgtcttcaa    720

agcaagtgga ttgatgtgat atctccactg acgtaaggga tgacgcacaa tcccactatc    780

cttcgcaaga cccttcctct atataaggaa gttcatttca tttggagaga acacggggga    840

ctctagatat ttttacaaca attaccaaca acaacaaaca acaaacaaca ttacaattac    900

tatttacaat tacatctctt acttccaaaa atcaaactca agttaacgcg tcgttggccc    960

cgcaagaaaa ttattccatt tctgaaggct gggggagtga cgaagatggt tctgggtgcc   1020

ataagaacgg caggtatttt cggattgcac ggtggtcagt tagcaaaacg gttggatgaa   1080

gaatttgaaa aattgggagc taccacttta ttgtcgcaaa ccggtagagc cggtgaagcc   1140

cgctgatgcg actgctgccg ctgtaccgcc agctgctgct gccaacgcca cggccactgc   1200

gccggcgacg aacgggctcg aacgagccga ctaattgtct ttaaacgcgc gatataagcg   1260

cacaatgctc gagaaacgat aaactctatc gctctgtcgc gtgcgtggca tcttcgcgcg   1320

cgttcgtcgc cggcgcagtg gccgtggcgt tggcagcagc agctggcggt acagcggcag   1380

cagtcgcatc agcgggcttc accggctcta ccggtttgcg acaataaagt ggtagctccc   1440
```

-continued

```
aatttttcaa attcttcatc caaccgtttt gctaactgac caccgtgcaa tccgaaaata   1500
cctgccgttc ttatggcacc cagaaccatc ttcgtcactc ccccagcctt cagaaatgga   1560
ataattttct tgcggggcca acgacgcgtt aacttgagtt tgatttttgg aagtaagaga   1620
gcgatcgcgt tatttggcct ctcgttggat ctccttatgt agctttctca atgtttcatt   1680
ttgtttttc ttagtttgaa aagagttttg gaattactat gctttgttat agtctcaact   1740
ctgaacagct ttggatcttt ttctgtatga ccataagata ttcaaaaatt ggtagtcatt   1800
ttatctcaca aaaaaacctt gaatttgtgc tgtatgattt tgtaaagtct taggtgccaa   1860
atctttgatt ggagttgata aaatattttt atttggttgt aattttgtaa tatcccagga   1920
tatttcacaa attgaacata gactacagaa ttttagaaaa caaactttct ctctcttatc   1980
tcacctttat cttttagaga gaaaaagttc gatttccggt tgaccggaat gtatctttgt   2040
ttttttgtt ttgtaacata tttcgttttc cgatttagat cggatctcct tttccgtttt   2100
gtcggacctt cttccggttt atccggatct aataatatcc atcttagact tagctaagtt   2160
tggatctgtt ttttggttag ctcttgtcaa tcgcctcatc atcagcaaga aggtgaaatt   2220
tttgacaaat aaatcttaga atcatgtagt gtctttggac cttgggaatg atagaaacga   2280
tttgttatag ctactctatg tatcagaccc tgaccaagat ccaacaatct cataggtttt   2340
gtgcatatga aaccttcgac taacgagaag tggtctttta atgagagaga tatctaaaat   2400
gttatcttaa aagcccactc aaatctcaag gcataaggta gaaatgcaaa tttggaaagt   2460
gggctgggcc ttttgtggta aaggcctgta acctagccca atattagcaa aaccctagac   2520
gcgtacattg acatatataa acccgcctcc tccttgttta gggtttctac gtgagagaag   2580
acgaaacaca aaagaggcta cttgattcaa catattcata atttaaatac atcagaagat   2640
cagtataact ttacttcagt taaagctcaa gaaactattc ctgtttcttt atgtagagcc   2700
agtgaaaccg gctgacggtt cagcagttcc agttactcca gtaccagcaa cggccacggc   2760
aatggatgga acggctacgg gatcaacgag tagtattgag cgatattcaa tggatgactg   2820
gcgtcacttc agacgaaggt gctttaagga ctcctggaat tttcggtctc ttcgacggtg   2880
aattagcaga gcgtgcgcgc gaaacaacgg taatcaaccg gcaattatta atcgtacatg   2940
cgcggcgcag gcgcgcctgc attatccctc gtcatcacca aagcgccaca ttatgcttct   3000
tcacgctctg ctaattcacc gtcgaagaga ccgaaaattc caggagtcct taaagcacct   3060
tcgtctgaag tgacgccagt catccattga atatcgctca atactactcg ttgatcccgt   3120
agccgttcca tccattgccg tggccgttgc tggtactgga gtaactggaa ctgctgaacc   3180
gtcagccggt ttcactggct ctacataaag aaacaggaat agtttcttga gctttaactg   3240
aagtaaagtt atactgatct tctgatgtat ttaaattatg aatatgttga atcaagtagc   3300
ctagagactc ttatcaagaa tcccatctct tgcttgcttt tttttgttgt cttccctttg   3360
atagggtttg tttttcttgt ttcagtgact ttctatgtta aaagataatg tcagtaaaag   3420
gatttggttt tctattattc tgaatcgatt acggaagatt cttgcttaat tccaatctat   3480
acaagtatcg tgaaataatg accgtttatg tgattaggag acgtgtttca ttaataaaat   3540
ataagatcaa tacattgtta gtagtgataa actatgtaca aattgtattg attgtaaaag   3600
aaacacaata ggttcctttt ttctacaata tattgtgaca gactctctgt tttaacgaat   3660
gaattaaatt tgtcaacgaa aaaattaaag aatgatgtga tcactttgca ccttggttca   3720
tcttcagagg cttctgcatg ttccatgcat tgaggctctc tacggtcaca ggttgtgagc   3780
cgttgttaaa gacaaacaaa tgagcttttt ctcctactgc ttttgtcgga tacactctaa   3840
```

```
gatgttatca ctgtctttcc ttttgctcca aagctctcca caaccgagtg atcaatctgc   3900

aaattcactc aattatgtta cctatttgct tctctataca agagtaatat tcagtaaaat   3960

gagtcgacta gataaacaat acactttaca cacattattt tcttagaatt gggtctcata   4020

tagaacactc acaaaggtga cttataaaaa atgcttcaaa gatcctagtc ttttagtgtg   4080

cattcctcaa aatcgtagtt gatatgtatc ttgctcctat tcgggttttg gtcttagaat   4140

tttggtttca ggaattttca attaactcat taaaacattt ataacataaa aagatatatc   4200

acgaaaaccg atcaatcatt taatatattt ttattttatt ttattttttg tcacaataaa   4260

atcctagaca atagtgttta aacatttatc aaaaaattca ccttacgatt aatttgtttt   4320

atattttgtg atgatgcaat ttaatctata taaattataa aacatatcga taatctgtgt   4380

ttttcttttt ctacatataa aattcataaa aatgagagtt ttgaagctct taaaatggac   4440

tagtcaacaa ttggccaatc tttgttctaa attgctaata aacgaccatt tccgtcaatt   4500

ctccttggtt gcaacagtct acccgtcaaa tgtttactaa tttataagtg tgaagtttga   4560

attatgaaag acgaaatcgt attaaaaatt cacaagaata aacaactcca tagattttca   4620

aaaaaacagt cacgagaaaa aaaccacagt ccgtttgtct gctcttctag tttttattat   4680

ttttctatta atagtttttt gttatttcga gaataaaatt tgaacgatgt ccgaaccaca   4740

aaagccgagc cgataaatcc taagccgagc ctaactttag ccgtaaccat cagtcacggc   4800

tcctcgggct aattcatttg aaccgaatca taatcaacgg tttagatcaa actcaaaaca   4860

atctaacggc aacatagacg cgtcggtgag ctaaaaagag tgtgaaagcc aggtcaccat   4920

agcattgtct ctcccagatt ttttatttgg gaaataatag aagaaataga aaaaaataaa   4980

agagtgagaa aaatcgtaga gctatatatt cgcacctgta ctcgtttcgc tttccttagt   5040

gttagctgct gccgctgttg tttctcctcc atctcttact tccaaaaatc aaactcaagt   5100

taacgcgtcg ttggccccgc aagaaaatta ttccatttct gaaggctggg ggagtgacga   5160

agatggttct gggtgccata agaacggcag gtattttcgg attgcacggt ggtcagttag   5220

caaaacggtt ggatgaagaa tttgaaaaat tgggagctac cactttattg tcgcaaaccg   5280

gtagagccgg tgaagcccgc tgatgcgact gctgccgctg taccgccagc tgctgctgcc   5340

aacgccacgg ccactgcgcc ggcgacgaac gaggctactt gattcaacat attcataatt   5400

taaatacatc agaagatcag tataacttta cttcagttaa agctcaagaa actattcctg   5460

tttatttatg tagagccagt gaaaccggct gacggttcag cagttccagt tactccagta   5520

ccagcaacgg ccacggcaat ggatggaacg gctacgggat caacgagtag tattgagcga   5580

tattcaatgg atgactggcg tcacttcaga cgaaggtgct ttaaggactc ctggaatttt   5640

cggtctcttc gacggtgaat tagcagagcg tgagctcgaa tttccccgat cgttcaaaca   5700

tttggcaata aagtttctta agattgaatc ctgttgccgg tcttgcgatg attatcatat   5760

aatttctgtt gaattacgtt aagcatgtaa taattaacat gtaatgcatg acgttattta   5820

tgagatgggt ttttatgatt agagtcccgc aattatacat ttaatacgcg atagaaaaca   5880

aaatatagcg cgcaaactag gataaattat cgcgcgcggt gtcatctatg ttactagatc   5940
```

<210> SEQ ID NO 38
<211> LENGTH: 6052
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<223> OTHER INFORMATION: Gall Wasp DNA construct #2

<400> SEQUENCE: 38

agattagcct tttcaatttc agaaagaatg ctaacccaca gatggttaga gaggcttacg     60

cagcaggtct catcaagacg atctacccga gcaataatct ccaggaaatc aaataccttc    120

ccaagaaggt taaagatgca gtcaaaagat tcaggactaa ctgcatcaag aacacagaga    180

aagatatatt tctcaagatc agaagtacta ttccagtatg gacgattcaa ggcttgcttc    240

acaaaccaag gcaagtaata gagattggag tctctaaaaa ggtagttccc actgaatcaa    300

aggccatgga gtcaaagatt caaatagagg acctaacaga actcgccgta aagactggcg    360

aacagttcat acagagtctc ttacgactca atgacaagaa gaaaatcttc gtcaacatgg    420

tggagcacga cacacttgtc tactccaaaa atatcaaaga tacagtctca gaagaccaaa    480

gggcaattga gacttttcaa caaagggtaa tatccggaaa cctcctcgga ttccattgcc    540

cagctatctg tcactttatt gtgaagatag tggaaaagga aggtggctcc tacaaatgcc    600

atcattgcga taaaggaaag gccatcgttg aagatgcctc tgccgacagt ggtcccaaag    660

atggaccccc acccacgagg agcatcgtgg aaaaagaaga cgttccaacc acgtcttcaa    720

agcaagtgga ttgatgtgat atctccactg acgtaaggga tgacgcacaa tcccactatc    780

cttcgcaaga cccttcctct atataaggaa gttcatttca tttggagaga acacggggga    840

ctctagatat ttttacaaca attaccaaca acaacaaaca acaaacaaca ttacaattac    900

tatttacaat tacaccggtg gcgtggtgcc ggatctgttc gagatactgc ccaacggaga    960

gaccgagatc gtcaacgctg attttcacac tccggttcac atgctgctgt tcgcgccagt   1020

tgaccagcga cgttagcaag ttgctcaaat tcccgctcaa gccgatccgc gaggaatgga   1080

acagcggtat cgaagcactt actgatgctc tcaacatggt attgcgaccg tggacctggg   1140

tgaagacgta cttttacagc ttttggccgt cgctgttgcc tgaggacgaa atcccgcgta   1200

tgttccccct gctcggctcg aacgagccga ctaattgtct ttaaacgcgc gatataagcg   1260

cacaatgctc gagaaacgat aaactctatc gctctgtcgc gtgcgtggca tcttcgcgcg   1320

gagcaggggg aacatacgcg ggatttcgtc ctcaggcaac agcgacggcc aaaagctgta   1380

aaagtacgtc ttcacccagg tccacggtcg caataccatg ttgagagcat cagtaagtgc   1440

ttcgataccg ctgttccatt cctcgcggat cggcttgagc gggaatttga gcaacttgct   1500

aacgtcgctg gtcaactggc gcgaacagca gcatgtgaac cggagtgtga aaatcagcgt   1560

tgacgatctc ggtctctccg ttgggcagta tctcgaacag atccggcacc acgccaccgg   1620

ctcgagggaa acaagtgatg attcttgatt catgtttctg tgtttggtta ctttgcctcg   1680

atctttcttg ttttgtttgg agtttggtcc ggtttcgttg taatttttat ccaatttgta   1740

tgaatattat ttaatggatg gctgttttgg ttataaatta actaatggat gtatgaatat   1800

atagtttcac ctaaataggt agttgtaatg ttgtatagct aattatcgat ccatatatat   1860

aaaaaataga tcgttacaat tttatgatat agtaacaact aacaacaatg acaaattaat   1920

ggatggtttc aagtagaagt ttcgagatca tcgtcattag gtatattctt agggatgttc   1980

cactcatgag ctttccactc tggcaattgt tgtatgacaa cctatgcaat aatttattaa   2040

tatcaataaa tcacatgcat gtatagaaaa aaatgaagat tatatattat agacagagaa   2100

aaagagaggt tatatattat taccaatccg gtagaatctg gatttcccac gttggtttga   2160

caagctagtc tccaattttt tggtttctgt gaaaacatta ttcgatttta ctcccataac   2220
```

```
caagatgata caagattact aaatactata ggataatttc ttaaataaaa ctataccctt   2280
ttgagtttct ccttctcaat atcagttcgc ggatttagaa gctcctttcc atttacaatc   2340
tgaaaagaaa tatccatcaa tatctcataa accatcataa gcttcgttgg aagctgtata   2400
tcctctgacg ccgcattaaa tgcgtctgat acgtatctcc atctctcttt gctcgcgctt   2460
tttattgtca catccgggaa tttttctaat aatttctct tatgttttct ttccaagttg   2520
ctccgatatg attattgtga ttttaaaaca tcacatgttg tttccgtagt acttgtgctg   2580
tttaccaaat cgtagtactt ctgctggtca tagattcaag gtaaaagccc attcaccttg   2640
ttgaataatc aatccagtac aatactcacc cgaaaaagtt accagcccaa tatcgtggta   2700
tatactccat ttcaatacta attttttgt tttttaatga ttattttttt aaaaaaaaaa   2760
tgaaataaat cctttcatag tacatgctgc tgcagttgta aattgcatgt attttatgaa   2820
acgttcagta caaacttaga aagttgtagt aatgaaagct ctaaattgag atctacactc   2880
ataaatagtt catgctttat ttagtagtaa ctgcataagt aatgcatgct tttttttttt   2940
gatacgttgt aatcattgcc ctacaatctc tagctcccct acatctacaa gtctgctgtc   3000
gggaatatgg ttttgccgcc catccgtaga ggctatatcg gatatttcgc atggtaaaaa   3060
aacgttatat acccaacttt tctgggagaa ggtcattctc ttaataagga tgtcaaattt   3120
ggtcattcag taaattaacc cttaaaaaaa tgcaaaataa tttgtttatg tgacaaagaa   3180
atggatttta tctataacta tcaagaagaa gaaaacactc ggctatatat atacgtacaa   3240
cacataagaa aaacaaacca atcacttcac tctctctaat caaaaaggct tttaacctca   3300
gccgttaaat ctttctccga tcccgggtct gatgtcgaga aacaaaaaca aggatgagtc   3360
gcgtcgtttt gtgctggtac tcgtcgatct agctgcactg gctgcacaaa caacagcttt   3420
cgtcgttgtt gactagcgac gttagcaaac tgctcaaatt ccctctgaaa ccaatccgtg   3480
aagaatggaa cagcggtgtt gaggctctga gcgatgctct gaatctttta tgtattactg   3540
ggtacccaac aaagctacca gtgccttccg gatttactct gaaactttga acaagcacag   3600
catgaagtat aaaatggata acgtaccgcg cgcgaaacaa cggtaatcaa ccggcaatta   3660
ttaatcgtac atgcgcggcg caggcgcgcc tgcattatcc ctcgtcatca ccaaagcgcc   3720
acattatgct tcttcggtac gttatccatt ttatacttca tgctgtgctt gttcaaagtt   3780
tcagagtaaa tccggaaggc actggtagct ttgttgggta cccagtaata cataaaagat   3840
tcagagcatc gctcagagcc tcaacaccgc tgttccattc ttcacggatt ggtttcagag   3900
ggaatttgag cagtttgcta acgtcgctag tcaacaacga cgaaagctgt tgtttgtgca   3960
gccagtgcag ctagatcgac gagtaccagc acaaaacgac gcgactcatc cttgtttttg   4020
tttctcgaca tcagaagacg tcaaattcaa cgttgttaat ctgatgaatt tttcgtgatt   4080
tgctttttta atttgcatcg taatgggttt ctggccgttg gatcattttt agatgaatct   4140
ttgtctattg attgatcatt tatgtgtctt tgggtttgtt gttggagttg taatatctct   4200
ggaaggcttt tgtgcaattg tattgtacgg tttaataact ataattgaga aaaccaggga   4260
atgtgaatta tgaaaatgaa tttttttgtt attgtttatt ttacttaaag agccctaact   4320
aatttagatc ataatttacg agacatggaa attttaatga ataataaaca ttgtgattga   4380
tatttttggt tttcatttcc gttttttata ttttatatca acacactaca gtagtacata   4440
tttacacatg atttatgtcc aggctaaaat tgtatattaa gcgttgaaaa atcatcgagt   4500
gttacactta ggaggggttc gacttccatg tgtaaaaata atactagcaa ttcgcaaata   4560
actttacaaa cacaagtcat gactcatgag ctaaggttca aattactttg ggttgcaatg   4620
```

tatgcgtttc atttctatat cgttccaatc acagcattat tatttccttc tttgtgagtc 4680
ttcttccaac atttcggcgg gaatctgtag ggagattttc gtcattcgga tttcattttg 4740
tttggtttca aaacgtgaat agcaatagat ggatgggaat agattcgcta aaatctttgt 4800
ggggttaatg gataataaag ttcgtgaaac gtctggacag tatacgaacc atctacctct 4860
ataagggccc aagcttttta cagtaagaac tgataacaaa aattttactt atttccttag 4920
aattaatctt aaaggtgata gtaaacaagg acgattagtc cgttggcaaa attggttcag 4980
caagtatcaa tttgatgtcg aacatcttga aggtgtaaaa aacgttttag cagattgcct 5040
cacgagagat tttaatgctt aaaaacgtaa gcgctgacgt atgatttcaa aaaacgcagc 5100
tataaaagaa gccctccagc ttcaaagttt tcatcaacac aaattctaaa aacaaaattt 5160
tttagagagg gggagtgccc gggccggtgg cgtggtgccg gatctgttcg agatactgcc 5220
caacggagag accgagatcg tcaacgctga ttttcacact ccggttcaca tgctgctgtt 5280
cgcgccagtt gaccagcgac gttagcaagt tgctcaaatt cccgctcaag ccgatccgcg 5340
aggaatggaa cagcggtatc gaagcactta ctgatgctct caacatggta ttgcgaccgt 5400
ggacctgggt gaagacgtac ttttacagct tttggccgtc gctgttgcct gaggacgaaa 5460
tcccgcgtat gttcccccctg ctctctgatg tcgagaaaca aaaacaagga tgagtcgcgt 5520
cgttttgtgc tggtactcgt cgatctagct gcactggctg cacaaacaac agctttcgtc 5580
gttgttgact agcgacgtta gcaaactgct caaattccct ctgaaaccaa tccgtgaaga 5640
atggaacagc ggtgttgagg ctctgagcga tgctctgaat cttttatgta ttactgggta 5700
cccaacaaag ctaccagtgc cttccggatt tactctgaaa ctttgaacaa gcacagcatg 5760
aagtataaaa tggataacgt accgagctcg aatttccccg atcgttcaaa catttggcaa 5820
taaagtttct taagattgaa tcctgttgcc ggtcttgcga tgattatcat ataatttctg 5880
ttgaattacg ttaagcatgt aataattaac atgtaatgca tgacgttatt tatgagatgg 5940
gtttttatga ttagagtccc gcaattatac atttaatacg cgatagaaaa caaaatatag 6000
cgcgcaaact aggataaatt atcgcgcgcg gtgtcatcta tgttactaga tc 6052

<210> SEQ ID NO 39
<211> LENGTH: 3645
<212> TYPE: DNA
<213> ORGANISM: Apis mellifera
<220> FEATURE:
<223> OTHER INFORMATION: Honey Bee Apis mellifera; Coatomer subunit alpha (Alpha-coat protein); XM_623195

<400> SEQUENCE: 39
atgttgacaa aatttgagac aaaatctgct cgcgtaaaag gattatcttt tcatccaaaa 60
cgtccgtggg ttcttgcaag tttgcacaat ggagttattc agttatggga ttatcgtatg 120
tgtactttat tagataaatt tgatgaacat gatggaccag ttcgtggaat atgttttcat 180
aatcaacaac cattatttgt atctggtgga gatgattata agattaaagt atggaattac 240
aaacaaagaa gatgtatctt tactttatta ggtcatttag attatattag aacaactgta 300
tttcatcaag aatatccatg gattttaagt gcatctgatg atcaaactat tcgtatttgg 360
aattggcaaa gtcgcacgtg catttgtgtc ttaactggac ataatcatta tgtaatgtgt 420
gcacaattcc atcttactga agatattatt gtatcagctt ctttagatca aacagttaga 480
gtatgggaca tttctggttt aagaaagaaa aatgtagctc ctggaccagg aggattagaa 540
gatcatttaa aaaatcctgg taccacagat ctatttggtc aagctgatgc tgttgtaaaa 600

```
catgttttgg agggtcatga tagaggtgtt aattgggcat gtttccatcc aacattacca    660
ttgattgttt ctggagcaga tgatcgtcaa attaaaatgt ggcgaatgaa tgatgctaaa    720
gcttgggaag ttgacacttg ccgtggacat tacaacaatg tttcttgtgt tttattccat    780
cctagacaag atttaattct ttcaaattca gaagataaaa gtattcgtgt ttgggatatg    840
tctaaacgta cttgcttgca tacatttagg agagaacatg aaaggttttg ggttcttgct    900
gcacatccta ccttaaatct ttttgctgct ggtcatgatt ctggaatgat tattttcaaa    960
ttagaaagag aaagacctgc atatgccgta tatggaaatg ttctttatta tgtaaaagaa   1020
cgttttctta gaaaactgga ttttactact tcaaaagata catctgttat gcaaatacgc   1080
ggaggtggaa agacacctcc ttatagtatg tcatataatc aagctgaaaa tgccgtttta   1140
atctgtacaa gatcacctaa taatgtcgaa aatagcactt atgatctata tataatacca   1200
cgtgaaggtg attcaaacac tgatgctgat acaaaacggg cttcgggtgt cacagctatt   1260
tgggttgcaa gaaatcgttt tgctgtatta gatagagcat attcattggt catcaaaaat   1320
ttaaaaaatg aagttacaaa aaaagtgcaa attccaaact gtgacgaaat attttatgct   1380
ggcactggaa tgcttctttt acgtgatgct gatcaagtaa cactctttga tgttcaacaa   1440
aaaagaacat tagctgaagt aaaaatttct aaatgtcgat acgtcgtttg gtctagcgat   1500
atgtctcatg ttgctttact tgcaaaacat actgttaata tttgtaatcg acgattagaa   1560
tccttgtgtt ctgtacatga aaacactaga gtaaaatctg gagcatggga tgattctgga   1620
gtgtttattt atactactag caatcatatc aaatatgcaa ttaacaatgg tgatcatggc   1680
attattcgta ctttagatct cccaatatat gtaacacgag tcaaaggcaa tcaagtttat   1740
tgtttagata gagaatgcag accaagaatt cttcgaatag atccaactga atataaattt   1800
aaattggctt taattaatag gaagtatgag gaggttttgc atatggttcg caatgcaaat   1860
cttgttggcc aatctataat tgcatatttg caacagaaag gatatcccga agttgcttta   1920
catttcgtta aagatgaaaa gactagattt ggtcttgcac tcgaatgcgg aaatatcgaa   1980
gtcgctctag aagctgcaag atcgcttgat caaaaatctt gttgggaaag cttagctcaa   2040
gcagctttat tgcaaggcaa tcatcaagtt gttgaaatgt gttatcaaag aactaaaaat   2100
tttgaaaaat tagcattcct ttatcttata actggtaatt tggaaaaatt acgtaaaatg   2160
ataaaaattg cagaaattag gaaagatgta tctgggcaat atcaaggtag tttgttactt   2220
ggtgatattt atgaacgtgc aaaaatatta cggaattctg gtcaagcttc tttagcttat   2280
gtaacggaaa aaattcatgg tatatcatct ccggaagacg atattcaata tagttctatg   2340
agcgaagaac tttctgctct tgaaaaagga gcagaatatc ttcgacctcc agtaccaatt   2400
caacaagccg agaataactg gccattatta acagtatcaa aaggtttctt tgaaggagca   2460
atgatgtcac gtggaaagag tcaagtagct gctgctttag ctccggaaga tgacaatgcc   2520
gagccagccg aaggatgggg taatgacgaa gaattaggaa tagatgatga agaaggtgtt   2580
gaaaatgaaa acgttcctga aggtgaagat actgctggat gggatgtcga agaagtagat   2640
ttaccaccag aacttgaaac cacaacagtt gtggtggaag atggctatta ttcaccgcca   2700
acaaaaggaa tatcacctac tcaacattgg gtgaataatt ctcaattagt tgtagatcat   2760
atattagctg gatcgttcga aacagcattt agattattaa atgatcaaat tggcgtagtt   2820
gaatttgaag catatcaaag tcttttcatg aatactttcg tacgtgctaa aacatcgttt   2880
gcttcgttac caaatatacc ttcattgtat ggatatcctc aaagaaattg gaaagataca   2940
```

```
agtccaaaaa atggtcttcc tgcagttgga ttacatctta ctgatttagt tcaacgactt   3000

caaatatgtt atcatttgac aactggcgga aaatttccgg aagcaataga aaaattacaa   3060

gcgattttac tcagtgtatc gttattagtt gttgatacaa gacaagatat tgtagaagca   3120

caacagttga ttcagatttg tagagaatat attctaggtt tgaaaatgga aactgaaaga   3180

aaaaatctac ctaaagctac tttagctgaa caaaaacgga tttgtgaaat ggcagcttac   3240

tttacacatt gtaatttgca acctgttcat caaattctta ctttaagaat agctgtaaat   3300

atgtttttca aattaaaaaa ttataaaact gctgcttcat ttgctagaag actacttgaa   3360

ttaggtccta aacctgaatt agcacaacaa gttagaaaaa ttttacaggc atgtgataaa   3420

aatccgatag atgaacatca attagtatat gatgaacata atccattttc attatgtgca   3480

agtacgtatg ttccaattta tagaggaaaa ccagaagtca aatgtccgtt gtgcggcgca   3540

acttacttac cgcaatttaa agatacaata tgtaaagttt gtgaagttgc attaattgga   3600

aagcaatgta tgggtttaag gataagtcct atacaattac gataa                    3645
```

<210> SEQ ID NO 40
<211> LENGTH: 5901
<212> TYPE: DNA
<213> ORGANISM: Apis mellifera
<220> FEATURE:
<223> OTHER INFORMATION: Honey Bee Apis mellifera; Chromodomain helicase-DNA-binding protein (Cdh3); XM_624411

<400> SEQUENCE: 40

```
atggcatccg atgaggaggt agacgagagc tacgcgggag aagatgattt agatgaaact     60

ggaggtcaag tttcaaatgt taatcaacaa gtggatggtt catctgatgc agaggaatct    120

caaagattag aagaagatga tgattatgaa ccagaagaaa gaaaaaaaaa gaaagggaaa    180

aaacgaaaag cacgtagtga agataagaag gggaagaaaa aaaagaaaaa gaaaaaatct    240

gattctggag atgaaagtga ttttggaggt ggtggtgaaa ctggtgatat agctggagat    300

gatagtgatt atgcaggaaa tagaaaaagt agaaagtctt cttccaggaa atcatctagt    360

cataatgcat cagctccacc tagccaagaa cctacaactg gaatgcccac aattgaagaa    420

gtctgtaaca catttggatt gacagatgta caaattgaat atactgatgc agacttccag    480

aatttaacta cctataaatt atttcaacaa catgttagac cacttctagc aaaggagaat    540

ccaaaagttc caatgtcaaa gcttatgatg ttagtagctg ctaaatggcg tgatttttct    600

gaattaaatc ctcatacgca accagataca gatgtatcat cagcaaatgt agatgaggat    660

agtagaaatg caagagcaaa tcgtagtagt gcagtccagg aaggtgaaga tgaagaagaa    720

gatgatgaag atagcgatag aaaacgaaaa tcacgaggat ctagagcaaa aaaaggaaaa    780

aaagcttcta aagtaccaac acttaaaatc aaacttggaa aacgtaaacg gggaagttca    840

gatgaagaag cagaaggtag tggtgttggt actgatagag attcagatat ggaatttgag    900

cagatgttag cagatgcaga agaacctgtt ggtgcagatg ggacaaataa aggaaataca    960

gaagaaagcg ggattgaacc accggcagaa ccacctgttc gtaggaaggc gaaaaccaaa   1020

atcggaaata aaactaaaaa gaagaagaaa acaaaaacta catcaaagtt tccagatgga   1080

gaagaaggtc ttcagactga tcatcaggat tattgcgaag tatgtcaaca aggtggagaa   1140

attattcttt gtgacacatg tcctagagct tatcatttgg tatgtttaga acctgaatta   1200

gaagaaaccc ctgaaggaaa atggagttgt cctcactgtg aaggagaagg tattgcaggt   1260

gcagcagaag atgatgacga gcatatggaa ttttgtagaa tatgtaaaga tggtggtgaa   1320
```

-continued

```
ttgctatgtt gtgatagctg tactagtgct tatcatacac attgtttgaa tccaccactt   1380
tcagaaattc ctgatggtga ttggaagtgc cctagatgtt cttgtccacc tatacgtgga   1440
aaagttgcga agatcttaac atggagatgg aaagattgtc cagaaacacc ttctgaagaa   1500
ccttcaacga gtaaagctac tcccaaacaa cgtagaatgc gtgaattctt tgtgaaatgg   1560
gcagatatgt cctattggca ttgtgattgg attacagaat tacagcttga tgttttccat   1620
cctcttatgt ttagaaatta ttcacgaaaa tatgatatgg atgaaccacc gaaattggaa   1680
gaaccattgg atgaaagtga ttctcgtgta aaacgactga aagaacagga cggtgctact   1740
aatagagatg aatacaattt agaagaacga ttttatcgtt atggagttcg tccagaatgg   1800
cttgtagtac atagagtaat caatcataga ctttcaagag atggtagagc gacatatctt   1860
gttaaatgga gagaattagg atatgatcag gcaacgtggg aagatgagca tgaagatatt   1920
cctggattaa aacaggctat tgaatattat ttggatctca gagcagcaaa ttgttgtgat   1980
ggtagttctt cacgcaaggg caagaagggt aaaggcaaga aatcgaagac tcgtgaactt   2040
attgatgatg aagaaagaac gcctaaaaga tatactcctc cacctgataa acctactaca   2100
gatctcaaga aaaaatacga acggcagcca gaatatttag atcagactgg aatgcaatta   2160
catccttatc agctagaagg tttaaattgg ttaagatatt catggggcca aggcatagac   2220
actattttag cagatgaaat gggactggga aaaactattc aaactattac atttctctat   2280
tctttgtaca aagaaggaca ttgtaaagga ccattcttgg tatctgttcc cctatcaact   2340
attattaatt gggaacgtga atttgaaact tgggcacctg atttttattg tgttacttat   2400
gttggtgaca aagatagtcg tattgtaatt cgagagaatg aattatcatt tgaagagggt   2460
gctgttcgtg gaggtcgagc atcaaagatt cgatcgaatc aaattaaatt taatgtactc   2520
cttacaagtt atgaactgat ttcaattgat tctgcatgtt taggatcaat agattgggcc   2580
gtgttagtag tagacgaagc acataggctt aaatctaacc aatcaaagtt ttttagatta   2640
ttagcatctt acaatattgc atataaatta ttattaactg gaactccttt acaaaacaat   2700
ttggaagaat tgtttcattt attgaatttt ctatgtcgtg ataaatttaa tgacttagct   2760
gcgtttcaaa atgaattcgc tgatatttcg aaagaagaac aagtaaagaa attacatgaa   2820
ttacttggac cacatatgtt aagaagatta aaggctgatg tgctgaagaa tatgccaagt   2880
aaatcggaat tcattgtccg cgtcgaatta tctcctatgc aaaagaaata ttataaatat   2940
atattaacga gaaatttcga ggcattaaat cctaaaggag gaggccaaca agtatcgtta   3000
ttgaatatta tgatggattt aaaaaaatgt tgcaatcatc cttacttatt cccagctgca   3060
tctcaagaag caccaaccgc accaaatgga agttatgaaa catctgcatt aattaaagca   3120
gcaggaaaac tcgttctatt gagtaaaatg ttaaagaaat taagagatga cggacataga   3180
gtattaatct tttctcaaat gacaaaaatg ttagatattc tcgaagatta tttagaagga   3240
gaaggctata aatatgaaag aatagatggt aatattactg gtgctcaacg acaagaagct   3300
attgatagat ttaatgcacc tggtgcacaa caatttgtgt ttcttctttc tactcgtgct   3360
ggtggtttgg gtataaactt ggctaccgct gacactgtaa tcatttatga ttctgattgg   3420
aatcctcata acgatattca agcatttagt agagctcata gaattggcca agctaacaaa   3480
gtcatgattt atagattcgt aactcgtaat tctgtcgagg aacgagttac acaagtggca   3540
aaacgtaaaa tgatgttaac gcatttagtc gtaagacctg gcatgggcgg aaaaggtgct   3600
aacttcagta aacaagaact tgatgacatt ttacgatttg gtactgagga attatttaaa   3660
gaggaagaag gtaaagaaga tgaagctatt cattatgatg ataaagctgt ggctgaatta   3720
```

```
ttagatagaa gcaaggaagg tattgagcag aaagaaaatt gggccaatga atatttaagt   3780
tcattcaaag tagcatcata tgtaacaaaa gaaggcgaaa cagaagaaga agctgatact   3840
gaaattatca aacaagaagc tgaaaatact gatccagcat actggatcaa attattaaga   3900
catcattacg aacaacaaca ggaagatata gccagaacac ttggaaaagg taaacgaata   3960
cgtaaacaag taaattataa tgatggagga gtaactggag accaaagtac aagagacgac   4020
caaccttggc aggagaatct ctccgattat aacagtgatt tcagtgctcc tagtgatgat   4080
gataaagaag atgacgattt tgatgaaaag ggtgatggag atttattatc tcgaagaagt   4140
agaagaagat tagaaaggag agacgaaaaa gatcgacctc tacctccatt acttgctaga   4200
gttaatggaa atattgaagt attgggtttc aatgctaggc agagaaaagc atttcttaat   4260
gcgattatgc gttacggtat gccaccacaa gacgcattta attctcaatg gttggtgcga   4320
gatttaagag gcaaatcgga aaaaaacttc aaagcatatg tttctctttt tatgcggcat   4380
ctctgtgaac ctggtgcaga caatgccgaa acgtttgcag acggtgttcc aagagaaggt   4440
ctcagtagac agcatgttct aacaagaatt ggtgtaatgt ctttgataag aaaaaaggtg   4500
caagaatttg aacatattaa tggatattat tcgatgcctg aaatgatacg aaagccagta   4560
gaacctgtaa aagtagatgg tagtggagat ggagcaactg ggactagtag tactagtgca   4620
acaccagcta cttctaatgc tgctagtcca agtcctgctg cgactccaac tccaacagcc   4680
atatctggaa ctacaattac tgatactaat aaatctaatt ctgatagttc tgaaataaaa   4740
gaatgcaaag aagaacaaaa ggataaagaa attacagaaa caaaagatgt gaaagaagaa   4800
tcaaaggatt ctaaagaaga agaagaaaat aatacagaga aagataaaga taaagatgat   4860
gtgaaaaagg aggagaaaga tgcagaatca gaaacaatag ataaagaaaa ggataaattg   4920
gatattaaag aagaaaagtc attaacaaaa catgacgaaa aagttgaaaa tactgaaaat   4980
aaaacaaagc aagattctga agaagatgta gttatcgtta aagatgatga agaagaaact   5040
gaaaaacgag aagagaaaga taataaagaa aaagatataa aggattgtga ttcagaaacg   5100
ataaaaccta aacgtaaatt catgttcaac atagctgatg gaggtttcac agaattgcat   5160
acattatggt taaatgaaga aaaagctgca gttcctggtc gtgaatatga aatctggcat   5220
cgaagacatg attattggtt attagctggt attgttacac atggttatgg tcgttggcaa   5280
gatattcaaa acgatatcag gttcgcaata attaatgaac catttaaaat ggatgtgggt   5340
aagggtaact tcttagaaat aaagaataaa tttttagcta gacgctttaa attgttggaa   5400
caagcattag tgatagaaga acaattaaga agagctgcat atctgaattt aacacaagat   5460
cctaatcatc ctgcaatgag tttaaatgca agatttgccg aagttgagtg ccttgcagaa   5520
tcacatcaac atcttagtaa agaaagtctt gcaggaaata aaccagccaa tgctgtcttg   5580
cataaagtac taaatcaatt ggaagaatta ttatctgaca tgaaatctga cgtaagccgt   5640
ttaccagcta ctttagctcg tattccacct gttgcgcaaa gacttcaaat gtcagagaga   5700
tctatattga gtcgattagc agctactgca ccaggcggaa ataattctca atcgggtcaa   5760
gcagcattgt tagcgcaaca atttccagca ggtttttctg gtggacaatt accagctaca   5820
tttgctggtg cagctaactt cggaaatttt agaccacaat actcagtacc aggtcaacca   5880
ccgcagggat tcacagcttg a                                             5901
```

<210> SEQ ID NO 41
<211> LENGTH: 462
<212> TYPE: DNA

<213> ORGANISM: Apis mellifera
<220> FEATURE:
<223> OTHER INFORMATION: Honey Bee Apis mellifera; Ferritin; XM_624041
<220> FEATURE:
<221> NAME/KEY: modified_base
<222> LOCATION: (332)..(332)
<223> OTHER INFORMATION: a, c, t, g, unknown or other

<400> SEQUENCE: 41

```
atgaagctac tttatgttct ttttattgtt ttcgtttaca tcaatggatc actaggaaat     60

gacagtgcaa caagatcatg tataataagt aatatagctg ctgatgaaaa tgcgacaaaa    120

cattggttgg atatggataa aaattgtatt aaaagcttgg aatctcaggt gaatgttgaa    180

attaaagctg caatgactta tcttgcaatg ggtgctcatt ttgctcttga tgtaattaat    240

cgacctggat tcagcaaatt cttttttgaa tctgctacag aagaaagaga acatgcaata    300

aaagttcttg aatatttatt aatgcgtggt cnattaacta atattaatga ggataatgtt    360

cttttaagat ttcctttgtc atctttaggt aaaatgatac aaacacatgg aatgttagga    420

gagtttctat ttgataaaaa acttttaaac aatgaaattt aa                       462
```

<210> SEQ ID NO 42
<211> LENGTH: 1341
<212> TYPE: DNA
<213> ORGANISM: Apis mellifera
<220> FEATURE:
<223> OTHER INFORMATION: Honey Bee Apis mellifera; Juvenile hormone epoxide hydrolase; XM_394922

<400> SEQUENCE: 42

```
atgtattatt ttcattttat ttatttattt tctgtgaacg aacttaatgt tccaacttta     60

ccggaaacaa attggggatc aaaaaaaaat gaaaaggaat ctatagaaat ccgacctttc    120

aaaattgatg tatcaaaatc ggttttagac gatttaaaat atcgcctggc acacagaaga    180

acgtttaaaa aaccattgga aaatgtaggc tggacttacg gtatctcaac tacatatttg    240

aatacagtac ttgattactg gagagataaa tacaactgga ctgagaggca agctttgtta    300

aataagtatc ctcagtttat gactactatt cagggtttgg atatacattt ctatcatgta    360

aagccaaatt taccaaataa taaaaactta aaagttttac ctttactcat gctacatgga    420

tggcctggat ctgttgtgga attccaaaaa attataccca tgttaacaaa accttggcct    480

aatcaaaact ttgtgttcga agttattgta ccgtcacttc ctggatacgg tttctccgaa    540

ggtgcggtac gaccaggcat ggctaatgct cagatagctg taatattcaa gaatctgatg    600

cagagacttg gttttgaaaa attttacgtt caaggaggtg attggggatc tgttattgct    660

tctgatatgg ctgttctctt cccagaaaag ataattggtc tacataataa tatgtgtact    720

tctttaaatt tatctaatct tttctggtta tttgtcggta cctatttccc atcgttaata    780

ggagcaaatg aacattactc aaaattcttt cctgtgagtg aaattttgtc cttcttaatt    840

gaagaaagtg gttactttca tatacaggct acgaaaccag atactatagg tgctgcattg    900

actgcttcac ctgatgcatt agcagcatat attttagaaa aattttctgt gtggacaaat    960

aaaacatata aaaaacaaga tgatggtggt ataacagaaa aatttgtact agatgagcta   1020

ttagataata taatgatata ttggatcact aatagtatta ctacaagtgt tagactttat   1080

gctgaaaatt atacttcatc atatagatct ctgaaaattg accaattgcc tataaaagtg   1140

tttacagctt gtgcagtctt tcccaatgaa atacttgttc tgcctgaaag tttgcttaaa   1200

caaaaatatc ctaatataat tcaatacaac attatatcac gtggtggaca ttttgcagct   1260
```

```
tttgaagaac ccagactttt agctgatgat attttcagtt ttgttaaaaa aatagaaaac   1320

cttacatcaa aatcttcata g                                              1341


<210> SEQ ID NO 43
<211> LENGTH: 3252
<212> TYPE: DNA
<213> ORGANISM: Apis mellifera
<220> FEATURE:
<223> OTHER INFORMATION: Honey Bee Apis mellifera; Chitin Synthase;
      XP_395677

<400> SEQUENCE: 43

atgtcaaaaa ttcaacaaca aaatggaatg atgccaggca atggaacaat gccagatgat     60

gatgattttt cagacggtga gagtactcca ttgactcagg actatggcga cagtcaaaga    120

acagttgtgg aaacaaaagc atgggacgtc tttcggaatc caccgccgaa gatcgattcc    180

ggttcaatgg ctaatcaaag atgcctggaa gtgacggtac agataacgaa ggtgatcgtg    240

tacctattag ttttcgtgat agtattagga agcggtgtag ttgccaaagg aactattcta    300

tttatgacat cacagttgag agcgaatcga actatcgttc actgcaacag ggatattggc    360

cgagacaaat actttgaagt gacgttacca gaacaagaga ggatagcgtg gatctggtgc    420

atcataatcg ctttcgcggt gcctgaattc ggcacgttaa tccgtagcat tagaatatgt    480

atcttcaaat catggaagaa accgcctgca tcccatttcc ttgtcgtttt cgtcatggag    540

acatttcacg tggtcggttt ggctttgatg ttcatggcag tgctacctga tttggacgtg    600

gttaaaggtg cgatgctgac aaattgtgta tgcttcgtac ccggtgtgct agggctactt    660

tctcggaata agaaaaaaga cgaatcacga tttgttctgg tgctaatcga tattgctgca    720

cttgtcgctc aagggacaag tttcgttctt tggccattat tggacagttc acgattctct    780

ttgtggctaa taccaccatc tttattccta gtttcatgtg gctggtggga aaattatgtt    840

tcgacgcaga gtccgattgg attcgttcga tctctaggaa aaataaaaca agaaatgcaa    900

ttgacaagat actttaccta catgttcatg tcggtttgga aaattatagt attctttact    960

agtacgatat taatattata tattaaaggt gaaactgttg gacatttatt cagcatgttc   1020

ggtgatgctt ttggaaatca cacaattgtt gtaagatcaa tgtatgatgt tactggcaga   1080

acaacagata tcgctgatat agttgatatc gatgataata agatagccat accggcaaat   1140

gtgaaaagtc ctatatacgt tctattgttg caaatattca gcgcctattt catgtacata   1200

ttcggtaaat tcgcgtgcaa gattttgata caaggtttca gttacgcgtt ccctgtaaat   1260

ctaactatac cggtatcgat ctcgttattg attgccgctt gcggtttaag gcataccgat   1320

ccttgcatat ttcacaacac aattccggat tatctgttct acgagtcacc accattgcat   1380

ttcctcaacg atttcgtttc gaagcaatat gcctgggtat ggctgctgtg gttgctgtcg   1440

caaacttgga ttactttgca tgtttggacg ccgaaatgcg aacgtctcgc ttccacagag   1500

aaattgttcg ttgtacctat gtacaactca ttgctgatcg atcaatcgat gggcttaaac   1560

aggaaaaggg atgatcaacc ggaagtgaaa gtggaggatt tggcggagat agagaaagaa   1620

aagggagatg gagattatga gactatatac gagcaaacgg atggcacaac cacacctcca   1680

tcaactgtaa gaagcagcga tcacgtaact agaatatatg cttgcgcgac gatgtggcac   1740

gaaaataagg aagaaatgat ggaatttttg aaaagcattc ttcgattgga tgaggatcag   1800

tgtgcacgac gtgtagccca aaaatatctg aaagttgtcg atccggatta ttatgaattc   1860

gaaactcaca tctttttcga tgatgccttc gagttatcgg atcacgatga gaacgagtcg   1920
```

```
caagtgaaca gattcgtgaa attattggta ggcactttgg atgaggctgc gtctgatgtc   1980

catcaaacac ggatgcatgt tagggcacca aagaagtacc caacacctta cggtggtcga   2040

ttagtttgga cacttcctgg taaaacgaaa atgatcgccc atttgaaaga caagagcaag   2100

attcgtcaca gaaaacgatg gagtcaggtc atgtacatgt attacttatt gggtcaccgg   2160

ttaatggagc taccaatcag cgttgatcgg aaggaagtga tcgcggaaaa tacttatctg   2220

ttaactctcg atggtgatat cgattttcaa ccagctgctg tgaaattact cgtcgacttg   2280

atgaaaaaga ataaaaatct tggcgcagct tgtggtcgta ttcatccagt tggttcaggt   2340

cctatggtgt ggtatcaaat gttcgaatac gctattggtc attggctgca aaaagcaacg   2400

gagcacatga ttggttgtgt gctttgtagt cctggttgtt tctcactttt tagaggaaaa   2460

gctttaatgg acgataatgt gatgaagaag tacacgacaa gatcggacga ggctagacat   2520

tacgtgcaat acgatcaagg ggaagatcga tggctttgta cacttctctt acaacgtggt   2580

tacagagttg aatattcagc agctagtgac gcttatactc atgcacctga aggctttaat   2640

gaattttata atcaacgtcg tcgatgggta ccttccacca tagccaatat catggatctt   2700

ttaatggacg cgaaacggac cattaaaatc aacgataata tttctctccc ttatatttct   2760

tatcaaatct tactcatggg tggtaccatt ttaggaccag gtacgatttt tctcatgtta   2820

gtaggtgcct tcgtggctgc tttcaagatc gataattgga ccagcttcta ctacaatatc   2880

attcccattc tcctcttcat gctcgtatgt tttacttgta aagcaaacat tcaacttctg   2940

tgcgcgcaga tattatcgac aggatacgcg atgataatga tggccgtcat cgtaggtacg   3000

gctctccagc tcggagaaga cggtatcggt tcaccctcgg ccatattttt gatagcctta   3060

tccggttcct tctttatagc ggcctgttta catccacaag aattctggtg tatcgtacct   3120

ggtatcattt atctcctttc gataccttcc atgtaccttc ttcttatcct ctattcgatc   3180

ataaatttga atgttgtctc atggggaact cgcgaagtcc aagtgaaaaa gaccaaaaag   3240

gcattggaat ag                                                        3252
```

<210> SEQ ID NO 44
<211> LENGTH: 1749
<212> TYPE: DNA
<213> ORGANISM: Apis mellifera
<220> FEATURE:
<223> OTHER INFORMATION: Honey Bee Apis mellifera; venom carboxylesterase-6 isoform 1 (VCE-F2); XM_391943

<400> SEQUENCE: 44

```
atggcacaat atcgaagagt cctaattttt tgtttgttga gctgtatata ctttttttgag     60

catgtcacga ctgatgaacc aatagtaaaa ataaaaaatg gtactttatt gggtttgact    120

ttgaaaacta gaaagggcag agaaattgct gcctttcggg gtataccata cgcacttcca    180

cctcttgaaa aattaagatt tgagccaccg aaacctgcag cagcttggaa cgatgtgcga    240

tcagctaaag aagacgccaa catatgcgta caaaggaata tttacattta tcaagaagag    300

atcgttggtg acgaggattg tctctatttg aatgtctata cgccaaaatt accaactgag    360

aatgataaat taaaaggacg atatccggtt atgatttggt ttcatggctg tggatggatt    420

tgtggtgctg gtcattcgga attttataat cccaaatttt tattagacca tgatctagtt    480

ctcgtgacag taaattatag actcggacct ttgggatttt tgagtacaga agatactgta    540

tgtcctggaa ataatggatt gaaagatcaa tctttgtcca ttcgttgggt acacgaaaat    600

attgcggctt ttggtggtga tccaaatagc gtgaccatct ttggagaaag cgcgggtggc    660
```

```
gctagtgtgc attatcatat gataagtaat ttgacaaaag gacttatcca tcgagcgatc    720
tctcaaagtg gtaatggcca ttgtttatgg actttaactc gaccaggttt agcaaaaaaa    780
aaagccgcca aggttgctga acttttgggt tgtccttcga atgattcaaa acagcttgtc    840
gattgtctgc ggaagaagaa agccattgac ataatcgcga ccgatcgtgc tttccaaata    900
tttggttatt gcccaatgat acccttcaga ccggtaattg agcctgttca tcctggtgct    960
ttcttaactg aagatccagc aatttcttcg aaaaatggcc gcatgttaga tataccatgg   1020
atgacaggaa ttacatccca agaaggttcc ctcgtagcac cagcattata tggaagaaac   1080
aacggagctt tgattaaaaa attgaacaaa gatttctcga acattgctcc aattacgtta   1140
ctatacgagg atacgtgctc taaagataaa cagaaacgga tgacatccga aatacggaaa   1200
ttctattttg gtgatggacc aattgatact tcaacgcggt tcaaagtgat cgatatgtac   1260
agtgacgcct ggttcaatca tgcagcttac acctctgtgc gtaattatct cgcgaaacaa   1320
tcttctcccg tgtattatta ttacctcgcg tacaaaggaa gcgcgtcgtt cagtattata   1380
ttcggcgatc ctaacaacga ttacggtgta tcgcacgcgg atgaacttca atatttgttc   1440
cctgtcggtg aacaattgtt caagaacatt tcattgagca agcaagatca caaaatggtg   1500
gatatcatca caaatctttg gtacaacttc gcaaaatttg gcaatcctac acccgaagtg   1560
tcagaagata taccgattaa atggaaaccc gtgagaactc aggccctaga atatcttcac   1620
ataggacaag ataacattag aatgtcggaa aatcttatct cagagagaat gaaattttgg   1680
gaaagtttac cggtacgatc cggtttggag gatggcgggt caaaatatcg aggaaaagag   1740
gaattataa                                                           1749
```

<210> SEQ ID NO 45
<211> LENGTH: 1641
<212> TYPE: DNA
<213> ORGANISM: Ophelimus maskelli
<220> FEATURE:
<223> OTHER INFORMATION: Blw Hydrogen-exporting ATPase activity

<400> SEQUENCE: 45

```
atggccctgt tgaccgtacg tcttgctgcc tcggtagcga gacaactacc cagcacccag     60
gtgagctggc ctgctgctgc tattgcctca aggaaatatc atgtatcgtg cagccgcaga    120
tccgctgaga tctcttccat tctggaggag cgtattcttg gcgctagctc caaggccaac    180
ctggaagaaa ctggccgtgt gctcagcatt ggtgacggta tcgcccgtgt atatggtctg    240
aagaacatcc aggccgatga gatggttgaa tttagctccg gtctcaaggg tatggccttg    300
aatttggagc ccgacaacgt cggtattgtc gtattcggta acgacaggca catcaaggag    360
ggtgacatcg tcaagcgtac aggtgctatc gtcgacgtac ccgttggtga ggagctactt    420
ggacgtgtag tcgatgctct gggtaacccc atcgatggca aaggcccact caacagtaag    480
ctcaggttcc gaattggtac caaggcccct ggtatcattc ccagggtatc tgtacgagag    540
cccatgcaga ccggtattaa ggccgtcgac tcactagtac caattggtcg tggacagcgt    600
gagttgatca ttggtgacag gcagactggt aagaccgccc ttgccattga caccatcatc    660
aaccagaaac gattcaacga tgctggtgaa gaaaagaaga agctgtactg tatctacgtt    720
gccattggtc agaagaggtc taccgtcgcc caaatcgtca agcgccttac tgacagcggt    780
gccatcggct actccatcat tgtgtcggct accgcgtcag atgctgcccc tctacagtac    840
ctcgccccgt actctggctg tgccatgggt gaatatttca gggacaatgg caagcacgct    900
ctcatcatct acgacgactt gtcgaaacag gccgtggcct accgtcaaat gtccctgttg    960
```

```
ctgaggcgac cccccggtcg tgaggcctac cccggtgacg ttttctacct tcactcccgt   1020

cttcttgagc gtgccgccaa gatgaacgag tccctgggtg gtggttccct tactgccctg   1080

cccgttatcg agacccaggc tggtgacgta tcagcttaca ttcctaccaa tgtcatttcc   1140

attaccgacg gacagatctt cttggaaacc gagttgttct acaaaggtat ccgaccagcc   1200

atcaacgttg gtctgtctgt atcccgtgta ggatcggccg ctcagacgaa ggccatgaaa   1260

caggtcgccg gttccatgaa actggagttg gcccagtacc gtgaagtagc tgccttcgcc   1320

cagttcggtt cggacttgga cgctgccacc cagcaactgc taaaccgtgg tgttcgtctt   1380

actgaactgt tgaaacaggg acagtacgta cccatggcca ttgaagaaca ggtcgcagtc   1440

atctactgtg gtgtccgtgg ataccttgac aaaatggacc ctgccaaaat cacgcagttc   1500

gagaaggaat tccttgccca cgtcaaatcc acgcagcaag atctgttggc caccattgcc   1560

aaagaaaata ttatcagtga atcatcagac gcaaaactga aaaggttgt caccgacttc   1620

ttagctggat ttaatgcgta a                                             1641
```

<210> SEQ ID NO 46
<211> LENGTH: 1641
<212> TYPE: DNA
<213> ORGANISM: Leptocybes invasa
<220> FEATURE:
<223> OTHER INFORMATION: blw; Hydrogen-exporting ATPase activity

<400> SEQUENCE: 46

```
atggccctgc ttaccgtgcg tctcgctgcc tcgttggcga ggcagctgcc cagcatccag     60

gtgagctggc ccgctgctgc ccttgcctcc agaaagtacc atgtctcctg cagccgcaga    120

tctgctgaga tctcctccat tcttgaggag cgtatcctcg gcactgccac caaggccaac    180

ctcgaggaaa ccggccgtgt gctcagcatc ggtgacggta tcgcccgtgt ctatggtctc    240

aagaacatcc aagccgacga gatggtggaa ttcagctctg gtctcaaggg tatggctttg    300

aatttggagc ccgacaacgt gggtattgtc gtcttcggta acgacaggca catcaaggaa    360

ggtgacatcg tcaaacgtac cggtgctatt gtcgacgtgc cagtcggtga ggagctgctt    420

ggtcgtgtcg ttgacgcttt gggtaacccc attgacggca aaggcccact cggcagcaag    480

ctgaggttcc gtattggtac caaagctcct ggtatcattc ctagggtatc cgtacgagag    540

cccatgcaaa ccggtatcaa ggccgtcgac tctctggtac cgattggtcg tggtcagcga    600

gagttgatca tcggtgacag acagactggt aagaccgctt tggccatcga caccatcatc    660

aaccagaagc gtttcaacga cgccggcgag gagaagaaga agctgtactg tatctacgtt    720

gccatcggtc agaagcgttc caccgtcgct cagatcgtca agcgtcttac cgacagcggt    780

gccatcaact attccatcat cgtctcggcc accgcctccg acgccgctcc cctgcaatac    840

cttgcaccct actctggctg tgccatgggt gaattcttca gggataacgg caaacacgcc    900

ctcatcatct acgacgattt gtcgaagcag gccgtggcct accgtcaaat gtcactgttg    960

ctgaggcgac cccccggtcg tgaggcctac cccggtgacg tattctacct tcactcgcgt   1020

cttctcgagc gtgccgccaa gatgaacgag tcgttgggtg gtggttccct cactgcctta   1080

cccgtcatcg agacccaggc cggtgacgtg tccgcctaca ttcccaccaa cgtcatctcc   1140

atcactgacg gacaaatctt cttggaaacc gagttgttct acaagggtat ccgacctgcc   1200

atcaacgtcg gtctgtctgt atcccgtgtc ggttcagctg cccagaccaa agccatgaaa   1260

caggtcgccg gttccatgaa attggagttg gcccagtatc gtgaggtcgc cgccttcgcc   1320
```

```
cagttcggtt cggacttgga cgctgccacc cagcaactgc tcaaccgtgg tgttcgtctt   1380

accgagctgt tgaaacaggg acagtatgta ccaatggcca ttgaagaaca ggtcgccgtc   1440

atctactgtg gtgtccgtgg atacctcgac aaaatggaac ccactaaaat cactgccttc   1500

gagaaggaat tccttgcaca cgtcaaatcc acgcagcaag accttctggc aacgatcgcc   1560

aaagagaaca tcatcagtga agcgtcagac gcgaagctga agaaggtcgt cactgacttc   1620

ttggcctcgt tcaacgcgta a                                             1641
```

<210> SEQ ID NO 47
<211> LENGTH: 867
<212> TYPE: DNA
<213> ORGANISM: Ophelimus maskelli
<220> FEATURE:
<223> OTHER INFORMATION: CG10881 translation initiation factor

<400> SEQUENCE: 47

```
atgccaaaca attacgaact agtttcaagt tgggctgatg aagtagaaga cgagggaaat     60

gttactcttc cagctccaac tgttgttcgt gaaaatgatt ttaaaatagt gacagaatac    120

aaattgaatg atgacaacaa aagaattaaa gtagtgcgta catctaaaat agaacatcgc    180

acagtttcca agacaattgc tgttcgaaaa aatttggcca aatttggaga ttcagcaaat    240

gatggtccag gtccaaatcc agcaacaaca gtcattgctg aagatgtttt catgcaattc    300

ttgtcaaaca aagaggaaga caacaaggtg gaggaagatt cactggacaa attgaagagt    360

atgggagaca aaggtgttgt caagtgtcgt aattgtaatg gagatcactg gacctctaag    420

tgtccattca aagatacagt tcttggaggc acaaacaaag ctccagatga caagaaacct    480

ctcaatccag ctgctggagc tggtatggct gatattagta aaccaacagg taccaaatat    540

gttcctccaa gcatgcgaga tggaggtaac aaaagaggtg actcaatgca aatgcagcgt    600

agagatgata caacagccat tcgaatatct aacttatctg aaagtacaac cgatcaagat    660

ttggaagacc ttgttaagca atttggtgca attcagaaac tttatttggc aaaagaaaag    720

aatacaaatg tctgtaaagg atttgcatac gtacatttca aatgcgagc tgaagctgct    780

aaggccattg atgccctcaa tggtcatgga tatgaccact tgatcttgag tgttgattgg    840

tctaaaccac cagctcaaaa taattaa                                        867
```

<210> SEQ ID NO 48
<211> LENGTH: 864
<212> TYPE: DNA
<213> ORGANISM: Leptocybes invasa
<220> FEATURE:
<223> OTHER INFORMATION: CG10881 translation initiation factor

<400> SEQUENCE: 48

```
atgccgtcta attacgaacc aatttccaac tgggcggacg aggtggaaga tgaaggaact     60

attagtctcc ctcctccaac agttgtttat gaaaatgact ttaaaataat gacagaatat    120

aagctgaatg atgacaacaa gaaagtcaaa gtagtgcgta catacaaaat tgaaaagcgc    180

actgtttcca aaaatattgc tgttcgtaag aattggccca agtttggaga ttctgctaat    240

gatggaccag gtccaaaccc agccactaca gttattgctg aagatgtatt catgcaattc    300

ctctccagca aagaggaaga caacaaggtt gaagaagatt ccctcgacaa actgaagagc    360

atgggagata aaggagttgt caagtgtcgt aactgtaatg gagatcactg gacctcaaaa    420

tgtccattca aggatacagt tcttggaggc accaaagctg tggatgacaa gaccaagcca    480

ctcaaccctg ttgcaggtgg accaggtatg gcagacaaac ctacaggtac caaatacgtt    540
```

```
cctccaagta tgcgtgacgg tggtaacaaa aggggtgact ctatgcaaat gcaaaggaga    600

gatgacacca cagccatcag aatatccaat ttgtctgaga gtaccacaga cgcagatttg    660

gaggaacttg tcaagcagtt tggtgccatt cagaagcttt atttggctaa ggaaaagaat    720

acgaatgttt gcaaaggatt tgcttatgtt cactttaaat ctcgagctga ggctgctaga    780

gctatcactg cgctaaatgg tcatggatat gatcacttga ttctcagcgt agattggtcg    840

aagcctcccg cgcaaagtaa ttga                                           864
```

<210> SEQ ID NO 49
<211> LENGTH: 921
<212> TYPE: DNA
<213> ORGANISM: Leptocybes invasa
<220> FEATURE:
<223> OTHER INFORMATION: RagA GTPase activity. positive regulation of cell growth

<400> SEQUENCE: 49

```
atgaagaaga aggtcttgtt gatgggcaaa agtggctcgg gaaagacgag tatgcgaagt     60

attatcttcg ccaattacat tgcaagagat actcgtcgtt taggggcaac aattgacgtt    120

gagcacagtc atgttcgttt ccttggaaat ctggttctca atctctggga ttgtggtgga    180

caagaggcct tcatggaaaa ctactttgca tcacagcgag acaacatttt tagaaatgtc    240

gaagtgctca tttatgtatt tgatgttgaa tcccgtgaac ttgacaaaga catgcactat    300

taccaaagct gtctggaggc tattttacaa aacagtccag atgcaaaagt gttctgcctc    360

atacacaaaa tggatttggt tcaagaagat caaagagact ctattttcag ggaaagagaa    420

gaggatttga ggagactgag caaaccatta cagtgtacct gttttaggac aagtatttgg    480

gacgaaactt tgtatagagc atggtcttcc atagtttata tgttaattcc aaacgttaaa    540

gagcttgaac agagtttaaa tcaatttgcc aatattattg atgctgatga agttctcctc    600

tttgagcgtg ccacattcct tgttattagt cattgtcaga gaaggtatca tagagatgtt    660

catcgctttg agaaagtttc aaacataatc aaacagttca agctgagttg cagtaaactg    720

gctgctcaat tctctagtat ggaagtaagg aacacaaatt tcgcggcttt tatcgacgtt    780

ttcacatcga acacgtacgt tatggtcgtc gtgtctgatc ctaccatacc atccgcagca    840

acgctgatca acatccgcaa tgcccgcaag cactttgaga agctcgagag agcaagtcag    900

agttcgtctt tgagcagata g                                              921
```

<210> SEQ ID NO 50
<211> LENGTH: 874
<212> TYPE: DNA
<213> ORGANISM: Leptocybes invasa
<220> FEATURE:
<223> OTHER INFORMATION: CG2931 nuclear mRNA splicing, via spliceosome

<400> SEQUENCE: 50

```
atgaaacttc ggcaaatgga agatgagatg agtcggtttg aagccgaaat aggagggcag     60

ttgattcctg ccatggggag acctgtgatt ggagcaaata catacaatca agtagcaaga    120

cgacttgagc aacacgaggt accagctaat gttattgcag ctgccgcaac agccgcatca    180

ttagcttttc ctccaatttt gggctttcca cctccaccac cgccacctcc gcctcctcca    240

gctccattga tgattccagc ccaagttgct agacagagta cagttcccat ttcgacctac    300

tcatccccag cacagataag tactcctttc atatcgaata tggtagagcc aattctaagt    360

gctactccta aaacttatga accagctcct gcagctccaa ttattcatcc agaaataatg    420
```

```
gagaaaatta taaacacaaa aataccagac gatgattcta agaaaaaacc aaaggtaaaa    480

ggtgtaagta ctgctgctga attagctatt agtcaaggaa aagctagttc aattatggct    540

aatgctagtg ctgaagagtc tcatccgaaa ggtaaaggca aaaagaataa aaaaataatt    600

aggacagcag gtggtcaaac ttgggaagat ccttcgctac ttgattggga cgatgatgac    660

tttcgaatat tctgcggaga tctgggcaac gacgtcacag acgagatgct cgtccgtgtg    720

tttggcaagt atcccagctt ccaaagagcc aaagtcgtgc gcgataaacg caccaacaag    780

accaagggct tcggtttcgt ctcgttcaag gatcctcagg atttcatcag ggcaatgaag    840

gaaatgaacg gtcgttatgt tggttcaaga ccca                                874
```

<210> SEQ ID NO 51
<211> LENGTH: 1188
<212> TYPE: DNA
<213> ORGANISM: Leptocybes invasa
<220> FEATURE:
<223> OTHER INFORMATION: CG31524 procollagen-proline 4-dioxygenase activity. oxidation-reduction process

<400> SEQUENCE: 51

```
gagacgcatc aggtcgcttg cggtgtgctc aacggcgtgc agtacagcac gggactgtcg     60

gcgagcgact gcttcgagtt gggcaggcag tcgtacaaca ccggcgacta ctatcacacg    120

gtgctctgga tgcaggaggc gatggaccgt ttacaagagg agcagaatcg caccagcgta    180

tccaagcccg acattctcga gtatcttgcc ttttctacct acatgcaagg taacgtggtg    240

agagcgttga gcatgacgaa cgagctgttg gatctagtgc cgacgcatca gcgtgccatt    300

ggtaatcgtg cctactatct cgatgaaatt caaaagcgta ccaaagacgg tagacgcaaa    360

cgcggcgagg atggcggcgc tgaggattta cccgatcagc cgttcacggt gccggagaag    420

aagataaaaa gcgtgagcga gatgacggag cgcgagaggt acgagatgct ctgccgcggt    480

gagatcaaga tgccgctgag catgcagaag gagctcaagt gtcgctacgt cgatcgcggc    540

aatcctttcc tcaagatagc gccgttcaag gaggaggaag cctaccacga gccgcgcatc    600

gtcatttacc acgacgtcat ttacgacgac gagatcgaga ccatcaagag aatggcacag    660

ccgaggttca aacgagcgac ggtgcagaac tacaagaccg gcgagctgga aatagccaac    720

taccgcatta gcaagagcgc ctggctacag gagcacgagc acaagcacgt gcaagcggtg    780

agccagcgag tcgagcacat gacgagcatg agcgtcgata ctgccgagga gctgcaggtc    840

gttaattatg gcatcggcgg acactacgag cctcacttcg atttcgccag aagagaagaa    900

acgaatgcat tcaagagcct tggcactggt aaccgaatcg caactatttt atattacatg    960

agcgacgttg aacaaggtgg tggtactgtg tttactcgaa tcaacatttc actctggccg   1020

aaaaaaggta gcgctgcttt ctggtacaac ttgaaaccca acggcgaggg agattacatg   1080

acgcgccatg ctgcctgtcc tgtactcact ggttccaaat gggtggcgaa taagtggttg   1140

cacgagagag gccaagagtt ccatcgacca tgcacgttag aaaatcaa                1188
```

<210> SEQ ID NO 52
<211> LENGTH: 1719
<212> TYPE: DNA
<213> ORGANISM: Ophelimus maskelli
<220> FEATURE:
<223> OTHER INFORMATION: Fred friend of echinoid; adult chitin-based cuticle pattern formation

<400> SEQUENCE: 52

```
gtcgccaaca acctgcgcga aaccgccaac gtgacatgta aagttcaagc ctggcccaag     60
cccgaattcc agtggagctt cggtacgaac gcagcacctc tgcaaggttc atcgagcgac    120
ggtcactacg agatctcgac gacgagcgac gactacgacg tgtacacctc ggtactcaaa    180
attaccaaca tccgtgacag cgactacggt gactactcgt gtcgagtcac caatgttcag    240
ggtagcatca cctccacgat caagttgcaa cccaaaggag cacccgagag acccacgaac    300
gtccgtgcca tggatgtagg cccaactcac gttgctctcg tttgggacct cggtttcgac    360
ggtggtctac ccataaccaa atacttcgtt tcgtacaaga ggatcgcggg tggtgacgag    420
gttatagctt ccgactgctc gcctccgcgt ggaccgactg gtcagtggca ggaaatggac    480
tgtcgcagat ctaatccatg caacatttcc gatctcgaac agcaccagac ctacgttttc    540
aaggtaaaag tatacaacac gaacaatcac tcggactact cggacgaagt gacagcgaca    600
acagcggttg caaaaattcc aacaccacag cgagtcacgt acgatcctga gggtaataca    660
ttggcgataa gcgtaggtcc aacgtgttta gcactcgtag catcgatcga gaagtcggat    720
tctggttcgg acaacacgtg gcgtatcgtt gacgactggc cgctcgagac tctcggtggc    780
tccagcactc aaagagagga cgagctcaac gatcctgctg cttctagttc ggagccaagg    840
atcagggtga gactttgcct caaggctgat aggcagaggt gtggcgatta cttcgaggct    900
gagatcggag cctcttacat agcacacgcc ggtgcgatgg caactccaac attaattgct    960
ctggtggtaa gcggtgccgt attcctattg ttcgccgcgt tgctgcttct gttctgccgc   1020
tgccgcagga aacacgctgc caaagccaaa gactacgaga tggattcgaa tgcggtccgg   1080
ccgagtttgg tgacgggtaa cggccagcaa accccaagcg cctcgcccta ttacgcggag   1140
aacaaggcgc tcgagcacag cctcgatcac gctcttgccc tcgaggactc caagacaccg   1200
gcctacggac agactggcta tggctatcat ccgcctaatc ataacatcaa cggtgtcaac   1260
atgggctaca tggagaacag ctactcgaac tcgaataacg gcggctcggt aaactcgcaa   1320
gactcgatat ggcagatgaa atcagcagcg gcggcaaacg gcgttggcgt gaacgccggt   1380
aacgtcggcg tggtcggcac accgtacgac atgggcggtt acgccaccac cgagtccgat   1440
tacccggccc acccgcacta cctgccgcag agggaagatt acagggagag tcacaacctc   1500
agtcggcagc aattctgcga gccattcgcc gcggttgtca agtcccagaa gcatgtcgac   1560
tcgccttacg acgtgtccgg tctcccgtac caagagaact acgacgagga cagcaaaccg   1620
ccgcagcagg tgagcctgtc gtacgacgag tcgctggaat cgggctactc gacttcgaac   1680
agccggggtc gccgtatcat ccgtgaaata atagtctga                           1719
```

<210> SEQ ID NO 53
<211> LENGTH: 3549
<212> TYPE: DNA
<213> ORGANISM: Leptocybes invasa
<220> FEATURE:
<223> OTHER INFORMATION: Fred friend of echinoid; adult chitin-based cuticle pattern formation

<400> SEQUENCE: 53

```
atgcgctcct ttgctgtgct tctccttgcc ttctcgtgct accacctcgg agcgatccaa     60
gcgtacggcg tggacgagac gtcgatagac acgaaggagg gggcaacggt gaatctgcca    120
tgtaaattcc caccgcccac ggtgaacgcg acgttcttct ggctgacgca cacgaacggc    180
gcgcacgaca atgcggccat cgagcagacg gccttggcgc cgcactaccg cgtgcacatg    240
catcccgacc gaggcgagta caacctgcag atccgcaacg tgtcgtactc gcgcgacaac    300
```

```
ggcaagtacg agtgccgagt gaaggtgagc ggcaccggcg agaatctcta ccacaagaac    360

atcacgctga ccgtgctgcg agcgccgagc gcgccggtca tcgtcctcgg ctcgccgatc    420

gtgcgcgagg aggagcgttt ggagcttcac tgcaagacca acggtggtag ccccgagccc    480

gacgtcaagt ggtaccgcgg cgagtccaac gtgctcgtgc acaccggacg cacctacgtc    540

ctcataccga gcaaggacga cgacggctcc aagctgcgct gcaccgtgtg gaatcgagcc    600

atggacgacg gccacaccct ctcggctagc atcaccctca acgtgcagta cttcccgcga    660

gtgtccctcg gctccgacaa tccgctgagg gtcgaggtca acaacatggc cacgctcaag    720

tgcaaggtcg actccaagcc cgccgtcacg tccgtcaggt ggctcaagga caacagcttc    780

gtcgccatga gcttcaatca catcctgccc aaggtcacgc ttcaggacgc cggcaagtac    840

acttgccaag ccgacaacgg attgtccaag aagggcgaga gcttcttgta cttggacgtg    900

ttgttcccgc ctagcgtgtc catcgaaggc gaccggatta ggactgtcga ggtcgaggac    960

agtgtcactg tgcactgcaa cgtcacctcc aatccggagc ccacgaagat cgagtggctt   1020

cgcgaaggtc ggccggagtt ccgtatcgag ggctcgattt tgcgcctgtc acgagtcaca   1080

gctgagcaag ccggcaatta cacctgccgc gcaatcaact cgatccatcc gtctggaggc   1140

gagcgtcgaa actactcggc cacctcgagg gtggagatcc gcgtgcgtca caagcctggg   1200

ccggcgcgca tcacgcccga cgccccggtc gccgtggaga acaccaaggt catcctgaat   1260

tgcgtggcca atccaccggg ctacccggag ccgacgttcc agtggacccg cgaaaccgag   1320

ggaggcctct cgtcgaccga gtacgtcggc cagaagtacg agattcactc ggtgcacctg   1380

ggcagcgagg gcatctacag gtgtcacgct ttcaacgaga tcggcaacgg cgagtccgcc   1440

tcggtcaacc tcaccgttca ccagtcgccc aagatcctca ccaagctcca gcctcacgtc   1500

accaggaagg tcggtgaatc gtccttccaa gtgtcgtgcg tagcgcaagg taagccccga   1560

ccgtcggtcc gctggatgaa ggacgacaac gagctgaccg ccgaccaaag cctttacaaa   1620

gtctcgacga ccctgtcaga gggtcacggc cgagtgatca cggtcaactc gacgctgagc   1680

ttcctgggca acgcccggcc ggagaccgat cgcatgatcg ccaacgaccg tggcaagtac   1740

acttgcgtgt tcgagaacga ggtgaagaga gtcgagtcgc aaatgatgct caaagtcgag   1800

cacgcgccga tcaagctgaa cctctacgac aaagtggcga gcaacttcca cgagaccgcc   1860

aatgtgacgt gcaaggtgca ggcttggccg aagccggagt tccagtggag cttcggcacc   1920

aacgcggctc cgctacaagg ctcctcgagc gacggccact acgagatctc caccgcgagc   1980

gacaactacg acgtgtacac gtcggtcctc aaaatcacca acatccgtga caccgactac   2040

ggggagtacg gctgtcgagc ggccaacgct cagggcagca ccacctccgt catcagatta   2100

cagccgaaag gcgcgcccga gaggcccatc aacctcaggg ccatggacgt cggaccgacc   2160

tacgtagctc tcatgtggga tcttggcttc gacggtggac tgcccatcac gaagtacttc   2220

gtctcctaca agagggtcgc cccggccgac gagatcattg ccgccgattg cgcgccgccc   2280

agggggccgt ccaatcaatg gatggaggtc gactgccgca ggtcgaatcc ctgcaacgtt   2340

tccgacctcg agcaacatca aacttacatt ttcaaggtaa aagtatacaa cacgaacaac   2400

cactcggact actcggacga ggtgacggcg accacagcgg tggcgaaaat tccaagtccg   2460

ttgcgcgtga gctacgaccc cgaaggcggc actctcggcg tcaacgtcgg accgacgtgc   2520

ttggcgctcg tcgcttcgat cgagaaatcc gactcgggct ccgacaacac ctggcgcatc   2580

gtcgaggatt ggacgctcga ggtcctcggc ggcgcgagca cgcagaggga agaggttctg   2640

caagactcgg ccgcgtcgag ttcagagccc agaattcgcg tgaggctgtg cctgaaggcc   2700
```

```
gatcggcaga ggtgcggcga gtacgtcgaa gctgagatcg ggccgtcata catagcccgg   2760

gcgggtacac tggcaactcc aactttaatt gctctggtag tgagcggagc cgtgttccta   2820

ttgttcgccg ctctgctgct tctgttctgc cgctgtcgca ggaaacacgc tgccaaagcc   2880

aaagactacg agatggattc aaatgcagtg aggccgagct tggtgaccgg aagcggaggt   2940

cagacgcagg cgccgccacc ctactacgcc gagaacaagg cgctcgagca cagtttggat   3000

cacgctctcg ccctcgagga ctcgaagaca ccggcttacg gccaaagtgg ctacggctat   3060

catcagccca atcacaacat gaatggtgta aacatgggtt acatggagaa cagctactcg   3120

aattcgaaca acggtggctc ggtgaattct caagactcga tctggcagat gaagcaagcc   3180

gcggcaaacg gcggcgtcgg cgtgaacgtc ggtaacgtcg gcgtggtggg cacaccctac   3240

gacatgggcg gctacggcac cactgaaccc gactatccgg cccacccgca ctacatgccg   3300

cagcaagatt acagggacac ccacaacctc agccgccagc aattctgcga gcccttcggc   3360

acagtcgtca agtcccagaa gcatgtcgat tcgccgtacg acgtgtcggg tcttccttac   3420

caagagaact acgacgagga cagcaagcca ccgcagcagg tgagcctgtc gtacgacgag   3480

tcgctggaat cgggctactc gaccccgaac agccggggtc gtcgcatcat ccgcgaaata   3540

atcgtctga                                                           3549
```

```
<210> SEQ ID NO 54
<211> LENGTH: 1368
<212> TYPE: DNA
<213> ORGANISM: Ophelimus maskelli
<220> FEATURE:
<223> OTHER INFORMATION: CG3590 AMP AMP-lyase; purine nucleotide
      metabolic process

<400> SEQUENCE: 54
```

```
tttcagcgat caaaacaatt tagcacgtgg cgtaaactat ggatttacct agctcaagct     60

gaaatgagtt tgggattagc cataaagcaa gagcaaatcg atgagatgac caagcacgtc    120

aatgatatcg actttgatgc tgcagctaag gaggagaaag ctacgagaca tgacgtcatg    180

gctcacgtac acgtttttgg taatcagtgt cccaaagctg cacccatcat tcatcttgga    240

gctaccagtt gttacgttgg agataatacg gacctgatag tcctgcgtga cggattcgac    300

atcctgctac cgaaactcgg tgccgtgata aatcgtcttg ccaaattcgc cctcgacaac    360

cgttcgatac caacattggg ttttactcat ctgcaaccgg ctcagctgac gaccgttggt    420

aaaagagcta cactctggct gcacgatctg ctgatggacg agcgggctat tcgcagggct    480

aggaatgatt tacggttccg tggtgtcaag ggtaccactg gtactcaggc atcgtttttg    540

cagcttttca atggagacgg agaaaaagta aaacagttag acaatttggt gacgagaatg    600

gctggatttg aaaaacgtta tgccgtgacc ggtcaaacgt acagtagaaa agtcgacctc    660

gaatgcttga acgctctcag ttctttgggt gcaacggtgc ataagatctg cagcgacatc    720

cgtatcctag cgaacatgaa agaaatcgag gagcccttcg agtcaacgca aatcggttca    780

tcggcaatgc cctacaaacg taatccaatg cgtagcgaac gctgctgcag catagctcgt    840

cacctgatga cacttgtcaa taatacgctt caaacggctg ccaatcaatg gatggaacgt    900

actttggacg actcggctaa tcgtcgtatt accttggctg aagctttctt atctgccgat    960

gttatactta tgactctgca gaatattacc gagggcctcg ttgtttatcc gaaggttatt   1020

gctaggcata tagcacagga attaccgttt atgtcggcgg agaatgttat tatggcgatg   1080

gtcaaggctg gtggtgatag acaggtctgc cacgaaaaaa tacgtgtgct gtctcacgaa   1140
```

```
gccggtgccc aagtcaagca gcacggtaaa gataacgatc tcgtcgatag aatccgcaac   1200

gacaaatact ttgaacctat tctcgaccaa ctggacgctc ttttggatcc atcgactttt   1260

gtcggtagag cacccgatca agttgtcgaa tttctcgaag aagaagtcta tcccgtactc   1320

aagaattacg agggccaaga tatcaaacca gttgaactga gcatttaa                1368


<210> SEQ ID NO 55
<211> LENGTH: 1374
<212> TYPE: DNA
<213> ORGANISM: Leptocybes invasa
<220> FEATURE:
<223> OTHER INFORMATION: CG3590 AMP AMP-lyase; purine nucleotide
      metabolic process

<400> SEQUENCE: 55

ttcaatttca gcgaccaaaa caagttcagt acgtggcgta aattgtggat ttaccttgcc     60

aaagctgaaa tgtctttggg tttggctata acgcaagagc aaataggcga aatggaagag    120

cacgtgagcg acatcgactt cgttgccgcg gctaaggaag aaaaggccac gagacacgac    180

gtgatggctc atgttcatgt tttcggtgcc cagtgcccga aagctgcgcc tatcattcac    240

ctgggcgcaa ccagctgcta tgtgggagat aacacggatc tcattgttct ccgtgacggc    300

ttcgacatcc tgttgccgaa gttggcagct gttatcaagc gattggccaa tttcgcgaaa    360

gaataccgat cactgcccac ccttggcttc actcatcttc agcccgctca actgacgacc    420

gtcggcaaga gagccactct ttggctgcat gagttgctaa tggatgaacg tgcgattcgc    480

cgggcgagga atgatttacg ttttcgtggt gtcaagggta ccactggtac tcaggcttcc    540

ttcttgcaac tctttaatgg cgagggtgaa aaagtgaagc agctagatga tatggttacg    600

aggatggcca gattcgagaa gcgttacgct gtcaccggcc aaacttacag caggaaggtc    660

gacgtcgagt gtctcaattg tctggcttct ctgggtgcca cagtttacaa gatctgcaca    720

gacatcagaa tcttagcaaa catgaaagaa ttggaagaac cgttcgagtc aactcaaatc    780

ggttcctcgg caatgcctta caaacgtaac ccaatgcgta gtgagcgttg ctgcagcata    840

gctcgccacc tgatgacact cgtgaataat ggactgcaga ccgcagcgaa ccagtggatg    900

gagcgaaccc tcgatgattc ggctaaccgg cgtattaccc ttgccgaggc attcctctcg    960

gctgatgtcg tacttatgac tttgcagaat atctgcgagg gcttggtcgt ctatcctaag   1020

gttatcgcca ggcacatcgc tcaggagctg cctttcatgt cggctgagaa cgttattatg   1080

gccatggtca aggccggcgg agaccgacag gtgtcccacg aaaaaatacg cattctctcg   1140

caagaggctg ctgctcaggt aaaacagcac ggtaaagata atgatctggt cgagcgcatt   1200

cgcaaagaca agtactttga gccaatactt gcccaaatgg ataccctctt ggatccttct   1260

actttcgttg gcagagcacc tgatcaagta gtcgaatttc tgcaggagga agttaaccct   1320

gtcttggcaa actacgagtg cttcaatgat gttccagttg aattgagcat ttaa         1374


<210> SEQ ID NO 56
<211> LENGTH: 1170
<212> TYPE: DNA
<213> ORGANISM: Ophelimus maskelli
<220> FEATURE:
<223> OTHER INFORMATION: CG5451 nuclear mRNA splicing, via spliceosome

<400> SEQUENCE: 56

tatattcatt tagaaaatct tctggctcgg tcgtacttcg atccaagaga agcatatcca     60

gatggaagta caaaagaaaa gagaagagca tacatagcca catctttagc aggagaagta    120
```

```
tccgtagtac catccagtag attgttagct ttgctaggac aagctttaaa atggcaacag    180

catcaaggac ttttaccacc aggtactact attgacttgt tcagaggtaa agctgcagta    240

cgtgatcaag aagatgaaca ttaccctaca caattatcaa aacaaatcaa atttggtaca    300

aagtcacatg tggaatgtgc tcgattttct cctgatggtc aataccttgt cacaggatcc    360

gtcgatggtt taattgaagt ttggaatttt acaactggta aaataagaaa agatttaaaa    420

tatcaagctc aagaatgctt tatggtgatg gaagatccag tagtatctct agcttttagt    480

agagacagtg aaatgttagc tggtggtgca caagatggaa aaatcaaaat ttggaaagta    540

caaagtggtc agtgtttgag aaggtttgaa aaagctcact ccaaaggtgt cacctgttta    600

cagttcagca gggataacag ccaaatactt tctgcatctt ttgataccac tattagaatc    660

catggactga agtctggaaa aacattaaaa gaatttagag gacatacttc atacgttaac    720

gaagttatat ttcttccga tgcccacaat atcattagtg catcttcaga tggaacagta    780

aaagtttgga gtttaaaaac aactgaatgt attggtactt ataagtccct tggagcagct    840

gatttgaacg taaatagtgt gctctcatta cccaaaaacc cagaacattt tgtagtgtgt    900

aatcgttcaa atacagttgt aattatgaat atgcaaggac agattgttag atcattttca    960

agtggtaaac gtgagggagg tgattttgtt tgtgcagttg tatctccaaa aggggaatat   1020

atatactgtg tgggtgaaga tagagtgtta tattgtttct caactacttc tggcaaatta   1080

gaaagaacat taaatattca tgaaaaagat gtcattggaa tagcacatca tcctcatcaa   1140

aatttattat gttcatacag tgaagatggt                                    1170
```

<210> SEQ ID NO 57
<211> LENGTH: 540
<212> TYPE: DNA
<213> ORGANISM: Leptocybes invasa
<220> FEATURE:
<223> OTHER INFORMATION: CG5451 nuclear mRNA splicing, via spliceosome

<400> SEQUENCE: 57

```
ttggccttca gtagagacag tgaaatgtta gctggaggat cacaagatgg caaaattaaa     60

atttggaaag ttcaaagcgg tcaaactttg agaaaatttg aaaaggcaca cactaagggt    120

gttacgtgtc tacaatttag tagagacaac agtcaaattc tttcagcatc atttgatgcc    180

acaatcagga tccatggact gaaatcaggc aaaacactga aagaatttag aggacattct    240

tcgtatgtca atgaagttat attctcttca gatgcacaca acatcattag tggatcttca    300

gatggaactg taaaagtttg gagtctaaaa acaactgaat gtattggaac gtataagtcg    360

ttaggggcag ccgatttaac tgtaaatagt gtacattcat taccgaaaaa tcctgaacat    420

tttgtagttt gtaatcgatc aaacacagtt gtgattatga atatgcaagg gcaaatagtc    480

agatcatttt cgagcggtaa gcgcgaaggc ggcgacttcg tttgtgcagt tgtttcacct    540
```

<210> SEQ ID NO 58
<211> LENGTH: 1170
<212> TYPE: DNA
<213> ORGANISM: Leptocybes invasa
<220> FEATURE:
<223> OTHER INFORMATION: Wls cuticle pattern formation

<400> SEQUENCE: 58

```
tggaaacact atgcttcttc tatagttgaa aggaatttag actgtaccat tgataagctt     60

cacgaagagt acaattacaa ttgcagtaca ttgtcacttt ttgaattggg atcattacat    120
```

```
catgattact atctacttaa tatacgctta cccaatgatc ctcggaaaaa ggagaatcaa    180

gatttaggac atgtaactga tctatggctc acagtcatca accagaatgg aggatttaca    240

aaagtatggg tcagcttgaa aaccgttttc ttcccaatca ctcttttgac tctttgctgg    300

tactggcgaa gaatccacat gctatcaaga tctccagctt tgctggaata catgttgctt    360

ggtttaggct gtgctttaag ttttctgaat atgccactgg aatattttac attggttttt    420

gatatgccat atatgctgct gctagaagat attagacaag gagtatttta cgcttcacta    480

ttgtctttct ggtttgtctt cgctggtgaa catttgatgg ttcaggacgg cgatcaaatg    540

aattctctga aatgttattg gcggcacttg tctgcagttg ggttggctg  cttatcatta    600

ttattcttcg atatgtgcga acgtggcgtg cagcttcgaa atccatttta ctcgatctgg    660

gtgacaagtg ctggagccaa aacagctttg gcgtttataa ttatggctgg aatatcagca    720

ggagcctacc ttttattctt gacgtacatg atttacaagg tatttgtaaa cataagcgcc    780

aagagagcgg tattaccaag tatgagttca gctcggcgtt tgcattacga gggagttatt    840

taccgcttca agtttttgat gatcgccact ctcttgtgcg cctcgttgac cgtcattggt    900

tttatcctgg gtcaggttgc cgaaggtcat tggaaatggg atcaagacat tgagttagaa    960

atgacatcag ctttcttcac tggagtttat ggcatgtgga atatttatac catcgctctg   1020

ctgtgtttgt acgcgccatc tcataagcaa tggcccgtcg aaccttcaga aaatagcgtt   1080

agtgaagaaa ttgagttttc aagattgccc actgaaccca atgagatgct ctctttgacg   1140

gcattcacgc gaaaaacggc gatagattaa                                    1170
```

<210> SEQ ID NO 59
<211> LENGTH: 1869
<212> TYPE: DNA
<213> ORGANISM: Ophelimus maskelli
<220> FEATURE:
<223> OTHER INFORMATION: CG6690 flavin-linked sulfhydryl oxidase
      activity; multicellular organism reproduction

<400> SEQUENCE: 59

```
atgattgttt tcgtcgtctt tgatgtaacc tccaatgttg ttgttcctaa ggatcaggat     60

aatcaaggcc tctttaattc cagtgatttg gtcgttgtat tgaacgacac gaattttaaa    120

accagtgttt ataatagcag aagggcatgg cttgtcgaat tttacaacag ctggtgtggt    180

ttctgccatc ggtttgctcc gatttggaag tccttggcta aaagtgttca tggctggaga    240

gatatagtag cgatagctgc tattgattgt gcaaatgatg ataataatcc tctctgtcgg    300

gagtatgagg ttatgaatta tcctacattg aagtttttc  ctataaattc aaagaaagat    360

tttctgggtt tagacattga caaagctatg gatgaagtgt ttataatgca cgctttgatt    420

gatcaattag agaaagaaca gcaagaacaa cgagcagatg tcttgtggcc aaatattatt    480

ccatacagaa gtaatgatgt agaaacgtta tggagtggag caccaagtag tattcaatat    540

caatttctga catttgaaga acctaagtca tatttaggag ctgcagttat tttagatttg    600

cacaaattaa gtaatattcg aattagaaga gtctcgacag agaatgaatt tttacgtgtg    660

ataatgaaag taacaaaatt tcccagtgta attgctgtaa ataaagataa ctcacaagag    720

tttatgaagc ttgattcact cactcgagaa ggtattaaag aagcaattgt agaattttta    780

aaatctaagg gattacctgt ggaactgaaa gatgaaattg aagaaaattt ttctataaat    840

attgttcctg aatcattaat caaacgtgaa tcaagagaac ctactcttac aggagacaag    900

ctttatcaat tagatctaga aagtgctctt caattttcat taaataacga aattccattg    960
```

```
tctaaaatca ttgccggtga aaagatgaaa gcattgaaag cttatttaaa agtgttaact   1020

acttattttc ctgtatattt acccaaagcc aaaacatact tgcaagtttt atatgagata   1080

gtggaaagtc gaaataatat tactggtaaa gaatttaaag aacatgtgaa acaaaaggaa   1140

aacggactta tgcctgtata ctcgggacct ccaagaactt ggattggatg caagggaagc   1200

tctgaaactt acagaggtta tccttgtggg ttgtggacta tgtttcatac attaactgta   1260

gcagctggtg aagatataga tgaaacatat gataataatc atccatcagt gttagcagca   1320

atgcatgggt acattaaaaa tttctttggt tgctcggatt gctcaaatca ttttcaagag   1380

atgtctcaga acagaaaatt gttcgaggtg catggaaaaa atgaaagtat tttgtggctg   1440

tggagggcac acaatgaggt aaataagaga ttagccggtg atgagactga agatccagaa   1500

cataaaaaga ttcagtatcc tgcagaatat tactgcccta aatgtagatt gccagatgga   1560

aaatgggatg agattgaggt tttgaaatat ctcaaaatca agtacaataa attacatata   1620

gaccttcaag gtattagtga cgatttactg cagcatgaaa tcgataccag tgcatctagc   1680

tcaggtgtta gtcatcgtaa aattggctgg aatttcacaa tgtttgattt tagtatttgt   1740

gtgatactat atgccatttc agccacaata ctaacattgg tttgtttaaa atttgcttat   1800

agaagatctt acaagaaaaa atatcgattc aacatttatt tggtaaagca tcaatgtaaa   1860

aaaagatga                                                           1869
```

<210> SEQ ID NO 60
<211> LENGTH: 1197
<212> TYPE: DNA
<213> ORGANISM: Leptocybes invasa
<220> FEATURE:
<223> OTHER INFORMATION: CG6690 flavin-linked sulfhydryl oxidase activity. multicellular organism reproduction; 5' fragment from same gene as SEQ ID NO: 235

<400> SEQUENCE: 60

```
atggggaagc gtcaacagca gttcctccgg gagacgttca taggttacct aattttcggt     60

ctccttgttg tcgtaagcgg cgtctctgcc aatgccattg gccagaagga cgagaacgcc    120

ttggagaata ccaccgggct ttacaacgct agtgatgaag tttatgtctt ggacaacatc    180

aatttccagt ccagtgtttt gcaaagcaag agagcatggc tggttgagtt ttacaacagc    240

tggtgtggtg cctgccacaa atttgctgca aaatggaaag ctctagctaa gagcgctcac    300

ggctggagaa aaatagttac tatagctgct attgattgtg ccaatgatga caatacccct    360

gtatgcaggg aatacgaagt aatgaaatat cctactctaa aattcttccc agtgaatgca    420

aaatcagact ttttaggctt acagctacca aaagctaatg atgaagtgct tataatgcaa    480

gcactgattg atcagcttga aaaagaacag caagagcaac gtggaggttc agactggcct    540

aatcttgctc cataccgaaa cagtgatatt gaaactttat ggcatggagt acctgcaaat    600

atcgattatc agtttttgat tttgaagag cctaaagcct atttaggcgc tgaagttatt    660

ttagatctat ataaattgaa taacatacgg ataagaagag tcacatcgga aaatgttctt    720

cttacagttg caagtaaagt caataaatat cccagtgttt tagctatcaa caagcacctc    780

acacaaacta ctttgaaaat tgataaatta acacgagaag gactgaaaga atcaatttta    840

gagtttctca aatcaaaagg aatatctaca gatataaaaa atgatatttt tgatgatatt    900

atcaatcata aagcaacaag tggacattat aatgtagagc ttgttaaatc agaggataaa    960

ctgtaccagt tagatttaga aactgcagtt cggtatactt taaataacga aattccactt   1020

tcaaagaaca ttacaggtga aaaattaaaa gctctacaaa actacttaaa agtattagct   1080
```

```
cactactttc ctagtaattt accaaagatg aaaacgtatt tacaagtttt aaaagaaatt   1140

gttgagagta aaagtaacat aactggtaaa gaatttagaa aagaagtcaa gacaaag      1197


<210> SEQ ID NO 61
<211> LENGTH: 699
<212> TYPE: DNA
<213> ORGANISM: Ophelimus maskelli
<220> FEATURE:
<223> OTHER INFORMATION: Cic sequence-specific DNA binding; regulation
      of transcription

<400> SEQUENCE: 61

cgaaaagcaa ataagcctaa agttaaaaca gacttttcac agcctacaaa tattaaggaa     60

ttaagagcac ttgataaacc ttttcgtatg cacaagctaa atttggtttg gataaaggca    120

aaacatagat taacagatcc taaattacaa tcactcttta gtgatttaaa gattcaagat    180

aaagaagaaa taacttttaa acatatgaaa tcggatggga aagatgaaag tggattggaa    240

gaagctaggc tacgaaaaaa gctcattggt atcatgagta cgtatgattt acttgaacac    300

tttgaagatg tcaaagatcc taaatattta agtaaaccca aaccatttaa cgatggtagt    360

aattatgtag caaagcaagt atttaaagac aagcgattaa accaattgtg ggcaaaagct    420

gaaagaggag gatttactca tgaagaacta gaaactttga aagaagaatt tagtcaccac    480

caagacaaaa ttgacgagta tatgagttta ctatcagaag ttgaagctgg agatccagat    540

agacatgaaa acagtcttca tgaaaaacct gacagttgga atgaattgga aactgaagag    600

gaagaaagta atgatgttcc aggaaggaaa aaagattatt tatccaaagc caatttgctc    660

aaagagaaac atttagatgt ccgaagtgga tttgatcat                           699


<210> SEQ ID NO 62
<211> LENGTH: 1131
<212> TYPE: DNA
<213> ORGANISM: Leptocybes invasa
<220> FEATURE:
<223> OTHER INFORMATION: Cic sequence-specific DNA binding; regulation
      of transcription

<400> SEQUENCE: 62

atgtcttcct ttgtgaaagc tagtctgttg agtatagttt taatgatagt tttaattgac     60

tgtgctgagg gactcagcaa atattccgaa caggctaata agcctaagcc taaacaaaag    120

ccaaaaactg atttctcact tccgactaac ataaaagagt tgcgggcgct cgacaagcct    180

tttcgtatgc acaaattaaa tttgttgtgg gtcaaagcga aaaacagatt gacggatcct    240

aagctgcagt cccttttag tgatctgaag attcatgaca aagaggagat agcatttaaa    300

catgccaagt ctgatggtaa agatgatact ggtctggaag aggctagaat gcgtaaaaat    360

ttactggtat tatgagtagg tacgatttgt tggagcattt tgaacaaatt gaccatgata    420

catattacaa acctaaagta aaaaccagac tatgggaatt atgttaccca agaagttttc    480

aaagataaaa gattgaacca cttgtgggcc aaagctgaga gagctgggtt tcatcatgaa    540

gagctggaag ctttgaaaga agaattcact catcatcaag agaaagtgaa cgagtatcta    600

agtctattat ctgaggtaga agctggagat cagaatagac atgagaatag tcttcatgaa    660

aagcctgtaa gttggaatga attagaatct caagaagaaa ttagcaatga agttccaggc    720

aagaataagg attatttagc aaaagccaag ttactaaaag aaaaacattt agaagttaga    780

actggttatg accatttaga aaacattgca gctaaagggc caacagccaa ggagttcatt    840
```

```
gatcctaaag ttcaagagct atggaatatg gcacttgaat caaaattttc agctaatgaa    900

ctgctgtcgt tgagagaaga gcttttacac tatgaaaaaa gattattgaa attacggcat    960

ctgcacacag aagcagcttt ggaagctgct cgacagggaa agaatataag ccaaaatact   1020

actcatgtga cttacattaa aaaacataca agggatgttg agaagttaca caaagacctt   1080

gaagataaaa tactgcaaaa acacacggag ctagtaaaaa gtttagaata a            1131
```

```
<210> SEQ ID NO 63
<211> LENGTH: 1329
<212> TYPE: DNA
<213> ORGANISM: Ophelimus maskelli
<220> FEATURE:
<223> OTHER INFORMATION: Crc DNA binding transcription factor;
      metamorphosis; molting cycle, chitin-based cuticle

<400> SEQUENCE: 63

aaagctcatc ataactggat tgcaatagct tatgcacact ttgtaacatg ttatcggtta     60

aaagattcat ctggttggca gcaggttttt accagtccac atatcgaatc tgtgattgaa    120

cgagttgcga taaatgcaaa aatggggatg ggagcggatg gaaaaatgat agctatttct    180

tatggaagtc aagtgagatt gtggtgcatt actgaagatg gagtaaaaaa cgacattggt    240

acttttaatc tgaatgtgcg tgtagaatat ttattttta ttggaagcca gttggttgct    300

ttatcaccaa cgggaaaaat tggtgtttgg catgctatga ctcaccactg gcaaattcaa    360

gatgtagtgt cgatctcgtc ttttgacact gctggatctt ttcttttact tggatgcaat    420

aatggctcta ttaattatat tgatatgcaa aaatttcctc tcagaatgaa agacaatgat    480

ctgcttgtaa cgcagctgta caaagatcca agtcatgatc ctattactgc aatatcagta    540

tatctaacac caaaaacaac gcaaggcctt tgtggtaatt ggatcgagat agcttatggt    600

acaaagtcgg gaagtgtacg tgtgatcgta cagcatccag aaaccgtcgg tcatggacct    660

caactttttc aaacctttac cgtacatcag agcagtgtta caaaagtgac cttgtcagaa    720

aaatatttag tatcggtttg ctcagaatat aatcacgtta gaacttgggc tgttacacga    780

tttagaggta tgatttcaac tcaacccggt tcaactcctg aggctagttt caaaattgtc    840

tcattggatg cagttgagcc ttgtattagt tataatgctg gaaatgactt tggtccattt    900

ggcgagcaag acgacgagca agtattcgta caaaaagttg taccagagac tgatcaactt    960

ttcgtgagat tggcatcgaa cggaaagcgt gtttgcgtta ttcaatcggt ggatgggagc   1020

gtcataacgt cattctgtgt acatgagtgc gaaggttcaa gtcgcatggg atctagaccg   1080

aggcgattta tattcacggg tcactcgaac ggtgcgattc aaatgtggga tctctctacg   1140

gccctggttt caccgtccaa gctttcggtc aaagaatttt ctggaggacc aacgccggaa   1200

gaattatgga aattattaga tcaatgtgat ttgagcaaca gtcattgttc gacaccttgc   1260

atcagtccat ctccgtcttt aatcgcatcc gggccaagga taaaagcaag caacgtacta   1320

tttctaaat                                                           1329
```

```
<210> SEQ ID NO 64
<211> LENGTH: 558
<212> TYPE: DNA
<213> ORGANISM: Leptocybes invasa
<220> FEATURE:
<223> OTHER INFORMATION: Crc DNA binding transcription factor;
      metamorphosis; molting cycle, chitin-based cuticle; 5' fragment
      from same gene as SEQ ID NO: 236

<400> SEQUENCE: 64
```

```
ataaaagcac atcacaattg gatagcaata gcttacgcgc acttcataac ttgttatagg      60

ttaaaggact cgtctggatg gcaacatgtt tttacaagtc cacatgttga gtcagtcata     120

gaacgagttg cgataaatgc caaaatggga atgggtgctg aagggaaaat ggtggctatt     180

tcttatggta gccaagtgag attgtggtgt gtgactgagg atggaataaa aacaaacatt     240

ggtactttta atttgaatgt gcgcgtagag tatttatttt ttattggaag ccagttagtt     300

gccttgtcac caactggaaa aattggagtt tggcatgcaa tgactcatca ctggcaaata     360

caggatgtag tacctatttc gtcctttgat actgcaggat cattcctttt gctaggttgt     420

aataatggat ctattaatta cattgatatg caaaaatttc cactgaggat gaaagataat     480

gatttgcttg ttacacaact ctatcgagat cctagccaag atcctataac ggcaatatca     540

gtttacttga caccaaaa                                                   558
```

```
<210> SEQ ID NO 65
<211> LENGTH: 954
<212> TYPE: DNA
<213> ORGANISM: Ophelimus maskelli
<220> FEATURE:
<223> OTHER INFORMATION: ATPase activity, positive regulation of growth

<400> SEQUENCE: 65

gacgagccaa tttcaaccct gactcaagat tttcacacgc gactagacaa cttgttaagg      60

actttggtgc acgcgagacc gcatttcgtt cgatgcgtga gaagtaacgg cactgaaaca     120

ccaatgcaat tcgatcgtaa tgttgccatg cgtcaaatac gatcccttca agttttggaa     180

accgtcaatc ttatggctgg tggctacccg catagaatgc gtttcaaagc tttcaacgcg     240

cgttaccgac tgatagcacc gtttaagcag ctacgccgca gcgaggagca ggcaatcgaa     300

gatacaaaac tcattttaca aaatgctcag cagctcaaga gcaactttaa cgcgagtaca     360

agttgggctc ttggaaagcg acacatattc cttagcgaag gcatcaggca gcaacttgag     420

aatctgcgat ccgaaattcg taggagagct gctaccgata ttcaggcaag ttggcgaggt     480

tggcgcatca gacgaagatg gacgttacgt catccaaaac taggtttgag ttccggtatt     540

ggaccgaaga gtacgcagca atcgtcatca acggctaata tcgtcacggg tagtggaacg     600

ttacagagaa gcatcactgc tggaactaac ggtgctggtt taggtggtgc aagaccgaga     660

ccacaaccga tcgccggtac accgccgccg gatcctactg aaaagtgcgc tgatcctaag     720

atgatacagc agacttgcac actttttggt ctcgatctgg aacggcctcc accagtacca     780

cctagcagat catacaccgt aaccggaaat acaaaacttg gctacccgca aacgaggatt     840

atgaaagcac ccttcccgga agagggcgag ggcgaagtcg ttcttctgaa aggagaaaca     900

gttttagtta ttggagcgtc gcagagacgc ggacacttac ttgtcgagca caat           954
```

```
<210> SEQ ID NO 66
<211> LENGTH: 2661
<212> TYPE: DNA
<213> ORGANISM: Leptocybes invasa
<220> FEATURE:
<223> OTHER INFORMATION: ATPase activity, positive regulation of growth

<400> SEQUENCE: 66

accttgacca gcacgagggc tatgccgctt acgtctcatc tcaatagggt tgtacaggag      60

gcggtgaggc aacagtccga gactggatat cctcaggcta ttatactttc tggtacgagc     120

ggtagcggca agacatacgc gtcgatgtta cttctacggc agttgttcga cgtcgccggt     180

ggcggacctg aaaccgacgc gttcaaacac cttgctgctg ccttcactgt actacgatct     240
```

```
ctgggttctg ccaaaactgc cacgaactcg gagagttcga gaatcggtca ctttatcgaa    300
gtacaggtga cggacggcgc gttgtacaga acgaaaattc attgttactt tttggaccag    360
acgagggtta ttcgaccgtt gcccaacgag aagaattatc acattttta ccaaatgctc     420
gccggtctgt cgcacgagga gagagtaagg ctgaatcttg agggatacaa cgtgaagaat    480
ttgaagtacc tgcagcatgg tgacacgaag caggacgagg ccgaggatgc gatgaggttt    540
caagcttgga aagcttgtct gggtgtcctg ggtattccat ttctcgacgt agttcgtgtg    600
ctggcagctg tactgattct cggcaatgtt aacttcactg acggtccgaa tgttgaagtg    660
agtgtgaacg gtgaaaatga acttgcttcg gttgcgacat tactcggtgt cacacccgct    720
gcgttactac gtggtctcac ttcgcggacg cacaatgcca gaggtcaact tgtcaagtcc    780
gtctgcgatg ctaatatgtc caacatgacg agagattcgt tggcgaaagc attgtactgt    840
cgcacagtcg caacgatcgt cagacgagct aacagtttga agaggcttgg ctcgactctc    900
ggcactttgt cgtcggactc gaacgaatct gttcacaatc aggctgaggt cgctagccag    960
catgcctcta cgattggcag tggcgcaggc tgcacgggtt cgcgtagcat gacggcgctg   1020
aacaacgcgg tacgtcacgc gacagacggt ttcatcggga ttctcgatat gttcggcttc   1080
gaggatccaa agccgtcgca gctggaacat ctgtgcatca atctctgcgc cgagacgatg   1140
cagcatttct acaacaccca catattcaag agctcgatcg agagctgccg cgacgagggc   1200
atcaggtgcg acgtcgaggt cgattacgtc gataacgtgc cttgcatcga cctcatctcc   1260
tctttgcgaa cgggtttgtt gagtatgttg gacgtcgagt gctcgataag aggcacagcc   1320
gaaagctacg tgtcgaaggt caaagttcag cacaagcaaa atccgcgatt attcgaaacg   1380
agaatgatgg actgccgctc ctttggaata caacatttcg ccggtcgtgt cgtctacgac   1440
gcttccgact ttctcgacac gaataaagat gtagtgccgg atgacctagt agcagtattc   1500
tacaagcaca cgtgtaactt cggcttcgca actcacctct ttggcagcga gttgaaggca   1560
ctttacgcga gcgacacagt gccgaggggc gtcagttttc gcatctcgcc tacttctcac   1620
accgacttat taaacggcga cgagccaatc tcgactttga cccaagactt tcacactcgc   1680
ctggacaatc ttcttcgcac cctcgtgcac gcgcgaccac acttcgtgcg ttgcgtgcgc   1740
agcaacgcca gcgagacgcc gatgcaattc gatcgaaacg tcgcgatgcg ccagattcgc   1800
tcgttgcaag tattggaaac cgtgaacctc atggccggtg gctatcctca ccgcatgcgc   1860
ttcaaagctt tcaactcgag gtacagactc atcgcgccgt tcaagcagct gaggcgcagc   1920
gaggagcaag ccatcgagga taccaagctg attctacaaa acgctcagca gcttaagagt   1980
agcttcaacg cgagcactag ctgggccttg ggcaagaggc acattttctt gagcgagggt   2040
atcaggcaac agcttgagaa tttgaggtct gacattagga gacgcgcggc tactgacata   2100
caggcaagtt ggcgcggctg gcgaatacga cgaagatgga cactgcgtcg ttcgaagcgc   2160
agtctcgtcc attcgagttt gattccaaag cagctgacga cgagtctgca ccaaccgtca   2220
tcggcgaacg catcgatcgg atcgttaggt actttgcaga gaagcctcca ttcgacgagt   2280
agcggaagta ttacaaggcc aaggccacaa ccgattgctg gcacaccgcc gcctgatcct   2340
tcggaaaaat gcgctgatcc caagatgatt cagcagactt gtacgctttt cggactcgat   2400
ctcgaacgac caccacccct accaccgagc agatcgtaca cggtcacggg aaatacaaaa   2460
ttgggttatc cacaaacgag ggtgatgaaa gctccgtttc ctgaagaagg tgaaggcgaa   2520
gtgattctgc taaaaggcga gactgtctta gtaatcggag catcccaacg tcgtggtcat   2580
```

```
ctgttagtcg aacacaatgg cactaatctt cacgtgcctt atcaattcat ggagctgaaa   2640

ccgtgcaaca tcagcgtttg a                                             2661


<210> SEQ ID NO 67
<211> LENGTH: 1224
<212> TYPE: DNA
<213> ORGANISM: Ophelimus maskelli
<220> FEATURE:
<223> OTHER INFORMATION: Dad transforming growth factor beta receptor;
      instar larval or pupal morphogenesis

<400> SEQUENCE: 67

ttggaaaaag cagccagtaa tacagaaatt tcaagtaaat ttacaaccat acctctaagt     60

ttcgatggta gggtacaagt atcacatcgt aaaggattgc ctcacgtaat ctactgcaga    120

gtatggagat ggccagattt acaatcacac catgaactaa aaccattaga aatctgccag    180

tatcagttct cagctgaaca aaaataagtg tacatcaatc cttatcacta taaacgagta    240

gagagtccag tactaccttc agttttagta ctcagacact cggaatatgc tccagaaaga    300

ttacccatga ctttccaaca gcacagtgaa tctgctatgc cacagaatat gtcttactat    360

tcaaacgact ttaacagtgg tggcatgggt ggaaacagtg gcaactcacc agtctcttct    420

tatggttctg tatccagtcc tattaacgca gctaacaatc acaatcataa tccttatgga    480

gctaatagtg gcttatctga aacaccacca ccagcttact ctccttcaga agatggttcg    540

cagtacggtc agtctccatc gcctaactca atgatggcca tggacacaag caatgcccag    600

gatgttgcac cagtgcctta tcaagagcct cgttactggg cttcgatagc ctactacgag    660

cttaattgtc gtgttggtga agtttttcat tgtcagtcac cttccgtgat agtagatggc    720

ttcactgatc ccagaaataa ttcggcaaga ttttgcttgg gacagttgtc taatgttaat    780

agaaattcaa cgatcgagaa cacaagacga cacattggta aaggtgtgca acttcattac    840

gtcggaggcg ctttgtttgc cgagtgcatt tccgactctg caattttcgt acagtcaaga    900

aactgtaatc atcaacgagg ctttcatttg agtactgtta tcaagatacc accaacgtgc    960

tcattgaaaa tttttgataa tcagctgttt gctgatttgc tagctcagag tgtctgccat   1020

ggattcgaag ctgtttacga gttaacgaaa atgtgcacga taagaatgtc gtttgtaaaa   1080

ggttggggag ctgaatatca ccgtcaagac gtcacatcaa ctccctgctg gatcgaaatg   1140

catcttaatg gtccacttca gtggctcgat aatgtcctca ctcgtatggg tacacctcat   1200

aatgccataa gttcagtgtc ttaa                                          1224


<210> SEQ ID NO 68
<211> LENGTH: 714
<212> TYPE: DNA
<213> ORGANISM: Leptocybes invasa
<220> FEATURE:
<223> OTHER INFORMATION: Dad transforming growth factor beta receptor;
      instar larval or pupal morphogenesis

<400> SEQUENCE: 68

gacacaccgc cccctggcta catcagcgaa gacggcgaca acatggacca caacgacaat     60

atgtcgctgt cgcggctgtc gcccagcccc gtggacgcgc aaccggtgat gtactgcgag    120

ccggccttct ggtgttccat tagctactac gagctcaaca cccgggtcgg cgagaccttc    180

catgcctctc agccgagcat caccgttgat ggcttcacgg acccgagcaa ctcggagcgc    240

ttctgcctgg gtttattgtc caacgtcaac cggaatacgg tcgtcgaaca gacgcgcaga    300

cacattggga agggagtccg cctgtattac atcggcggcg aggtctttgc cgagtgcctc    360
```

```
tccgactcga gcatcttcgt gcagagtccc aactgcaatc agcgctacgg ctggcatccg    420

gccaccgtct gcaaaatacc gcctggctgc aatctcaaaa tattcaacaa ccaggagttc    480

gcggcgctgc tctcgcagtc ggtatcgcag ggcttcgagg cggtttacca gctgacgcgc    540

atgtgcacca tccggatgag cttcgtgaag ggatggggtg ccgagtaccg ccggcagaca    600

gtcacctcaa cgccctgctg gatcgagctc catctgaacg ggccgctcca gtggctcgac    660

agggtactca ctcagatggg ctcgcctcgg ctgccttgct cctccatgtc atag          714
```

<210> SEQ ID NO 69
<211> LENGTH: 1230
<212> TYPE: DNA
<213> ORGANISM: Ophelimus maskelli
<220> FEATURE:
<223> OTHER INFORMATION: Dhc64C Dynein heavy chain 64C; microtubule motor activity; biological regulation; cell cycle; 5' fragment from same gene as SEQ ID NO: 237

<400> SEQUENCE: 69

```
gaatatttgt cgaaccctga cgaacgtctt cgttggcaag ccaatgcact acctgcagat     60

gagttatgta ctgaaaatgc aatcatgctt aaacgattca acaggtatcc attgataatc    120

gatccatcag gacaagcaac tgaatttctt attgatgaat ttaaagatcg aaaaattaca    180

aaaacaagtt ttctagatga ttcttttaga aaaaatttag aaagtgcctt acgttttgga    240

aatccattac ttgtccaaga tgttgaaaac tatgatccta tcttaaatcc agttttaaat    300

agagaattga gacgtaccgg cggtagagta cttataacac ttggagatca ggatattgac    360

atatctcctt catttgttat tttcttatcc acaagagatc caactgtaga gttttctccg    420

gacatctgct ctcgagtaac gtttgtaaat tttacagtta ctcgctcttc attacagagt    480

cagtgcttaa accaagtctt aaaagccgag cgccctgata tagatgaaaa acgctctgat    540

ctcctaaaac tgcaaggtga atttcattta cgtttacgac aactagaaaa atctttatta    600

caagctctta atgacgctaa aggtaaaata ttagatgatg attcagtaat tacaacactc    660

gaaaccctca aacacgaagc cgcagatata agtaaaaaag ttgaagagac tgacaaagtt    720

attgcagaga ttgaaactgt atctcaacag tactatccct tgtcacaggc ttgttcaaat    780

atatatttta caatggacag tttgaatcaa atacatttct tgtaccagta ttccttaaaa    840

atgtttctag atatttttac ttctgtttta actaaaaatt cgaagttatc tggtgtctca    900

gattatgttc aacgactgtc atatataaca agtgatttat tttctgtttg ctatgaaaga    960

gtagcccgag gaatgattta taatgataga attacatttg cattgttatt atgtcgcatc   1020

cacatgaaag gtttaagttc tgaactcaca tatgatgatg aattttcatt ctttttgcga   1080

ggaaaggaag gagttttaaa tattcgattg gatcacattt ctaatttaag ttcagaacag   1140

caagaagcac taatgcgctt gagtattaag ttatcggtat ttcgaaaact tcaggatact   1200

ataaaaaata acgaagaatt taatacatgg                                    1230
```

<210> SEQ ID NO 70
<211> LENGTH: 1116
<212> TYPE: DNA
<213> ORGANISM: Leptocybes invasa
<220> FEATURE:
<223> OTHER INFORMATION: Dhc64C Dynein heavy chain 64C; microtubule motor activity; biological regulation; cell cycle

<400> SEQUENCE: 70

```
ttaccaccag aaaaggttcc atgggatgcg ttaataactt tactgtcaga gtgcatttat     60
```

```
ggtggcaaaa ttgataatga attcgatcaa aggttactga cctcatttct tcgtaaactt    120

tttacctcta gatctttcga atctgatttt gctcttgttg caaatattga tggaacttta    180

ggatgtcaac ggcatataac tatgccggat ggaaccagaa gagatcactt tttgaaatgg    240

atcgaatctc tttccgataa acaaacgcca tcctggttag gtttacctaa taatgcagaa    300

aaagttcttt tgactacaag aggaaccgat ttaatatcaa aattgttaaa gatgcaacag    360

ttagaagatg aagatgaact agcttactgt aatgatgaat cattagatac acatagagaa    420

gcagattcag atgggcgccc tacgtggatg aaaacgcttt ataactctgc tacaacatgg    480

ttacaacttc ttccgaaaag tttagtgatt ttgaaaagaa ctattgaaaa cataaaagat    540

ccattataca gatattttga gcgagaggta aatagtggat ctagactatt aaaaaatgtt    600

atttatgatt tgcaagatgt ggtattaata tgtaagggtg aaaaaaaaca aacgaactac    660

catagaacga tgctatctga gttaataaaa ggaattatac caaccgggtg gagaagatac    720

acagtaccac gaggatgtac agttattcaa tggataacag atttcagcca tagagtttca    780

cagttacaag aagtgtctag attagtttct caaaatggag ctaaagaaat aaagaatttt    840

cctgtatggc ttggtggctt atttaatcca gaagcttata taacagcaac aaggcaatgt    900

gtagcacaag caaataattg gtctttagaa gagttacagt tggatgtttt tgtttgtaac    960

aacgataaca ctgaggcaga tgattactgt tttgcagtaa ctggattaaa attacaagga   1020

gcacaatgta aaaataatat gttatactta acatcaacaa taatgactga cttgcacgtg   1080

actatattaa aatgggttag acgtactact gcagat                             1116
```

<210> SEQ ID NO 71
<211> LENGTH: 1071
<212> TYPE: DNA
<213> ORGANISM: Ophelimus maskelli
<220> FEATURE:
<223> OTHER INFORMATION: dlg1 protein binding.anatomical structure development

<400> SEQUENCE: 71

```
atgacaggta gccttatgag gacctcgcaa aagaaatccc tctacgttaa gacgctgttc     60

cactacgacc ccaacaagga cgatggcttg ccgtcgcacg ggctggcgtt caagtacggc    120

gaaatcctgc acgtgaccaa cgcgtcggac gacgagtggt ggcaggcgcg caaggtcacg    180

gccctcggcg agcaggagca cctcggcatc ataccgtcgc gcaagcgctg ggagcgcaag    240

cagaaggcga gggatcgaca ggtcaagttc cagggacacc agcccgtcat cgtcgacaag    300

caatcaacgc tcgagaggaa aaagaagaat ttcccgttcg ggcgcacgct gccgttctcc    360

aagcacaaag acgggaagtc cgaggagggc tcggtgcagg aacaaataac gaacgaaaat    420

aagaacaaga gtgccgaagg cgaggagaac gtgttgtcgt acgaggcggt gcaacgagta    480

tccattcagt acacgcggcc tatcataatc gtcggcccgc tgaaagatcg catcaacgag    540

gatctcatct ccgagttccc cgataaattc gacagctgca taccacatac gacaagaaag    600

aagagagaat acgaggtgga tggacgagac tatcattttg ttgcatcaag ggaacaaatg    660

gaaagagaca tacaaaacaa tctctttatt gaagcaggcc agtacaacga caatatttac    720

ggcacggcga ttgcatcggt tagagaagta gctgaaaagg gaaaacactg cattttagac    780

gtaagtggaa acgctataaa aagattgcaa gttgcccagt tatatcctat cacgatctac    840

attaagccta aatcagtgga atcaatcatg gagatgaata agagaatgac agaggatcaa    900

gctaaaaaag tatttgacag agctgtgaaa gtggagcaag aatttggaga atacttcaca    960
```

```
gctgtcgtcc aaggtgacac gccagaagac atttacgcaa tggtgaagaa agttattgct   1020

gaacagtcgg gtcctaatat ctgggtaccc tgccgggatc agcaattgtg a            1071
```

<210> SEQ ID NO 72
<211> LENGTH: 1073
<212> TYPE: DNA
<213> ORGANISM: Leptocybes invasa
<220> FEATURE:
<223> OTHER INFORMATION: dlg1 protein binding.anatomical structure development

<400> SEQUENCE: 72

```
atgacaggca gccttatgag gacctcgcaa aagaaatcgc tctatgtcaa aacactattc     60

aactatgatc cggccaagga cgacggattg ccgtctcacg gtctgtcgtt cgcctacggc    120

gagatcctgc acgtgaccaa cgcctcggac gacgaatggt ggcaggcgcg aaaagtcacc    180

cacctcggcg agcaggaggc gctcggtata ataccgtcga agaaacgatg ggagcgaaag    240

caacgagcca gagatcgaca agtcaagttt cagggacatt ctcagccggt tattgtcgat    300

aagcaatcga cgttagagag gaaaaagaag aacttcccgt tcggcagaac gctcccgttc    360

tccaagcaca aagacgggaa gtccgaggag agttccgtgc aggaacagat cacaaatgaa    420

aacaagaata aaaatgccga tggcgaagag aatgtattat cctacgaggc agtgcagcga    480

gtgacgatag agtacacgcg gcctataata atcgttggtc cgttgaaaga ccgcatcaac    540

gaggacttga tctccgaatt cccagacaag tttgacagct gcataccaca tacgacgagg    600

agtaagagag aatacgaggt agacggccgt gattaccatt tcgtcgcgtc gagggaacaa    660

atggaaaggg acatccagaa caatctgttc atcgaggctg gccagtacaa cgataatatc    720

tatggcaccg ccgttgcgtc agtgcgagaa gttgccgaga agggaaaaca ttgtattctc    780

gatgtcagcg gaaatgctat caagagattg cagatggcac aattgtatcc tattactatc    840

tacattaaac ctaaatcggt tgaatctatc atggagatga ataagaggat gaccgaggat    900

caagctaaaa agtattcgat agagccgtta aggtcgagct ggagtttgga gagtatttca    960

cagcggtcgt tcaaggagac acgcctgaag acatatatgc aatggtgaag aaagttatag   1020

cagagcaatc gggtccaaca atttgggttc cgtgtcgaga tcaacagttg tga          1073
```

<210> SEQ ID NO 73
<211> LENGTH: 504
<212> TYPE: DNA
<213> ORGANISM: Ophelimus maskelli
<220> FEATURE:
<223> OTHER INFORMATION: Dnc 3',5'-cyclic-AMP phosphodiesterase activity. Synaptic Transmission; 5'fragment from same gene as SEQ ID NO: 238

<400> SEQUENCE: 73

```
tctctgcgct cggttcgaaa caacttccta tcactcacta atgtaccgac gaacaaatcg     60

aggagaagca gcggcgctca gggcagcagt acgccacagc cacggatcct tgcccccgga    120

gaggaaccct acatgaagct tgctgtcgag acaatagagg aacttgattg gtgtctagat    180

caattggaaa ctattcaaac tcatcgatcc gtgtccgaca tggcatcgct gaagttcaag    240

agaatgctaa acaaagaatt atcccacttt tcggaatcct caaaatccgg aaatcaaatt    300

tccgagtatc tctgcaatac tttcctcgac aaacaacagg agctggatct gccgtcgctg    360

cgcatcgacg aagcggtgcc gggcagcatg gacgcgcgag cagccaagaa gaaggaccga    420

gcacagcgcg gcccggcagc catgtcgcac atcagcggtg tcaagcgacc gctaacccac    480
```

accaacagct tcacgggcga acgc 504

<210> SEQ ID NO 74
<211> LENGTH: 1677
<212> TYPE: DNA
<213> ORGANISM: Leptocybes invasa
<220> FEATURE:
<223> OTHER INFORMATION: Dnc 3',5'-cyclic-AMP phosphodiesterase activity. Synaptic transmission

<400> SEQUENCE: 74
cgttcagtta gaaacaactt cctgtccctc actaatgtac caacgaacaa atctcgaagg 60
agtagcggcg ctcaaggcag cactacgcca cagccacgga tccttgcccc cggagaggaa 120
ccctacatga agctcgctgt cgagacaatg gaggaacttg attggtgttt agatcaattg 180
gaaaccattc aaactcatcg atccgtgtcc gacatggcat cgttgaagtt caagagaatg 240
ctgaacaaag aactgtcgca cttttctgaa tcttcgaagt ccggaaatca aatttccgaa 300
tatctctgca atactttcct cgacaagcag caagagttgg atttgccgtc gctgcggatc 360
gatgagcaag tgccggctct catggacacc cgtgcggcca agaagaagga tcgagtgcag 420
agagggccag ctgccatgtc gcacataagt ggcgtgaagc gaccgctcac ccacaccaac 480
agcttcaccg gcgagcgcgt gcccatctac ggcgtagaga cgccccacga ggaggacctc 540
ggcaagctgc tgagcgatat cgacaaatgg ggcatcgaca tcttcaggat aggtgaactg 600
agcaataatc gaccgctgac cagcgtcgcc tacacggcct tccagagcag agatttgttc 660
aagctcatca tgataccgcc gaagactttc gtcaccttca tgatgaccct cgaggatcac 720
tacgtcaagg ataatccgtt ccacaacagc cttcacgcag ctgatgttac ccagtccacc 780
aatactctgc ttaatactcc tgctctcgag tctgtattca cgccgttaga gataacagct 840
gctctattcg ccgctaccat tcatgacgtc gatcatcctg gtctcactaa tcagtttctc 900
attaactcaa gttcagaatt agctttgatg tacaacgacg aatccgtatt agagaatcat 960
catttggcag tcgcgttcaa actgctccaa aatgaaggtt gcgatattct tgtgaactgc 1020
tcgaagaagc aacggcagac tcttcggaag atggtgatcg acatggtact atcgactgat 1080
atgtcgaagc acatgtctct tctggctgac ctgaaaacca tggtagagac gaagaaggtc 1140
gctggctctg gcgtgctatt actcgacaac tacactgacc ggattcaggt actggagaat 1200
ctggtgcact gcgcggactt gtcgaaccca acgaagccgc tgccgctgta ccggcgctgg 1260
gtggacctgc tgatggagga attcttcctg cagggcgaca aggagcgcga gcagaacatg 1320
gacataagcc cgatgtgcga ccggcacaac gcgacaatcg aaaagtcgca ggtgggcttc 1380
atcgactaca ttgtgcaccc actctgggag acctgggccg atctcgtaca tcccgacgct 1440
caggagatac ttgacaccct cgaggagaat cgagactggt accagtcaat gataccccc 1500 tcgccgccac ccgactcctc ctcccactgt tccgagcagc agctgggcga acggatacac 1560
tatcaggaga cgctggagga gggcgacgag tgcgtcactc cggagaaagc gcggagcatg 1620
tcggccgacc agggcaacag cgactccgag gacgtgccag gcgatgctgg gatgtga 1677

<210> SEQ ID NO 75
<211> LENGTH: 3369
<212> TYPE: DNA
<213> ORGANISM: Leptocybes invasa
<220> FEATURE:
<223> OTHER INFORMATION: Ds cell adhesion molecule binding. epithelial cell Differentiation; 5' fragment from same gene as SEQ ID NOS 239 and 240

<400> SEQUENCE: 75

```
aacgcgcaga tcaggtactc tctggaatct ggcggcgacg gtctgttcgc cgtggacgag     60
cgaacgggcg agatcttttt gcaaggctcc atgaggcaag cgcgcaagca tctgttcgaa    120
ttgacgatat ccgccaagga catcggcgac agaccggcca tcaagaacgc actggtcgag    180
atctgtcggg aggagagcct gcagagcttg gaattcggcg gcggtgcgta cagcagcaac    240
ggttatcact acaagatcac ggagaatcgg ggcgaatgcg gcgagcgcac gtcttacgac    300
agagaagtcg gcagtgcaca ggtagtaact agcagcagca gcagcagcag caacagcacg    360
aaagtctctt acgccatagt gtacggcgac ccggcgggta gcttcaagat aaacaaattt    420
acgggatcaa taagcactgc cggttgcctc gatcgcgagc tcacttccta ctacagcctg    480
cagatcgtcg ctcgagccgg cctcgcgcac gccgtcacga gcgtgaacat cacgatcgtc    540
gacattaatg ataatccacc gaggttcccc accgaggagc gcgacgagga ggtctcgctc    600
aaggagtacg cggcggtcgg ccaagaggtt tgcttggctc gcgcgcgcga caaggacgcc    660
gctgccaacg cccgaatcac gtactccctc acgcaaaatc cggccaagca atttcgcata    720
gccgagaact cggggatcat ctatctggac aaaccgatca agtcgccgcc cggcacgtcg    780
ctgcacctcg aggtgacggc cgtggactct ggccctcaat cgctgtcggc gactcagcag    840
attcgcgtga tcatcgagga cgtgaacgat cacgcgcctg tattccgatt gaccagctac    900
gagacctcgc tgcccgagtc gacgcccgtg aacgagcgat ttttcgcctt gatcgcctcg    960
gacgacgatc gcggcgagaa cgggcgggtg gtgtactccg tcagcgaggg taattccgag   1020
ggtcgcttcg acatctttcc cgatggccag ctgtacgtga agagcgcgct cgatcgagag   1080
gagcaagact actacgcgct cgaggtgacg gcgcgagatc agggcagtcc agcgcgcagc   1140
tcgaccgtgc cggtggtcgt gcacgtgatc gatgagaacg acaacgcccc gcaattcagc   1200
aatgccagct tcacctttca cctgcgggag aacgagccgc ccgacacttt cgtcggcaaa   1260
ctgttggcca gcgatcggga cgtcgatcgc aacgccgatc tgaccttctc cctgagctcc   1320
cctcatcagc aggacttcgc catagatccg cgcaacggct tcatccgatc tctgcgagcc   1380
ttcgaccgcg agcacttgat cgcgacgagc ggcagcaacg tcatcgtcct cgaggcgagc   1440
gtcatcgaca acggcgaggt gcgtctgatg gacaaggtaa aggtcagcgt gtacatcaac   1500
gacgtgaacg acaatgcgcc gcagttcaag cggctgccgt acaaggtgca agtgagcgag   1560
ggcgcggccg tgggcacgca attgttgcgg gtgtacacca cggacgcgga cgagggcctg   1620
aacggcgacg cattctactc gctggaaaag cagtcgtccg atgcgcagcg gcgtaacgac   1680
ggcggggccg tggaggagca ggaggagggc ggccaattta cgattgacga ggcaacggga   1740
cagatctcgc tggcgaggcg gctcgatcgt gagacacgag acaattacca tctcacggtc   1800
gtggcccgtg acgccggatt agagacgagg ctgtcctcga gcgcaatcgt gcacgtcgag   1860
gtgctcgacg agaacgacaa cacgccccgt ttccaccacg gcagcgagcc gagaatctcg   1920
gtactcgaga gcgcgccgat gagcgagcaa ttgctgcgat tcggcgcgag cgacgacgac   1980
ctcggcgtca acagcgagct cacctacggg atttcggctg gcaatcgacg cgacgccttt   2040
cacgtggatc ccgtcagcgg cgcgctctat ctgagaagac ctctggacta cgaggagcag   2100
caggtctatc atctgaacgt cacgtgcagc gacgccggtc acccgaggct gagcagcgtg   2160
atcacgctgc aggtggacgt cgtcgacacc aatgacaatc cgccggtctt tcccaacacc   2220
gcgatcgtgc gtcaaatcct cgagggcatt cccgtgcaca ggccggtggt gaccgtcacc   2280
```

```
gccgaggatc cggattccgg cgacaatggc attgtcagct acgccattgc cagtcaagag   2340

ccggacgatc agaagcggcg attcggcatc aatcctacga gcggcgtgat tcacactctg   2400

ctgccgatcg atcgcgagga gatcgacacg ttcaaattgg tcgtcgtcgc gacggacaac   2460

gccaagccgg cctcggcgcg gctgaccgcg gagaagcaag tgatcgtcat cgtcacggac   2520

gtcaacgaca acgcgccgat tttcgtcagc atgtcctcgg gcatcttgcc gatcagcagt   2580

ggcatcccct atcagccggg caaacagatc agcgtagccc agctccacgc gcgagactta   2640

gactccagca cgaacggcct cgtcacctac gagctgctgc gtctcggtgc caattacacg   2700

gaggacatgt ttcgcattca gcgcaacagc ggcgaattga cgatgcgtct gccgcgctcg   2760

ccggcgatct tcgagaaatt gtcgaggctg caagtcggcg tgagagcgac cgacgaggcc   2820

gtgcaagccg agagacgctc cgcggagacg tacgtgacgt taattctacc gggggagggc   2880

gacgactcgc cgatttggga gcacagcggc caattggagg gaagcgtgca cgagaacgag   2940

gctgcgggcg ccagtataat gcgcgtgaaa gctcgcagtc gtcgctcgaa cgaggagctc   3000

gagtactacg tgacgaacgt caccgcagtc gtcaccgcgg acgcggctgg tggtccgcaa   3060

gtcgacaggc tgttcgacgt cgacgcgaag agcggcgttc tgacgaccgc tggcccgctg   3120

gatcgcgaaa ctggagtcga gcgctacgag gtcgagatct acgcggtcgt cagctccggt   3180

ggcaaagcca gcacatcgtc aactaaggtt cgcgtgagcg tgttggacaa aaacgacgtg   3240

gcgccaagtt ggggttcggg accatggagg tacgaaatat ccgaggatgc gccagccaac   3300

acaatcgttg ctattctcaa agcacacgat cccgacagta ttggtactct caagtacgcc   3360

attgtatct                                                           3369
```

<210> SEQ ID NO 76
<211> LENGTH: 309
<212> TYPE: DNA
<213> ORGANISM: Leptocybes invasa
<220> FEATURE:
<223> OTHER INFORMATION: e(r) regulation of transcription from RNA polymerase II promoter

<400> SEQUENCE: 76

```
atgtctcaca ctattcttct tgttcaacca gcaaacagac ctgaaacaag gacgtattcc     60

gattatgaaa gtgtcaacga gtgtatggaa ggcgtatgca aaatatacga agagtaccta    120

aagaggcaaa atccaaacac accaacaatc acctatgaca taaaacaact cttcgacttc    180

cttgatgatc tgacagactt gtcgtgctta gtttaccaaa agtcaactaa cacttatgcg    240

ccgtacaaca agaactggat aaaggataaa attcacgttc tacttcgtcg agcagccgaa    300

ctcgaatga                                                            309
```

<210> SEQ ID NO 77
<211> LENGTH: 639
<212> TYPE: DNA
<213> ORGANISM: Leptocybes invasa
<220> FEATURE:
<223> OTHER INFORMATION: E(z) histone methyltransferase; cuticle hydrocarbon biosynthetic process

<400> SEQUENCE: 77

```
gtcaagataa tcaatgcagt gtctcccatt ccaacaatgt acacatgggc accaattcag     60

cagaacttta tggtcgagga cgagactgtt cttcacaata tcccatacat gggtgatgag    120

attcttgatc aagatggcac cttcatcgaa gaattgatca agaactacga tggcaaagtg    180

cacggcgaca gagagtctgg ctttatggat gatactctgt tcgttgacct tgtgcatgct    240
```

```
ttggccgctt atgagaaaga agacaaggag aaagaggctc caaagaaagg gagagacttg    300

aaagacaagg ataaggataa ggacaaaagt aaggataggg acaaagatga ggttgaggat    360

aaaaagactg ataataaagg agaagacgat gcaactcctt ttccttctat gcaaattttc    420

acggcaatat ccagcatgtt tcctgacaaa ggtaggccag aagaattgaa agagaagtac    480

attgaactca cagaaagatc agatcccaat gctctgccac ccgaatgcac gccaaacatt    540

gatggaccca atgcaaaaag tgttccaaga gagcagacta tgcattcatt ccacacatta    600

ttttgcagaa gatgtttcaa atatgactgt tttcttcac                           639
```

```
<210> SEQ ID NO 78
<211> LENGTH: 1539
<212> TYPE: DNA
<213> ORGANISM: Ophelimus maskelli
<220> FEATURE:
<223> OTHER INFORMATION: Ebi regulation of epidermal growth factor
      receptor signaling pathway; regulation of cell cycle

<400> SEQUENCE: 78

atgagttttt caagcgatga ggtgaatttc ctcgtctaca ggtacctgca ggagtcagga     60

tttcaacatt ctgcatacac atttggaata gaatcgcata tatctcaaag taacattaat    120

ggtgccttag tacctcctgc tgcacttttg tgtatccttc aaaaagggct tcagtatacc    180

gaggctgaaa tctctatagg ggaagacggc acagagcaac gaatggtaga gtcactatca    240

ttaattgatg ccgttatgcc agatgtggtt gcatcgagac aaaatcaaca gaatcaacaa    300

aaacaacagc ttaaaacaga agttcaagac acaaatggag aagaagttgt tccttcaaat    360

gaaggtgtag gggctaatga caagggagga gagagggcag aaatggaggt tgatgatcaa    420

caacaaggac agggtggtgg gccaaatgct aattcagtga aaatacctcc aagcaaagct    480

actaaattat gtggtcacga atcagaagta tttatttgtg cttggaatcc tacaacagat    540

ttgctggcct cgggatctgg tgatagtaca gctaggatat gggatatgtc tgataactcc    600

cagtcaccta atcaactagt cttgagacat tgcattcaaa gaggaggcac agaagttcca    660

agtaataagg atgtaacctc cttggactgg aattgtgatg gaactttatt agcaactggt    720

agttacgacg gctatgctcg tatctggaca accgatggta gattagcatc aacgttaggg    780

caacacaaag gacctatttt tgcattaaaa tggaataaac gaggcaatta catactcagt    840

gccggtgtcg ataaaacaac gattatctgg gatgccgcga gtggtcagtg cactcaacaa    900

tttagttttc atttagcacc cgctctagac gttgattggc aaacaaacac atcttttgcc    960

agttgttcta cagatcaatg tattcatgtt tgtaaacttc acgttgataa accaatcaag   1020

agcttccaag gacatacgaa tgaagttaat gctatcaaat gggaccctca aggaaatcta   1080

ctagccagtt gctcagatga catgactcta aaaatttggt ccatgaaaca ggactcatgc   1140

ttgcatgatc ttcaagcaca tagtaaagaa atttacacta ttaaatggtc tcctactgga   1200

ccaggtacac agaatccaaa catgaactta actctggtca gtgcatcctt tgattccact   1260

gtaagattat gggacattga tcgaggtgcc tgcatatata ctctaactaa gcataccgag   1320

ccagtataca gtgtagcttt tagtcctgat ggaaaattct tggctagtgg aagttttgac   1380

aaatacgttc atatatggtc cactcaaagt ggtcaactag tgcatagtta caaaggaacc   1440

ggaggaattt tcgaagtgtg ctggaacagt aggggagaca aagttggagc ttcagcttca   1500

gatggcagtg tatttgtcct tgatcttcgc aaactatga                          1539
```

<210> SEQ ID NO 79
<211> LENGTH: 1434
<212> TYPE: DNA
<213> ORGANISM: Leptocybes invasa
<220> FEATURE:
<223> OTHER INFORMATION: Ebi regulation of epidermal growth factor receptor signaling pathway; regulation of cell cycle

<400> SEQUENCE: 79

```
aacattaatg gtgccttagt gcctcctgca gcacttttat gcgtcctaca gaaaggattg      60
ttatacactg aagctgaaat atcgattggg gaagatggaa ctgaacaacg aatggttgag     120
tcgctgtcac ttattgacgc tgttatgcct gatattgttg catctcgaca aaatcagcaa     180
aatcaacaga atcaacaaaa gcaacagctg aaaactgaaa ttcaagatac aaatggagaa     240
gaagtacccc caaacgaggg agtaggcagc aatgacaaag gaggtgatcg tgcagaaatg     300
gatgttgacg accaacagca aggacaaggc ggcggaccca atgccaattc cgtcaaaatt     360
ccagctaata aagccaccaa actctgtggg cacgagtcag aagtattcat ttgtgcttgg     420
aaccccacca cagatctgtt ggcttctgga tctggagata gcacagctcg aatatgggat     480
atgtctgaca attctcagtc tcccaatcaa ctagtcttga gacactgcat acagagaggt     540
ggtactgaag tccctagtaa taaggatgtt acttctctcg attggaattg tgatggaact     600
ctcttagcta ctggtagtta cgacggatat gcgcgcattt ggacgactga cggccgacta     660
gcgtcaacgt taggacaaca caagggacct atattcgcat tgaaatggaa taaaaaaggc     720
aactacattc ttagtgctgg agtcgacaaa accacaatta tttgggatgc tgcaagtggt     780
caatgtaccc aacaatttag ttttcatcta gcacctgccc tagacgttga ctggcagtcg     840
aatacgtctt ttgctagttg ctcaactgat caatgtattc atgtatgcaa acttcatgtt     900
gatagaccaa tcaagagctt ccatggacat acgaatgagg tgaatgccat caagtgggat     960
ccccaaggaa atctattagc cagttgttca gacgatatga cattgaaaat ctggtcaatg    1020
aaacaagaca cgtgtctgca cgatctgcaa gctcatagta aagaaattta tacaatcaag    1080
tggtcgccaa ctggtcctgg tacgcaaaat ccgaacatga acttgacttt ggtcagtgcg    1140
tcctttgatt cgacagtgag actttgggac atcgaccgcg gtgcctgcat ttatactcta    1200
acaaaacata ccgaaccagt atacagcgta gcttttagtc ccgatggcaa atttttggct    1260
agtggcagtt tcgacaaata cgttcacata tggtccacgc agaatggtca actagtgcat    1320
agctacaaag gaacaggagg aattttcgaa gtgtgctgga acagtagggg agacaaagtt    1380
ggtgcttcag cttctgatgg cagtgtattt gtcctcgatc ttcgtaaact atga          1434
```

<210> SEQ ID NO 80
<211> LENGTH: 1574
<212> TYPE: DNA
<213> ORGANISM: Leptocybes invasa
<220> FEATURE:
<223> OTHER INFORMATION: EcR repressing transcription factor binding. anatomical structure development; biological regulation

<400> SEQUENCE: 80

```
cttttcgccg gtatcgcgcc gagcaatcaa gccaaacggc ctaggactga ggattggctt      60
gcgcccgaat cgccgcaagg tcctctgcca cagcagcatc tctatctgcc gacgcaacag     120
cagcagcagc agcagcagca gcagcctcag caacaacaac agcaacagcc gcctatggcg     180
cattccacgc ctattgtaca gccacagcag aatcagcagc agccgcagca gcagagtgtc     240
attggtacac agccacccag taataatggc tacgcgagtc caatgagctc gggaagctac     300
```

```
gatccttaca gtcccaacgg aaaaattgga agggacgatc tgtcgccgcc gagctcgctg    360

aacggctaca gcgccgacag ttgcgacgcg aagaagaaaa aagggccgac gcctcgtcag    420

caggaggagc tgtgcctggt gtgcggcgat cgtgcgtccg gctaccatta caatgccctc    480

acgtgcgagg gttgcaaggg cttcttcagg cgcagcatca ccaagaacgc cgtctatcag    540

tgcaagtacg gcaacaattg cgagatcgac atgtacatga ggcgcaagtg ccaggagtgc    600

cggctgaaaa agtgcctgca cgtcggcatg cgacccgagt gcgtcgtacc cgagttccag    660

tgcgccgtca agcgcaagga gaaaaaggca cagaaggaga aggacaagcc gaacagcacg    720

acgatgaacg gctcgcccgt gggtctggta gccgagccaa tgggcgtgaa aatggagcca    780

gcggaggcgg acggctactc gatgtcgagt ggcagcggcg tggtcgtggc gtcgatcggc    840

tcgcaaaacg gcatcaatta cgtcagtccc gagcaggagg agctgatcaa caggctcgtc    900

tatttccagg acgagtacga gcagccgaac gaggaggacg tgaaaaggat cacgaacgcg    960

acgtcggaaa acgaggaccc cagcgacgtg aggttcaggc acataaccga aatcacgata   1020

ctgacggttc agctgatcgt cgaattcgcg aagcggctgc cgggcttcga caagctccgc   1080

cacgaggaca aaatcgtcct gctgaaagcg tgctcgagcg aggtgatgat actgcggatg   1140

gcgcgcaaat acgacttcca aacggacagc atcatattcg ccaacaatca gccgtactcg   1200

cgcgacagtt acaccctcgc cggcatcggc aacatcatcg acgacctgct gcactttggc   1260

cgcctcatgt actccatgaa ggtcaacaat gccgagtacg ccctgctcac cgccatcgtc   1320

atattttcag agaggccgaa cgtgtcggaa ggctggaagg tcgagaagat ccaggagatt   1380

tacctggacg cgctgaaggc ctacgtggag agcaggcgga agcctaaagc ctcggcgatg   1440

ttcgccaagc tgctgtccgt tctcaccgag ctgcgcaccc tcggcaatca gaacagcgag   1500

acctgctcga acctcaagct caagaacaaa aagctgccgc cgttcctcgc ggaaatctgg   1560

gacgtggcgt ccta                                                       1574
```

<210> SEQ ID NO 81
<211> LENGTH: 1386
<212> TYPE: DNA
<213> ORGANISM: Ophelimus maskelli
<220> FEATURE:
<223> OTHER INFORMATION: Ef1alpha48D translation elongation factor activity. determination of adult lifespan

<400> SEQUENCE: 81

```
atgggtaagg aaaagattca cattaacatc gtcgtcattg gacacgtcga ctctggtaaa     60

tcgaccacca ctggtcattt gatctacaaa tgtggaggta tcgacaaacg taccattgag    120

aagttcgaga aggaagccca ggagatgggt aagggttcct tcaaatatgc ctgggtactc    180

gacaagctga aggcagagcg tgaacgtggt ataaccatcg acattgctct atggaaattt    240

gaaaccgcta aatactatgt caccatcatt gacgctcctg gacacagaga tttcatcaag    300

aacatgatca caggtacgtc gcaggctgac tgtgccgtgt tgatcgttgc tgctggtact    360

ggtgaattcg aagctggtat ctccaagaac ggtcagaccc gtgagcatgc tctgctcgcc    420

ttcactcttg gtgtaaagca gttgatcgtt ggtgtcaaca agatggactc tactgaacca    480

ccatacagcg aagctcgttt cgaggaaatc aagaaggaag tatcttcata cattaagaag    540

atcggttaca acccagctgc tgttgctttc gtacccatct ctggttggca cggagacaac    600

atgttggagc catccaccaa aatgccatgg ttcaagggat gggctgttga gcgtaaggaa    660

ggcaaggctg acggtaaatg ccttattgaa gctcttgacg ccattcttcc accatccaga    720
```

```
cccaccgaca aagccctccg tcttccactt caggacgttt acaagattgg tggtattgga    780

acggtaccag tcggtcgtgt cgaaactggt gtgttgaaac ccggtatggt tgtcactttt    840

gctccagttg gtttgaccac tgaagttaag tccgttgaaa tgcaccacga agcccttcaa    900

gaggctgtac ccggagacaa cgttggtttt aacgttaaga acgtctctgt caaagacttg    960

cgtcgtggtt acgtcgctgg tgactcaaag aacaacccac ccaagggtgc tgctgacttc   1020

actgcacagg tcatcgtgct caaccaccct ggtcaaatca gcaacggtta cacgcctgtt   1080

ctcgactgtc acaccgctca cattgcctgc aaattcgcag aaatcaagga gaagtgtgac   1140

cgtcgtaccg gtaaaactac tgaagaagcc cccaaggcta tcaagtctgg tgatgccgcc   1200

attgtcaacc ttgtgccaag caagcccatg tgcgtagaag ctttccagga gttccctccc   1260

cttggacgtt tcgccgtacg tgacatgcgt caaactgttg ctgtcggtgt catcaagtcc   1320

gtcaacttca aagatgtctc cggcaaggtc accaaagctg ccgagaaggc ctcaaagaag   1380

aagtag                                                              1386
```

<210> SEQ ID NO 82
<211> LENGTH: 1386
<212> TYPE: DNA
<213> ORGANISM: Leptocybes invasa
<220> FEATURE:
<223> OTHER INFORMATION: Ef1alpha48D translation elongation factor activity. determination of adult lifespan

<400> SEQUENCE: 82

```
atgggtaagg aaaagattca tatcaacatc gtcgtcattg gacacgtcga ctccggcaag     60

tccacgacca ctggtcactt gatctacaaa tgcggtggta tcgacaagcg taccatcgag    120

aagttcgaaa aggaagccca ggagatgggc aaaggttcct tcaaatatgc ctgggttctg    180

gacaaactga aggccgagcg tgagcgtggt atcaccatcg atatcgctct ctggaagttc    240

gagaccgcca agtactacgt caccatcatc gacgcccccg gacacagaga tttcatcaag    300

aacatgatca ctggtacgtc gcaggctgac tgtgctgtgt tgatcgtcgc cgccggtact    360

ggtgaattcg aagccggtat ctcgaagaac ggtcagaccc gtgagcacgc tctgctcgcc    420

ttcacccttg gtgtcaagca gctcatcgtt ggtgtcaaca agatggactc caccgagccc    480

ccatactccg aggctcgttt cgaggaaatc aagaaagaag tctcctccta catcaagaag    540

atcggttaca acccagccgc cgttgccttc gtccccatct ccggatggca cggagacaac    600

atgcttgagc catccaccaa gatgccatgg ttcaagggat gggctgtcga gcgcaaggaa    660

ggcaaggccg acggcaagtg cctcatcgaa gctctcgatg ccatcctccc acccagccga    720

cccaccgaca aagccctccg tcttcccctc caggacgtgt acaagattgg tggtatcgga    780

acggtacccg tcggtcgtgt cgaaactggt gttctcaagc ccggtatggt cgtcaccttc    840

gcccctgttg gtctgactac tgaagtcaag tccgtggaga tgcaccacga agccctcacc    900

gaagctgttc ccggagacaa cgttggtttc aacgttaaga acgtctccgt caaggacttg    960

cgtcgtggtt acgtcgctgg tgactccaag gctaacccac ccaagggtgc tgctgacttc   1020

accgcacagg tcatcgtgct caaccaccct ggtcagatca gcaacggcta cacgcccgtg   1080

ctcgattgcc acacggccca catcgcctgc aaattcgcag agatcaagga gaagtgtgac   1140

cgtcgtaccg gtaaaaccac cgaggagaac cccaaggcca tcaagtccgg tgacgccgcc   1200

atcgtcaact tggtgccaag caagcccatg tgcgtagagt ccttccagga gttcccaccc   1260

ctgggacgtt tcgccgtgcg tgacatgcgt caaaccgtcg ccgtcggtgt catcaagtcc   1320
```

gtcaacttca aggacgtctc cggcaaggtc accaaggccg ccgagaaggc cgcgaaaaag 1380
aagtag 1386

<210> SEQ ID NO 83
<211> LENGTH: 1278
<212> TYPE: DNA
<213> ORGANISM: Ophelimus maskelli
<220> FEATURE:
<223> OTHER INFORMATION: Ef1gamma translation elongation factor
autophagic cell death; salivary gland cell autophagic cell death

<400> SEQUENCE: 83
atggcgtctg gtacactcta cacgtatccg gagaacttca gagcctacaa ggcacttata 60
gcggcccagt tctccggggc tcaggtcaag gtagctgaaa attttgtatt cggtgagacc 120
aacaaatccg aggcttttct taaaaagttt ccctttggca aggtaccagc ctttgaaaca 180
aaagatggca aatatattac tgaaagtaat gcgattgctt attatgtcgc taatgatcag 240
ttgagaggaa aaactgacat cgaacgtgct gaagtaatcc aatggtttag ctttgccgat 300
tcggaaatct taccagctag cagtgcatgg gtattccctc ttcttggaat catgccctac 360
aataaacagg caattgaagc tgcaaaggaa gatgtcgaaa aggcccttac gtatttaaat 420
tctcacttat tgaccaggac ttacttagta ggagaaaggt tatcgctagc tgatatcagt 480
gtctccatga cccttctgta tttgtaccag tatattttag acccaaatct acgtaagccc 540
taccagaatg ttaccagatg gttccaaaca gtcataaatc aaccagaagc agttgctgta 600
atcggtacct tcaaactggc agataaaaca cttgaatacg accctaagaa atatgcagac 660
gcacatggca agagtaagaa agacaagaaa gaaaaggagc acaaagaaaa agagcccaag 720
aaagaaaagg aatctaaaaa ggaaccagct gaagaactgg atgctgccga agctgccttg 780
gctgctgaac caaaatcttc aaatccattc gatagcatgc caaagggtac ctttgacatg 840
gatgacttca aacggtgtta cagtaatgag gatgaagcaa agtctattcc ttacttctgg 900
gagaagtttg acccacaaaa ttacagcatt tggttctgtg aatacaaata cgcagacgaa 960
cttacaaaag tttttatgtc gtgtaacctt attagtggaa tgtaccaacg tttggataaa 1020
atgagaaagg ctgcttttgc cagcgtttgt ctgtttggaa gtgacaataa cagcacaatt 1080
agtggaatct gggtttggcg tggacaagat cttgcattta ctttgtctcc tgattggcag 1140
attgattatg aatcttatga ttggaaaaaa ttgaacccat cagatgaaaa aactaaagaa 1200
cttgtaaaac aatatttcag ctggactggt aaagataagg gtggtcgccc attcaaccaa 1260
ggaaagattt tcaaataa 1278

<210> SEQ ID NO 84
<211> LENGTH: 1284
<212> TYPE: DNA
<213> ORGANISM: Leptocybes invasa
<220> FEATURE:
<223> OTHER INFORMATION: Ef1gamma translation elongation factor
autophagic cell death; salivary gland cell autophagic cell death

<400> SEQUENCE: 84
atggcgtctg gtacactcta cacttatccg gagaacttca gagcctacaa ggccctcatc 60
gcggcccagt tctcgggggc caaggtcaag cttgcccagg atttcgtctt cggcgagacc 120
aacaagtccc ccgacttcct caagaagttc ccacttggca aggtaccagc ctttgaaaca 180
agtgatggca agtacattac tgaaagtaat gcaattgctt attatgttgc taatgatcag 240
ctgagaggaa agtcagactt ggagcgtgct caagtcatac agtggttagg ttttgccgac 300

```
tctgatattt tgcctgctag cagtgcatgg gtttttcctc ttcttggcat catgccttac    360

aacaaaaata ctgtcgaggc ggcaaaggag gacattaaaa aatgcctgac gtttttgaac    420

gactatctgc tgactagaac ttacctggtt ggcgagagaa taacgttagc tgacatcagc    480

gttgccatga ctctccttta cttgtatcag tacattctgg aacccagtct acgtaagccc    540

tacacaaatg tcaacagatg gttccaaact attatcaatc aacctcaatc tattgccgtg    600

attggtgcct tcaaattggc cgacaaaacg ctagaatacg atcctaagaa atactcagaa    660

gctcaaggaa aggttaagaa agataagaaa gaaaaggagg ccaaaaagga gaaagagccc    720

aagaaagaaa agaaggcaga gaaagaaact gaaaaagaag agcctgatgc agctgaagct    780

attctggcag cagaacctaa atcttcaaat ccatttgaca gcatgccaaa gggtaccttt    840

gacatggatg acttcaagcg gtgttacagt aatgaagatg aggctaaatc tattccttac    900

ttttgggaaa agtttgaccc tcaaaactat agcatttggt tctgtgaata taagtatcca    960

gatgaactta caaaggtctt tatgtcctgc aatttaatta gtggaatgta tcaacgtttg   1020

gataaaatga gaaaggctgc ttttgccagc gtttgtcttt ttggtacaga caacgacagc   1080

actatcagtg gaatttgggt atggcgtgga caggagcttg cattcacgct gtcccctgac   1140

tggcaaatag attatgaatc ttatagttgg aagaagttgg atgcaaaaga tgagaaaact   1200

aaggaacttg tcaaacaata tctcagctgg tctggtgctg ataaggatgg tcgtaaattc   1260

aaccaaggaa agatttttaa ataa                                          1284
```

<210> SEQ ID NO 85
<211> LENGTH: 1002
<212> TYPE: DNA
<213> ORGANISM: Ophelimus maskelli
<220> FEATURE:
<223> OTHER INFORMATION: eIF-2alpha translational initiation

<400> SEQUENCE: 85

```
atggtgttat cctgtcgatt ttataaagaa aaatacccag aagttgagga tgttgttatg     60

gtcaatgtcc ggagtatagc agaaatgggt gcctatgtgc acctactaga atacaacaac    120

attgagggta tgatattact ctctgaattg tccaggagac gtattcgatc tattaataag    180

ttaattaggg taggaaaaac agaaccagtt gttgtaattc gagttgataa agaaaaaggt    240

tacattgatc tgagtaaacg cagagtatca gctgaagacg ttgaaaaatg tacagagcga    300

tatgcaaaag caaaagctgt aaattcaatt ttaagacacg tggcagaact tttacactac    360

gagaacgatg atcaattaga agaactgtat caaaaaacag catggtattt tgaagagaaa    420

tataagaaac aaaaagcatc tgcctatgac tttttcaaac aatcagtatt ggatccttct    480

attttagcag agtgtgatct tgatgaacac accaaagagg ttttattgaa caatattaag    540

agaaagttaa cttctcaagc tgttaaaata agagcagatg ttgaggttgc ttgttatgga    600

tatgaaggca tagatgcagt caaaactgca ttgaaggctg gtttggcctt atccacagaa    660

gagcttccca ttaaaattaa tttaattgct ccccctcttt atgttatgac tacatcaaca    720

ccagaaaaaa cagagggttt gaaagcactt aatgatgcta ttgaagttat taaagaaaaa    780

atagtatcga tgggtggtgt tttcaacata caaatggctc caaaagttgt tactgcaaca    840

gatgatgcag aacttgctaa gcaaatggaa agagctgaac ttgaaaacgc ggaagttgct    900

ggtgacgatg atgaggaaga aaatgaaggc atgggtaact tcagtggtga tgatgaaaat    960

gacgaaaatg acaaagaaaa tcaatctgga gaggatgatt aa                      1002
```

<210> SEQ ID NO 86
<211> LENGTH: 768
<212> TYPE: DNA
<213> ORGANISM: Leptocybes invasa
<220> FEATURE:
<223> OTHER INFORMATION: eIF-2alpha translational initiation

<400> SEQUENCE: 86
atggttttgt cgtgtagatt ttataaagaa aagtacccgg aggtggagga tgttgtcatg 60
gtcaatgtcc gtagtatagc tgaaatgggt gcctatgtgc acctactcga gtacaataac 120
atagagggta tgattttact ctctgagttg tccaggagac gtattcgttc tattaacaaa 180
ttaattaggg taggcaaaac agaaccagtt gttgtcattc gtgttgacaa agaaaaaggt 240
tacattgatt tgagtaaaag aagagtttca cctgaagatg ttgaaaaatg tacggaaaga 300
tatgcaaaag caaaagctgt aaattccatt ttaagacatg ttgctgaact attgcattat 360
gaaactgatg aacagttaga agaactctat caaaagacag catggcattt tgaggaaaaa 420
tataagaaac agaaagcttc ggcttatgat tttttcaaac aatcagtatt ggatccatcg 480
atattagcag agtgtgattt agatgagaaa acaaaagaag ttttattgaa caatatcaaa 540
aggaaattaa cttctcaagc tgttaaaata agagcagatg ttgaagttgc atgctatggt 600
tatgaaggca tagatgctgt caaagctgct ttaaaagctg gtttggcact ttcaacagaa 660
gagcttccga ttaaaatcaa tctcatagca cctccattat atgttatgac tacatcgact 720
ccagaaaaaa ctgatggctt acaagcatta aatgatgcta ttgaagta 768

<210> SEQ ID NO 87
<211> LENGTH: 2373
<212> TYPE: DNA
<213> ORGANISM: Ophelimus maskelli
<220> FEATURE:
<223> OTHER INFORMATION: eIF3-S8 translation initiation factor activity

<400> SEQUENCE: 87
atgagctgca tgcttagcac ttttgaggat ctccagaaag cctatcaaaa agctttgcct 60
gtaatatcaa aggaagaaaa tggaacaacc cctcgttttt atgtacgttg tttagttgaa 120
atggaagatt ttattaatga agtatgggag gacagagaag gtcgtaaaag tatgtccaaa 180
aataattcaa agtcattgac ttcattacgt cagaagctta gaaagtataa taaggaattt 240
gaagaagaca ttgctaaatt tcgtgaaaat cctgatcaag aagatgacga ggaagaagag 300
aaggctgatg atggtgattt agacgatgat gacaatcgta tttctgactt taaaaaacaa 360
gaatctagtg ttccagatgt ttctaaattt aagaaaggag ctgatgatga tggcagtgaa 420
agtgattcag aatggggcag tgattcagac agtgacagct caagaagttc tgatgatgat 480
aaacctcaac atgttggtgc tgattacttc agaaaaacac aaaaagaagg tgatgaagag 540
aaaattggtg gtggtggtgg taagagagat cggcctcgta aagagcggcc aaagaaaatc 600
gaagaagatg atggccaagg taaatgggaa actgttaaag gaggagtagc cattccctta 660
gaaaagccaa aaatgtttgc aaaggacgca gagattaata ttgcagctgt actgaaaaag 720
ttgggtgaaa tcatagctgc acgtggtaaa aaaaggactg accgaaggga acaaattgag 780
ttgcttcatg aattgcaatc aattactgaa actcacaatc ttggagcacc agttttaata 840
aaaattaaat tcactattgt ttcttcaatt ttcgattaca atccaaaagt ttctgatgca 900
atgaaacctg aatattggtc aaagattttg gaacgcataa cagaaatgtt gaatctagta 960
ttggctactc ctgatatgat tattgctgat tcagttcctg aagatgaaga agaatacgaa 1020

```
aaaccaccat tcaagttaca tggatgtgta ctcacattgg ttgaaagatt ggatgaggaa   1080

ttcataaaac ttttgaaaga atgtgatcct cacagtaatg aatatgtaga aagattgaaa   1140

gacgaaaaat tggtttcttc aactattgat aaagttcagg aatatctgga aagaaaaggt   1200

tcagtatcag aactatgccg tatctacctt cgtaaaatag aacatcttta ttataagttt   1260

gatccaactg ttttaaaaca aaaagacgga gaggttccag cagacgttgt tacctctata   1320

caagttatgg acaaactttg taaatatatt tatgcgcatg acgaaaccga tcgcctaaga   1380

acaagagcaa ttctgtcgca tatctatcat catgcacttc atgataattg gttccaagct   1440

cgtgatttaa tattaatgtc acatttacaa gaaaccatcc aacattcaga ccctgctacg   1500

caaattttat ataaccgtac aatcgcccat cttggtctct gtgcattccg tcacgcaaat   1560

atcaaagatg cacatggttg cttattagat ttaatgatga ctggaaaagt taaggaactt   1620

ttggctcaag gtctactgcc acagagacag cacgagcgca gcaaggaaca agaaaaaatt   1680

gagaaacaac gtcaaatgcc attccatatg cacatcaact tagagttgct tgaatgtgta   1740

taccttgttt cagctatgtt aattgaaatt ccatacatgg ctgctcacga gttcgatgca   1800

cgaaggagaa tgatctcgaa gaccttctac caacaactca ggtcaagtga aaggcaatct   1860

ttagttgggc cacctgaatc tatgagagaa cacgtagttg cagctgctaa agctatgcgt   1920

aatggaaatt ggtcggcttg caataccttc attatcaatg aaaagatgaa tgctaaagtc   1980

tgggatctat tttatcaagc tgataaagta cgtgatatgc ttacgagatt aatcaaagaa   2040

gaagctttga gaacatatct tttacttat tctcatgttt atgattcaat atccatgcca   2100

actttggctg aaatgttcca gttgaagaaa ccggttgtgt attcgataat cagtaaaatg   2160

attattaatg aagaactaat ggcatcacta gatgatccaa cagaaactgt agtaatgcac   2220

cgcagtgaac ctagccgtct gcagtcatta gcagtccaac taacagataa aattaataac   2280

tttgttgatt caaacgagcg tatcttcgaa atgaagcaag gtaacttctt ctcgagaggt   2340

aaccaaggta atttccgcga tcgtcaaaat tac                                2373
```

<210> SEQ ID NO 88
<211> LENGTH: 2382
<212> TYPE: DNA
<213> ORGANISM: Leptocybes invasa
<220> FEATURE:
<223> OTHER INFORMATION: eIF3-S8 translation initiation factor activity

<400> SEQUENCE: 88

```
atgagcatgt tactgacgac cttcgaagac ttacagagag cttatcaaaa ggctttgcct     60

gtcgtttcaa aagaagaaaa tggacaaact ccgagctttt acgtacgttg cttggttgaa    120

atggaagact ttatcaatga agtctgggaa gacagagagg ggcgcaagaa tatgtcaaaa    180

aataactcaa agtcattgac ttctctgcgt caaaaactga ggaagtacaa taaagacttc    240

gaggaagata ttatcaagtt ccgtgaaaat ccagaacagg aagatgaaga agatgagaaa    300

gctgaggaag ttgattcaga tgatgaaaat cgtgtatcag aatttaagaa acaagaactc    360

agtgttccag atgtatccaa attcaagaaa ggtgctgtcg atgatgaagg cagttcaagt    420

gactcagact ggggcagtga ttctgagagc gaaagctcta gtagttcaga cgatgacaaa    480

cctcagcatg ttggagctga ctacttcaga aaaactgcgg caaaagacgg tgatgagaat    540

gagaagcacg tcaaagaaag gaaggagcac cgcaaagatc gtaaagacaa agataagaag    600

aggcgacgtg aagaggacga tggagaaggc gaatgggaga ctgtgaaagg aggagttgcc    660
```

```
attccttctg agaagccgaa aatgtttgcc aaggatgccg agatcaacat tgctgcggtg    720

ctgaaaaagc tcaatgaaat catagctgct cgtggcaaaa agaggaccga cagaagagaa    780

cagattgaac tgttgcatga gttgcagtct ataactgaga gtcacaatct cggaaatgca    840

gtattagtga aaataaagta ctctatagtt tcttcaattt tcgactacaa tcccaaagtt    900

tctgatgcaa tgaagcctga atattggtcg aaattattgg agcgcataac agaaatgttg    960

aatttgcttt tggccacgcc agatttgacc attgctgaca ctgttaacga ggaagaagaa   1020

gagtacgaga aggcaccttt caagatccac ggctgcgtcc ttacgttggt ggaaagattg   1080

gacgaggaat tcacgaaact cttgaaagag tgtgatcctc acagtaacga atatgtagaa   1140

agattgaagg atgaaaaatc agtctcctca atcatcgaca aagtgcagca gtaccttgaa   1200

agaaacggtt cgatgtcgga gttgtgtcgt atttatcttc gcaaaatcga gcatctctac   1260

tacaagttcg acgcgaacgt gcttaagcaa aaagacggtg aagttccaaa ggatactgtc   1320

acgtctattc aagtgatgga caagctctgc aagtacatct acgctcacga cgagaccgat   1380

cgtttgagaa cgagagctat cctgtcgcac atctatcatc acgctcttca cgacaactgg   1440

ttccaagctc gcgatttggt tctgatgtct cacttgcagg aaaccatcca acactctgat   1500

cctgcaacgc agattttata caaccgtacg atcgctcatc tcggtctctg tgccttccgt   1560

cacgctaaca tcaaagacgc gcatggttgt cttttggatt taatgatgac tggtaaggtc   1620

aaagaattgt tggcgcaagg tctaatgccg caaagacaac acgagcgcag caaggagcaa   1680

gagaagatcg agaagcagcg tcagatgcca ttccatatgc acatcaactt ggagcttctc   1740

gagtgtgtct acctcgtctc ggctatgctc attgagatcc catatatggc tgctcacgaa   1800

tttgatgccc gaagaaggat gatctccaag accttctacc aacaactccg gtcgagcgag   1860

cgtcaatctt tggttggtcc accagaatcc atgagagagc acgttgttgc cgcagctaaa   1920

gctatgagga atggcaactg gtctgcctgc aataacttca ttatcaatga gaagatgaac   1980

gccaaggtct gggatctgtt ttatcaagcg gacaaagttc gtgaaatgtt gaccaaactg   2040

atcaaggagg agtctctgag aacatatctt ttcacttact cccatgttta tgactcgata   2100

tctatgccta cactggcaga tatgttccaa ctgaaaagac ccattgttca ttccattatc   2160

agtaaaatga ttataaacga ggaacttatg gcatcgctgg acgacccatc ggaaacagta   2220

gtgatgcacc gtagcgagcc cagccgtcta cagtcattgg cagtacagtt gactgacaaa   2280

gtcaacaact tcgttgattc caacgagcgc atctttgaaa tgaagcaagg taacttcttc   2340

tcgagaggca accaaggcaa cttccgcgac aggcaaaatt ac                       2382
```

<210> SEQ ID NO 89
<211> LENGTH: 1176
<212> TYPE: DNA
<213> ORGANISM: Ophelimus maskelli
<220> FEATURE:
<223> OTHER INFORMATION: eIF5 translation initiation factor activity

<400> SEQUENCE: 89

```
atgggtagtg tcaacgtaaa ccgcggcgtt agcgatgcct tctatcgcta taaaatgccg     60

cgcatccagg cgaaagtcga gggtaagggt aatggtatca agaccgtaat cgtaaacatg    120

gtcgaggttg ccaaggccat tggtcgtcca gcgacctatc caaccaagtt tttcggttgc    180

gaactcggcg cccagaccca gtttgacttt aagaatgaga gattcatcgt taatggtagt    240

cacgatgctt ccaagttaca agatttactc gatggtttca tcaggaagta tgtactgtgt    300

cccaactgcg ataatcccga gactgaattg cttgttaatg cgaagaaagg aactatttcg    360
```

```
cagggctgca aagcttgtgg tcaccatggc atgctcgaga gcaaccacaa gttgaacact    420

tacatactga agaatccgcc aagtcttgat cctgcagccc agggtagctc attgaccgaa    480

ggtaagcgcg gtaagagatc taaacgcaca aacggtgaca ccaatggcga tcgttcgggt    540

tctcccgaga acgataacaa caccagcact actgatatcg tcgtcgaggc acccgagaaa    600

atggcaagta aggacgatga cgacgacgat gcgaactggg cagttgatgt atcggcggaa    660

gcagtacgcg ctcgtatgca agatctgacc gatggtgcca agggcatgac aataagcgag    720

gaccttgaca agagtgagaa ggaacgcatg gatatattct acaagctggt taagtgtcgt    780

cgggatgctg gtcagctcga caatcacaag gagcttgtga gtgaagctga acgtctcgag    840

atcaagacca aggcacctct cgtacttgct gagctgctgt tcgatcagca catcgctgct    900

caggtgaaga agtatcgctt gttgcttttg cgttttactc tgaatgacat caaggcacag    960

aaatatctca ttagaggtat tgagcaggtt atcgctcttc ataaggatgt tctcatgccc   1020

aaggtgcctg gtattttgaa gcttttctat gacagtgaca tcttggaaga aaaggctctt   1080

ctcgaatggg ctagtaaagt cagtaagaag tatgtttcta aggatatttc tcaggagatt   1140

cacgataagg ctgcaccatt tctcacatgg ctcaag                             1176
```

<210> SEQ ID NO 90
<211> LENGTH: 1191
<212> TYPE: DNA
<213> ORGANISM: Leptocybes invasa
<220> FEATURE:
<223> OTHER INFORMATION: eIF5 translation initiation factor activity

<400> SEQUENCE: 90

```
atgggtagcc tcaacgtcaa tcgaagcgtc agcgacgctt tctaccgtta caagatgccc     60

cgcatccagg ccaaggtcga gggcaagggg aacggcatca agaccgtcat cgtcaacatg    120

gtcgaggtcg ccaaggccat cggccgcccc gccacctatc ccaccaagtt cttcggctgc    180

gagctcggcg ctcagactca gttcgacttc aaaaacgagc gcttcatcgt caatggcagc    240

cacgatgcca ccaagctgca ggacctcctc gacggcttta tccgcaaata cgttctttgc    300

cccaactgcg acaatcccga gaccgacttg atcgtcaacg ccaagaaggg caccatctcc    360

caaggctgca aagcttgcgg tcaccacggc atgctcgaaa gcaaccacaa actcaacact    420

tacatactga aaaatccgcc aagtctcgat ccagctgcgc agggtagctc cctcaccgaa    480

ggtaaacgtg ccaaacgctc caaacgcccc aatggcgacg ccaatggcga gcagcgctca    540

agatcgcccg agaacgacaa caactccagc accactgaca tcgtcgtcga agctcccgag    600

aagatggcta acgagaacga tgatgaagac gacgatggaa attgggccgt cgacgtatcc    660

gaggaggcgg tgcgcgcacg tttgcaagac ttgaccgatg gcgccaaagg tatgaccatc    720

agcgaggatc tggaaaagag cgaaaaagaa cgcatggata ttttctacaa gttggtcaag    780

tgccgtcgcg acggtgatca actcaacaat cccaacagcc acaaggagct gctgaccgag    840

gcagagcgcc tcgaaatcaa gtccaaggca ccgcttgtcc ttgctgaact cttgttcgac    900

cagcacatcg ccgccgaggt taaaaagtac cgagttctcc ttctgcgttt cacccacgat    960

gatgtcaagg cccagaagta tttgatcaga ggcattgaac agatcatcgc tttgcacaag   1020

gatgtgctta tggccaaggt gcctggcatt ttgaagctct tctatgacag cgacatacta   1080

gaagagaagg ctttgtttga atgggctagc aaagtaagca agaagtatgt ttctaaagat   1140

gtatctcaag agattcacga taaggctgca ccattcctta cttggctcaa g            1191
```

<210> SEQ ID NO 91
<211> LENGTH: 1113
<212> TYPE: DNA
<213> ORGANISM: Ophelimus maskelli
<220> FEATURE:
<223> OTHER INFORMATION: Faf cellularization ubiquitin-specific protease activity

<400> SEQUENCE: 91

```
tcgattagtg ctgcattcga cctactcgtt agtctgtgtt cgggctgcgt acccaacatg      60
aaacttctag tcagcatgct ctgcgatatg ttctactcgg acaaagacga gcctctggtc     120
gagtgggatt acctgccacc cgtcgggccg agaccgcctc agggcttcgt tgggctgaag     180
aatgccggag caacttgcta catgaattcg gtacttcagc agctttatat ggtcgagagt     240
ataagggtag gtctgctcgc ggcggaagga gcggctacgg atataaatga ggacttttcg     300
ggcgaggaga ggatcgacgg agagcagacc atagaagcga ctgataatga taccaacgag     360
gaaaagtgta ctgctgacga atcgcgtaaa gaatataaca taggtattct taaacaggtt     420
caagcaatct ttggacattt agcttacagt aagttgcagt actacattcc tcgtgggctt     480
tggaaacatt tcaaactcca aggtgagcct gtgaatcttc gagagcagca ggatgctgtt     540
gaatttttca tgagcctaat tgagagtctc gatgaagctt taaaagcttt aggtcatgag     600
caaatcatga gcaagatcct tggtggttct tatagtgatc aaaaaatctg caaaggctgt     660
cctcacagat actctaaaga agagccattt agtgtaataa gtgtggatat tagaaatcat     720
agtaatttat tggattcttt ggagcaatat gtgaagggag aactgctgga aggagcagat     780
gcatatcact gtgataaatg taacaaaaaa gttgtgacag ttaagcgatt gtgcgttaag     840
aaactacccc ctattctggc aattcagcta aaacgattcg agtatgactt cgaaagagta     900
tgtgctataa aattcaatga ttactttgaa ttcccaaggg atctagacat ggaaccctac     960
acagtctcag gtttggccaa actagaagga gaaattatag attgggacca tgaagaaaca    1020
attaaaggaa cttgtactaa atatcagcta actggtattg tagttcacag tggacaagcc    1080
agtggaggtc actactattc ttatatttta cac                                 1113
```

<210> SEQ ID NO 92
<211> LENGTH: 2754
<212> TYPE: DNA
<213> ORGANISM: Leptocybes invasa
<220> FEATURE:
<223> OTHER INFORMATION: Faf cellularization ubiquitin-specific protease activity

<400> SEQUENCE: 92

```
gaatttttc aactgttatg taggctatta aattatgcac atatctctgg ttacccgatc      60
aatgccgagc agtggctgaa ctatgaaatc gtttggctga aaaatgtacg tgaccgcgtt     120
cgtgaaaccg gcgatactca ggtggacgag gcagttttag aaggtcatct ggcgtatgct     180
aaagaactgt tatcgttttt accagccagc aaaaagtacg agtatggatc ggacgagaag     240
cgcggtgtta atttaattaa ggaactagtg gaggacttca tattcccggc gtcgataagc     300
atgctgcagc tgcgcaatac aggtgagctg ggctcatcgc aagcgtgccc ggtatgcacg     360
acgccccagt caatcagcgc ggcgttcgac ctgctggtca gtctgtgcac gggttgcgtg     420
cccaacatga aacttctagt cagtatgctc tgcgacatgt tctactcgga taaggatgag     480
ccgctggtcg agtgggatta tttgccacca gttggcccaa ggccaccgca aggtttcgtc     540
ggtctcaaga atgctggtgc cacttgttac atgaattcgg tgcttcagca actctacatg     600
```

```
gttgagagca tacggattgg tctgctcgcg gccgaaggag cggctaccga tttgaacgag    660
gatttctcgg gcgaggagag ggttgacggt gaacagacca ttgaagctac ggacaatgat    720
acgaacgaag agaagtgcac tgccgacgag tcgcgcaagg aatacaatat tggcatatta    780
aagcaagttc aggcgatctt tggccacttg gcctacagca agctgcaata ttatattcct    840
cgtggacttt ggaagcactt caaacttcaa ggtgaacctg ttaatttgag agaacagcag    900
gacgcagtcg aattttttat gagcctcgtt gaaagtttgg acgaagcact gaaagctctt    960
ggccatgaac aaataatgag caagatcctt ggaggttctt acagcgatca aaaaatttgt   1020
aaaggctgtc cccataggta ttctaaagaa gagcctttta gtgtaataag tgtggatatt   1080
agaaatcata gtaatttatt agactctttg gagcaatacg tcaagggcga actgcttgaa   1140
ggggcagacg catatcactg tgataaatgt aataaaaaag ttgtgacagt aaaacgtctg   1200
tgtgtgaaaa agttacctcc tgttctggcg attcaattga aacgttttga atacgatttc   1260
gagagggtct gcgccataaa gttcaacgac tacttcgaat tcccgaggga acttgatatg   1320
gagccttaca cagtttcggg actcgccaaa atggaaggag agatcacaga ctgggatagc   1380
gaggaggcaa tcaaaggaac ttgcaccaag tatcaactgt cgggtattgt tgttcacagt   1440
ggacaagcta gcggaggcca ttactattcg tacattttac atagacaaag tgatggatca   1500
ggaaaatggt acaagtttga tgacggtgac gttactgagt gcaaaatgga agaagaggaa   1560
gaaatcaagt ctcagtgctt tggcggcgat tacatgggtg aagtgtttga tcacatactc   1620
aagcggatga gttatcgtag acagaaacga tggtggaacg cttacatgct cttctacact   1680
cgagttgatg tagagcaaaa ttcacaattg aaaaaagtta acgaattatc gctttatacg   1740
aaattgggag tgacaaagat gccaccagca attgagcaaa gcgttaggaa acaaaacatt   1800
aaatttatgc ataatagaaa ccagttcaat gccgagtatt ttcaatttgt cagaaaactt   1860
gtgtcatgta atccgtacaa cgttaaccga cctaatcacg aaaaaattag ccaagatgct   1920
gaagaattat cgatgttatc tgttcagctg gcgtcaaaat ttctattttt taccggcttt   1980
catacaaaga agactttacg tgggactgcg acggattggc atgacatact ttgccatcat   2040
ttattgggca gtaaagcagt tcgatcgtgg ttcgctcaca atgtcttatt caaccatccg   2100
catagatttt gcgaatatct gttgagctgc ccaagtacgg aagtaagaaa tgccttttttg  2160
aaaatattag tcttcttggc tcacttttct ttacaagatg ggccctgttt accgcctctt   2220
aatgcaccaa ctatgctact ggacccgaca gcaacattga gtgaccattt attgcacgca   2280
gtgctcatgt tgcttcatcg agagatttcg gatcatggcc ggcacttacc gcattacttt   2340
gcattgttcc ttacttatgc gtccattggt ctgcctcaaa agttacagct cttgaagctg   2400
aatgtgccag tgacgttcat gttggtagcg atcgatgaag ggccaggtcc agtgattaag   2460
tatcaatacc cggagcttgc caagttacac caagttgtga gcattttaat acgttgctgc   2520
gacgtttcgt caaaggcgca gtctagtaac gctcagaaca atgtcgctcc actgccgaac   2580
ccctacggag atccagcttg tggtcaagat tacctaatgc ctattcagcc gtcggcttcc   2640
gagatattat ttagccggac gagttacatg aagaaactta tcgaggacgc gagtgttact   2700
gaggagacag tcaagttgct gcagttctgc tgttgggaga atccacattt ttca         2754
```

<210> SEQ ID NO 93
<211> LENGTH: 1236
<212> TYPE: DNA
<213> ORGANISM: Ophelimus maskelli
<220> FEATURE:

<223> OTHER INFORMATION: Hel25E RNA helicase activity nuclear mRNA splicing, via spliceosome

<400> SEQUENCE: 93

```
cagaccgagc agattgtgga aggaaatgga gaagtcgttc cagccaaaaa ggaggtgaaa     60
ggaacttacg tctcaatcca cagtagtggc ttcagagatt tcttattaaa gccagaaatt    120
cttcgtgcaa ttgttgattg tggttttgag catccttcag aagttcaaca tgaatgtatt    180
ccacaagctg tgcttggtat ggacattcta tgccaagcta aatctggtat gggtaaaact    240
gcagtatttg tcttggccac cttgcaacaa ttggaattgg cagaaaatca agtatatgta    300
ctagtaatgt gtcatacaag agagctggca ttccaaatta gtaaagagta cgagagattt    360
agtaaataca tgccacaagt caaagtatca gtatttttg gtggattacc tatccaaaaa     420
gatgaagagg tcttaaaaag tacacaacct cacatagttg tgggaacacc aggacgtatt    480
ttagccctca ttaaaagtaa aaaactcaac cttaagaaca taaagcattt tattctagat    540
gaatgtgaca aaatgctaga gcaactagat atgcgcaaag atgtacaaga aattttccga    600
agcactcctc atggcaagca agtaatgatg ttcagcgcta ctttatccaa ggagatacgt    660
ccggtctgca aaaaatttat gcaagatcct atggaggtct atgttgatga tgaagcaaaa    720
ctcacgcttc atggattgca gcagcactat gtcaaattga aagaaaacga aaagaacaaa    780
aaactgtttg aactgttaga tgttcttgaa tttaatcaag ttgtgatatt tgtaaagtca    840
gtacagaggt gtatggcact tgcacaactg ctaaccgaac aaaacttccc tgccattggt    900
attcacagag ggatgacaca agaagaaagg ttaactagat atcaatcatt caaggacttc    960
cagcagcgaa tactagtggc aacaaatctg tttggacggg gtatggacat tgaacgagtc   1020
aacattgtgt tcaattacga tatgccggag agttcagata catatcttca tcgagtagct   1080
cgagctggac gttttggtac aaagggcttg gctatcacgt tagttagtga cgaaagtgac   1140
gccaaaattc tgaatgacgt acaagaaaga tttgatgtga acataacaga actaccagaa   1200
gagatagact tagcatccta cattgaaggc cgataa                             1236
```

<210> SEQ ID NO 94
<211> LENGTH: 1236
<212> TYPE: DNA
<213> ORGANISM: Leptocybes invasa
<220> FEATURE:
<223> OTHER INFORMATION: Hel25E RNA helicase activity nuclear mRNA splicing, via spliceosome

<400> SEQUENCE: 94

```
cagactgagc aggttgtcga gggtaatgga gaagttgctc cagcaaagaa ggaagtcaag     60
ggtacctacg tatccatcca cagcagtggt ttcagagatt tcttgcttaa gccagagatc    120
ctgcgagcca ttgttgactg cggttttgaa catccttctg aagttcaaca cgagtgcatt    180
ccacaagctg ttcttggcat ggacatcctt tgccaagcca agtctggtat gggaaagaca    240
gctgtttttg tcttggctac tttgcagcag cttgagttga cagagaacca ggtttacgtt    300
cttgtcatgt gccataccag agaattggct ttccagatca gcaaggaata tgagcggttc    360
agcaagtaca tgcctcaagt caaggtgtca gtattctttg gtggtctgcc aattcagaag    420
gacgaagaag tattaaaaag tacatgcccg catatagtgg ttggaacacc tgggcgtatt    480
ctcgctctca tcaagagcaa gaaactcaac ttaaaacatt tgaaacactt cattcttgat    540
gaatgtgaca aaatgctgga gcaattagac atgcggaaag atgtgcagga aattttccgt    600
agtacccccc atggcaagca agttatgatg ttctctgcaa cattgtcaaa ggaaattcgt    660
```

```
ccagtctgca agaaatttat gcaagatcct atggaagttt atgtagatga cgaagccaaa     720

ctcactctgc acggtttaca acagcattac gtcaaactca aggaaaatga aaagaacaaa     780

aaactctttg aactgttgga tgttcttgag ttcaatcagg ttgtcatttt cgtgaaatca     840

gtacaaagat gtatggctct ggcgcaactt ctgactgagc aaaacttccc agcaattggc     900

attcataggg gcatgacaca agaggaacgg ttaacaaggt atcagtcatt caaggatttc     960

caacagcgaa ttttggtagc cacgaatctt tttggccgtg gcatggatat tgagcgagtg    1020

aatattgtct tcaactacga tatgccggaa aattcagaca cctacctcca ccgagtagct    1080

cgtgcagggc gttttggtac aaagggattg gctataactt ttgtcagcga tgaaagtgat    1140

gctaaaattt tgaacgacgt gcaagaaaga ttcgacgtta acattacaga actccctgaa    1200

gagattgact tagcttccta cattgaagga cgataa                              1236
```

```
<210> SEQ ID NO 95
<211> LENGTH: 1941
<212> TYPE: DNA
<213> ORGANISM: Ophelimus maskelli
<220> FEATURE:
<223> OTHER INFORMATION: HLH106 sequence-specific DNA binding
      transcription factor activity fatty acid biosynthetic process

<400> SEQUENCE: 95

gaacccgatg cgatacaaaa cgtgcgcaag gtcacagctt catcgaacaa tggcttacca      60

gatcacacac gtgtttcact gtgtgctttc ctctttatat tcctggcttt taatccactt     120

ggctttgtca tgaataacgt gggacgattc aattatgatt attcaaggag tcgtgaaagt     180

cgaacgatat tggactatga tgaacaactg gatactgaat caaacgtatg gagcagcatg     240

attctctggt tgatgaacgc agttctcctg gcatttggac tctgtcgact tttgctttac     300

ggagatcccg ttctaccagc cgacagcaaa gtatccgtag aacttcaccg ctggagacgt     360

caggctgagt tcaacatgtc gaaggatgat tacgagcaag cttatcgcga tcttagtcaa     420

tgccttcagt acttctctcg acagctgcca ctgactcgca tggatatctt tttcgcgacg     480

ttgtggcaaa tgttccgaca aggtcttcac cgtctctaca tcagcagatt agtgacatat     540

atcggcaaaa agttcataga taaatctgaa cgacatctgg ctgaaatatc tgcgatggag     600

ttagctatag tgtatcaaaa tatgctgtgc ttgaagcttt cacgagcctc taaagattcc     660

gtggtctaca ttgctctttc ggctgttaac tatgcggagg cagccggtga aactatacct     720

aaatccatgt tggctgaaat ttacgttaat gcgactctat gtttcaagca gtcaattttc     780

ccatttatcc acaagttcta cctgaacaaa gctcgtagtc tcttggcttc ttgcgttgtt     840

ccacagaagc tcagatggat cgtcaatgac gacggtatga aattcttggt ctcgcaaaaa     900

ttgagctacg ggcaaagaga ggagagtgac ttcactgtgc agaataacaa atcggatcca     960

ctgtcttacg ctgcacgagc gtacagagaa catcttatca gtcaaggatt gagattatta    1020

gctggtaccg ttggtgatgc tcatgcttcg ggactactcg atatagcacg caagataatg    1080

atttcggcac gaattgattt gtgcatctgc agtgaagaga agatcggagt taccaaagtg    1140

gaagatgaag taggactatg gtggggtgcc gttatgtccg tggcagctaa ctttagatta    1200

ggagatgaag attcagatgc gtggaatatt gttgaaggta aatttccttt tgaaaagaat    1260

tctcagttag gaaattgcaa tcctctccca catgctgtac ttctccttct gcagtctgca    1320

aggtgcttat caaaaagaac aacagttcga ctgattgatc aagctagtac attccttgaa    1380

cactcaactg tgtacaataa ttgtaagcag caatcgtctc aaaacgtttt gctgacccag    1440
```

```
ttgtgggtat gcgactggct cttagagatg agaacaacac tgtgggaaga tctcaaggaa   1500
gacattgaaa agccagctat taattctact cttgttggtt tccaaagaga ccttgcatgt   1560
atgcgacaat tgtgtcaaca tataccttca atcctacccc gagttttctt atatgaagca   1620
acagcaagaa taatggctgg tgcgacaccg gtaaaaactc aaatcttact ggaccgcagc   1680
ctacatcata gaaattcacg ttcatccata atctgcggta aggaccgatc acacgaacaa   1740
ggcagtggtg aacgtgagca tgcggctgct ttatgtttgg cttgtcggca tctgccggtt   1800
ttgctcttgg cttcacctgg cgaacgtgct ggcatgttag ccgaagcagc caagacgcta   1860
gaacgcatag gcgatcgaaa gagactacaa gaatgttatg agctgataaa gcagcttaca   1920
cctgcaatgt cttcaaatta a                                              1941
```

```
<210> SEQ ID NO 96
<211> LENGTH: 1806
<212> TYPE: DNA
<213> ORGANISM: Leptocybes invasa
<220> FEATURE:
<223> OTHER INFORMATION: HLH106 sequence-specific DNA binding
      transcription factor activity fatty acid biosynthetic process

<400> SEQUENCE: 96
```

```
gataatatgg cgagattcaa ctatgattac tcaggaagct cgagggaagg gacaatattg     60
aatttccaag atcctgctga taccgagtcg aacatgtgga gcaatgtatt catctggtta    120
tcaaatgctt tactcttggc ttttggcatg tgtcgactgt tgctgtacgg agatccagtg    180
ctaccagccg acagcaaagt tggtctcgaa cttcaccgct ggagacgtca agctgaattt    240
aacatctcgc gaaatgacta tgaacaaggc catcgcgacc tcagccagtg ccttcagtac    300
ttctcgcgaa ctttacctct cacgcggatg gacactttct tcgtgacgat gtggcagctg    360
tttcggcaag ttttgcatcg actgtacatt aatcgtctag taacgttcat cggcaagaag    420
ttcttcgaca agtccgagag gtcattggct gaaatgtctg caatggaact gtcgacggtt    480
taccagcaca tgctatgtct caagctatct caaggctcga ctgactcgat tgttcatatt    540
gcactatcgg cactcaatta tggcgaagct gctggtgata ccatgcctaa gtcaatgctg    600
gccgagattt acgtgaacgt tgcactctgc ttcaaacagt cgcttttccc attcgtgcac    660
aagttctatc tcaacaaggc aaaaagtatt ctagcttcgt gtgttgtacc gcagaagctc    720
aagtggatca tgaacgacga tggtatgaaa ttcttggtct cgcagaagtg gagttacgaa    780
cagagagacg acagtgactt taccgtgcag aacaacaagt ctgatccact gtcttacgct    840
gctagagctt acagggagca tttgatcagc cagggtttga gattgttggc aggcactgtc    900
agcgatgctc acgcttctgg gcttttggat atttcaaaga aaatcatgac atcagctcaa    960
attgatctgt gcatttgcag tgagggaaag atcggtatca cgaaagtgga agatgaaatt   1020
ggattgtggt ggggcgctgt aatgtgcgta gccgcgaact tcagattagg cgaggaagat   1080
tctaacgttt ggaatatcgt cgaagggaaa tttccattcg agaaaaattc tcagctaaac   1140
aatggcaatc ctttgcctca cgccgttttg ctgcttcttc agtcggcaag gtgcacgtcg   1200
aagcacacga aaatgcgtct tgtcgaccaa gctagtacat tccttgagca ctcgacggtt   1260
tacaacaatt gtaaacagca gtcgtcccaa aacgttttgc ttacccagct gtgggtatgc   1320
gattggttgc tggagatgag gacgacactg tgggaggagc tgagtgaaaa catcgaaaga   1380
ccagctatca attcgtctct cgttggtttt cagcgagatc tcgcatgcat gcggcaactg   1440
tgtcagcaca taccgtccgt tctaccgcga gttttcttat acgaagcaac agcaagaata   1500
```

```
atggccggcg ctacaccagt caagactcag atacttctgg atcgaagtct gcaccatcga   1560

aactcacgct cctcgatcat ttgtggaaag gatcgatcgc acgatcaagg tagcggcgaa   1620

cgcgaacacg ctgctgcttt gtgcttggcc tgccgacact taccggttct gctgctggct   1680

tcacctggcg aacgcgctgg catgctcgcc gaggctgcta agactctgga acgccttggc   1740

gacaaaaaga ggctgcaaga atgctacgaa ctcatcaagc aactgacccc agcgatttcg   1800

aattaa                                                               1806
```

<210> SEQ ID NO 97
<211> LENGTH: 669
<212> TYPE: DNA
<213> ORGANISM: Ophelimus maskelli
<220> FEATURE:
<223> OTHER INFORMATION: Hr38 ligand-dependent nuclear receptor epidermis development

<400> SEQUENCE: 97

```
tatgcagata tgcctattga attgattctt gaagcagaaa aacgttttga atacttgatt     60

gaaaatcaag cctcttacga gcaatttagt aatcaaagta ataaacaaat acgacacatg    120

gtcgaatggg caaagcgact tccccaattt acgtcgcttc cgattgagga tcagacgctt    180

cttttacgcg ctgggtggaa cgagctgctg attgctgcat ttctcatcgg ttcaatcgac    240

attgaagatg gtatcatcct tagcacaggt ataacgttgc acaaaaattc agctcaacag    300

gctggtgtgg gcgctatctt tgagcgcgtg cttactgagc ttgtgcacaa gatgaaaagc    360

atgaaaatgg acaaagcaga acttggatgt ctgagggcta ttattctttt caacccagag    420

gtacgtggtt tgaaagctcc tcaagaagtc gatttgctta gagaaaaagt ttacgttgcc    480

cttgatgaat atactaagct gcatcgccca gatgagccta gtcgattcgc caagctatta    540

ttaagacttc cagcactacg ttccattggc ctaaaatgta ctgaacacct ctgtgttttc    600

agactgctag gtgataagca acttgatgaa ttactcactg atatgcttga ggttcctctt    660

gactcttaa                                                            669
```

<210> SEQ ID NO 98
<211> LENGTH: 558
<212> TYPE: DNA
<213> ORGANISM: Leptocybes invasa
<220> FEATURE:
<223> OTHER INFORMATION: Hr38 ligand-dependent nuclear receptor epidermis development

<400> SEQUENCE: 98

```
ttgataagtc ctggtaattt cagtccttca aatccaaata gcccagggtc tctcattgga     60

gtcccaggca acatgaataa ctcatcacca ggtaatcgca atgcagccaa tgcaggcaca    120

gcttatccac caaatcatcc attgtcaggt agcaaacatc tctgctcaat ttgtggcgat    180

cgggccagtg gtaaacatta cggcgtttac agttgtgaag gctgcaaagg cttcttcaag    240

cgcaccgtgc gcaaggatct gacctacgcc tgccgcgaag aaaggcactg cctaattgat    300

aagcgtcagc gtaaccgctg ccagtactgc cgttaccaga agtgtctcac gatgggtatg    360

aagcgcgaag ccgtccagga ggaacggcaa cgcacaaagg agcgcgaggc ttcaggtgca    420

aatccgggct cagtcgccgg gtctgaagca gagagttgta ccagcagctc gcacgccgac    480

atgcccgtcg aactgattct cgaggctgag cgacgttttg actttctcgg ggagaatcag    540

gcgtcgtacg atcagtac                                                  558
```

<210> SEQ ID NO 99
<211> LENGTH: 1146
<212> TYPE: DNA
<213> ORGANISM: Ophelimus maskelli
<220> FEATURE:
<223> OTHER INFORMATION: La 5S rRNA primary transcript binding RNA processing

<400> SEQUENCE: 99

```
gatgaaaaac cggcaaaaat taccgaaaca gaaaaaaatg gatctaataa tgaagaaaaa     60

acaaatggtg aagaaaaaga aaatggtgaa gaaaaaacta atggtgaaga agaaaaaaat    120

gatgaagaaa aaagtaatga tgccgagaaa gctaatgatg ctcctacaaa tgtagttcaa    180

gagccttcag aagagttact taaaaaaatt aagaagcaag ttgagtttta ctttggagac    240

gtcaatatgc aacgtgataa gtttcttatc gaacagacga gactcgatga agggtgggtt    300

ccaatgactg tgatgttaaa ttttaaaatg cttgcctcga tgagtaaaga cattgatctt    360

attttgaaag ctcttgaagg tagtgaactc attgaaatat ctgaagacag aaaaaaaata    420

agacggtcac tggacaagcc tctgcctgta tatgatgatg aatacaggaa agctcaagaa    480

gctaggacaa tttatttgaa aggttttcca actaatacga aaatcgaaat gttaaaaaat    540

cattttgaat caaatgatag tattgaaaat atcatgatga ggaagtacaa gaaaaacaag    600

gaatcatttt ttaagggttc aatatttgta caatttaaaa cattagatga tgcaaaagca    660

tttatggaac aggagtccat aaaatataat gacactgagt tgatcaaatt atggtcagct    720

gagtatgcag cgtcaaaaga aaaagaaagg gaagaaaggc gtcaaaagaa aaataagaat    780

caaaatgatt cgaagaatga aaatgcaaaa acatccaaaa attctaaagc aaacgcccaa    840

gataagatca aactgccaaa aggttgcatc atacacattt caaatttacc aaaggatatg    900

aagagggaag atataaaaaa acagttaatg gaattggata cggaagtagc ttacatcgac    960

ttcaacatgg gagatgttga aggctgggtt cgcttgcaag gagaaaatgc tgctgtagaa   1020

ttactgaaga aattagaatc tgacacaatt aaagttaatg attgtgatgt gaaatgtaaa   1080

ttattagaag gagaagaaga agattcatat ttagcaaaga cacaagaaaa tatgcttaat   1140

cttaga                                                              1146
```

<210> SEQ ID NO 100
<211> LENGTH: 1014
<212> TYPE: DNA
<213> ORGANISM: Leptocybes invasa
<220> FEATURE:
<223> OTHER INFORMATION: La 5S rRNA primary transcript binding RNA processing

<400> SEQUENCE: 100

```
gaggttaaag ccgacgctaa accggcagat gaaacagcag acaagcaaac ggatgaacca     60

aaggaagaac cttctgcctc attgcttgag aaactgagaa aacaagttga gttctacttc    120

ggcgatgtga acatgcaacg tgacaaattc ctcattgagc aaacgaagtt ggacgaagga    180

tgggtcccga tgactgttat gctcaatttc aaactattag catctatgag caaagacgtc    240

gatgttattt tgaaggcttt ggaagaaagt gagctgatcg aaatttcaga agataggaaa    300

aaaattcgca gagcgctcga caagccactg ccggcgtacg acgacgagta tagaaaggct    360

caagaagcta ggacgattta tttgaaaggc tttcctcttg actctaccat tgaaacctta    420

aagacttact ttgaatctac agacactatt gagaatatca ttatgaggaa gtataaaaaa    480

ggcaaagagc acttgtttaa aggatctgtc tttttacaat tcaagactct tgatgatgct    540
```

```
aaggcgttca tggaacaaga atctgtcaaa tacaaagaca cagaattgat taaaatgtgg    600

tcaaaagagt atcttgctat gaaggaaaaa gagaaagaag aagttcgtct aaagaaactt    660

cacaaacaga tggataatga tgccaaagca gcaaagaaaa acaagtctca gaataaaatt    720

gaacttccaa aaggatgtgt tttacgtatt tcaaacatag aaaaggttga tagagaaaaa    780

gtaaaggaga agttcacaga gctagaagct gaggtatctt ttgtagattt caaagctgga    840

gatactgaag gtttcattcg tttacaaaaa gagaatgctg ctgtagagtt cttgaaaaaa    900

ttagaatcaa acaagataac cgtgggagat tctgaaattg aatgtaaatt aatagaaggt    960

gaagaagaag aaacttacct gtctaaggta gttgagaaca tgactaacgt tagg         1014
```

<210> SEQ ID NO 101
<211> LENGTH: 1035
<212> TYPE: DNA
<213> ORGANISM: Ophelimus maskelli
<220> FEATURE:
<223> OTHER INFORMATION: lin19 ubiquitin protein ligase binding mitotic cell cycle G2/M transition DNA damage checkpoint

<400> SEQUENCE: 101

```
attactcaaa aaagcagcaa aaatccagaa gaagctgaac ttgaagatac tctaaaccaa     60

gtgatggtgg tatttaaata tatagaagac aaggacgtgt accaaaaatt ctacagtaaa    120

atgttggcaa aaagattggt acaacacatg tctgctagcg atgatgcaga ggcttccatg    180

atttcaaaac tgaaacaggc ttgtggcttt gagtacacct ctaaacttca aagaatgttc    240

caggatattg gagtttcaaa agacttgaat gagcatttta gaagacatct aacaaactca    300

gctgaacccc tagacataga ttttagtata caggttttgt catctggttc atggccattt    360

caacagtcgt ttacattttc tcttccaaca gagctggagc gatctgtgca taggtttaca    420

accttctata gttcacaaca cagtggtcga aaattgaatt ggttgtataa tatgtctaag    480

ggtgaacttc acacaaactg ttttaagaat aggtacacac tgcaagcatc gactttccaa    540

atggcagttc tgttgcaata taatacatca acatcttgga caatacagca gttacatgaa    600

tctacccaaa taaaaatgga ctttctatta caagtcatac aaattttact aaaagcaaaa    660

cttcttgtaa caaatgatga tgaatctgaa ttaggaccat cttctacagt agacctcttc    720

acaggttata aaaataagaa actaagggta aatattaaca taccaatgaa aactgagttg    780

aaaattgaac aagaaaccac acataaacat atagaggaag accgtaaact tcttatccaa    840

gcagcaattg tgagaattat gaaaatgcgc aaagttctaa agcatcaaca acttgttgca    900

gaagttttaa accaattaaa ttcaaggttt aagccacgtg tgcatgttat taagaaatgt    960

atagatattt taattgaaaa agagtatctg gagcgtacag aaggtcagaa ggacacatac   1020

agttacttag cgtga                                                    1035
```

<210> SEQ ID NO 102
<211> LENGTH: 1377
<212> TYPE: DNA
<213> ORGANISM: Leptocybes invasa
<220> FEATURE:
<223> OTHER INFORMATION: lin19 ubiquitin protein ligase binding mitotic cell cycle G2/M transition DNA damage checkpoint

<400> SEQUENCE: 102

```
gattcatttg aaaacttgtt tcttgaagat acagaaaggt tttatacacg tgaaagctct     60

gaatttcttc gtcataatcc agtcacagaa tatatgaaaa aagttgaaca gaggttgcaa    120
```

```
gaagaacaaa acgagttcag gttttattta catcaaacaa cacatgaaag attagcaaaa    180
acgtgtgaaa gagttttaat agaaaaacat ttagacattt ttcatgcaga gtttcagaat    240
ttgttagatt ctgacaaaaa tttagatttg ggaagaatgt accaactggt tgccagaata    300
ccaaatggtc taggtgaatt acgaaatctt ttagaaagtc acatagctaa tcaaggtctg    360
gctgccattg ataaatgtgg ggattctgca gcaaatgatc caaaaattta tgtaaacact    420
attttggagg ttcacaaaaa atataatgct ttagtattag ttgcatttaa taacgatagc    480
ggttttgtag cagctttaga taaggcttgt ggtcgattta taaatgctaa ttctgtaact    540
aaagcagcaa atagtagtag taaatcgccg gaattattag cgaaatattg cgatttgcta    600
ctcaaaaaaa gcagtaaaaa tccggaagaa gcagaacttg aagacactct aaatcaagtt    660
atggtagtat tcaaatatat cgaagataaa gacgtatacc aaaagtttta tagcaaaatg    720
ctagcgaaaa gattggtgca acatatgtct gctagtgatg atgctgaagc ctctatgatt    780
tcaaaactca agcaagcttg tggatttgaa tatacatcta aacttcagag gatgtttcaa    840
gatattggag tttcaaaaga cttaaatgaa cactttagaa ggcaccttac taattcagct    900
gaacctttgg atatagattt tagtatacaa gtcttatcat ctggttcatg gcctttttcaa   960
caatcattta catttttcttt gccaacagag ttggagagat ctgttcatag gtttactaca  1020
ttttatagtt cacaacatag tggaagaaaa ttgaattggt tgtataatat gtctaaaggt  1080
gaactcctta ctaactgttt taaaaatcgg tatacgcttc aagcttcgac ttttcaaatg  1140
gcagttttgc tgcaatataa tacttcaaca tcttggacga tacaacaatt acatgaatcg  1200
acccaaataa aaatggattt tctattacag gttattcaga ttttattgaa agctaagctt  1260
ctaataacca gcgacgatga atctgaatta ggatcatcat caacggtaga acttttcaca  1320
ggatataaaa ataagttaag ggtaaacatt aatataccaa tgaagacaga attagaa     1377
```

<210> SEQ ID NO 103
<211> LENGTH: 1800
<212> TYPE: DNA
<213> ORGANISM: Ophelimus maskelli
<220> FEATURE:
<223> OTHER INFORMATION: Mor transcription coactivator activity chromatin remodeling

<400> SEQUENCE: 103

```
atagcagaat gtgaagatga tgctactcac ataatctatc catctgctga tcctctagaa     60
gaagaatacg caaggccgtg ttttcgaaga gatcgatctg ttttacttca ctggtattat    120
tttccagata gttatgattc gtgggtcaac attgaacttc catgggattt tcctgaaact    180
gctcttggaa accctcctcc aaagtcacca tataaagttt ctgctacttg ggcactagat    240
ttagaacaat acaatgaatg gatgaatgag gaagattatg aagtagatga aagtggtcag    300
aaaaaagtac ataagtacag gttaagcgtt gaagacatga tgacacaatc agcaccacct    360
tctgttaaaa agcagaaaag gaagaggtct ccgactccac caccaaaact aggcaaacga    420
aaaagtgggc gagctcctgc tggtcctcaa ggtataaatt cttctacggg tccaaagaaa    480
tcacgtggaa ctggagatga agaagaagac ttaactcaag gcatggatga tccacctgca    540
gaacccagga taatggaagt cgtctctaca aatgctaaca caccaaactc agctcaaaac    600
agtactggtc ctatcatttc cagtagcaaa aaacaggata atgaattgca gccattaaaa    660
tctggaaata tggccgatct tgatgaacca gtggatggtg aaaaaagtaa ctcacaaacg    720
tctcaagacc gagaagaaag ggatacgagt aaagaaagga atgatggtag caaaagcgat    780
```

```
gaaccagaag ataatgttac agaacaaact catcacattg ttgtacccag ttactctgcg    840

tggtttgatt acaattccat tcacacaatc gagaaacgag ctctgtctga atttttcaat    900

ggcaaaaaca aatcgaaaac accagaaatt tatttggcgt atagaaattt catgatcgac    960

acttatcgtt tgaacccaac agagtacatc acgtcaacag cgtgcaggcg aaatttggct   1020

ggtgatgttt gtgcgataat gcgcgtacat gctttcctcg aacaatgggg tctaattaat   1080

tatcaggtgg atgccgattc aaggccgacg cctatgggtc caccgccaac ctcacacttc   1140

cacgtgcttt cagacacacc gtcaggttta gcaccagtta atcctaatcc tcctaaaacg   1200

ccacagccat ccgcagcgaa aactcttttg gatctcgaaa agaagcctgt tattacggat   1260

gaaaaagttc ctccggtcgg acccatggca aactttggtc tcaagatcga tcagtattcg   1320

aaaaaaccag ccgtactgaa aaataaacaa gctgctggtg caactcgtga ttggacggaa   1380

caagaaacgt tattattact agaggcttta gaacttcata aggacgattg gaataaggtg   1440

tgcgagcacg ttggctcgag gacacaagat gagtgcattc tgcatttctt aaggctaccc   1500

attgaggatc catacettga ggagccggag ggtctaggcc cgttggcata tcagcctatt   1560

cctttctcta aggctggaaa tcctgttatg agtacagtag ctttcctggc atcagtggtt   1620

gatccaagag tagcggcaag tgcggccaaa gctgcaatgg aagaattcgc tgcgataaag   1680

gatcaggtgc cagcagcact tctggatcaa catttaagga atgtgcaggc tagcgcgaat   1740

tcggatggta aattcgatcc ggcagctggt cttgcacagt cgggtatcgc cggaaccggt   1800
```

<210> SEQ ID NO 104
<211> LENGTH: 1530
<212> TYPE: DNA
<213> ORGANISM: Leptocybe invasa
<220> FEATURE:
<223> OTHER INFORMATION: Mor transcription coactivator activity chromatin remodeling

<400> SEQUENCE: 104

```
cagtacaatg agtggatgaa tgaagaagat tatgaagtag atgatagtgg acagaaaaag     60

gtacataaat atagactatc agttgaggac ttgatggctc caacacctgc atcaggtaaa    120

aaacaaaaga gaaaaagtcg cccagtcctc ctccaaaact tggaaaaaga aaagtggcag    180

agctcctgga ggaactcaag gtgggttgtc cggcccaaaa aatcacgagg tggagacgaa    240

gaagaagact tgacacaagg aatggaggat cctccgtctg agccgagaat aacggaagtt    300

gtaaattcga atacgaatgc atctatctct ggacagaata gcagctcagg catggtgtcc    360

agcaaaaaac aggacaatga catgcagcca ctcaagtctg gaaacatggc cgatttggat    420

gaaccagttg atggtgataa aagcaattcg caaaattcac aagacagaga agaacgtgac    480

acgagcaagg aaagaggcga cggcagcaag agcgatgagc ccgaggataa cgtgaccgag    540

cagactcatc acattgtgat tccgagctac tcggcgtggt ttgactacaa ctctattcac    600

atgattgaga agcgagcact atcagagttt ttcaacggca agaacaagtc taagacacca    660

gaaatctacc tcgcttacag gaatttcatg atcgacacct atcgcctcaa tccgaccgag    720

tacattactt ccacagcctg taggcgaaac ttagctggtg atgtatgcgc tatcatgcgc    780

gtgcacgctt ttctcgaaca gtggggtctg atcaattatc aagtggatgc cgattcaaga    840

ccgacaccta tgggacctcc acctacttcg cacttccatg ttttgtcaga tacaccgtct    900

gggttagctc cagttaatcc aaaccctccc aaaacaccgc agccgtcagc ggcaaagacg    960

ttacttgatc tcgaaaagaa accgattatt gacgagaaga ttccagctgc tggagcgatg   1020
```

```
gccaacttcg gcctgaagct cgatcaatac gcgaggaagc ctgcggtttt gaaaaacaag   1080

caagctgctg gtgctactcg cgagtggacg gaacaagaaa cgctgttatt gcttgaagct   1140

ttggagttac acaaggatga ctggaataag gtttgtgagc atgttggttc aagaactcag   1200

gatgaatgta tcctacactt tttgcgatta cccattgaag acccgtacct tgaagaacca   1260

gaaggtcttg gtccactggc atatcagccc ataccttttt ctaaggctgg taaccctgtc   1320

atgagcaccg ttgcattttt ggcttcggta gtggatccta gagtagcagc tagtgcggca   1380

aaggctgcta tggaagagtt tgctgccatc aaagaccagg tgcctgctgc tttactggat   1440

caacatttga gaaatgttca ggctactgct gctgatggaa aattcgaccc agccgccggt   1500

cttgcacagt caggtatcgc aggcacagga                                    1530
```

<210> SEQ ID NO 105
<211> LENGTH: 2715
<212> TYPE: DNA
<213> ORGANISM: Ophelimus maskelli
<220> FEATURE:
<223> OTHER INFORMATION: NAT1 translation initiation factor activity autophagic cell death

<400> SEQUENCE: 105

```
ggaagggacg ataatcgctc cctatccact gagcaacgct ggatccctcc ttcaactatt     60

agacgcgatg cgctcacccc agaaagccga aacgatgtca tcttccgaaa ggtgcgggga    120

attcttaaca agctcacacc ggaaaaattc gcaaagctga gcaacgactt gctcaacctt    180

gagctcaatt ccgatgtaat tctcaaaggc gtcatatttc tgatcttcga aaaagctctc    240

gatgaaccga aatacagttc tatgtatgca cagctgtgca agcggctgtc cgaggaggct    300

gcgaactttg agaactcgca gcggcagcag cagcatggcg gagtcgggct gcaaggccgc    360

atcggagccg gagctaataa gcccggcgct gaggctgggc ggcgcagcca caacagtacc    420

ttcgaccgca tcctgctcaa caaatgcaag gacgagttcg agaaccgatc caaggcccac    480

gaggcgttcg agcgccaggc cgagctcagc cctgaggacg aggaacgccg gcaggcggcc    540

aagcgcaaaa tgctgggtaa catcaagttc atcggcgagc tcggcaagct ggagatcgtt    600

tccaactcga tcctgcacaa gtgcatccta cagcttctgg acaagaggcg ttgcggatcc    660

cgggggtacc cgcccgagga catcgagtgc ctctgccaga ttatgcgcac ttgcggtcgc    720

atcctcgata cggacaaggg caaccagctc atggagcagt acttcgaacg gatgagccag    780

ctagcgaaga gcagcaagct gccacttcgt atccgtttca tgctgcggga cgtgatcgag    840

ttgagggccg atggctgggt gccgcgtaaa gccaccagca ccgagggccc gatgcccata    900

caccagatcc gcaacgacaa cgacgaccac gggggcggcc ggctgggcgg cggcggtgga    960

cccggcatgg gtggccccgg caacatgccc aatgcctact acgcgcgcaa ccgcgacgac   1020

cagggccgcg gcggcgtcgg caccgacctc ttccgacgta tgggccgtgt cagcctggat   1080

gttgacagtc tcggtggcat aatcccactg tcctcatcga gcttctccat cggctctccg   1140

ttcagcccga acggcttcgg accaggcacg ccgtcggcgc cctacggtcg ccacggtcag   1200

cgcaacaacc agcaaggcgc gcccttctac cccaatcaaa atcgacagca gaacaactac   1260

caggccaagc ataaccaaca gcaacaccaa cagcaccagc agcataactt gccacagaac   1320

tacaacaaca atgccaataa ggagccagtg cgttttaata aaaacaagat gctcatcgga   1380

ccgccggagg aggtctcact cagaccctcg gccaactcta tgaccttcaa gcaacccaac   1440

atcaatccca atatgtctct gaataatgga ggaatagact tgttccctgg tcgtattcct   1500
```

```
gagtcaccat tgatgcgagc atcggcaatg cgcaagccaa gtccgccgct tctaccgaaa   1560

gaaaccccgg ccagtatcgt gatcaagcag ggcccgttag ataagcgcga aaaggcgcgt   1620

gaacgcaaag ataagggtcc gaccaaggag gagattatga aaaaagtcaa ctcgatgatg   1680

gacgatttca tgtcccaggg taacatgcct gacgccatta tggccttcaa agagcttaag   1740

ataccggagc gcttctcgcg atgcgccgtc tacacgatct actccaacag tctcgagcgt   1800

aacgactcag aacgcaatct cgctgctgat ctagttaacc agctgcgaaa ggacaacatc   1860

gtcaacaacc tgcagtatca cgatggttgg aaggaggtgg ttaactcgat tgccgagaaa   1920

gagagcgctg tgccctgtat tgcctcacac atcgctcagc tgacggcgcg cgccattgtc   1980

gatggcctgc tgcagctgtc cgacctggcc accgtgaccg agaacggcca gcagtatccg   2040

cttttcctgc tcacgcttca gcagctgcac aagagccaag gcaaagctgc tctcacgcag   2100

atcttcaacg agagcaaggt taatctcata agtcagctac ctgaggccga gaagaccaag   2160

gaacgacttg gcgaaatact tgaagatagg gatcttacct tcctataccc actgctaaga   2220

attcagggtg atatgtggag gcagcttgag agcgatccag cacccaacag cctctacaag   2280

tggattaagg aaaagcttga cccttcgcac cattccgatc caggatttat caatgctctc   2340

atgactgtat tactcaaata tattacccag gaaacaacat tcccagctgg ctccaaacca   2400

tcagtcattc ctgagaaatc attgctggaa aaagagttag ctttactggg taaataccag   2460

cgaatgctgc aaatgcttct gccaactatc gattcacagg tcactgccgt acactcattg   2520

caagtcttct gcctgtcgct aggcttcccc aagggaatgc tgttgcgttg gttcatagct   2580

ctttatgacc tttcaattat tgatgaagag gccttcatgc gttggaaaga agacgttaat   2640

gatgcttatc caggaaaggg tgacgccttg ttccaggtaa atgcctggtt aacatggctt   2700

gccgagcaac catct                                                     2715
```

<210> SEQ ID NO 106
<211> LENGTH: 2791
<212> TYPE: DNA
<213> ORGANISM: Ophelimus maskelli
<220> FEATURE:
<223> OTHER INFORMATION: NAT1 translation initiation factor activity autophagic cell death

<400> SEQUENCE: 106

```
ggaagggacg ataatcgctc cctatccact gagcaacgct ggatccctcc ttcaactatt     60

agacgcgatg cgctcacccc agaaagccga aacgatgtca tcttcagaaa ggtgcggggt    120

attcttaaca agctcacacc ggaaaagttc gcaaagctga gcaacgactt gctcaacctt    180

gagctcaatt ccgatgtaat tctaaaaggt gtcatttttt tgatcttcga aaaagctctc    240

gatgaaccga aatacagttc tatgtacgca cagctgtgca agcggctgtc cgaggagagt    300

gcgaactttg agaacacaca aaagcaaagc ggcttgcgtc agcagcagca gcagcagcat    360

cagcagcagc atcgaggact caatagcagc ggcacaacat caggcggcaa tcatccagcg    420

cataaccatg tacacgaggc agcgggaagg cgcagcatcg acagtacctt cacccgtctg    480

ctactcaaca agtgtcgaat tgagttcgag aatcgttcca aggcgaacga ggcattcgag    540

ctcaagcagg gcgaactctc ggccgaggac gaggagcgcc ggcagaatgc caagcgcaaa    600

atgctcggca acatcaagtt catcggcgag ctcggcaaac tggagatcgt gtcgaactcg    660

atactgcaca ggtgcataca gcaattactg gacaagaggc gtggcggatc ccggggggac    720

caggccgagg atatcgagtg cctttgtcaa attatgcgca cttgcggacg catcctcgac    780
```

```
accgacaagg gcgcccagct tatggagcag tacttcaaac gtatgagcgt acttgcgaag    840

aacggcgagc taccactgcg catacgtttc atgctgcgcg acgtgatcga gttgaggcag    900

aacggttggg taccgaggaa ggcgaccagc accgagggac ccatgccgat caatcagata    960

cgtaatgaca atgacgatca tcccggtcgt caggctcacc tcggcctgcc cggccaggga   1020

tccggcgcgg cgccgggctc cttttacaac cggaatcgcg gcgacgatcc cggctccagg   1080

ggcatgggca gcgacctgtt caggcgcatg ggtcgcgtca gcttcgacgt cgacaatctt   1140

ggtatcatac cactcacatc cgcgggcttc gccatgagct cgccattcag tcccaatggc   1200

tttggccatc ccggccagcc gacgcccacg cccaacactt acggacctgg caggcacaac   1260

cagcgcaacc agccaccggc caacttctat cccaatcaga atcgcaacca gaacaactat   1320

cagggcaaac acaaccagca acagcacaac tcgccccaga actacaacaa caacggcaat   1380

aaggagccag tcagattcaa taaacacaaa ctcatcggac cacccgagga aatatcgctc   1440

agaccttcgg ccaattctat gacttttaag cagcccagca tcaaccccaa tataaccact   1500

aacaatggag gaattgacct attcccgggt cgtattcccg agtcgccgct gatgcgcgcg   1560

gcagcaatgc gcaaaccgag tcctccgctg atccctaaag acccgccagc caccgtggtg   1620

atcaagcagg cgccattgga caagcagaag cgcgagcgca aggacaaagg ccctaccaag   1680

gaagaggtga tgaagaaggt gaacgcgttg atggacgact tcgcgtcgca cggcaacatt   1740

cccaacgcaa tcgcagcctt caaagagctc aagattcccg agcgttttct gcgctgggcc   1800

gtctacacga tctactcgaa cggcactgag cgcaacgacg ctgagcgtac tttggctgcc   1860

aatcttgtca gtcaaatgcg caaggacggt gtgattaatg ctcaacagtt tcacgatggc   1920

tggaaggagc tcgtgaattc gatcgccgag aaagagagtg cagtgccgtg tatttcttcg   1980

cacactgctc aactcactac tcgagctatc gtcgatggaa tgatgcaact ctctgacttg   2040

gcgtcggtca ccgagaacgg tcagcactat ccgctcttct tactcaccct ccagcagctg   2100

cacaagaccc aaggcaagca ggcgctcacg cagattttca gcgacagcaa ggttaatctg   2160

atcagccagc tgcccgaagc cgagaagacc aaagaacgtc tcggtgaaat tcttgaggat   2220

agagatctta ctttcttgta tccgctgctg agaatccaag gggacatgtg gaagcagctg   2280

gagagtgatc cttcgcccaa cagtctctac aagtggatca aggagaagct cgacccgtct   2340

caccattccg atccgggctt cattaacgcg ctcatgaccg ttctactcaa atatattact   2400

caggaaacaa cattcccagc tggctccaat ccatcggtca tccctgacaa gtctttacaa   2460

gagaaggagg ttgcattact gagcaaatat aagcggatgc tacacacgct tctaccgacc   2520

atcgaatcgc aggtcactgc cgtacactcc ctgcaagttt tctgcatgtc gcaaggtttt   2580

cccaaaggaa tgctattgcg ctggttcatt gcactttacg atctttcaat tgtcgatgaa   2640

gatgccttca tgcgctggaa ggaagacgtt aacgatgctt atccaggaaa gggcgaggcc   2700

ttattccagg taaacgcttg gttgacgtgg ctggcggaac aaccgtcaga ggacgaggat   2760

gaagaagagg atgagaaggc agataactaa g                                  2791
```

<210> SEQ ID NO 107
<211> LENGTH: 708
<212> TYPE: DNA
<213> ORGANISM: Ophelimus maskelli
<220> FEATURE:
<223> OTHER INFORMATION: Noi zinc ion binding nuclear mRNA splicing, via spliceosome; 5' fragment from same gene SEQ ID NO: 241

<400> SEQUENCE: 107

```
tcggagcatc gattgaagat gctcttggat cagtttatgg agagtactgg gcatctggta     60

gaattgtacg aagataaaga tgggcaacga aaggaagagg ttcaagcgct ttctggtcca    120

aatgaatttt cagaattcta cgcaaggctc aagtctataa aagaatttta tcgaagacat    180

ccgaatgaaa ttagtgttcc tatgtctgta gaatttgaag aactggccaa aatgagggaa    240

aaccctagtg aagaagcagc taaccttgtc gaattcacag atgaagaagg ttatggcaaa    300

tacctagatt tacatgaatg ctacgaaaag tatattaatt taaaaggtat agagaaagtt    360

gattatatca catatttgtc tacgtttgat catcttttcg atattccaaa ggatagaaaa    420

aatgcagagt accgtagata tgtagaggct ttgttagagt atttgttaga tttcttggga    480

agagttcgac cgctccttga tgtcgatgct gaattaatag aaactaataa tgactttgaa    540

gaaaagtggg aaactagcac ttttcccgga tggcctaaag aagctggtag tgcactgaca    600

aacgtaggag cacatttaga actgtctgca ttttcttctt gggaagagct tgcatcactt    660

ggtttggaca gattaaaatc tgctctgatg gctcttggat tgaagtgt                 708


<210> SEQ ID NO 108
<211> LENGTH: 1500
<212> TYPE: DNA
<213> ORGANISM: Leptocybes invasa
<220> FEATURE:
<223> OTHER INFORMATION: Noi zinc ion binding nuclear mRNA splicing, via
      spliceosome

<400> SEQUENCE: 108

atggagacga tcctggagca gcagagacgt taccatgaag aacgggagcg cctcatggat     60

gcaatggtca aggagatgtt gtacaaaaag ccaggacacc gcgaaaccat caattcggag    120

caccggctga agatgctcag cgatcagtac atggagagca ctacgcatct cgaggagatg    180

tatgaggaca aagatggtca aaggaaggat gaggtacaag cgctgtctgg gccaaatgag    240

ttttcagagt tctactccag gttgaaatcc atcaaagagt tttatcgcag acatccgaat    300

gagatcagtg ttcctatgtc agttgaattc gaagagcttg ccaagatgag agagaatcct    360

accgaggaga atgctaattt ggttgatttc accgacgagg agggatacgg aaagtacttg    420

gacttgcacg agtgctacga gaagtatatc aatctgaagg ggattgagaa ggttgactac    480

atcacgtacc tgtcaacctt tgatcacttg tttgacattc caaaagacag gaagaatgca    540

gagtacagaa gatacgttga gtctctgctc gaatacttga tggaattttt gggcagggtc    600

aaaccactgc tagacataaa caaagagctg atagaggcca acaaagactt tgagttacag    660

tgggagacga gcacctttcc cggatggccc aaggaggctg gcagtgcttt gactaacgtt    720

ggtgctcact tagaattgtc tgctttctct tcttgggaag aattggcgtc cctcggattg    780

gatagattga agagtgctct gatggctctt ggactcaagt gcggtggtac tttagaggaa    840

agagctcaaa gattattcag cacaaagggc gaatcgtcac ttgatcctaa cttactggct    900

aaaaagcaga ggaaacttgg caaaggcaag aatgtagaga aacaaaagga aattgcacga    960

ttggaagctc aggtttacaa gcttgctgag ttggtgagca gccagaggat ggctaccaaa   1020

gaaaacgtcc agaggaagca ggccagaaca gaaggtgagc gtggagactc tgatgttgaa   1080

gccagtgcaa gtgagtccga ggaggaagac gacaacgacg taccttacaa tcccaagaac   1140

ttgcctcttg gttgggatgg aaagcccatt ccctactggt tgtacaagct tcatgggctg   1200

aatattagct ataattgtga aatatgtggt aattttactt acaaaggccc caaagccttt   1260

cagcgtcact ttgcagagtg gaggcatgct catggtatga ggtgtttggg tattccaaat   1320
```

```
actgcccact ttgcaaacgt tacgcagatt gaagatgcat tggcactgtg ggaaaagtta   1380

aagacacaga agcaagctga aaggtggcag ccggaacaag aagaagaatt tgaggattct   1440

ctaggaaatg ttgttaatag gaagacctat gaggatttaa aaagacaagg gctattgtaa   1500
```

<210> SEQ ID NO 109
<211> LENGTH: 1221
<212> TYPE: DNA
<213> ORGANISM: Ophelimus maskelli
<220> FEATURE:
<223> OTHER INFORMATION: Pit ATP-dependent RNA helicase activity

<400> SEQUENCE: 109

```
aaccctaccg aaagtttgcc tggttcatca gttggtctag aactcacaaa agacagatct     60

ttttcagcat taaaagacat ggtttgtgaa aatacattaa aaggaatagc agaaatgggc    120

tttactcata tgactgaaat tcaagcaaaa gcaatacctc ctttacttga aggaagagat    180

attgttggtg ctgcaaaaac tggttcggga aagactttag cttttcttat tcctgccatt    240

gaacttattt ataaactcaa atttatgcct agaaatggca cgggttgtat aattatttca    300

ccaacacgag aattatcaat gcagactttt ggtgtactca aagagctaat gaaatatcat    360

tatcacactt ttggtttatt aatgggtggt gcaagcagac agactgaagc tcaaaagtta    420

tcaaaaggag taaacataat tgtagcaaca cctggaaggt tactcgatca tttgcaaaat    480

actccagatt ttctgtacaa aaatctacaa tgtctaatta tagatgaagc ggatagaatt    540

cttgatattg gatttgaaga agagctcaaa caaatagtta atattttacc aaaaagaaga    600

cagacaatgc tttttagtgc cactcaaacg aaaaaaactg aagcattgac agctttggct    660

ttaaaaaaag aacccgtcta tgtaggcgtc gatgataata aagaaaaggc tacagtcgaa    720

ggtttagagc agggttatgt agcttgtcct agtgaaaaga gatttttatt attgttcaca    780

tttttaaaaa agaatcgaca aaagaaagtt atggtcttct tcagctcttg tatgtctgta    840

aaatatcatc acgagctttt gaactacata gatttaccag ttatgagtat tcatggtaaa    900

acaaaaaacaa acgaaaagaa caacaacttt cttccaattt tgcaatgcac aatcaggtat   960

tcttttatgt acggatgtag ctgccagagg tcttgatatt cctgatgtgg actggattgt   1020

gcagtatgac cacctgatga tccaaggaaa tacattcaca gagttggtag aacgggctcg   1080

aggagaaggt agcagtggac acgcttttga ctgatacttc gcccagagga gcttggtttt   1140

ctccgttacc tgaaacaagc tagagtacca gttaatgaat ttgagttttc atggaataaa   1200

attgctgata ttcaactaca g                                             1221
```

<210> SEQ ID NO 110
<211> LENGTH: 2202
<212> TYPE: DNA
<213> ORGANISM: Ophelimus maskelli
<220> FEATURE:
<223> OTHER INFORMATION: Psi mRNA binding negative regulation of nuclear mRNA splicing, via spliceosome

<400> SEQUENCE: 110

```
atgagcgact attcagccgt tgcaccaccg caaaatttct cgcaaagctc tgcctttgca     60

gccgcacttc agcgagctaa acagattgca gctaagataa accctcaagg ttcacaaaat    120

aatcaagatg cacaaaagaa acgttcattg gaagatggtt cagaacccga tgcaaagaaa    180

attgcttcta tgctacctga cccattgatg agcctacgtg gaaacaccac tcctggtgtt    240

gcttcaagta tcggtgatag tcctatttca aggccttcag gacctacgac acctaatcca    300
```

gtttctttgg gaggtatttg caatgaagaa atcagagttc ctgacaaaat ggttggattg 360
ataattggaa gaggaggaga acaaatatcc agattacaaa gtgaaacagg atgtaaaata 420
caaatggctg cagaaagtgg gggtcagtct gagcgtacat gcacgctaac cggctcccga 480
gaagctgtca atcgagccag agaacttgtc ttatctattg tcaaccaaag gaacaaaccg 540
gatgatgtaa taccaggagc caatcctcct tacccaggtc ctgccgcagg atctgctgca 600
gcatcaatcc tttcgggaca tccaggctac caagaaatca tgattcctgg tcctaaagtt 660
ggtctaatca ttggaaaggg tggtgaaact attaaacagc ttcaagaaaa atctggagca 720
aaaatggtca tcatccaaga tggcccaggt caggaaacag aaaaacctct gagaatcact 780
ggagatccgc aaaaagtgga gcatgcaaag cagctagtct atgaattaat agctgaaaaa 840
gaaatgcaga tgtataatag aggttcaaga aattccaatt ttaataattt taatcaagat 900
caaagtggaa ctgaggtgtt cgtgccgaag acagctgtag gcattgttat tggcaagggt 960
ggtgaaatgg ttaaaaaaat tcagcaagaa accggcgcta aactgcagtt cgtgtcaatc 1020
gatggtcaag acgcttctca cggagatcgt aaggtcctta tcaacggtag tatggagtgc 1080
gtcgaaaatg ctcggcaaag gatagaggaa ctgatcgaag gcgcgaataa aggacgcaat 1140
caacgtggta atggttttaa tccaggacga ccgaatgagt atggtggtgg ttggaacaac 1200
agaggtccag acatgggaaa caaaatcgag ttcagttatg cagtccctgc taacaagtgt 1260
ggtattatca ttggaaaagg cggtgaaacg attaagcaga ttaatcaaca aactggcgca 1320
cattgtgaac tagataggcg aaatccaggc aatgaaacag agaagttctt cataatcaaa 1380
ggaactcctg agcaaataga acatgcgaag agagtatttg cagaaaaatt aggaggaatg 1440
cagggtggca acatgtatgg tcagaatcaa atgggctaca acactggatg gaatgcacct 1500
gctggctatc aagcttggcc tggtcagcca acaggagatc caaatgctac acaacctgct 1560
tctgtgcaaa ttaatccagt gactggacaa cccgattaca gtgcacagtg ggcagaatat 1620
tatagatcgt taggtagaca tatggaagcc gatatgattg agcaacaggc aaaacagcag 1680
cagcagcaaa tggctgcgaa aggcgatatg aatcaggtgc cagctggaca aaacccacca 1740
aatccagcac cagctccagc tccagctcaa gctccgcagc aacaagctca gccacagcct 1800
cagcagcaag ctcaacagaa tggtagccaa gctgattata gtgcacagtg ggcagaatat 1860
tataggagta taggaaaaat aaaagaggct gaggatatcg aagctacaat gaaaaacaag 1920
ccgagtggtg gaatgccaaa tagtcagatg ggacagcagc aagcgcagca gccaatgcaa 1980
cccaatccga tggtgaatcc cggtggtgga gcaggtgctg gcggtccagg tggcacgcct 2040
aatgcctatg ctccacctta cggtggttat ccaggcatga atccagcttc tggtggttac 2100
tacacacctc aagctcaggg tgggggacaa cctggacaaa atcctccctt cccaggcaat 2160
taccaaaact atcagtatcc tcagcccaac tctgacaact ga 2202

<210> SEQ ID NO 111
<211> LENGTH: 2160
<212> TYPE: DNA
<213> ORGANISM: Leptocybes invasa
<220> FEATURE:
<223> OTHER INFORMATION: Psi mRNA binding negative regulation of nuclear mRNA splicing, via spliceosome

<400> SEQUENCE: 111
atgagtgatt actcggctgt agctccgcca accaacctct ctcagagttc agcgtttgcc 60
gctgcgctgc agcgcgccaa gcagattgca gctaagatta atcctcaggg ttcgcaaaat 120

```
aatcaagaac caaagaagcg ttcattggaa gatggcacag aacctgaagc caagaagcat    180

atacctgatc cattaacaaa tcttcgtgga cctattggat taaatcttgg tctagacaat    240

ccatcgaggc ctggttctac agtctctaat gcttctagtg ttggaggtat ttgcaatgaa    300

gatattagag ttccagacaa aatggttggg ttaatcattg gcagaggagg agaacagata    360

tccagattgc aaagtgaaac aggatgtaaa atacagatgg cttcagaaag tgggggtggg    420

cttgagcgta tttgcacgct aactggccca cgagatgctg tcaaccgagc caaagaactt    480

gtcttgtcaa ttgtcaatca gaaaaaggat gaacccatcc caggagctaa tcctccttac    540

ccaggcccag caggcccagc agcttcggct attttgtcag gacacccagg ttaccaggaa    600

atcatgattc caggtcccaa ggttggtctc atcattggaa aaggaggtga aaccattaag    660

cagctccagg agaaatctgg ggctaaaatg gtggttatcc aggatggtcc aggacaagaa    720

tcagaaaaac ctttgagaat caccggtgat ccgtcaaaag tagaacacgc aaaacagtta    780

gtttacgaac taatcgctga gaaagaaatg caagcctaca gtagaggagg aaggggaggt    840

tttggccgag atggaaattc tgacgaggtt accgtaccga agaatgtggt tggcttggtg    900

atcggcaaag gcggcgaaat gataaaaaag ctgcaacaag aaacgggtgc taagattgta    960

tttttaaatc taaatgaaga cggccccgaa gaccgcagat gttctatctc cggtaatgac   1020

gatgccgtgc aaaatgcgcg ccaaaggatc caggagcttg ttgacaacgc tatgaatcgg   1080

ggcaacggtt acaattccgg aaggtctaat gagtacggcg gttgggatgg caggcgaaac   1140

gatatgaccg gtaaaattga attcagctat cctgttccta cgaacaagtg tggtatcata   1200

attggaaaag gtggtgaaac aatcaaacaa atcaacgcgt caacgggtgc ccattgcgag   1260

ctggacaggc gaaatccagg caccgagtcc gagaaattct tcacgatcaa gggtacgcct   1320

gaacaagtcg agcatgccaa gagaatattc agcgagaaac ttggtggtgg catgacttca   1380

acgaatagta tgtacggcgc acaaaacgct atgggttaca gtcagtggaa tccggcgggt   1440

taccaagctt ggccaggtca acaaccagca gctgatccga atgcagcgag tcaaggtcaa   1500

gtacagatca atccggcgac tggtcagcct gactatagtt cacaatgggc tgagtactat   1560

aggtcgatgg gtatgcatcg agaagccgaa atgatcgagc agcaggccaa gcaacaaaat   1620

gcaactgcgg cagctaaacc tgacatgaat cagcaaactc cacaaggtgc caatccatcg   1680

gctcctcaac cagcacagca gcaacaacca cagcagcagc agcaacaaca acaacaacaa   1740

caacagcaac aacagcaatc ccagcaaaat ggtagtcaac aagattacag tgcgcaatgg   1800

gccgaatact ataggagcat tggaaaaatt aaggaagctg aagctattga agctcaaatg   1860

aagaataaaa ccggcgcgag catgccaaat aatcaaatgc cacagcagca gcagcagcag   1920

cagcagcaga ccatgcaaaa taatccaatg caggcaggcc aaggtggcgc gccaggtggt   1980

cctggtggcg cacctaatgc tttccccggt tatggtggtt atccaggaat gaatccatcg   2040

gctggcggtt attacacgcc tcaggctcag ggtcaggcgg cacccggtca aaatccagcg   2100

tatccaggcg caggtggcta ccagaactat caatatcccc aggctagccc cagcaactga   2160
```

<210> SEQ ID NO 112
<211> LENGTH: 954
<212> TYPE: DNA
<213> ORGANISM: Ophelimus maskelli
<220> FEATURE:
<223> OTHER INFORMATION: Rb protein transporter activity determination
of adult lifespan

<400> SEQUENCE: 112

```
gtgattgtaa atatgttaac acgatactca catactcaat ttataaaccc taatatagat     60

gatattgagg tacgatgagg aacgttcatt ttatgattct gactctgaat ccagtacaaa    120

aaaccaaaat tcacacttga tactgatcac agacttcttt tgcgcaatac aaaaccattg    180

ttacaaagtc gtaatgctgc agtagtaatg gcagtagccc aattgtatca ccatgctgct    240

gctcgaagtg aagcaatgat cgcagcaaaa gctatgataa gactgttaag aggtcataga    300

gaagttcaaa gtgttgttct tcactgtatt gctagtatat cagtaaagag aaaaggaatg    360

tttgaacctt tcttaaaatc atttttcgta cggacttcag atccaactca tataaaatta    420

ttaaaactag atattttaac caatttggca actgaaacaa gtattggtgt tatattgaga    480

gaatttcaaa cttacatctc aagcagtgat aaagaatttg ttggtgccag catccaagct    540

attgggcgat gtgctagcaa tataaaagaa gtaactgaca cttgtttaaa tggattagtc    600

tcactgttaa gtaatcgaga tgaagctatt gtagcagaaa gtgtggtagt tataaaaaaa    660

cttttacaaa cacagccaag tgaacataaa gatattatag ctcatatggc caaattaatg    720

gatttcatta cggtaccaca agctcgagca tccattttat ggttacttgg agaatattcg    780

aacagagtgc caaaaatagc tccagatgta ttaagaaaaa tggctaaaac atttatcaat    840

gaagaagaca ttgttaaatt acaaacgtta aatttagctg tgaaattgta tcttaataac    900

ccagaacaaa cgaaaaagat ttgtcaatat gtatttcagt tagctaagta tgat          954
```

<210> SEQ ID NO 113
<211> LENGTH: 795
<212> TYPE: DNA
<213> ORGANISM: Leptocybes invasa
<220> FEATURE:
<223> OTHER INFORMATION: Rb protein transporter activity determination of adult lifespan

<400> SEQUENCE: 113

```
gtggcaccca tgacccccat aatgacaccg agcttaggtg gtttccttac acctatgctg     60

ccgacgtcaa ccaaatcttc ggatggtgtt aaggaagtgt cgccctcatt tattccagtt    120

cgaaagtatg agctgtttaa taaagtcagt ggtcgcggtt tgaaagccga attcaggttc    180

actagatcgc aacatttaat tagctcttct cttgttaacg tcgagctaac ttttacgaat    240

gaaagtagcg atgttataac ggaagttcga gttggaaata agaatttacc gtctggaatg    300

tctattcacg acttctcgcc aatctctatg ctccagccaa gcatgtcttt ggcgtgcagt    360

ttaggcatca attttaacga ctcaactcaa ccggctccgt ttaatattga ttacaaaatt    420

aaagacgagc aaacgtctcg tactgtggaa ataagagcac caattggtga aattattaga    480

tctgtgcttc tacctgaatc aatgttcctg tctgaaaaag acaagctgaa aggtatgaat    540

gaacatagta ccacagttaa ttactctgaa aataggaaga gtttgtctca gaagattctg    600

gaagctgcca atttagctgt tatttcaagt gatgatgata ctattaggtt tgctgctaat    660

actctttctt ccaaatcgct agttttagtg acaataaaaa cagttgatga taaaaaattg    720

aatatttgta taaattgtga aaaaatggtg ataggctcga tgctgttgaa cgaactgaag    780

agtaacttga agtaa                                                     795
```

<210> SEQ ID NO 114
<211> LENGTH: 4464
<212> TYPE: DNA
<213> ORGANISM: Ophelimus maskelli
<220> FEATURE:
<223> OTHER INFORMATION: Sas receptor activity instar larval development

<400> SEQUENCE: 114

```
acaactgaaa gtggagagcc gacaagtgaa ggaacaacag aattcacaag tacaccacca     60
gaaggcacaa ctgaagaacc aggaacatcc tctcctatgg atatatttac gccaagctcc    120
gttgattcgg cactttcaac ggaacataaa cttcccaagt gtaaacctag aaaacctaaa    180
ccatgcaaag gcacagaatt tggatgctgt ttcgacggta ttacaatcgc gaaaggacca    240
ttctctcaag gttgtccaac tgcgcacact tgtaaagaaa ccaaattcgg ttgttgtcct    300
gatggagttt cacctgctct tggtcacaaa aacaagggct gtcctgatca acactgcaat    360
gaaactctgt tcggatgttg tccagataac gttacacctg cagagggcaa tgactacgaa    420
ggttgcaaga aaccgtgcaa ccagactgaa tttggatgct gccctgataa agaaacgcca    480
gcacttggca aaaataatct tggttgctgc aatactacga aacatggatg ttgtccagat    540
gacaaaaccg cggcctctgg tcccaaagga aaaggatgcc caaaagttga aatgggcgga    600
cgtcttaaat atgattgtgt taattcaact tacggatgtt gtcctgatgg tgagaagact    660
gcaaacggta ctaacttcga aggatgtgac gttattaata ccgaaaactg tactgcatcg    720
tactttggat gctgtcctga caatgttact gccgctcttg gaccaaacaa caccggatgt    780
gcattaccat gtgacaacac gacctacgga tgctgtgacg ataagaaaac ggcagctcac    840
ggatataaca aagaaggctg ttgcctgtcg agtccgttca agtgttgccc tgataatatc    900
acaccagctc gcggacctga ctattacggt tgcgaatgtc aatggtctag attcggatgc    960
tgccctgaca acaaaaccgc tgccaccgga tctaataaag agggatgtgg ttgcgcctat   1020
gcagaacacg gatgttgtcc aaacagaatt acgcctgcaa caggaccaaa ttacgaagga   1080
tgtccttgtt atacatatca attcggctgt tgccctgatg gcattactgc tgcaaaagga   1140
cctcgtaacc taggttgtgg atgcgaaaac tccgaattca agtgctgctc cgatggaaaa   1200
accccggcta aaggaccaaa ctacgccggc tgtacttgtg acgcctctaa atacggctgc   1260
tgccccgacg gaattgagga agctcaagga gaaaactttg agggatgtct caaagtgccg   1320
ccgaatatgc aagccgcatg cgctttgcca agggacaggg gcacatgccg cgagttcagc   1380
gtcaagtggt tctacgacac tgagtacggt ggttgctcga gattctggta cggaggctgc   1440
ggtggcaacg acaatcgatt caagacccaa gaggactgca aagccacttg cgtcgagccc   1500
caaggaaaag atttttgtaa attacccaag attggtggac cttgcgaagg ctattatcca   1560
tcttggtact acgatgccga cagaaaacaa tgtggtcagt ttatttactc tggctgtctt   1620
ggaaataaaa atagattcaa gactcaccaa gaatgtgaag agctttgttc tgaacctatt   1680
gacgctgatc cttgcactct tgacaaagaa cctggccctt gcgaaggcaa cttcacaagg   1740
tggttctata ataaagaatc gcaaaactgt gaacaattca actacggagg atgcaaggcc   1800
aatgctaaca attatcctac agaattggct tgccgtcaac aatgcttaca ccctggacaa   1860
agtcgagaat catgttcgct accacgtacg gagggcaact gtacggagaa gctttcgcgt   1920
tggtccttcg atcaacagga aaatcgttgc atgccatttt attacactgg ctgtggtgga   1980
aataataata actttggctc tagagatgca tgtgaatcaa attgtccatc gaaaattgaa   2040
caagacactt gcttattgcc ggcgcttctt ggcgaatgtc ataactacac acaacgctgg   2100
tacttcgatt cttacgatga aagatgtaag ccattctatt acggcggttg cggaggaaat   2160
cacaacaact tccgaacgga agaagaatgt gagggcagat gttctagaag agcacctttt   2220
actactacca gtgctcctta tcctattccc ggtgaaaacg tcgagccttc attctcgtca   2280
gaattctgct tcttgcctga gcaacgaggc tcctgtcaac aatacactac caaatggttc   2340
```

```
tatgacagca gagaaggtct ttgcaagcag ttcgtctaca gcggctgcgg aaacaatgga   2400

aacaacttca attcccgcga agactgcgag taccgatgtg gcgaagttca agatccgtgc   2460

acgatgccag ctattcccgg tccatgcaac gaatcactgc ctcgattcta ctacgaccgt   2520

cgcgtggatg cttgctacca gttcgcctac agcggttgtc aaggaaacaa gaacaacttt   2580

gaagagctac gtacatgcga gcagcgttgt cgcagaaggc aaaccggacc acagactgtt   2640

gtgccaatat cggcagcacc accgacaagg ccaccaccag tgcaaagtgc acaactggag   2700

gcttgtctcg aagcagctga tcctggcccg tgtcgcgacc agattaccgc ttattactac   2760

gataggaaca atcaagcgtg ccaggcgttc atttatggag gttgcgaggg taacgctaat   2820

agattcgaga ctgaagagca gtgccagagg ttgtgcggaa cgttcagaga ccaagatatt   2880

tgcaatctac cacgcgatca aggtccttgc cgaggagcgt tccagaaata ctattacgat   2940

gctacttata gagcttgccg cgaattcatc tatggtggct gcgatggaaa cgctaatcga   3000

ttcagcacca ttaacgagtg cgaatcggtt tgcattcatc acgaggagcc agctcaaact   3060

ggaaacagaa ctgcaattac cgatttgaca atctgcaaag aacctgttga tattggatca   3120

tgctctgttg gcaattacaa gagattctat tatgatgatg agtatcaaac atgcagagca   3180

tttatttaca ctggttgcgg tggaaatcgc aacaacttta agaccattga ttcttgtctt   3240

aaagtttgtc gtcaagtcaa cacgattccg gacgacggac aggacactaa ggatccttgc   3300

gcggaagcta cggaatactg ccagcgactt cactgtccct acggccagga agattacgtc   3360

gattcacaga actgccaacg ctgtcgttgc tccgaaccat gtcaatctat ttcttgtcct   3420

gaaggtcaaa aatgcgccgt tatccttgtg cagaccagag acggcaccga atatagagga   3480

ctttgtaatc ccgttaccaa acccggaaag tgtcctgttg tgtcgagcag cacgagatgc   3540

gagacggaat gtttcacgga cgctgactgt tcgggcgagc agaagtgttg ccataatgga   3600

tgtggtgctt cttgcctaag tccagcagca gaagaaatag tcacaactcc actaccctat   3660

cgtcaaaatc aaggaacact acctcctgga tatgttccac ctgcgataga gcaaccagca   3720

acgccgaatg tcaccgctga ggagggcgga tacgttacga tgacttgtgt ggcgatcggt   3780

aaccccaaac caagcattat gtggaaaaaa gatgccaaaa tcattgaaca tgaagagaat   3840

agaagacgca tactgggaga cggatctttg cagattacta atctgtatcc agttgacagt   3900

ggcatttata tttgtacagc agacaatgga attacagcac caatcgacat acaatatcag   3960

ttagaagtta cagagccgca cgataacccg ccagcgataa tagacgagcc aaatcggcct   4020

atcacagtca acctgaactc accaatcgta ttgcactgct acgcggttgg ctggccgcga   4080

ccgatggtca cttggtggcg taacgacagc atgctcccac tgaataccga gcaatatcat   4140

cagggctccg agaacacctt atccatacac actgtcacgc ttactatgct tggtatctac   4200

acttgccaag cgttcaatgg cattggcaag ccagccgagt ggtcgactgt cctacaagca   4260

gtcggtcctg tggctaacgt tccacccgac caggagaaat acactaagta cctggtacaa   4320

ccaccccaga gacctgaaaa acctagctat ccctacagac ctgaccgtaa tcaggttcaa   4380

cagaaccaaa cttatgctcc catctacact actaaacaat acgacgttcc agctgtcata   4440

ccgcttacaa ctctgtctcc ttcc                                           4464
```

<210> SEQ ID NO 115
<211> LENGTH: 519
<212> TYPE: DNA
<213> ORGANISM: Ophelimus maskelli
<220> FEATURE:

```
<223> OTHER INFORMATION: SCAR actin binding cytoskeleton organization;
      5' fragment from same gene as SEQ ID NOS 242 and 243

<400> SEQUENCE: 115

atgccgctgc cgaagcgagt ggtggagccg gtgcacgtgg cgcgcggtac gatacccgag     60

gactttccgt tgccctcgga gctcgaggcc gtaacgaatg gtaccctcgc caacgccatc    120

aggcagctgt ccagcttgtc gaggcacgcc gaggatatgt tcggcgaact ggccaaggag    180

gcgcatggac tcagcgatcg ggccaactcg cttcaggcta ggatcgatag gttggctgtc    240

aaggtcacgc agttggacag caacgtcgag gaagtctcgc tccaagatat tcacatgcgg    300

aaagccttca agagttcggt ggtgttcgat cagcaggtcg tctccaggga cacgatgccc    360

acggcgatgc tcgaaactta ccagcagtgt gacactccac caccgctcga caaactcaac    420

gtttacaggg acgacggaaa agacggctta aagttttata cggatcccaa ttacttcttc    480

gacttgtgga gtcaagaaat gctcaaggat acagaaaaa                           519


<210> SEQ ID NO 116
<211> LENGTH: 1794
<212> TYPE: DNA
<213> ORGANISM: Leptocybes invasa
<220> FEATURE:
<223> OTHER INFORMATION: SCAR actin binding cytoskeleton organization

<400> SEQUENCE: 116

atgccgctac caaagcgagt agtcgagccg gtgcacgtgg cacgcggcac gatacccgag     60

gactttccat tgccatcgga gctcgaggca gtgacgaacg gcaccctcgc caacgcgatc    120

aggcagctgt cgagtctgtc gaggcacgcc gaggatttgt tcggcgagct cgccaaggag    180

gcgcacaacc ttagcgaccg cgccaattcg cttcaggcga ggatcgatag gctcgccgtc    240

aaggtcactc agcttgacag caatgtcgag gaagtttcgc tacaagacat ccacatgcgc    300

aaggccttca agagctccgt cgtgttcgac cagcaggtcg tctccagaga caccatgccc    360

accgctatgc tcgagactta ccagcagtgc gacatgccgc cgccgctcga caaactcaac    420

gtttacaggg atgacggaaa ggacggtttg aagttctaca ccgatcccaa ttacttcttc    480

gagctgtgga gccaagagat gctcaaggac acagagaaaa aattgcacga tcgaggaaag    540

aagccgcata ggcctcggaa cgacggtggc agtggaggag gaggcagtcg gcacaagaag    600

cgtgtaaggc agccgcacaa tacgcgcgag cgtcaacgtc agatcgccgt gggtcacggc    660

gaatacatta tgccgtcgca aggaatccaa taccgtgcgc aacacactat tcccgacgaa    720

gctttgctgg gtatggtaat gacggatcca cgaccaccac gacccaacag catcgaattg    780

aggcgcagct atccgcccga ggaacatcag ctctacagcc cccctataac tgggcattac    840

ggccaagcga attatgccgc tcagttgcaa ggctacgaag acagcgcgta cggctcgcat    900

tatgctcccg gtcaaggcca ctcgggtagc gatacttacc agagtcctgg aggtccaggc    960

acgccaagtc gaagaaacag gccatcgcag ccgccacccg caccgcctag caatgcatct   1020

agtaactcga cgccgacgat cgcttccgcg aacaatacgc caacgagggg caggtccatg   1080

agcacaggca gggacaatct accaccgccg ccgccgcctc ccggtgaaac aatgtcgccg   1140

cccgctatga atggcgctct tccgtctcac ttgctgcaga gaaacggtag ccgttctaac   1200

agcccgctgc cgaatcatca gtcaacgccg acagcgggta tgatgcacat ggttcagatg   1260

atgccgatcg gcgtagacga aacggagtcg gtggcacaag atcttccacc gccacctcca   1320

actccagatc cagcaccacc tcacgagcga ccagtctcac caccgtgcaa cataccaccg   1380
```

ccaccgccgc caccacctcc tccgccaatt ttgaacggtc caccagcgtc actcagccaa 1440
atgccgataa cgaatggtga cattgctaaa atgattgtca acaatccgcc gattctcaag 1500
ccgctcaaga gcatcgtcga cggccaactc aggaagccca acaatcccaa catgcctgct 1560
gtggtcgacc cgaggaacga tctactaaag gccatccgag acggtatcaa actacgaaag 1620
gtagaaaaaa tcgaacaaaa ggaagtggag cgagtgaatg cattgaacga cgtggcatcg 1680
atcctggctc gacgagtagc cgtggaattc agcgacagcg actcagcatc cgaaagcgag 1740
tgcgacagcg aaggttgggg tgagcatgat acgaccgcga ctaatgctgc gtga 1794

<210> SEQ ID NO 117
<211> LENGTH: 1407
<212> TYPE: DNA
<213> ORGANISM: Leptocybes invasa
<220> FEATURE:
<223> OTHER INFORMATION: Shi actin binding epithelial cell migration, open tracheal System; 5' fragment from same gene as SEQ ID NO: 244

<400> SEQUENCE: 117
atggcgggca acacgggaat ggagcagctg atcccgatcg ttaataaact ccaggatgcc 60
ttcactcagc tcggggtcac gatgcagctc gacttgccgc agatcgccgt ggtcggcggt 120
caaagtgctg gcaagtcgtc tgtccttgag aacttcgtcg gcagggattt cctgccacga 180
ggctcgggta tcgtcaccag gaggccgctc attcttcagc tcatcaacgc cactagcgaa 240
tttggtgaat tcttgcattg caaaggcaag aagttcgtcg acttcgaaga ggtgcgaaaa 300
gagattgaaa atgaaacaga ccgcattacc ggcagtaaca aaggcatctc caacgtaccc 360
atcaacctca gagtctactc gcccaacgtg ctgaatttga ctctgatcga tctgccgggt 420
ctgacaaagg tgccgatcgg cgatcagcca gcagatatcg agcagcaaat caaagggatg 480
atctttcagt ttatcaaacg tgacaactgc ttgattctgg ccgtaacgcc tgctaatact 540
gatctagcta atagcgatgc tctcaaactt gccaaggagg tcgatcccca gggtgtacgt 600
actattggtg tcatcactaa gctggatctt atggacgatg gcaccgacgc gagagatatt 660
ttggaaaata aattactgcc cctgcgaaga ggctacatag gtgtaattaa taggagtcaa 720
aaggacattg agggtagaaa agacatcaag gcagctctgg cagctgaacg taaattcttc 780
ttgagccatc cttcatatcg acacctcgca gacaggtcag gcacgccata cctgcaacgc 840
gtactcaacc agcagctgac gaatcacatc cgagatacgt tacctgctct tcgtgatagg 900
ctgcagaagc agcaacttgc tctagaaaag gacgttgaac agtacaaaca tttcaggccc 960
gacgatcctg ctatcaagac aaaagccatg ttgcagatga tacagcaact acaatcggat 1020
ttcgagagga ccatcgaggg ttcgggatct gctcagatca acactatgga gttgagcggt 1080
ggtgctaaga tcaaccgatt gttccacgag aggtttccct tcgaaattgt caagatggaa 1140
tttgacgaga aagaattgcg aagagaaatt gcttttgcca ttcgaaacat ccacggtatt 1200
cgagtcggtc tcttcactcc ggatatggct ttcgaagcta ttgtcaaaaa acaaatcaac 1260
aggctcaagg agcctagtct taaatgtgtg gacttagtcg tacaagaact tagtaatgtc 1320
gttcgcattt gtacagatag gatgtcgcga tatccgagac tgcgcgagga aacagagcgc 1380
attatcacaa cccatgtcag gcaacga 1407

<210> SEQ ID NO 118
<211> LENGTH: 1282
<212> TYPE: DNA
<213> ORGANISM: Ophelimus maskelli
<220> FEATURE:

<223> OTHER INFORMATION: su(w[a]) RNA binding nuclear mRNA splicing, via spliceosome

<400> SEQUENCE: 118

```
cgctgggtcg tcgactccgg gattctgcgt aaaaaggtgg agatggggaa ccgcaggagc     60
tactggtctt tggttacagc tgtaaattat ttcgcgacga cgaacgagcc aaattgatcg    120
atcaaggcaa acatttgata ccatggatgg gcgatagcac tctgaagata gacaggtccg    180
tttctctaac ctaacaaaaa cacacaaaac aattcaatct atctagtata tcgttaatat    240
taacgtatat cttaatccac gaggccttag tctagtggaa agaatacgat tttttattga    300
cttgtttcaa ccagcttgag acagagcttt acaactctgt ctccttcaat atttcttaag    360
cctgatgcac atatagacaa tctggagact atttaagggt ttgcgcaggt gtacctcagc    420
caaatcaagt gtggcagtgc gttttgtatg cgctcccaca acacacagac taaggggtgc    480
cttatgtgag cgtttgtggt gactttgtag ctgagagcgt ctgaaggcat cagcaaggta    540
tgatggccga ggagctttgg gagacttacg gctgtatgaa ccgccacctg gtggttttga    600
tcaacgaact ttccttactg aagatgaata caaaattgag caagcatgtg atgaagagcg    660
atatagatct ctctacaata atgatgcaga agaatctatg taccacgagg aagaaatgaa    720
acgtcttcat caagctcttg atgaggaaaa cacatacagc caagttggat tcaattatga    780
tgacgagaaa aaattaacag aagattcaca aagttcaaag cagtcagaag gctcgcaaga    840
agaagatgaa ccatttctac ctgaagctga attagaagtc ccagaagata tgatagttcc    900
tgaaacgcaa aaactgaatg caatcataac caaaactgca ttgttcatta gtcgtcaagg    960
tagccaaatg gaaatactga taaaagcaaa gcaggccaat aacgatcaat tctcgttttt   1020
gtcaatcgat ggaaagttgc atccctacta taagcacgtc ttagaagcta taaagaatgg   1080
gacatataat ccagacaaac aacctgaaaa ggaagaatct gactctgggg aacaatcaga   1140
ggaagatgga gacaatgctt atctgcatcc gagtctggcg tcctccctca aagttgaagc   1200
ggcaccaagt attccaacta ttaactataa gccatcagca aattgctcgt attctatgct   1260
tgtaaataaa ataaccggta aa                                            1282
```

<210> SEQ ID NO 119
<211> LENGTH: 579
<212> TYPE: DNA
<213> ORGANISM: Leptocybes invasa
<220> FEATURE:
<223> OTHER INFORMATION: su(w[a]) RNA binding nuclear mRNA splicing, via spliceosome

<400> SEQUENCE: 119

```
ttaattctat ggttttatgt ctatagatat gatggtcgag gagccttggg agatctacgg     60
atatatgagc caccacctgg tggacatgac attcggacta tccttactga ggaggagtac    120
aaagttgagc aggcatgtga tgaggaacgc tatcgatctc tctacaacaa tgatgctgag    180
gaatcaatgt accatgagga agagatcaaa aggctacatc aggcattgga tgctgaaaac    240
tcatattctc aagtagcgtt caactatgac gatgaaaaga aatttgcaga agattcacaa    300
agtccaaagc agtcagaagg ctctcttgaa gaagatgaag catatatagc tgatcctgat    360
ttggatgtcc cagctgatat gaaagtaccc gaaacgcaaa aacacaatgc aatcgttaca    420
aaaactgcat tgtttatcag ccgtcaaggg ggtcagatgg aagttttaat aaaagcaaag    480
caagcaaata ataagcagtt cgaatttctg tccatggatg atgagctgca cccttattac    540
aagcacgttt tagaggccat taaatctggc aaatttaat                           579
```

<210> SEQ ID NO 120
<211> LENGTH: 981
<212> TYPE: DNA
<213> ORGANISM: Ophelimus maskelli
<220> FEATURE:
<223> OTHER INFORMATION: Trip1 translation initiation factor activity translational initiation

<400> SEQUENCE: 120

```
atgaaaccac tgatgttaca tgggcacgag cgtgccatca caaaaatcaa atacaacaga     60

gaaggagact tactttttc tgctagtaaa gataaacaac cgaatgtttg gtattcgtta    120

aacggagaaa gacttggaac attcaatgga cacaatggtt cagtttggtg tattgatgtc    180

aattgggata caacacgctt tttatccggt agtggtgaca acactttaag attatgggat    240

tgtgcaacag gaaaagagat tagtcaattg tccacaaaca gttcagtaag agcttgtgca    300

tttagctatt caggcaatct tgctgtatat gccactgaca aagctcttgg acaccaatgt    360

gaaatgttta ttattgacat taggtctcct gaaagtgttc tttctcaaga tgataacgtt    420

tgtagaactt cagtcagtgg ttcaaggatt tcatctctct tgtggggagc tctcgatgaa    480

tctattatta ctggtcatga aaatggtgat ttaaacatct gggacagtag gactggaaag    540

aaattgagtg atgctcaggg tcacaagggt caaattaatg acatgcagtt caacaaggat    600

ggaactatgt tcgttacagc ctcaaaggac cacactgcaa agttgtttga cagtgaatct    660

cttgttccat tgaaaacgta taaaacagaa aggccagtta actctgccac gatatctcca    720

atctttgatc acgtcgtagt tggaggtggt caagacgcta tggacgtcac cacgacatcg    780

acgaaacaag gaaaattcga tgctcgtttt ttccatcttg tctttgaaga agaatttgca    840

cgtttaaaag gtcactttgg tccaattaac tcgctggcct ttcatccaaa tggacgcagt    900

ctgtctactg gaggagagga tggttatatt cgtataaata catttgatca gtcctatttc    960

gattttcatt ttgagtacta a                                              981
```

<210> SEQ ID NO 121
<211> LENGTH: 939
<212> TYPE: DNA
<213> ORGANISM: Leptocybe invasa
<220> FEATURE:
<223> OTHER INFORMATION: Trip1 translation initiation factor activity translational initiation

<400> SEQUENCE: 121

```
atgaaacctt taatgttgca cgggcacgag cgtgccatta caaaaattaa gtataacaga     60

gaaggagatt tactgttttc agccagtaaa gacaaacagc ctaatgtatg gtactctctc    120

aatggtgaaa gattgggtac attcaatggc cacaacggtt cagtttggtg cattgacgtc    180

aattgggata ctacacgctt cctttctggc agtggtgaca acacactgag aatatgggat    240

tgtcaaacag gcaaagaaat aagccagttg tcaaccaaca gttctgtaag agcttgcgct    300

ttcagttact ctggtaacct tgctgtttat gcaactgaca aagctcttgg tcatcagtgt    360

gaaatgttca ttattgatat taggactcct gaaagtgtac tttctcagga agataatgtc    420

tgcagaacta tgatcggtgg ttccaggatc tcatctctcc tttggggagc tcttgatgaa    480

accatcataa ctggtcatga gaatggtgac ttgaccattt gggatagtag gactggaaag    540

aaattgagcg acgctcaggg acacaaaggt caaataaatg atatgcagtt caacaaagat    600

gccactatgt tttgcactgc ctccaaagat cacactgcta aattatttga cagcgaatct    660
```

```
ctagtttcac taaaaactta caaaactgag cggcccgtta actcggctac gatttctcca    720

atctttgatc atgtcgttgt tggaggtggt caagatgcca tggatgtaac aacgacgtcg    780

acgaaacaag gaaaattcga cgctcgtttt tatcatctcg tctttgaaga agaatttgca    840

cgtttaaagg gccatttcgg ccccatcaac tcattatcct tccacccgaa cggcagaagc    900

ttagccactg gaggagagga cggttacatt cgtatcaac                           939
```

```
<210> SEQ ID NO 122
<211> LENGTH: 1332
<212> TYPE: DNA
<213> ORGANISM: Ophelimus maskelli
<220> FEATURE:
<223> OTHER INFORMATION: protein phosphatase PP2A 55 kDa regulatory
      subunit-like isoform 1 (PPR)

<400> SEQUENCE: 122

ggcaacatgg actgcggcga ggcctcaagt aatggagaca ttcagtggag tttctcgcag     60

gtgaagggaa ccttagaaga tgatgtcaca gaagctgaca ttatctcatg tgtggagttc    120

aaccatgatg gtgaccttct ggcaacaggt gacaaaggtg gtcgtgtagt aatattccaa    180

agggatccac ttagcaaaac aactattcca agacgaggcg aatacaacgt ttacagtact    240

ttccaaagtc atgaacctga atttgattac ctgaagtcct tagaaataga agagaaaata    300

aacaaaataa gatggttaaa aagaaaaaac cctgctcact ttctactttc aacaaatgac    360

aaaaccatca aactttggaa agtcagtgaa agagataagc gagtcgaggg ttacaacaca    420

aaagaggaaa atggcgctat ccgcgatcct gcgtgcgtca ctgctttgag ggtacccact    480

ataaagccaa tggaactgat ggttgaagct tcaccaagga gaatatttgc taatgcgcac    540

acttaccaca taaacagtat aagtgtcaat agtgaccaag agacgtatct tagtgcagat    600

gaccttagaa ttaatctttg gcatttggag ataacggatc aaagttttaa tattgttgac    660

attaagccta ctaatatgga ggaactgaca gaagtcataa cggcagctga gttccatcca    720

gttgagtgta acctgctggt ttacagtagt agtaaaggaa caattcgtct gtgcgatatg    780

agatcggcgg cgctctgtga tcggcatagt aagctgtttg aagaacctga agatccgaca    840

aacagaagct tttctcgga aattatttca agtataagcg atgtcaagct tagtaactct    900

ggccgatata tgattagtag agactacctc agtgttaaag tgtgggattt gcatatggaa    960

acaaaaccca tcgaaagtta tcctgtacat gagtatttaa gatcaaagct gtgttcgttg   1020

tatgaaaatg actgcatctt tgataaattt gagtgctgct ggagcggcaa cgattcagcc   1080

ataatgactg gttcatataa caatttcttc cgcgttttcg atcgttcaac gaaacgagat   1140

gtaacattgg aagcgtcgcg ggacgttgct aagccaaaaa cccttctgaa accacgcaag   1200

gtctgtaccg gtggtaaacg taagaaggat gaaattagcg tggactgtct agactttaat   1260

aaaaagatcc tgcatactgc atggcatccc accgaaaaca ttgttgcggt agcggccaca   1320

aataatctct tt                                                       1332
```

```
<210> SEQ ID NO 123
<211> LENGTH: 1356
<212> TYPE: DNA
<213> ORGANISM: Leptocybe invasa
<220> FEATURE:
<223> OTHER INFORMATION: protein phosphatase PP2A 55 kDa regulatory
      subunit-like isoform 1 (PPR)

<400> SEQUENCE: 123

atgatcaaca ctgctgtcaa caagcgtgca ggtaatgggg acatccaatg gagtttctca     60
```

caggtgaagg gaaccctaga agatgatgtc acagaagctg acattatttc ctgtgtggaa 120
ttcaaccatg atggtgacct cttggcaact ggtgacaaag gtggtcgtgt agtcatattc 180
caaagggatc ctgttagtaa atcaattatt ccaaaacgag gcgaatacaa tgtatacagt 240
accttccaga gtcatgagcc tgagtttgat tatctgaaat cattagaaat agaggaaaaa 300
attaataaaa tacgatggct caagagaaaa aacccagctc actttttact ttcaacaaat 360
gacaaaacaa tcaaactgtg gaaagtcagt gaacgagaca agcgagttga gggttacaat 420
actaaggaag aaaatggcgc catccgcgat cgcgcttgta tcactgcctt gagggtaccc 480
actataaagc ccatggaact gatggttgag gcttcgccaa gaagaatatt cgctaatgcg 540
cacacctacc acataaacag tataagtgtc aatagtgacc aagagacgta tctcagtgcg 600
gatgacctaa ggatcaatct gtggcacctt gagattacgg atcaaagttt taatattgta 660
gacattaagc cgaccaacat ggaagagctg acggaggtca taacggcggc cgagttccat 720
ccagtcgagt gtaacttgct ggtctacagc agtagcaagg gaacgatccg cctgtgcgac 780
atgagatcag cagctctttg tgaccggcac agcaaactct tcgaggagcc cgaggatcct 840
accaaccgaa gcttcttctc tgaaatcatc tctagcataa gcgatgtcaa gctcagtaac 900
tctggcagat atatgattag cagagactac ctcagtgtta aggtatggga tttgcacatg 960
gagacgaaac caatcgagag ctatcctgta cacgagtatt tgcgatcgaa gttatgttcg 1020
ttgtacgaaa atgactgcat ctttgataag ttcgaatgct gctggagcgg caacgactcg 1080
gccataatga caggttcata taacaacttc ttccgcgttt tcgatcgctc aaccaaacga 1140
gacgtaacac tcgaagcatc gcgcgacgtc gccaagccaa aaactcttct aaaaccccgc 1200
aaggtgtgta ccggtggtaa acgcaagaag gatgagatta gtgtggactg tctggacttc 1260
aacaagaaaa tcttgcacac tgcatggcat cccaccgaaa atatcgttgc ggtcgcggcc 1320
acaaataacc tctttctgtt tcaagataag ctctag 1356

<210> SEQ ID NO 124
<211> LENGTH: 6103
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Gall Wasp DNA construct #3

<400> SEQUENCE: 124
agattagcct tttcaatttc agaaagaatg ctaacccaca gatggttaga gaggcttacg 60
cagcaggtct catcaagacg atctacccga gcaataatct ccaggaaatc aaataccttc 120
ccaagaaggt taaagatgca gtcaaaagat tcaggactaa ctgcatcaag aacacagaga 180
aagatatatt tctcaagatc agaagtacta ttccagtatg gacgattcaa ggcttgcttc 240
acaaaccaag gcaagtaata gagattggag tctctaaaaa ggtagttccc actgaatcaa 300
aggccatgga gtcaaagatt caaatagagg acctaacaga actcgccgta aagactggcg 360
aacagttcat acagagtctc ttacgactca atgacaagaa gaaaatcttc gtcaacatgg 420
tggagcacga cacacttgtc tactccaaaa atatcaaaga tacagtctca gaagaccaaa 480
gggcaattga gacttttcaa caaagggtaa tatccggaaa cctcctcgga ttccattgcc 540
cagctatctg tcactttatt gtgaagatag tggaaaagga aggtggctcc tacaaatgcc 600
atcattgcga taaaggaaag gccatcgttg aagatgcctc tgccgacagt ggtcccaaag 660

```
atggaccccc acccacgagg agcatcgtgg aaaaagaaga cgttccaacc acgtcttcaa    720
agcaagtgga ttgatgtgat atctccactg acgtaaggga tgacgcacaa tcccactatc    780
cttcgcaaga cccttcctct atataaggaa gttcatttca tttggagaga acacgggga    840
ctctagatat ttttacaaca attaccaaca acaacaaaca acaaacaaca ttacaattac    900
tatttacaat tacaagaggc gacggcagca agagcgatga gcccgaggat aacgtgaccg    960
agcagactca tcacattgtg attccgagct actcggcgtg gtttgactac aactacgttt   1020
aaagggccat ttcggcccca tcaactcatt atccttccac ccgaacggca gaagcttagc   1080
cactggagga gaggacggtt acattcgtat caacgaagag ctgacggagg tcataacggc   1140
ggccgagttc catccagtcg agtgtaactt gctggtctac agcagtagca agggaacgat   1200
ccgcctgtgc gacaggctcg aacgagccga ctaattgtct ttaaacgcgc gatataagcg   1260
cacaatgctc gagaaacgat aaactctatc gctctgtcgc gtgcgtggca tcttcgcgcg   1320
tgtcgcacag gcggatcgtt cccttgctac tgctgtagac cagcaagtta cactcgactg   1380
gatggaactc ggccgccgtt atgacctccg tcagctcttc gttgatacga atgtaaccgt   1440
cctctcctcc agtggctaag cttctgccgt tcgggtggaa ggataatgag ttgatggggc   1500
cgaaatggcc ctttaaacgt agttgtagtc aaaccacgcc gagtagctcg gaatcacaat   1560
gtgatgagtc tgctcggtca cgttatcctc gggctcatcg ctcttgctgc cgtcgcctct   1620
gtgtgtcttg tcttatctgg ttcgtggtgg tgagtttgtt acaaaaaaat ctattttccc   1680
tagttgagat gggaattgaa ctatctgttg ttatgtggat tttattttct tttttctctt   1740
tagaacctta tggttgtgtc aagaagtctt gtgtacttta gttttatatc tctgttttat   1800
ctcttctatt ttctttagga tgcttgtgat gatgctgttt ttttttgtcc ctaagcaaaa   1860
aaatatcata ttatatttgg tccttggttc attttttttgg ttttttttttg tcttcacata   1920
taaatattgt ttgaatgtct tcaatctttt atttgtatga gacaattatt taagtatcgg   1980
gtgacaatgc agctattatg tattgtcgat tgttatattg gcgcccaaaa tatatactta   2040
gcctaagaat ttggtaagtg agtggcttat gttttactcc agcaaaaatt gtgtgtgtat   2100
taccattctg atgcgaaaca agaaaagaat ttgatctaag aaaccaagtt tattcactag   2160
ttaaaaaaca aatgacctaa tgtaatcgac tccacatatc aaaatacgta aaacaaacat   2220
tgtatgttga caaaagggaa aagaaatgat ttatttggtt aaaaagaaag ctggattcaa   2280
ttgcaacagt ttagtcgaaa tcattttgaa aggcttacaa tggattgaat gtgaatattc   2340
cattaagccg cttctgtcta cacagaatgt tacgcttgga gagcagcaat cattttcacg   2400
tttttatctt tttaggtgga catgtatatt attggttacg cctttggagt ttttcgaaat   2460
ttatttcttt caaatcacaa gatgactaaa catcacaatc tgtttatctt cctaactagt   2520
taaatttttg tccccaccat ttaaataata gagggaccca aaataacatt gttgaaatgg   2580
aatataatca taaatgagtc acatcttcaa aatctgatca aatcacttgg aaaaaaaaag   2640
atcaagtcac atgcaaccag taaccacaat catattttgg ccggtctatc accatacaca   2700
ttgtttacag ctcacacttg tccctcctta tatttgttcg tatccatttg ttttcttctc   2760
tctctactct aatctcatct ttatgtttat cccttttga attttgaagc tactctgtcc   2820
tttgggtcca ccctccacca cctctaattt caatcacgtt aaaccggcca tattacttta   2880
aaccgaccgt tttctactaa taggaaaatc cgacccaaat ttttgactaa ttataagaca   2940
taccgccgct ataccatgat attgtcaaag aaaaagtttc taaccaataa ccactataga   3000
```

```
ctaaaagatt tcaaataatt tgattgatac tgcattgaac attctacaat tctacttata   3060
ttgtgtagtt caaataatga gaacatatcg gaaagactag ccgctattag attatgaatg   3120
cgtatgaata cattatacat tatagtatat atatatatat atacacatat attaaaatgt   3180
attactatat aataatttgt cttagtatag tactcaaaga aatagagttt tcttacgtag   3240
atgtcatata ttttagtcat tttaggcacc ttcctaactc aaatcacgaa tagaacttat   3300
gtagcaaaat gtaaacacat gaaatcattt attaattcgg gtccaacgta acccaccaca   3360
ccacagaaac tcattaaata gtattttttt ataaaactta agttatattc ctggatacag   3420
gaacgatact cctatataaa gagaacagca ttcaaaaggt cttatcatct tcttcactaa   3480
acaaaaaaaa acccttcaaa acatttcctt attctttctt cttcatctac aacaatcgac   3540
acttatcgtt tgaacccaac agagtacatc acgtcaacag cgtgcaggcg aaatttggct   3600
ggtgatgttt gtgcgataat gcgcgtacat gctttgacat taggtctcct gaaagtgttc   3660
tttctcaaga tgataacgtt tgtagaactt cagtcagtgg ttcaaggatt tcatctctct   3720
tgtggggagc tgtcgcctag actttaataa aaagatcctg catactgcat ggcatcccac   3780
cgaaaacatt gttgcggtag cggccacaaa taatcgcgcg cgaaacaacg gtaatcaacc   3840
ggcaattatt aatcgtacat gaggcgcgcc gcgatcgctg cattatccct cgtcatcacc   3900
aaagcgccac attatgcttc ttcgattatt tgtggccgct accgcaacaa tgttttcggt   3960
gggatgccat gcagtatgca ggatcttttt attaaagtct aggcgacagc tccccacaag   4020
agagatgaaa tccttgaacc actgactgaa gttctacaaa cgttatcatc ttgagaaaga   4080
acactttcag gagacctaat gtcaaagcat gtacgcgcat tatcgcacaa acatcaccag   4140
ccaaatttcg cctgcacgct gttgacgtga tgtactctgt tgggttcaaa cgataagtgt   4200
cgatggaaac aagtgatgat tcttgattca tgtttctgtg tttggttact ttgcctcgat   4260
ctttcttgtt ttgtttggag tttggtccgg tttcgttgta atttttatcc aatttgtatg   4320
aatattattt aatggatggc tgttttggtt ataaattaac taatggatgt atgaatatat   4380
agtttcacct aaataggtag ttgtaatgtt gtatagctaa ttatcgatcc atatatataa   4440
aaaatagatc gttacaattt tatgatatag taacaactaa caacaatgac aaattaatgg   4500
atggtttcaa gtagaagttt cgagatcatc gtcattaggt atattcttag ggatgttcca   4560
ctcatgagct ttccactctg gcaattgttg tatgacaacc tatgcaataa tttattaata   4620
tcaataaatc acatgcatgt atagaaaaaa atgaagatta tatattatag acagagaaaa   4680
agagaggtta tatattatta ccaatccggt agaatctgga tttcccacgt tggtttgaca   4740
agctagtctc caattttttg gtttctgtga aaacattatt cgattttact cccataacca   4800
agatgataca agattactaa atactatagg ataatttctt aaataaaact ataccctttt   4860
gagtttctcc ttctcaatat cagttcgcgg atttagaagc tcctttccat ttacaatctg   4920
aaaagaaata tccatcaata tctcataaac catcatttta cagtaagaac tgataacaaa   4980
aattttactt atttccttag aattaatctt aaaggtgata gtaaacaagg acgattagtc   5040
cgttggcaaa attggttcag caagtatcaa tttgatgtcg aacatcttga aggtgtaaaa   5100
aacgttttag cagattgcct cacgagagat tttaatgctt aaaaacgtaa gcgctgacgt   5160
atgatttcaa aaaacgcagc tataaaagaa gccctccagc ttcaaagttt tcatcaacac   5220
aaattctaaa aacaaaattt tttagagagg gggagtggtc gacatcgaca cttatcgttt   5280
gaacccaaca gagtacatca cgtcaacagc gtgcaggcga aatttggctg gtgatgtttg   5340
tgcgataatg cgcgtacatg ctttgacatt aggtctcctg aaagtgttct ttctcaagat   5400
```

```
gataacgttt gtagaacttc agtcagtggt tcaaggattt catctctctt gtggggagct   5460

gtcgcctaga ctttaataaa aagatcctgc atactgcatg gcatcccacc gaaaacattg   5520

ttgcggtagc ggccacaaat aatcagaggc gacggcagca agagcgatga gcccgaggat   5580

aacgtgaccg agcagactca tcacattgtg attccgagct actcggcgtg gtttgactac   5640

aactacgttt aaagggccat ttcggcccca tcaactcatt atccttccac ccgaacggca   5700

gaagcttagc cactggagga gaggacggtt acattcgtat caacgaagag ctgacggagg   5760

tcataacggc ggccgagttc catccagtcg agtgtaactt gctggtctac agcagtagca   5820

agggaacgat ccgcctgtgc gacagagctc gatcgttcaa acatttggca ataaagtttc   5880

ttaagattga atcctgttgc cggtcttgcg atgattatca tataatttct gttgaattac   5940

gttaagcatg taataattaa catgtaatgc atgacgttat ttatgagatg ggtttttatg   6000

attagagtcc cgcaattata catttaatac gcgatagaaa acaaaatata gcgcgcaaac   6060

taggataaat tatcgcgcgc ggtgtcatct atgttactag atc                      6103
```

<210> SEQ ID NO 125
<211> LENGTH: 993
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: AtDelta TIP promoter including 5UTR

<400> SEQUENCE: 125

```
taaataatag agggacccaa aataacattg ttgaaatgga atataatcat aaatgagtca     60

catcttcaaa atctgatcaa atcacttgga aaaaaaaaga tcaagtcaca tgcaaccagt    120

aaccacaatc atattttggc cggtctatca ccatacacat tgtttacagc tcacacttgt    180

ccctccttat atttgttcgt atccatttgt tttcttctct ctctactcta atctcatctt    240

tatgtttatc cctttttgaa ttttgaagct actctgtcct ttgggtccac cctccaccac    300

ctctaatttc aatcacgtta aaccggccat attactttaa accgaccgtt ttctactaat    360

aggaaaatcc gacccaaatt tttgactaat tataagacat accgccgcta taccatgata    420

ttgtcaaaga aaaagtttct aaccaataac cactatagac taaaagattt caaataattt    480

gattgatact gcattgaaca ttctacaatt ctacttatat tgtgtagttc aaataatgag    540

aacatatcgg aaagactagc cgctattaga ttatgaatgc gtatgaatac attatacatt    600

atagtatata tatatatata tacacatata ttaaaatgta ttactatata ataatttgtc    660

ttagtatagt actcaaagaa atagagtttt cttacgtaga tgtcatatat tttagtcatt    720

ttaggcacct tcctaactca aatcacgaat agaacttatg tagcaaaatg taaacacatg    780

aaatcattta ttaattcggg tccaacgtaa cccaccacac cacagaaact cattaaatag    840

tatttttttta taaaacttaa gttatattcc tggatacagg aacgatactc ctatataaag    900

agaacagcat tcaaaaggtc ttatcatctt cttcactaaa caaaaaaaaa cccttcaaaa    960

catttcctta ttctttcttc ttcatctaca aca                                 993
```

<210> SEQ ID NO 126
<211> LENGTH: 921
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: AtActin7 Terminator including 3UTR

<400> SEQUENCE: 126
gtgtgtcttg tcttatctgg ttcgtggtgg tgagtttgtt acaaaaaaat ctattttccc 60
tagttgagat gggaattgaa ctatctgttg ttatgtggat tttattttct tttttctctt 120
tagaacctta tggttgtgtc aagaagtctt gtgtacttta gttttatatc tctgttttat 180
ctcttctatt ttctttagga tgcttgtgat gatgctgttt ttttttgtcc ctaagcaaaa 240
aaatatcata ttatatttgg tccttggttc atttttttgg tttttttttg tcttcacata 300
taaatattgt ttgaatgtct tcaatctttt atttgtatga gacaattatt taagtatcgg 360
gtgacaatgc agctattatg tattgtcgat tgttatattg gcgcccaaaa tatatactta 420
gcctaagaat ttggtaagtg agtggcttat gttttactcc agcaaaaatt gtgtgtgtat 480
taccattctg atgcgaaaca agaaaagaat ttgatctaag aaaccaagtt tattcactag 540
ttaaaaaaca aatgacctaa tgtaatcgac tccacatatc aaaatacgta aaacaaacat 600
tgtatgttga caaaagggaa aagaaatgat ttatttggtt aaaaagaaag ctggattcaa 660
ttgcaacagt ttagtcgaaa tcattttgaa aggcttacaa tggattgaat gtgaatattc 720
cattaagccg cttctgtcta cacagaatgt tacgcttgga gagcagcaat cattttcacg 780
tttttatctt tttaggtgga catgtatatt attggttacg cctttggagt tttcgaaat 840 ttatttcttt caaatcacaa gatgactaaa catcacaatc tgtttatctt cctaactagt 900 taaattttg tccccaccat t 921

<210> SEQ ID NO 127
<211> LENGTH: 100
<212> TYPE: DNA
<213> ORGANISM: Leptocybe invasa
<220> FEATURE:
<223> OTHER INFORMATION: i7 100 bp of Li MOR gene

<400> SEQUENCE: 127
agaggcgacg gcagcaagag cgatgagccc gaggataacg tgaccgagca gactcatcac 60
attgtgattc cgagctactc ggcgtggttt gactacaact 100

<210> SEQ ID NO 128
<211> LENGTH: 100
<212> TYPE: DNA
<213> ORGANISM: Leptocybe invasa
<220> FEATURE:
<223> OTHER INFORMATION: i8 100 bp of Li TIF gene

<400> SEQUENCE: 128
acgtttaaag ggccatttcg gccccatcaa ctcattatcc ttccacccga acggcagaag 60
cttagccact ggaggagagg acggttacat tcgtatcaac 100

<210> SEQ ID NO 129
<211> LENGTH: 100
<212> TYPE: DNA
<213> ORGANISM: Leptocybe invasa
<220> FEATURE:
<223> OTHER INFORMATION: i9 100 bp of Li PPR gene

<400> SEQUENCE: 129
gaagagctga cggaggtcat aacggcggcc gagttccatc cagtcgagtg taacttgctg 60
gtctacagca gtagcaaggg aacgatccgc ctgtgcgaca 100

<210> SEQ ID NO 130
<211> LENGTH: 100
<212> TYPE: DNA
<213> ORGANISM: Ophelimus maskelli
<220> FEATURE:
<223> OTHER INFORMATION: m7 100 bp of Om MOR gene

<400> SEQUENCE: 130
atcgacactt atcgtttgaa cccaacagag tacatcacgt caacagcgtg caggcgaaat 60
ttggctggtg atgtttgtgc gataatgcgc gtacatgctt 100

<210> SEQ ID NO 131
<211> LENGTH: 100
<212> TYPE: DNA
<213> ORGANISM: Ophelimus maskelli
<220> FEATURE:
<223> OTHER INFORMATION: m8 100 bp of Om TIF gene; C 98 change to G to eliminate SacI site [C 472 change to G in target sequence]

<400> SEQUENCE: 131
tgacattagg tctcctgaaa gtgttctttc tcaagatgat aacgtttgta gaacttcagt 60
cagtggttca aggatttcat ctctcttgtg gggagctgtc 100

<210> SEQ ID NO 132
<211> LENGTH: 81
<212> TYPE: DNA
<213> ORGANISM: Ophelimus maskelli
<220> FEATURE:
<223> OTHER INFORMATION: m9 81 bp of Om PPR gene; T2C change to eliminate XbaI site

<400> SEQUENCE: 132
gcctagactt taataaaaag atcctgcata ctgcatggca tcccaccgaa aacattgttg 60
cggtagcggc cacaaataat c 81

<210> SEQ ID NO 133
<211> LENGTH: 706
<212> TYPE: DNA
<213> ORGANISM: Leptocybes invasa
<220> FEATURE:
<223> OTHER INFORMATION: RNAi 3

<400> SEQUENCE: 133
agaggcgacg gcagcaagag cgatgagccc gaggataacg tgaccgagca gactcatcac 60
attgtgattc cgagctactc ggcgtggttt gactacaact acgtttaaag ggccatttcg 120
gccccatcaa ctcattatcc ttccacccga acggcagaag cttagccact ggaggagagg 180
acggttacat tcgtatcaac gaagagctga cggaggtcat aacggcggcc gagttccatc 240
cagtcgagtg taacttgctg gtctacagca gtagcaaggg aacgatccgc ctgtgcgaca 300
ggctcgaacg agccgactaa ttgtctttaa acgcgcgata taagcgcaca atgctcgaga 360
aacgataaac tctatcgctc tgtcgcgtgc gtggcatctt cgcgcgtgtc gcacaggcgg 420
atcgttccct tgctactgct gtagaccagc aagttacact cgactggatg gaactcggcc 480
gccgttatga cctccgtcag ctcttcgttg atacgaatgt aaccgtcctc tcctccagtg 540
gctaagcttc tgccgttcgg gtggaaggat aatgagttga tggggccgaa atggcccttt 600
aaacgtagtt gtagtcaaac cacgccgagt agctcggaat cacaatgtga tgagtctgct 660
cggtcacgtt atcctcgggc tcatcgctct tgctgccgtc gcctct 706

<210> SEQ ID NO 134
<211> LENGTH: 3030
<212> TYPE: DNA
<213> ORGANISM: Apis mellifera
<220> FEATURE:
<223> OTHER INFORMATION: Honey Bee Apis mellifera; SWI/SNF complex
subunit MOR; XM_393008

<400> SEQUENCE: 134

```
atgcttgcgt taggacctaa aaaggacggt ggacccaata caaaattttt tgagtcccag     60
gaaattctta cacaacttga tgcagttaaa cagtggcttt tgaaaaactg taaaaagtat    120
gtccaaacgg atcctccaac taataaaagt ttagctacat tgatagtgca attattgcaa    180
tttcaagaag ataatttagg aaaaaatgtt tcaaaaccac caatgacaag acttcctatg    240
aaatgtttct tagattttaa accaggaggt ggtttgtgtc atattcttgc tactgcatat    300
cgttttaaac aagaacaagg atggcgtcga tttgacttcc ctgttggaaa atcaggatct    360
cgtatggaca gaacagtaga aatgttaatg gctgctgaaa gagctttggt acagaatcga    420
tgtatgatta taccaagtgt atacgtgaga cctgatgtag ataaatcaac agctgcaaaa    480
gtgaaagaag cagttcgtcg acatcaagtt gatcctatgg aagaagaata cgcgcgacct    540
tgtatgagac gagaaagatc tgttcttctt cattggtatt attttcccga tagttacgat    600
tcttggacta cattagatct tccttgggac ttcccagaag gtacacttac aaatacaaac    660
atgaaatcag tatacaaagt agccgcaaca tgggcattag atttagatca atataatgaa    720
tggatgaacg aagaagacta tgaaatagat gaaaatggtc aaaagaaaat acataaatat    780
cgactttcgg tagaagattt aatggctcaa ccatctcatc ctcctccttc agcgaaaaaa    840
ccaaaaagga aacgatctcc tagtccatcg ccgaaaccag gaaaacgtaa aagcgcaaga    900
gcaccatcag gtgttcaaac ttcatcttca tcatcacttg cgactccgaa gaaatcccgc    960
ggtggtggag aagaagaaga cgatctcact caaggaatgg aagatccacc agcagaacct   1020
cgaatagtag aagtagttgc tactcctacg aatccgccag tgactggtca aggtaatatt   1080
ccaacaagtg gcaatacttt aacgacaaca ggtagtaaga aacaagataa cgaacttcaa   1140
ccacttaaat ctggtaatat ggcggatttg gatgaaccta tggaaggaga taaaggaagt   1200
tctcaaagta ctcaagacag agaagaacga gatgcaagta aagaaagagg agaaggaaat   1260
aaaggagatg aaccagaaga taatgtcact gaacaaacac atcatattgt tgttcctagt   1320
tattctgctt ggtttgatta taattcgatt catactattg aaaaaagagc tttatctgaa   1380
ttttttaatg gtaaaaataa atctaaaacg ccagaaattt atcttgcata cagaaatttt   1440
atgatcgata cctatagatt aaatcctaca gaatatatta catcgactgc ttgtaggcgt   1500
aatttagcag gagatgtatg cgcaatcatg cgtgtacatg catttttgga acagtgggga   1560
cttattaatt accaagtgga tgcagaatca agaccaacac ccatgggtcc acctccaaca   1620
tcacatttcc atgtattatc agatactcca tcaggtttag ctccagttaa tccgaatcct   1680
ccgaaaacac cacaaccttc agccgcaaaa acattacttg atttagaaaa gaaatcatcc   1740
ggtttgggaa cagaagagaa agcttcagct ggagtgatgg caaattttgg attaaaaatt   1800
gatcaatatt caagaaaacc agcagttttg aagaacaaac aagctgccgg tgctactcgt   1860
gattggacag aacaagaaac acttttgcta ttagaaggat tagaattaca caaagatgat   1920
tggaataaag tctgtgaaca tgttggttcg agaacacagg atgaatgtat cttgcatttt   1980
ctacgacttc ccatagaaga tccttattta gaagaaagcg gaccagaggg tttgggtcca   2040
```

```
ttagcttacc aaccagtacc attttctaaa gctggcaatc ctgttatgag tactgtggca   2100

tttttggctt cagttgttga tcctagagtt gctgcaagtg cagccaaagc tgctatggaa   2160

gaatttgcag ctattaaaga tcaagtacca gctgctttat tagatcagca cttaagaaat   2220

gttcaagcta gtgctaactc tgatggtaag tttgatccag ctgcaggatt agcacaatca   2280

ggtatagctg ggactggacc acccgaacct cctgatgata cagcaccacc ttcaactacg   2340

ggtgctacag ttacatctcc acattcagca acaacaactt ctatggaaat gaaaaaggag   2400

gaacaagaaa agcctaaaga atctgaaata gatcaaaatc aattggacat aacaaaaaaa   2460

gaagacgaat taaaagaaac cgaagaagat gcaaaatcaa ccatggatgc tgaaactatg   2520

gaggcaaaag aaaagagaga taaggtggtg cgagatgctc agcttcaatc tgcagctgca   2580

gcagcgttag cagcagctgc cgttaaagca aaacatttgg cagctgtaga agaacgtaaa   2640

attaaagctt tggtggcgct gcttgttgaa acacaaatga agaaattaga aattaaatta   2700

cgtcattttg aagaattgga aacgacgatg gaacgagaac gtgaaggact tgaatatcaa   2760

cgacaacaac tcattactga aagacaacag tttcatttgg aacaattaaa agcagccgaa   2820

tttagagcta gacaacaagc gcatcagcgt ttagctcaag agcaacagca acaacaacaa   2880

aatcaacatt ctgcatggca acctactgtg caacagcagc agcaacagca acaacaacaa   2940

caacagcaac aacaacaaca acaacaacca ccgagccctc aagcatcagc ccaacaacca   3000

ccatcacata cacctccaca acaagcataa                                    3030
```

```
<210> SEQ ID NO 135
<211> LENGTH: 981
<212> TYPE: DNA
<213> ORGANISM: Apis mellifera
<220> FEATURE:
<223> OTHER INFORMATION: Honey Bee Apis mellifera; Translation
      Initiation Factor 3 Subunit 1; XM_392780

<400> SEQUENCE: 135

atgaaacctt taatgttaca tgggcacgaa cgtgcaataa cacaaatcaa atataataga     60

gaaggagatt tattattctc ttctagcaaa gataaaaagc caaatgtttg gtattctttg    120

aatggggaac gtcttggaag ttttaatgga cataatggtt ctgtatggtg tattgatgtt    180

aattgggata caacaagatt tttatctgga agtggtgata atacattaag agtttgggac    240

tgtcaaactg gaaaagaaat aggtttactt catacaaaca gttcagtgag aacatgtagc    300

tttagttact cagcaaatct tgctgtttat tcaacagata aagctttagg acatcaatgt    360

gaaatgttta ttatggatat taaaaatgtt gatgcagttt tatcacaagc agatgcaatt    420

tctagaattg ctgtgaatgg tcctagaatt tctgctattt tatggggtgc attagatgaa    480

acaattatta ctggccatga agatggtgaa atcactcttt gggatgttag gacaagaaaa    540

aaattgacaa gtgttaaagg tcataaatca caaataaatg atatgcaatt caacaaggat    600

ggtactatgt ttgtaactgc atcaaaagat aatactgcca aattatttga tagtgaatca    660

ttaatgttat tgaaaacata taaaacagaa agacctgtta attctgctac aatttctcca    720

atttttgatc atgtcgttct tggaggaggt caagatgcta tggatgtcac aacaacatca    780

actcgtcaag gaaaattcga ttctcgattt ttccatttag tatttgaaga agaatttgca    840

cgtttaaaag gacactttgg tccaattaat tctttagcat ttcatcctaa tggtcgaagt    900

tttcaacgg gtggggaaga tggttatgtt cgtattaata catttgacca atcttacttt     960

gacttccatt ttgaatatta a                                              981
```

<210> SEQ ID NO 136
<211> LENGTH: 1410
<212> TYPE: DNA
<213> ORGANISM: Apis mellifera
<220> FEATURE:
<223> OTHER INFORMATION: Honey Bee Apis mellifera; TWS Phosphatase PP2A; XM_394082

<400> SEQUENCE: 136

```
atgaagagcc cctccaacat catgaggcag tctagcctca ccaagcttgg ttccatgatc     60

aataccgccg tgaacaagag agtcggcaat ggtgacatac aatggtgttt ctctcaggtg    120

aaaggaacat tagaagacga tgtcactgaa gctgatataa tttcatgtgt tgaatttaac    180

catgatggtg atcttcttgc aacaggagat aaaggtggtc gggttgttat ttttcaaaga    240

gacccagtta gtaaaaacag tatacctcgg agaggtgaat acaatgtata cagcaccttt    300

caaagtcatg aacctgaatt tgattacctg aaatcattag aaatagaaga aaaaattaac    360

aaaattagat ggttaaaaag aaaaaatcca gcacattttt tactttccac aaatgataaa    420

acaattaaat tgtggaaagt cagtgaacga gataaaagag tagaaggcta taatacaaag    480

gaagaaaatg gtacaattcg tgatcctgct tgtatcactt ctttaagggt tccaactata    540

aagccaatgg aattaatggt agaagcatct ccaagaagaa tatttgccaa tgcgcacacc    600

tatcacataa acagtataag tgtcaacagt gatcaggaga catacctcag tgctgatgat    660

cttagaatta atctttggca tcttgagatc acagaccaga gttttaatat agtagatatt    720

aagccaacta atatggagga gctaactgaa gtaataaccg ctgcggaatt tcacccggca    780

gaatgtaatg tcttggtata tagtagcagt aaaggaacaa ttagactttg tgacatgaga    840

tctgctgcgc tttgcgatca acatagtaaa ctctttgaag aaccagaaga tccaacaaat    900

agaagtttct tctctgaaat catttccagt ataagcgatg taaaacttag taattcagga    960

agatatatga tcagtagaga ctacctcagt gtgaaagtgt gggatttaca aatggaaaca   1020

agacctattg aatgttaccc tgtacatgaa tacctaagat caaagttatg ttcattatat   1080

gaaaatgatt gtatctttga caaattcgag tgttgttgga gtggtaatga ttctgctatt   1140

atgacgggtt catacaataa tttcttcaga gtattcgatc gtacgactaa acgtgatctc   1200

acattggaag cagcacgtga cattgccaaa ccaaaaacac ttttaaaacc acgtaaggtt   1260

tgtactggcg gtaaacgtaa aaaagatgaa attagcgttg actgtcttga tttcaataaa   1320

aaaatattac atactgcttg gcatccttct gaaaatgtag tagctgttgc tgctacaaat   1380

aatctcttcc tatttcaaga caaactctag                                     1410
```

<210> SEQ ID NO 137
<211> LENGTH: 706
<212> TYPE: DNA
<213> ORGANISM: Leptocybes invasa
<220> FEATURE:
<223> OTHER INFORMATION: dsRNA module from Li RNAi1

<400> SEQUENCE: 137

```
tctcttactt ccaaaaatca aactcaagtt aacgcgtcgt tggccccgca agaaaattat     60

tccatttctg aaggctgggg gagtgacgaa gatggttctg ggtgccataa gaacggcagg    120

tattttcgga ttgcacggtg gtcagttagc aaaacggttg gatgaagaat ttgaaaaatt    180

gggagctacc actttattgt cgcaaaccgg tagagccggt gaagcccgct gatgcgactg    240

ctgccgctgt accgccagct gctgctgcca acgccacggc cactgcgccg gcgacgaacg    300
```

```
ggctcgaacg agccgactaa ttgtctttaa acgcgcgata taagcgcaca atgctcgaga    360

aacgataaac tctatcgctc tgtcgcgtgc gtggcatctt cgcgcgcgtt cgtcgccggc    420

gcagtggccg tggcgttggc agcagcagct ggcggtacag cggcagcagt cgcatcagcg    480

ggcttcaccg gctctaccgg tttgcgacaa taaagtggta gctcccaatt tttcaaattc    540

ttcatccaac cgttttgcta actgaccacc gtgcaatccg aaaatacctg ccgttcttat    600

ggcacccaga accatcttcg tcactccccc agccttcaga aatggaataa ttttcttgcg    660

gggccaacga cgcgttaact tgagtttgat ttttggaagt aagaga                   706


<210> SEQ ID NO 138
<211> LENGTH: 708
<212> TYPE: DNA
<213> ORGANISM: Ophelimus maskelli
<220> FEATURE:
<223> OTHER INFORMATION: dsRNA module from Om RNAi1

<400> SEQUENCE: 138

aggctacttg attcaacata ttcataattt aaatacatca gaagatcagt ataactttac     60

ttcagttaaa gctcaagaaa ctattcctgt ttctttatgt agagccagtg aaaccggctg    120

acggttcagc agttccagtt actccagtac cagcaacggc cacggcaatg gatggaacgg    180

ctacgggatc aacgagtagt attgagcgat attcaatgga tgactggcgt cacttcagac    240

gaaggtgctt taaggactcc tggaattttc ggtctcttcg acggtgaatt agcagagcgt    300

gcgcgcgaaa caacggtaat caaccggcaa ttattaatcg tacatgcgcg gcgcaggcgc    360

gcctgcatta tccctcgtca tcaccaaagc gccacattat gcttcttcac gctctgctaa    420

ttcaccgtcg aagagaccga aaattccagg agtccttaaa gcaccttcgt ctgaagtgac    480

gccagtcatc cattgaatat cgctcaatac tactcgttga tcccgtagcc gttccatcca    540

ttgccgtggc cgttgctggt actggagtaa ctggaactgc tgaaccgtca gccggtttca    600

ctggctctac ataaagaaac aggaatagtt tcttgagctt taactgaagt aaagttatac    660

tgatcttctg atgtatttaa attatgaata tgttgaatca agtagcct                 708


<210> SEQ ID NO 139
<211> LENGTH: 108
<212> TYPE: DNA
<213> ORGANISM: Leptocybes invasa
<220> FEATURE:
<223> OTHER INFORMATION: L3 - loop #3 Li Chitin Synthase intron with
      Asc1 site

<400> SEQUENCE: 139

gcgcgcgaaa caacggtaat caaccggcaa ttattaatcg tacatgaggc gcgccgcgat     60

cgctgcatta tccctcgtca tcaccaaagc gccacattat gcttcttc                 108


<210> SEQ ID NO 140
<211> LENGTH: 100
<212> TYPE: DNA
<213> ORGANISM: Leptocybes invasa

<400> SEQUENCE: 140

agaggcgacg gcagcaagag cgatgagccc gaggataacg tgaccgagca gactcatcac     60

attgtgattc cgagctactc ggcgtggttt gactacaact                         100


<210> SEQ ID NO 141
<211> LENGTH: 706
<212> TYPE: DNA
```

<213> ORGANISM: Leptocybes invasa
<220> FEATURE:
<223> OTHER INFORMATION: dsRNA module from Li RNAi2

<400> SEQUENCE: 141
ccggtggcgt ggtgccggat ctgttcgaga tactgcccaa cggagagacc gagatcgtca 60
acgctgattt tcacactccg gttcacatgc tgctgttcgc gccagttgac cagcgacgtt 120
agcaagttgc tcaaattccc gctcaagccg atccgcgagg aatggaacag cggtatcgaa 180
gcacttactg atgctctcaa catggtattg cgaccgtgga cctgggtgaa gacgtacttt 240
tacagctttt ggccgtcgct gttgcctgag gacgaaatcc cgcgtatgtt ccccctgctc 300
ggctcgaacg agccgactaa ttgtctttaa acgcgcgata taagcgcaca atgctcgaga 360
aacgataaac tctatcgctc tgtcgcgtgc gtggcatctt cgcgcggagc agggggaaca 420
tacgcgggat ttcgtcctca ggcaacagcg acggccaaaa gctgtaaaag tacgtcttca 480
cccaggtcca cggtcgcaat accatgttga gagcatcagt aagtgcttcg ataccgctgt 540
tccattcctc gcggatcggc ttgagcggga atttgagcaa cttgctaacg tcgctggtca 600
actggcgcga acagcagcat gtgaaccgga gtgtgaaaat cagcgttgac gatctcggtc 660
tctccgttgg gcagtatctc gaacagatcc ggcaccacgc caccgg 706

<210> SEQ ID NO 142
<211> LENGTH: 708
<212> TYPE: DNA
<213> ORGANISM: Ophelimus maskelli
<220> FEATURE:
<223> OTHER INFORMATION: dsRNA module from Om RNAi2

<400> SEQUENCE: 142
tctgatgtcg agaaacaaaa acaaggatga gtcgcgtcgt tttgtgctgg tactcgtcga 60
tctagctgca ctggctgcac aaacaacagc tttcgtcgtt gttgactagc gacgttagca 120
aactgctcaa attccctctg aaaccaatcc gtgaagaatg gaacagcggt gttgaggctc 180
tgagcgatgc tctgaatctt ttatgtatta ctgggtaccc aacaaagcta ccagtgcctt 240
ccggatttac tctgaaactt tgaacaagca cagcatgaag tataaaatgg ataacgtacc 300
gcgcgcgaaa caacggtaat caaccggcaa ttattaatcg tacatgcgcg gcgcaggcgc 360
gcctgcatta tccctcgtca tcaccaaagc gccacattat gcttcttcgg tacgttatcc 420
attttatact tcatgctgtg cttgttcaaa gtttcagagt aaatccggaa ggcactggta 480
gctttgttgg gtacccagta atacataaaa gattcagagc atcgctcaga gcctcaacac 540
cgctgttcca ttcttcacgg attggtttca gagggaattt gagcagtttg ctaacgtcgc 600
tagtcaacaa cgacgaaagc tgttgtttgt gcagccagtg cagctagatc gacgagtacc 660
agcacaaaac gacgcgactc atccttgttt ttgtttctcg acatcaga 708

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: VCE-F2 primer; nucleotides 1026-1052 of Nv gene XM_001599205
<220> FEATURE:
<221> NAME/KEY: modified_base
<222> LOCATION: (7)..(7)
<223> OTHER INFORMATION: a, c, t, g, unknown or other

<400> SEQUENCE: 143
gataccntty agacctgtwa ttgarcc 27

<210> SEQ ID NO 144
<211> LENGTH: 28
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: VCE-F2 reverse primer; nucleotides 1628-1655 of Nv gene XM_001599205

<400> SEQUENCE: 144
ggatttccag awttkgcraa rttrtacc 28

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Chitin Synthase primer; Nucleotides 158-178 of Nv gene XM_001602240.2

<400> SEQUENCE: 145
ggrayccacc gccgaagatc g 21

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Chitin Synthase reverse primer; Nucleotides 1197-1220 of Nv gene XM_001602240.2

<400> SEQUENCE: 146
gcgaatttac cgaakatgta catg 24

<210> SEQ ID NO 147
<211> LENGTH: 670
<212> TYPE: DNA
<213> ORGANISM: Ophelimus maskelli
<220> FEATURE:
<223> OTHER INFORMATION: RNAi3

<400> SEQUENCE: 147
atcgacactt atcgtttgaa cccaacagag tacatcacgt caacagcgtg caggcgaaat 60
ttggctggtg atgtttgtgc gataatgcgc gtacatgctt tgacattagg tctcctgaaa 120
gtgttctttc tcaagatgat aacgtttgta gaacttcagt cagtggttca aggatttcat 180
ctctcttgtg gggagctgtc gcctagactt taataaaaag atcctgcata ctgcatggca 240
tcccaccgaa aacattgttg cggtagcggc cacaaataat cgcgcgcgaa acaacggtaa 300
tcaaccggca attattaatc gtacatgagg cgcgccgcga tcgctgcatt atccctcgtc 360
atcaccaaag cgccacatta tgcttcttcg attatttgtg gccgctaccg caacaatgtt 420
ttcggtggga tgccatgcag tatgcaggat ctttttatta aagtctaggc gacagctccc 480

```
cacaagagag atgaaatcct tgaaccactg actgaagttc tacaaacgtt atcatcttga    540

gaaagaacac tttcaggaga cctaatgtca aagcatgtac gcgcattatc gcacaaacat    600

caccagccaa atttcgcctg cacgctgttg acgtgatgta ctctgttggg ttcaaacgat    660

aagtgtcgat                                                           670
```

<210> SEQ ID NO 148
<211> LENGTH: 308
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148

```
atcgacactt atcgtttgaa cccaacagag tacatcacgt caacagcgtg caggcgaaat     60

ttggctggtg atgtttgtgc gataatgcgc gtacatgctt gcgcgcgaaa caacggtaat    120

caaccggcaa ttattaatcg tacatgcgcg gcgcaggcgc gcctgcatta tccctcgtca    180

tcaccaaagc gccacattat gcttcttcaa gcatgtacgc gcattatcgc acaaacatca    240

ccagccaaat ttcgcctgca cgctgttgac gtgatgtact ctgttgggtt caaacgataa    300

gtgtcgat                                                             308
```

<210> SEQ ID NO 149
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 149

```
atcgacactt atcgtttgaa cccaacagag tacatcacgt caacagcgtg caggcgaaat     60

ttggctggtg atgtttgtgc gataatgcgc gtacatgctt                          100
```

<210> SEQ ID NO 150
<211> LENGTH: 100
<212> TYPE: DNA
<213> ORGANISM: Leptocybe invasa
<220> FEATURE:
<223> OTHER INFORMATION: 736-835 of SEQ ID NO: 46

<400> SEQUENCE: 150

```
cgttccaccg tcgctcagat cgtcaagcgt cttaccgaca gcggtgccat caactattcc     60

atcatcgtct cggccaccgc ctccgacgcc gctcccctgc                          100
```

<210> SEQ ID NO 151
<211> LENGTH: 100
<212> TYPE: DNA
<213> ORGANISM: Leptocybe invasa
<220> FEATURE:
<223> OTHER INFORMATION: 443-542 of SEQ ID NO: 48

<400> SEQUENCE: 151

```
ttggaggcac caaagctgtg gatgacaaga ccaagccact caaccctgtt gcaggtggac     60

caggtatggc agacaaacct acaggtacca aatacgttcc                          100
```

<210> SEQ ID NO 152
<211> LENGTH: 100
<212> TYPE: DNA
<213> ORGANISM: Leptocybe invasa
<220> FEATURE:
<223> OTHER INFORMATION: 822-921 of SEQ ID NO: 49

<400> SEQUENCE: 152
taccatacca tccgcagcaa cgctgatcaa catccgcaat gcccgcaagc actttgagaa 60
gctcgagaga gcaagtcaga gttcgtcttt gagcagatag 100

<210> SEQ ID NO 153
<211> LENGTH: 75
<212> TYPE: DNA
<213> ORGANISM: Leptocybe invasa
<220> FEATURE:
<223> OTHER INFORMATION: 113-187 of SEQ ID NO: 50

<400> SEQUENCE: 153
tagcaagacg acttgagcaa cacgaggtac cagctaatgt tattgcagct gccgcaacag 60
ccgcatcatt agctt 75

<210> SEQ ID NO 154
<211> LENGTH: 100
<212> TYPE: DNA
<213> ORGANISM: Leptocybe invasa
<220> FEATURE:
<223> OTHER INFORMATION: 304-403 of SEQ ID NO: 51

<400> SEQUENCE: 154
aatcgtgcct actatctcga tgaaattcaa aagcgtacca aagacggtag acgcaaacgc 60
ggcgaggatg gcggcgctga ggatttaccc gatcagccgt 100

<210> SEQ ID NO 155
<211> LENGTH: 100
<212> TYPE: DNA
<213> ORGANISM: Leptocybe invasa
<220> FEATURE:
<223> OTHER INFORMATION: 187-286 of SEQ ID NO: 53

<400> SEQUENCE: 155
gacaatgcgg ccatcgagca gacggccttg gcgccgcact accgcgtgca catgcatccc 60
gaccgaggcg agtacaacct gcagatccgc aacgtgtcgt 100

<210> SEQ ID NO 156
<211> LENGTH: 100
<212> TYPE: DNA
<213> ORGANISM: Leptocybe invasa
<220> FEATURE:
<223> OTHER INFORMATION: 454-553 of SEQ ID NO: 55

<400> SEQUENCE: 156
ttgctaatgg atgaacgtgc gattcgccgg gcgaggaatg atttacgttt tcgtggtgtc 60
aagggtacca ctggtactca ggcttccttc ttgcaactct 100

<210> SEQ ID NO 157
<211> LENGTH: 64
<212> TYPE: DNA
<213> ORGANISM: Leptocybe invasa
<220> FEATURE:
<223> OTHER INFORMATION: 476-539 of SEQ ID NO: 57

<400> SEQUENCE: 157
tagtcagatc attttcgagc ggtaagcgcg aaggcggcga cttcgtttgt gcagttgttt 60
cacc 64

<210> SEQ ID NO 158
<211> LENGTH: 91
<212> TYPE: DNA
<213> ORGANISM: Leptocybe invasa
<220> FEATURE:
<223> OTHER INFORMATION: 247-337 of SEQ ID NO: 58

<400> SEQUENCE: 158
tgggtcagct tgaaaaccgt tttcttccca atcactcttt tgactctttg ctggtactgg 60
cgaagaatcc acatgctatc aagatctcca g 91

<210> SEQ ID NO 159
<211> LENGTH: 100
<212> TYPE: DNA
<213> ORGANISM: Leptocybe invasa
<220> FEATURE:
<223> OTHER INFORMATION: 712-711 of SEQ ID NO: 60

<400> SEQUENCE: 159
aatgttcttc ttacagttgc aagtaaagtc aataaatatc ccagtgtttt agctatcaac 60
aagcacctca cacaaactac tttgaaaatt gataaattaa 100

<210> SEQ ID NO 160
<211> LENGTH: 100
<212> TYPE: DNA
<213> ORGANISM: Leptocybe invasa
<220> FEATURE:
<223> OTHER INFORMATION: 1-100 of SEQ ID NO: 62

<400> SEQUENCE: 160
atgtcttcct ttgtgaaagc tagtctgttg agtatagttt taatgatagt tttaattgac 60
tgtgctgagg gactcagcaa atattccgaa caggctaata 100

<210> SEQ ID NO 161
<211> LENGTH: 100
<212> TYPE: DNA
<213> ORGANISM: Leptocybe invasa
<220> FEATURE:
<223> OTHER INFORMATION: 817-916 of SEQ ID NO: 64

<400> SEQUENCE: 161
gatccatcat tcaattcctc gccagctaaa gaatttcctg gtggcccgac gcccgaagaa 60
ttatggaagc tactggatca gtgcgatctg agcaatagcc 100

<210> SEQ ID NO 162
<211> LENGTH: 100
<212> TYPE: DNA
<213> ORGANISM: Leptocybe invasa
<220> FEATURE:
<223> OTHER INFORMATION: 2142-2241 of SEQ ID NO: 66

<400> SEQUENCE: 162
actgcgtcgt tcgaagcgca gtctcgtcca ttcgagtttg attccaaagc agctgacgac 60
gagtctgcac caaccgtcat cggcgaacgc atcgatcgga 100

<210> SEQ ID NO 163
<211> LENGTH: 100
<212> TYPE: DNA
<213> ORGANISM: Leptocybe invasa
<220> FEATURE:
<223> OTHER INFORMATION: 473-572 of SEQ ID NO: 68

<400> SEQUENCE: 163
aggagttcgc ggcgctgctc tcgcagtcgg tatcgcaggg cttcgaggcg gtttaccagc 60
tgacgcgcat gtgcaccatc cggatgagct tcgtgaaggg 100

<210> SEQ ID NO 164
<211> LENGTH: 100
<212> TYPE: DNA
<213> ORGANISM: Leptocybe invasa
<220> FEATURE:
<223> OTHER INFORMATION: 921-1020 of SEQ ID NO: 70

<400> SEQUENCE: 164
gtctttagaa gagttacagt tggatgtttt tgtttgtaac aacgataaca ctgaggcaga 60
tgattactgt tttgcagtaa ctggattaaa attacaagga 100

<210> SEQ ID NO 165
<211> LENGTH: 100
<212> TYPE: DNA
<213> ORGANISM: Leptocybe invasa
<220> FEATURE:
<223> OTHER INFORMATION: 902-1001 of SEQ ID NO: 72

<400> SEQUENCE: 165
aagctaaaaa gtattcgata gagccgttaa ggtcgagctg gagtttggag agtatttcac 60
agcggtcgtt caaggagaca cgcctgaaga catatatgca 100

<210> SEQ ID NO 166
<211> LENGTH: 100
<212> TYPE: DNA
<213> ORGANISM: Leptocybe invasa
<220> FEATURE:
<223> OTHER INFORMATION: 1482-1581 of SEQ ID NO: 74

<400> SEQUENCE: 166
ccagtcaatg atacccccct cgccgccacc cgactcctcc tcccactgtt ccgagcagca 60
gctgggcgaa cggatacact atcaggagac gctggaggag 100

<210> SEQ ID NO 167
<211> LENGTH: 100
<212> TYPE: DNA
<213> ORGANISM: Leptocybe invasa
<220> FEATURE:
<223> OTHER INFORMATION: 6779-6878 of SEQ ID NO: 75

<400> SEQUENCE: 167
atacggtcgg caacggcgtg gcctcggtgc cgatgggtct cacggccgag gagatcgaac 60
gcttgaattc gcgtcctcgc acgtccagcc tcgtgtcgac 100

<210> SEQ ID NO 168
<211> LENGTH: 100
<212> TYPE: DNA
<213> ORGANISM: Leptocybe invasa
<220> FEATURE:
<223> OTHER INFORMATION: 210-3009 of SEQ ID NO: 76

<400> SEQUENCE: 168
agtttaccaa aagtcaacta acacttatgc gccgtacaac aagaactgga taaaggataa 60
aattcacgtt ctacttcgtc gagcagccga actcgaatga 100

<210> SEQ ID NO 169
<211> LENGTH: 100
<212> TYPE: DNA

```
<213> ORGANISM: Leptocybe invasa
<220> FEATURE:
<223> OTHER INFORMATION: 280-379 of SEQ ID NO: 77

<400> SEQUENCE: 169

ccaaagaaag ggagagactt gaaagacaag gataaggata aggacaaaag taaggatagg     60

gacaaagatg aggttgagga taaaaagact gataataaag                          100


<210> SEQ ID NO 170
<211> LENGTH: 71
<212> TYPE: DNA
<213> ORGANISM: Leptocybe invasa
<220> FEATURE:
<223> OTHER INFORMATION: 228-298 of SEQ ID NO: 79

<400> SEQUENCE: 170

tacaaatgga gaagaagtac ccccaaacga gggagtaggc agcaatgaca aaggaggtga     60

tcgtgcagaa a                                                          71


<210> SEQ ID NO 171
<211> LENGTH: 100
<212> TYPE: DNA
<213> ORGANISM: Leptocybe invasa
<220> FEATURE:
<223> OTHER INFORMATION: 258-357 of SEQ ID NO: 80

<400> SEQUENCE: 171

cagtaataat ggctacgcga gtccaatgag ctcgggaagc tacgatcctt acagtcccaa     60

cggaaaaatt ggaagggacg atctgtcgcc gccgagctcg                          100


<210> SEQ ID NO 172
<211> LENGTH: 89
<212> TYPE: DNA
<213> ORGANISM: Leptocybe invasa
<220> FEATURE:
<223> OTHER INFORMATION: 1131-1219 of SEQ ID NO: 82

<400> SEQUENCE: 172

gaagtgtgac cgtcgtaccg gtaaaaccac cgaggagaac cccaaggcca tcaagtccgg     60

tgacgccgcc atcgtcaact tggtgccaa                                       89


<210> SEQ ID NO 173
<211> LENGTH: 100
<212> TYPE: DNA
<213> ORGANISM: Leptocybe invasa
<220> FEATURE:
<223> OTHER INFORMATION: 1156-1255 of SEQ ID NO: 84

<400> SEQUENCE: 173

gaatcttata gttggaagaa gttggatgca aaagatgaga aaactaagga acttgtcaaa     60

caatatctca gctggtctgg tgctgataag gatggtcgta                          100


<210> SEQ ID NO 174
<211> LENGTH: 100
<212> TYPE: DNA
<213> ORGANISM: Leptocybe invasa
<220> FEATURE:
<223> OTHER INFORMATION: 353-452 of SEQ ID NO: 86

<400> SEQUENCE: 174

tgcattatga aactgatgaa cagttagaag aactctatca aaagacagca tggcattttg     60

aggaaaaata taagaaacag aaagcttcgg cttatgattt                          100
```

<210> SEQ ID NO 175
<211> LENGTH: 100
<212> TYPE: DNA
<213> ORGANISM: Leptocybe invasa
<220> FEATURE:
<223> OTHER INFORMATION: 463-562 of SEQ ID NO: 88

<400> SEQUENCE: 175
agttcagacg atgacaaacc tcagcatgtt ggagctgact acttcagaaa aactgcggca 60
aaagacggtg atgagaatga gaagcacgtc aaagaaagga 100

<210> SEQ ID NO 176
<211> LENGTH: 100
<212> TYPE: DNA
<213> ORGANISM: Leptocybe invasa
<220> FEATURE:
<223> OTHER INFORMATION: 824-923 of SEQ ID NO: 90

<400> SEQUENCE: 176
aggagctgct gaccgaggca gagcgcctcg aaatcaagtc caaggcaccg cttgtccttg 60
ctgaactctt gttcgaccag cacatcgccg ccgaggttaa 100

<210> SEQ ID NO 177
<211> LENGTH: 100
<212> TYPE: DNA
<213> ORGANISM: Leptocybe invasa
<220> FEATURE:
<223> OTHER INFORMATION: 2516-2615 of SEQ ID NO: 92

<400> SEQUENCE: 177
gctgcgacgt ttcgtcaaag gcgcagtcta gtaacgctca gaacaatgtc gctccactgc 60
cgaaccccta cggagatcca gcttgtggtc aagattacct 100

<210> SEQ ID NO 178
<211> LENGTH: 100
<212> TYPE: DNA
<213> ORGANISM: Leptocybe invasa
<220> FEATURE:
<223> OTHER INFORMATION: 1-100 of SEQ ID NO: 94

<400> SEQUENCE: 178
cagactgagc aggttgtcga gggtaatgga gaagttgctc cagcaaagaa ggaagtcaag 60
ggtacctacg tatccatcca cagcagtggt ttcagagatt 100

<210> SEQ ID NO 179
<211> LENGTH: 100
<212> TYPE: DNA
<213> ORGANISM: Leptocybe invasa
<220> FEATURE:
<223> OTHER INFORMATION: 1134-1233 of SEQ ID NO: 96

<400> SEQUENCE: 179
gctaaacaat ggcaatcctt tgcctcacgc cgttttgctg cttcttcagt cggcaaggtg 60
cacgtcgaag cacacgaaaa tgcgtcttgt cgaccaagct 100

<210> SEQ ID NO 180
<211> LENGTH: 100
<212> TYPE: DNA
<213> ORGANISM: Leptocybe invasa
<220> FEATURE:
<223> OTHER INFORMATION: 399-497 of SEQ ID NO: 98

<400> SEQUENCE: 180
ggagcgcgag gcttcaggtg caaatccggg ctcagtcgcc gggtctgaag cagagagttg 60
taccagcagc tcgcacgccg acatgcccgt cgaactgatt 100

<210> SEQ ID NO 181
<211> LENGTH: 100
<212> TYPE: DNA
<213> ORGANISM: Leptocybe invasa
<220> FEATURE:
<223> OTHER INFORMATION: 746-845 of SEQ ID NO: 100

<400> SEQUENCE: 181
gtatttcaaa catagaaaag gttgatagag aaaaagtaaa ggagaagttc acagagctag 60
aagctgaggt atcttttgta gatttcaaag ctggagatac 100

<210> SEQ ID NO 182
<211> LENGTH: 85
<212> TYPE: DNA
<213> ORGANISM: Leptocybe invasa
<220> FEATURE:
<223> OTHER INFORMATION: 222-306 of SEQ ID NO: 102

<400> SEQUENCE: 182
tcatgcagag tttcagaatt tgttagattc tgacaaaaat ttagatttgg gaagaatgta 60
ccaactggtt gccagaatac caaat 85

<210> SEQ ID NO 183
<211> LENGTH: 100
<212> TYPE: DNA
<213> ORGANISM: Leptocybe invasa
<220> FEATURE:
<223> OTHER INFORMATION: 1537-1636 of SEQ ID NO: 106

<400> SEQUENCE: 183
cccgagtcgc cgctgatgcg cgcggcagca atgcgcaaac cgagtcctcc gctgatccct 60
aaagacccgc cagccaccgt ggtgatcaag caggcgccat 100

<210> SEQ ID NO 184
<211> LENGTH: 100
<212> TYPE: DNA
<213> ORGANISM: Leptocybe invasa
<220> FEATURE:
<223> OTHER INFORMATION: 379-478 of SEQ ID NO: 108

<400> SEQUENCE: 184
ttggttgatt tcaccgacga ggagggatac ggaaagtact tggacttgca cgagtgctac 60
gagaagtata tcaatctgaa ggggattgag aaggttgact 100

<210> SEQ ID NO 185
<211> LENGTH: 100
<212> TYPE: DNA
<213> ORGANISM: Leptocybe invasa
<220> FEATURE:
<223> OTHER INFORMATION: 1895-1994 of SEQ ID NO: 111

<400> SEQUENCE: 185
aaatgccaca gcagcagcag cagcagcagc agcagaccat gcaaaataat ccaatgcagg 60
caggccaagg tggcgcgcca ggtggtcctg gtggcgcacc 100

<210> SEQ ID NO 186
<211> LENGTH: 100

<212> TYPE: DNA
<213> ORGANISM: Leptocybe invasa
<220> FEATURE:
<223> OTHER INFORMATION: 252-351 of SEQ ID NO: 113

<400> SEQUENCE: 186
tgttataacg gaagttcgag ttggaaataa gaatttaccg tctggaatgt ctattcacga 60
cttctcgcca atctctatgc tccagccaag catgtctttg 100

<210> SEQ ID NO 187
<211> LENGTH: 100
<212> TYPE: DNA
<213> ORGANISM: Leptocybe invasa
<220> FEATURE:
<223> OTHER INFORMATION: 31-130 of SEQ ID NO: 114

<400> SEQUENCE: 187
ggaacaacag aattcacaag tacaccacca gaaggcacaa ctgaagaacc aggaacatcc 60
tctcctatgg atatatttac gccaagctcc gttgattcgg 100

<210> SEQ ID NO 188
<211> LENGTH: 100
<212> TYPE: DNA
<213> ORGANISM: Leptocybe invasa
<220> FEATURE:
<223> OTHER INFORMATION: 1212-1311 of SEQ ID NO: 116

<400> SEQUENCE: 188
gaatcatcag tcaacgccga cagcgggtat gatgcacatg gttcagatga tgccgatcgg 60
cgtagacgaa acggagtcgg tggcacaaga tcttccaccg 100

<210> SEQ ID NO 189
<211> LENGTH: 100
<212> TYPE: DNA
<213> ORGANISM: Leptocybe invasa
<220> FEATURE:
<223> OTHER INFORMATION: 199-298 of SEQ ID NO: 117

<400> SEQUENCE: 189
aggaggccgc tcattcttca gctcatcaac gccactagcg aatttggtga attcttgcat 60
tgcaaaggca agaagttcgt cgacttcgaa gaggtgcgaa 100

<210> SEQ ID NO 190
<211> LENGTH: 100
<212> TYPE: DNA
<213> ORGANISM: Leptocybe invasa
<220> FEATURE:
<223> OTHER INFORMATION: 63-162 of SEQ ID NO: 119

<400> SEQUENCE: 190
atatgagcca ccacctggtg gacatgacat tcggactatc cttactgagg aggagtacaa 60
agttgagcag gcatgtgatg aggaacgcta tcgatctctc 100

<210> SEQ ID NO 191
<211> LENGTH: 100
<212> TYPE: DNA
<213> ORGANISM: Ophelimus maskelli
<220> FEATURE:
<223> OTHER INFORMATION: 1-100 of SEQ ID NO: 45

<400> SEQUENCE: 191
atggccctgt tgaccgtacg tcttgctgcc tcggtagcga gacaactacc cagcacccag 60
gtgagctggc ctgctgctgc tattgcctca aggaaatatc 100

<210> SEQ ID NO 192
<211> LENGTH: 100
<212> TYPE: DNA
<213> ORGANISM: Ophelimus maskelli
<220> FEATURE:
<223> OTHER INFORMATION: 474-573 of SEQ ID NO: 47

<400> SEQUENCE: 192
gaaacctctc aatccagctg ctggagctgg tatggctgat attagtaaac caacaggtac 60
caaatatgtt cctccaagca tgcgagatgg aggtaacaaa 100

<210> SEQ ID NO 193
<211> LENGTH: 100
<212> TYPE: DNA
<213> ORGANISM: Ophelimus maskelli
<220> FEATURE:
<223> OTHER INFORMATION: 412-511 of SEQ ID NO: 52

<400> SEQUENCE: 193
ggtgacgagg ttatagcttc cgactgctcg cctccgcgtg gaccgactgg tcagtggcag 60
gaaatggact gtcgcagatc taatccatgc aacatttccg 100

<210> SEQ ID NO 194
<211> LENGTH: 100
<212> TYPE: DNA
<213> ORGANISM: Ophelimus maskelli
<220> FEATURE:
<223> OTHER INFORMATION: 303-402 of SEQ ID NO: 54

<400> SEQUENCE: 194
cctgctaccg aaactcggtg ccgtgataaa tcgtcttgcc aaattcgccc tcgacaaccg 60
ttcgatacca acattgggtt ttactcatct gcaaccggct 100

<210> SEQ ID NO 195
<211> LENGTH: 89
<212> TYPE: DNA
<213> ORGANISM: Ophelimus maskelli
<220> FEATURE:
<223> OTHER INFORMATION: 802-890 of SEQ ID NO: 56

<400> SEQUENCE: 195
actgaatgta ttggtactta taagtccctt ggagcagctg atttgaacgt aaatagtgtg 60
ctctcattac ccaaaaaccc agaacattt 89

<210> SEQ ID NO 196
<211> LENGTH: 100
<212> TYPE: DNA
<213> ORGANISM: Ophelimus maskelli
<220> FEATURE:
<223> OTHER INFORMATION: 837-935 of SEQ ID NO: 59

<400> SEQUENCE: 196
taaatattgt tcctgaatca ttaatcaaac gtgaatcaag agaacctact cttacaggag 60
acaagcttta tcaattagat ctagaaagtg ctcttcaatt 100

<210> SEQ ID NO 197
<211> LENGTH: 100
<212> TYPE: DNA
<213> ORGANISM: Ophelimus maskelli
<220> FEATURE:
<223> OTHER INFORMATION: 466-565 of SEQ ID NO: 61

<400> SEQUENCE: 197
gaatttagtc accaccaaga caaaattgac gagtatatga gtttactatc agaagttgaa 60
gctggagatc cagatagaca tgaaaacagt cttcatgaaa 100

<210> SEQ ID NO 198
<211> LENGTH: 100
<212> TYPE: DNA
<213> ORGANISM: Ophelimus maskelli
<220> FEATURE:
<223> OTHER INFORMATION: 574-673 of SEQ ID NO: 63

<400> SEQUENCE: 198
ggtaattgga tcgagatagc ttatggtaca aagtcgggaa gtgtacgtgt gatcgtacag 60
catccagaaa ccgtcggtca tggacctcaa ctttttcaaa 100

<210> SEQ ID NO 199
<211> LENGTH: 100
<212> TYPE: DNA
<213> ORGANISM: Ophelimus maskelli
<220> FEATURE:
<223> OTHER INFORMATION: 839-938 of SEQ ID NO: 65

<400> SEQUENCE: 199
ttatgaaagc acccttcccg gaagagggcg agggcgaagt cgttcttctg aaaggagaaa 60
cagttttagt tattggagcg tcgcagagac gcggacactt 100

<210> SEQ ID NO 200
<211> LENGTH: 100
<212> TYPE: DNA
<213> ORGANISM: Ophelimus maskelli
<220> FEATURE:
<223> OTHER INFORMATION: 615-714 of SEQ ID NO: 67

<400> SEQUENCE: 200
gccttatcaa gagcctcgtt actgggcttc gatagcctac tacgagctta attgtcgtgt 60
tggtgaagtt tttcattgtc agtcaccttc cgtgatagta 100

<210> SEQ ID NO 201
<211> LENGTH: 100
<212> TYPE: DNA
<213> ORGANISM: Ophelimus maskelli
<220> FEATURE:
<223> OTHER INFORMATION: 1016-1115 of SEQ ID NO: 69

<400> SEQUENCE: 201
gcatccacat gaaaggttta agttctgaac tcacatatga tgatgaattt tcattctttt 60
tgcgaggaaa ggaaggagtt ttaaatattc gattggatca 100

<210> SEQ ID NO 202
<211> LENGTH: 100
<212> TYPE: DNA
<213> ORGANISM: Ophelimus maskelli
<220> FEATURE:
<223> OTHER INFORMATION: 872-971 of SEQ ID NO: 71

<400> SEQUENCE: 202
agatgaataa gagaatgaca gaggatcaag ctaaaaaagt atttgacaga gctgtgaaag 60
tggagcaaga atttggagaa tacttcacag ctgtcgtcca 100

<210> SEQ ID NO 203

<211> LENGTH: 100
<212> TYPE: DNA
<213> ORGANISM: Ophelimus maskelli
<220> FEATURE:
<223> OTHER INFORMATION: 298-397 of SEQ ID NO: 73

<400> SEQUENCE: 203
atttccgagt atctctgcaa tactttcctc gacaaacaac aggagctgga tctgccgtcg 60
ctgcgcatcg acgaagcggt gccgggcagc atggacgcgc 100

<210> SEQ ID NO 204
<211> LENGTH: 78
<212> TYPE: DNA
<213> ORGANISM: Ophelimus maskelli
<220> FEATURE:
<223> OTHER INFORMATION: 414-491 of SEQ ID NO: 78

<400> SEQUENCE: 204
tgatcaacaa caaggacagg gtggtgggcc aaatgctaat tcagtgaaaa tacctccaag 60
caaagctact aaattatg 78

<210> SEQ ID NO 205
<211> LENGTH: 98
<212> TYPE: DNA
<213> ORGANISM: Ophelimus maskelli
<220> FEATURE:
<223> OTHER INFORMATION: 1130-1227 of SEQ ID NO: 81

<400> SEQUENCE: 205
agaagtgtga ccgtcgtacc ggtaaaacta ctgaagaagc ccccaaggct atcaagtctg 60
gtgatgccgc cattgtcaac cttgtgccaa gcaagccc 98

<210> SEQ ID NO 206
<211> LENGTH: 100
<212> TYPE: DNA
<213> ORGANISM: Ophelimus maskelli
<220> FEATURE:
<223> OTHER INFORMATION: 849-948 of SEQ ID NO: 83

<400> SEQUENCE: 206
caaacggtgt tacagtaatg aggatgaagc aaagtctatt ccttacttct gggagaagtt 60
tgacccacaa aattacagca tttggttctg tgaatacaaa 100

<210> SEQ ID NO 207
<211> LENGTH: 100
<212> TYPE: DNA
<213> ORGANISM: Ophelimus maskelli
<220> FEATURE:
<223> OTHER INFORMATION: 903-1002 of SEQ ID NO: 85

<400> SEQUENCE: 207
tgacgatgat gaggaagaaa atgaaggcat gggtaacttc agtggtgatg atgaaaatga 60
cgaaaatgac aaagaaaatc aatctggaga ggatgattaa 100

<210> SEQ ID NO 208
<211> LENGTH: 100
<212> TYPE: DNA
<213> ORGANISM: Ophelimus maskelli
<220> FEATURE:
<223> OTHER INFORMATION: 493-592 of SEQ ID NO: 87

<400> SEQUENCE: 208
gttggtgctg attacttcag aaaaacacaa aaagaaggtg atgaagagaa aattggtggt 60

```
ggtggtggta agagagatcg gcctcgtaaa gagcggccaa                          100


<210> SEQ ID NO 209
<211> LENGTH: 100
<212> TYPE: DNA
<213> ORGANISM: Ophelimus maskelli
<220> FEATURE:
<223> OTHER INFORMATION: 848-947 of SEQ ID NO: 89

<400> SEQUENCE: 209

ccaaggcacc tctcgtactt gctgagctgc tgttcgatca gcacatcgct gctcaggtga     60

agaagtatcg cttgttgctt ttgcgtttta ctctgaatga                          100


<210> SEQ ID NO 210
<211> LENGTH: 100
<212> TYPE: DNA
<213> ORGANISM: Ophelimus maskelli
<220> FEATURE:
<223> OTHER INFORMATION: 240-339 of SEQ ID NO: 91

<400> SEQUENCE: 210

tataagggta ggtctgctcg cggcggaagg agcggctacg gatataaatg aggacttttc     60

gggcgaggag aggatcgacg gagagcagac catagaagcg                          100


<210> SEQ ID NO 211
<211> LENGTH: 100
<212> TYPE: DNA
<213> ORGANISM: Ophelimus maskelli
<220> FEATURE:
<223> OTHER INFORMATION: 426-525 of SEQ ID NO: 93

<400> SEQUENCE: 211

agaggtctta aaaagtacac aacctcacat agttgtggga acaccaggac gtattttagc     60

cctcattaaa agtaaaaaac tcaaccttaa gaacataaag                          100


<210> SEQ ID NO 212
<211> LENGTH: 100
<212> TYPE: DNA
<213> ORGANISM: Ophelimus maskelli
<220> FEATURE:
<223> OTHER INFORMATION: 1037-1136 of SEQ ID NO: 95

<400> SEQUENCE: 212

atgctcatgc ttcgggacta ctcgatatag cacgcaagat aatgatttcg gcacgaattg     60

atttgtgcat ctgcagtgaa gagaagatcg gagttaccaa                          100


<210> SEQ ID NO 213
<211> LENGTH: 101
<212> TYPE: DNA
<213> ORGANISM: Ophelimus maskelli
<220> FEATURE:
<223> OTHER INFORMATION: 534-634 of SEQ ID NO: 97

<400> SEQUENCE: 213

gctattatta agacttccag cactacgttc cattggccta aaatgtactg aacacctctg     60

tgttttcaga ctgctaggtg ataagcaact tgatgaatta c                        101


<210> SEQ ID NO 214
<211> LENGTH: 100
<212> TYPE: DNA
<213> ORGANISM: Ophelimus maskelli
<220> FEATURE:
```

<223> OTHER INFORMATION: 867-966 of SEQ ID NO: 99

<400> SEQUENCE: 214
catcatacac atttcaaatt taccaaagga tatgaagagg gaagatataa aaaaacagtt 60
aatggaattg gatacggaag tagcttacat cgacttcaac 100

<210> SEQ ID NO 215
<211> LENGTH: 75
<212> TYPE: DNA
<213> ORGANISM: Ophelimus maskelli
<220> FEATURE:
<223> OTHER INFORMATION: 615-689 of SEQ ID NO: 101

<400> SEQUENCE: 215
aatggacttt ctattacaag tcatacaaat tttactaaaa gcaaaacttc ttgtaacaaa 60
tgatgatgaa tctga 75

<210> SEQ ID NO 216
<211> LENGTH: 100
<212> TYPE: DNA
<213> ORGANISM: Ophelimus maskelli
<220> FEATURE:
<223> OTHER INFORMATION: 1034-1133 of SEQ ID NO: 105

<400> SEQUENCE: 216
gcgtcggcac cgacctcttc cgacgtatgg gccgtgtcag cctggatgtt gacagtctcg 60
gtggcataat cccactgtcc tcatcgagct tctccatcgg 100

<210> SEQ ID NO 217
<211> LENGTH: 100
<212> TYPE: DNA
<213> ORGANISM: Ophelimus maskelli
<220> FEATURE:
<223> OTHER INFORMATION: 455-554 of SEQ ID NO: 107

<400> SEQUENCE: 217
tagagtattt gttagatttc ttgggaagag ttcgaccgct ccttgatgtc gatgctgaat 60
taatagaaac taataatgac tttgaagaaa agtgggaaac 100

<210> SEQ ID NO 218
<211> LENGTH: 100
<212> TYPE: DNA
<213> ORGANISM: Ophelimus maskelli
<220> FEATURE:
<223> OTHER INFORMATION: 179-278 of SEQ ID NO: 109

<400> SEQUENCE: 218
atattgttgg tgctgcaaaa actggttcgg gaaagacttt agcttttctt attcctgcca 60
ttgaacttat ttataaactc aaatttatgc ctagaaatgg 100

<210> SEQ ID NO 219
<211> LENGTH: 100
<212> TYPE: DNA
<213> ORGANISM: Ophelimus maskelli
<220> FEATURE:
<223> OTHER INFORMATION: 977-1076 of SEQ ID NO: 110

<400> SEQUENCE: 219
aaattcagca agaaaccggc gctaaactgc agttcgtgtc aatcgatggt caagacgctt 60
ctcacggaga tcgtaaggtc cttatcaacg gtagtatgga 100

<210> SEQ ID NO 220
<211> LENGTH: 85
<212> TYPE: DNA
<213> ORGANISM: Ophelimus maskelli
<220> FEATURE:
<223> OTHER INFORMATION: 852-936 of SEQ ID NO: 112

<400> SEQUENCE: 220
tgttaaatta caaacgttaa atttagctgt gaaattgtat cttaataacc cagaacaaac 60
gaaaaagatt tgtcaatatg tattt 85

<210> SEQ ID NO 221
<211> LENGTH: 100
<212> TYPE: DNA
<213> ORGANISM: Ophelimus maskelli
<220> FEATURE:
<223> OTHER INFORMATION: 738-837 of SEQ ID NO: 115

<400> SEQUENCE: 221
cgaacatcag ttgtatagtc cgcccatgtc cgagcattat cggcaggcga attacgctgg 60
acagatggca ggctacgaag atagtgcata cggttctcac 100

<210> SEQ ID NO 222
<211> LENGTH: 100
<212> TYPE: DNA
<213> ORGANISM: Ophelimus maskelli
<220> FEATURE:
<223> OTHER INFORMATION: 1101-1200 of SEQ ID NO: 118

<400> SEQUENCE: 222
aacctgaaaa ggaagaatct gactctgggg aacaatcaga ggaagatgga gacaatgctt 60
atctgcatcc gagtctggcg tcctccctca aagttgaagc 100

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
cgaacgagcc gactaattgt ctt 23

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
cacgcgacag agcgatagag ttta 24

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 225
caagaatccc atctcttgct tgc 23

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 226
agcaagaatc ttccgtaatc g 21

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 227
gaagatggtt ctgggtgcca taag 24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 228
ctggagtaac tggaactgct gaac 24

<210> SEQ ID NO 229
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 229
gcgcgaaaca acggtaatca ac 22

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 230
cgctttggtg atgacgaggg ataa 24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 231
gatctgttcg agatactgcc caac 24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 232
ctagatcgac gagtaccagc acaa 24

<210> SEQ ID NO 233
<211> LENGTH: 306
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 233
agaggcgacg gcagcaagag cgatgagccc gaggataacg tgaccgagca gactcatcac 60
attgtgattc cgagctactc ggcgtggttt gactacaact ggctcgaacg agccgactaa 120
ttgtctttaa acgcgcgata taagcgcaca atgctcgaga aacgataaac tctatcgctc 180
tgtcgcgtgc gtggcatctt cgcgcgagtt gtagtcaaac cacgccgagt agctcggaat 240
cacaatgtga tgagtctgct cggtcacgtt atcctcgggc tcatcgctct tgctgccgtc 300
gcctct 306

<210> SEQ ID NO 234
<211> LENGTH: 100
<212> TYPE: DNA
<213> ORGANISM: Ophelimus maskelli
<220> FEATURE:
<223> OTHER INFORMATION: m1* 100 bp of Om Alpha COP gene

<400> SEQUENCE: 234
aggctacttg attcaacata ttcataattt aaatacatca gaagatcagt ataactttac 60
ttcagttaaa gctcaagaaa ctattcctgt ttatttatgt 100

<210> SEQ ID NO 235
<211> LENGTH: 540
<212> TYPE: DNA
<213> ORGANISM: Leptocybes invasa
<220> FEATURE:
<223> OTHER INFORMATION: 3' fragment from same gene as SEQ ID NO: 60

<400> SEQUENCE: 235
ttatctgcaa tgcatggcta cataaaacac ttttttggct gctctaattg ctcggaccat 60
tttcaagaaa tgtctaagaa aagaaaactg tttgaagtcc gtggaaatga tgagagtatt 120
ctatggttgt ggaaagcaca taatgaagtg aataaaagat tagctggtga tgaatctgaa 180
gatccacagc acaaaaagat tcagtatcct tcttctgacc attgtccgca atgtaaacga 240
tttgatggta agtgggatga aaatgaagtt ttaatctatt tgaaaaccaa gtatggtagg 300
tctaatatag atctcaaagg tattaatggt cagatactta agcaagaaag agatatcagt 360
gcatcaagct ctggtgcgag tcatcgtaaa attggttggg actttacaat atttgatatt 420
agcatttgtg ttatgctgta tgttatatca gctgcaatac tgactctggt atgcataaaa 480
tttgcttata aaagaactta caagagaaaa atataccaac atatatttgg tctagcatga 540

```
<210> SEQ ID NO 236
<211> LENGTH: 441
<212> TYPE: DNA
<213> ORGANISM: Leptocybes invasa
<220> FEATURE:
<223> OTHER INFORMATION: 3' fragment from same gene as SEQ ID NO: 64

<400> SEQUENCE: 236

ggtccatttg gcgaacaaga cgatgagcaa gtatttgtac aaaaggtcgt gcccgagact     60

gatcaattgt ttgtaagatt ggcatccaac gggaaacgcg tttgcgtaat acaatctgtt    120

gacggcagcg ttatcacctc attttgcgta cacgagtgcg aaggttccag tcgtatgggt    180

tcgagaccac ggcgcttcat attcaccggc cactccaatg gagctataca aatgtgggac    240

ttgacgactg ccctcgatcc atcattcaat tcctcgccag ctaaagaatt tcctggtggc    300

ccgacgcccg aagaattatg gaagctactg gatcagtgcg atctgagcaa tagccattgt    360

tccactccgt gcattagtcc gtccccgtcg ctcattgcct ctggaccgag gatcaaagca    420

agtaacgtct tatttctgaa t                                              441


<210> SEQ ID NO 237
<211> LENGTH: 1359
<212> TYPE: DNA
<213> ORGANISM: Ophelimus maskelli
<220> FEATURE:
<223> OTHER INFORMATION: 3' fragment from same gene as SEQ ID NO: 69

<400> SEQUENCE: 237

gcttttcgac ctgatcgtgt tatagccgct gcatcactgg tagtttctgc tatctttgga     60

gaatcattta tgaacgcagc agaaaccgaa ttagatcttt cttttgtcgt tgagcacgaa    120

ttaaaatcat acgttccagc attgttatgc tcggttcctg gatttgatgc atcaagccgt    180

gtagatgatt tagcagctga gtctggcaaa caaattgtta gcatcgctat tggttcagca    240

gaaggattta gtcaagctga tagagctatt aatacagctg tgaaaactgg aagatgggtt    300

cttttaaaaa atgttcattt agctccacaa tggcttgtac aattagaaaa gaaacttcat    360

agtttacaac cacaccataa ttttagatta tttttaacta tggaaattaa ctcgaaagta    420

ccagtgaact tgcttagagc aggaagaata tttgtttttg aaccacctcc tggaataaga    480

gcaaatctat taagaacatt taatacagta ccagcttcac gaatgatgaa gccacctcat    540

gaaagagcca gattatactt cttattagct tggtttcatg caattataca agaacgctta    600

cgttatgtac ctctaggctg ggctaagcac tatgaattca atgaaagtga tctaagagtg    660

gcttgtgata cattagatgc atggattgag tctactgcaa tgggaagaac gaatctgcca    720

ccagaaaagg tgccttggga tgccataatt actctaatgt ctcaatgtac gtatggtggt    780

aaaattgata atgatttcga tcagagatta ctaacgtcgt ttcttcggaa actttttaca    840

ccaagatctt ttgagaatga ctttgcattg gttgctaata tcgatgggac tttaggaaat    900

caacgacata ttactatgcc agatggtacg cgaagagatc attttcttaa atggattgaa    960

gctctgtctg ataaacaaac accatcttgg cttggtttac caaacaatgc tgaaaaggtt   1020

cttcttacta caagaggaac aaatttagtt tcaaaattat taaaaatgca acagctagaa   1080

gatgaagatg aattagctta ttctgtcgat gaattattag atgttcaacg cgaagcagat   1140

tctgatggta ggccgtcttg gatgaaaaca ttacataatt cagcttcaac atggttgcag   1200

ctattaccga aaaacttagt tatattaaaa agaacagttg ataatataaa agatcctttg   1260

taccgatatt ttgaaagaga agttaatgga ggatcaaaat tgttgaagga tgtaattcat   1320
```

gatttagaag atgttgtttc gatttgcaag ggtgaaaaa 1359

<210> SEQ ID NO 238
<211> LENGTH: 768
<212> TYPE: DNA
<213> ORGANISM: Ophelimus maskelli
<220> FEATURE:
<223> OTHER INFORMATION: 3' fragment from same gene as SEQ ID NO: 73

<400> SEQUENCE: 238
aagctactca gcgacatcga caaatggggt atcgacatat tcaggatagg cgagctgagc 60
aacaacaggc cgctgacctg cgtcgcctac acggccttcc acagcagaga cctgttcaag 120
ctgataatga taccgccaaa gactttcgtc accttcatga tgacgctcga ggatcactac 180
gtcaaggata atccgttcca caacagtctt cacgcggccg acgtcaccca gtccacgaat 240
accctgctta atactcctgc actcgagtct gtgttcacgc cactagaaat aacagctgcc 300
ctattcgccg caaccattca cgatgttgat catcctggtg tcaccaatca gtttcttatt 360
aactcaagtt cagaattagc tttgatgtac aacgacgaat ccgtgttaga gaatcatcat 420
ctggcagttg cgttcaaact gctgcagaac gaaggctgcg acattttcgt caactgcacg 480
aaaaaacagc gtcagaccct gaggaaaatg gtcatcgaca tggtgctgtc gacggacatg 540
tctaagcaca tgtccctcct cgcggacctc aaaaccatgg tggaaaccaa aaaggtcgcc 600
gggtcgggcg tgttgttgct cgacaattat acagatcgaa tccaggtgct cgaaaacctg 660
gtgcactgcg ccgatctgtc gaacccaacg aaaccgctgc cactgtaccg tcgctgggtc 720
gatctgttga tggaggagtt cttcatgcag ggcgaccgcg agcgcgag 768

<210> SEQ ID NO 239
<211> LENGTH: 2160
<212> TYPE: DNA
<213> ORGANISM: Leptocybes invasa
<220> FEATURE:
<223> OTHER INFORMATION: Median fragment from same gene as SEQ ID NOS
75 & 240

<400> SEQUENCE: 239
gctagcatcg gcgctagtgt gctgcaggtg tccgcgagcg atcgcgacga gggtgcgaac 60
ggtcgcgtgc gctacagcat cgcgtccggc gacgagaatc gcgacttcgc gatcagcgag 120
gacacgggcg tggtgcgcgt gtcgaagaat ttgaattacg agcgcaagtc gcgctacagg 180
ctgcgcgttc gcgccgagga ttgcgccggg gacgcgcgtc cgcggctgga gtcgcgcgcc 240
gacgacgccg acgtgatcgt cagcgtgctc gacatcaacg acaacgcgcc cgcgttcttg 300
cactcgccct acgtggcgca cgtcatggag aacatgctac cgcccaacgc tggattcgtc 360
atgcaggtga aggcatacga cgcggacacg ccgccttaca acgatcaggt gcgttacttc 420
ctgaaggagg gtgacaccga cttgttccgc atcaacgcca gtaccggcga gatttttctg 480
cttagaccgc tcgaccgcga gcgcgtcgcc gagtacgtgc tcactctcgt cgcgatggac 540
accggtacgc caccgttgac gggcgctggt ctggtgaaga tcacagtgct ggacgtgaac 600
gaccacagtc cagaatttca caggcaggaa tacgtggcga gggtcagcga aaatcttaag 660
caaggtacct ggctcgctaa tcctcgagcg cgagacagcg acgagggact caacgccaga 720
atacgataca gtttactagg tgacaaagcc gagcgtttcc acgtgaattc gagtaccggc 780
gagatcgtca cactcgagcg tctcgatcgc gagcaaaccg ccgtttacca cctgacgctg 840
gtagctcaag actctagtcc aacggaacca cgtgcctcag ccgtcaatct gacgataatc 900

```
gttgacgatc tgaacgacaa tgcaccgagg ttttctagtc ccagatacac cgcttacgtt    960

cctgattcga caaccaaagg tgacttcgtg tttggcgcga aggcaattga cgacgacgtc   1020

ggcgagaatt cccggatagt ctatcgtctc cacggcaaag attctcatcg ctttaccatt   1080

gacgcgaaca acggcgtgat ccgctcgaga gaagttttat cgtctgcagg tcaaaacact   1140

taccaattgc aaatcgaagc gtcggattgc ggcgtcgagc cgcgttccgt cacggccgac   1200

ctcgttgttc atctgtggga gcggcaattg ttcccgagct ttcaaccggc caccgcgacg   1260

agattcatct tgaaggagga cgcgcccgag gggaaattag tgacgacgct cagtgctacg   1320

acaccaaaga ccgggccagc gagtgatttg gtattcggta tggctggcgg aaatgtcggc   1380

gaggctttgc gaatcgattc gcattccgga gaggtggcga tcgcgtctgg atttgacttc   1440

gagacagcgc cgtactacga agcttgggtc gaggtccgtg actccgggaa tccgtcgctt   1500

cgaagcgtca ttcaactgct cgtcaacgtg accgacgcca acgacaatgc accgctcatg   1560

gattcggcgg tttacaacgc ctcggtaccc gaggaggaat atccaccgca attcgtgagc   1620

aaaatctcag ccaaagacgc ggactctggg cagaatcgag agatcacgta tcacttggtc   1680

gacgacttcg aggagacgtt catcatcgac gagacgaccg gtgaaatcag caccaatgcc   1740

aaattagaca gagaagagat cccctcgtac gagctgatcg tggaagcgcg cgatcgcgga   1800

acgccaagcc tgacgggcac agccacggtg ctcgtgtcga tactcgacaa aaatgacaat   1860

ccgccgcgtt tcacgcgcct ctacagcgtg aacgtgacgg agaactcgga aatcggcgcc   1920

ttcgtcattc gcatcacgag cagcgatcag gacgagggac cgaacgctaa cgtgtcgtac   1980

agcttcaccg acaatccaag tggaaagttc gccgtcgatc cgctcagcgg caacgtgacg   2040

gtggccggac acctcgatcg cgaggtgcaa gacgagtacc tgctgaaggt gtcggtggtg   2100

gacggcgctt gggtcgccga gacaccgctg accatcagca ttcaggatca gaacgacaat   2160
```

```
<210> SEQ ID NO 240
<211> LENGTH: 1890
<212> TYPE: DNA
<213> ORGANISM: Leptocybes invasa
<220> FEATURE:
<223> OTHER INFORMATION: 3' fragment from same gene as SEQ ID NOS
      75 & 239

<400> SEQUENCE: 240

gccgacggcc gatggcacaa cttgacactg cactctcagg cccgaggact gaagatgtac     60

gtcgacggcg agttggccgg cgacgagtta gattcggccg gggttcacga cttcctggat    120

ccgtacttga ctctgctgac cgtcggcggc gtcaggcgcg acttgtatct cgcctacgac    180

ggctcgccga agtccttcga gggctgcttg gccaacttca cggtgaacgg cgaggcgcag    240

ccgttcaacg gctcgggctc gatcttcccg caggtgatct atcacggcaa cgttcatctc    300

ggctgccgcg gtcccatcgg catcgccgcg gccaccgccg ccgatccgct cagcgtcggc    360

atcaccctcg tcatcgtgtt cttcatcgtt ctcctcgtgg cgatactcgc gagcttcgtg    420

atctttcggc tgcgccgtca gaacaaggag aaatccgcga ccaccgtggt cgtcaacaag    480

aacaccaacg ccattctcac cggcaactcg ctggtgtcgt cgcaaccgga caatctgatg    540

accagacacg agaacacgta catctccgac ggctcggatc tgcgcaacgt gcgaccgccg    600

gagctggtct cgaagaagta caaagagcgc gaggtgtcgg cgccgcaacg accggacatc    660

atcgagcgcg agatcagcaa gaatccgccg atcagggacg agcatccgcc gctgccacca    720

acggcgcacg ctcaggagcc ggatttgccg gaacactacg acctcgagaa cgccagctcg    780
```

```
atcgcgccga gcgacatcga catcgtctac cattacaaag gctaccgcga cggcatgcga    840

aagtacaagg ccacgccgct gccgatcagc agctacgcca atcatcacaa gcacagcaat    900

cagcagcaca ggcacgccgg agcgtttcca cctcgcgcgc cgatgggtcc accgccgccg    960

tcggcggtcg gtcaaccgag cgccgcgccg aagctgctgc aaagcacgcc gctggcgagg   1020

ctgtcgccga gcagcgagtt gtcggcgcaa cagccgagga tactgacgtt gcacgacatc   1080

agcggcaaac cgctgcagag cgcgctgctg gcgaccacct cgtcgtcggg tggcgtcggc   1140

aaggacgcca tgaattccaa cagcgagcgc agcctgaatt cgccgataat gagtcagctg   1200

tccggctcga cagccagtcg caaggtcgcg caagcggcgg cggatacggt cggcaacggc   1260

gtggcctcgg tgccgatggg tctcacggcc gaggagatcg aacgcttgaa ttcgcgtcct   1320

cgcacgtcca gcctcgtgtc gaccctcgac gcggtgagct cgtcgagcga ggctcgcgga   1380

cccacgcacc atctgcaccg acgacacacg ccgccggcgc cgatcaaacg gcgaagctcg   1440

tcgacgaccg aggagagcgg caacgacgac agtttcacgt gctcggaaat cgacgagcga   1500

gtcgtcggcg tcgacgagga cgaggacgac gacgacgacg aggaggagga cgacgacgac   1560

gacgacattt acagcaaacc cgaggcaggc accgccggcg aggacgctaa gcgcggattc   1620

gacagctcgt ttcgcggctc tctcagcacg ctcgtcgcct ccgacgacga cacgtccacg   1680

cgcatgggtg ggctttatcg accggcgatc aatgccgaag cggccaacac cgcgctgagc   1740

tgggattacc tgttgaattg gggaccgaac ttcgagagcc tcgtcggcgt gtttatcgac   1800

attgccgaat tgccggatgg caatagtaga gtgccgaatt ctttgaggct accgaacaat   1860

atcaacaagc cgtccgagga gtacgtttga                                    1890
```

<210> SEQ ID NO 241
<211> LENGTH: 546
<212> TYPE: DNA
<213> ORGANISM: Ophelimus maskelli
<220> FEATURE:
<223> OTHER INFORMATION: 3' fragment from same gene as SEQ ID NO: 107

<400> SEQUENCE: 241

```
ttacaaaagg ccttgtcgtt ttaagtcctc ataagttttg cgattcacaa cattacccag     60

tgaatcctca aattcttctt cctgctcagg ctgccacctt tcagcttgtt tctgagcttt    120

cagtttttcc cacagtgcca aagcatcttc tatttgtgta acattagcaa aatgagcagt    180

gtttggaata cctaaacagc gcataccatg agcatgcctc cattctgcaa aatgcctttg    240

aaaagctttt ggtcctttgt atgtgtaatt accacaaatt tcacaattat aactgatatt    300

taatccatgc agtttgtata gccagtaagg aataggtttt ccatcccaac caagtggcaa    360

attcttagga ttataaggta cgtcattgtc atcttcttct tcagattcgc tagcacttgc    420

ttcggcatct gaatctcccc gttcaccttc tgttctggct tgcttccttt ggacattttc    480

tttagttgcc cctctttgac ttgaaactaa ttctgcaagt ttataaactt gtgcttcaag    540

tctggc                                                               546
```

<210> SEQ ID NO 242
<211> LENGTH: 711
<212> TYPE: DNA
<213> ORGANISM: Ophelimus maskelli
<220> FEATURE:
<223> OTHER INFORMATION: Median fragment from same gene as SEQ ID NOS
      115 & 243

<400> SEQUENCE: 242

```
aggcacaaga agcgcgtgag acagccgcac aacacgcgag aacgtcaacg tcagatagcc      60

gttggtcacg gcgagtacat aatgccatcg cagagcatac agtacagggc gatacccgac     120

gaagcgctac tcggtatggt catgacggag cagaggccgc ctaggcccaa cagtatcgaa     180

cttagaagga gttatccgtc tagttatgtg cctgacgaac atcagttgta tagtccgccc     240

atgtccgagc attatcggca ggcgaattac gctggacaga tggcaggcta cgaagatagt     300

gcatacggtt ctcactacgc acctggtcag ggacattcgg gcagcgatac gtaccagagc     360

cccggcccag gtacgccgag tcgaggtggc agaaaccgac cttcccaacc accaccggct     420

ccacccagta acgcgtccag caattcgacg ccgacgatcg cttcggcgaa taatacaccc     480

acgaggggca ggtcgatgag taccggtagg gataacttgc cgcctccacc tccacctcct     540

ggagagacaa tgtcaccgcc ttcgatgaat ggtacaattc catcgcacct gctaaacaga     600

aacggcagtc gttcgaacag tcccttaccg aaccatcaat caacaccaac atcgatatca     660

ttggtgggtc atctcggtca gatggtgcag atgggcgtag acgaaacaga a              711
```

<210> SEQ ID NO 243
<211> LENGTH: 357
<212> TYPE: DNA
<213> ORGANISM: Ophelimus maskelli
<220> FEATURE:
<223> OTHER INFORMATION: 3' fragment from same gene as SEQ ID NOS 115 & 242

<400> SEQUENCE: 243

```
atgcccatta caaatggtga tattgctaag atgatcgtaa acaatccgcc aaaactcaag      60

cctcttaaga gtatcgttga tggcagcta agaaattcaa ccaatccgaa tatcccagca      120

ccggttgatc cgagaaacga tctgttgaag gctattcgag atggtataaa attgcgaaaa     180

gtcgaaaaga tagaacagaa ggaagtagaa agagtaaacg cactgaacga tgtagcatca     240

atattggcac ggcgagttgc cgttgagttc agtgacagtg attccgcatc ggagagcgaa     300

ggtgatagcg aaggttgggg tgaacatgat agtacgagtg cgacgaatgt cgcgtga        357
```

<210> SEQ ID NO 244
<211> LENGTH: 876
<212> TYPE: DNA
<213> ORGANISM: Leptocybes invasa
<220> FEATURE:
<223> OTHER INFORMATION: 3' fragment from same gene as SEQ ID NO: 117

<400> SEQUENCE: 244

```
aaagagcagc tcattctttt ggtcgactgc gagctcgcat atatgaacac taatcacgaa      60

gattttatcg ggttcgccaa cgcccaacag tcgtcggaga atgcggtgaa atcgggacgt     120

agtactcttg gtaatcaggt cattcgcaaa ggttacatgt gcatacacaa tcttggtata     180

atgaagggtg gttcgaggga ttactggttc gtactcacct ctgagagcat ctcatggttc     240

aaagatgagg aggagcgaga gaagaagtat atgttgccat tggacggttt gaagttacgt     300

gacctcgagc agggtttcat gtcgcgacgt cacctgttcg cgctattcaa tccagacggt     360

agaaacgtct acaaggacta caaacaactt gaattgagtt gcgagactca agatgatgtg     420

gactcgtgga aggcatcctt ccttcgtgct ggcgtctacc ccgagaaatc gaccgaacag     480

gctaacggtg atggcgaagg aggcggcgag cagcagtcgt cgatggaccc tcagctagag     540

cgacaagtag agacgatcag gaacttggta gattcctaca tgaagatcgt cacgaagaca     600

actcgtgatc tcgttccaaa aacaattatg cacttgatca taaacaatgc caaagatttc     660
```

-continued

```
atcaatggag aacttttggc tcatctctat gctagtggag atcaggcatc gatgatggaa    720

gaatctccag aagaagcgca aaagcgagaa gaaatgttgc gcatgtatca cgcttgcaaa    780

gaagctctcc gaattattgg agacgtgtcg atggccacag tttcaacgcc agtacctcca    840

cctgtcaaga acgactggct gccagcaggc gacaat                              876


<210> SEQ ID NO 245
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245

aaaaaaaaaa a                                                          11
```

GALL WASP CONTROL AGENTS

CROSS REFERENCE TO PRIOR APPLICATIONS

This is a U.S. National Phase application under 35 U.S.C. § 371 of International Patent Application No. PCT/US2012/031413, filed Mar. 30, 2012, and claims the benefit of U.S. Provisional Application No. 61/469,469, filed Mar. 30, 2011 and U.S. Provisional Application No. 61/592,175, filed Jan. 30, 2012, all of which are incorporated by reference herein in their entirety. The International Application published in English on Oct. 4, 2012 as WO 2012/135600 under PCT Article 21(2).

REFERENCE TO SEQUENCE LISTING

Pursuant to 37 C.F.R. 1.821(c), a sequence listing is submitted herewith as an ASCII compliant text file named "SEQLST.txt" that was created on Sep. 30, 2013, and has a size of 312,759 bytes. The content of the aforementioned file named "SEQLST.txt" is hereby incorporated by reference in its entirety.

FIELD OF THE INVENTION

The present invention relates to the field of double stranded RNA (dsRNA)-mediated gene silencing in insect species.

BACKGROUND

Gall wasp infestations of *eucalyptus* trees have occurred in both the Northern and Southern hemispheres and pose a threat to commercial *eucalyptus* farming in China, Australia, Israel and Brazil. Efforts to control gall wasp infection of *eucalyptus* have included attempts to isolate naturally resistant plants and natural predators. These efforts have met with limited or no success. The protective environment of the gall in which gall wasps develop makes chemical pesticide control of gall wasps difficult.

Even when feasible, chemical pesticide control has disadvantages. Chemical pesticides are potentially detrimental to the environment, are not selective and are potentially harmful to non-target crops and fauna. Chemical pesticides persist in the environment and generally are metabolized slowly, or not at all. Chemical pesticides accumulate in the food chain, particularly in the higher predator species where they can act as mutagens and/or carcinogens to cause irreversible and deleterious genetic modifications. Crop pests, moreover, may develop resistance against chemical insecticides because of repetitive usage of the same insecticide or of insecticides having the same mode of action.

RNA interference or "RNAi" is a process of sequence-specific down-regulation of gene expression (also referred to as "gene silencing" or "RNA-mediated gene silencing") initiated by double-stranded RNA (dsRNA) that is complementary in sequence to a region of the target gene to be down-regulated. Down-regulation of target genes in multicellular organisms by means of RNA interference (RNAi) has become a well-established technique. U.S. patent application publications US 2009/0285784 A1 and US 2009/0298787 relate to dsRNA as an insect control agent and are hereby incorporated herein by reference in their respective entireties. U.S. Pat. No. 6,506,559, U.S. patent application publication 2003/00150017 A1, International Publications WO 00/01846, WO 01/37654, WO 2005/019408, WO 2005/049841, WO 05/047300 relate to the use of RNAi to protect plants against insects. Each of the foregoing patents and published applications is hereby incorporated by reference in its entirety.

SUMMARY

The present invention is based, in part, on the inventors' sequencing of genes from *eucalyptus* invasive species gall wasp pests, *Leptocybe invasa* (Li) and *Ophelimus maskelli* (Om). In certain aspects, the invention thus provides Li and Om nucleic acids, derivatives thereof and the use of such nucleic acids and derivatives as gall wasp control agents.

In certain aspects the invention provides isolated nucleic acids that hybridize selectively under high stringency hybridization conditions to a sequence set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 45-123, SEQ ID NO: 127-132, SEQ ID NO: 150-222, and SEQ ID NO: 234-244 and complementary sequences thereof.

In certain aspects the invention provides isolated nucleic acids that are 90-99.99 percent identical to sequences set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 45-123, SEQ ID NO: 127-132, SEQ ID NO: 150-222, and SEQ ID NO: 234-244, and complementary sequences thereof.

In certain aspects the invention provides isolated nucleic acids that include at least 17 contiguous nucleotides of the sequences set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 45-123, SEQ ID NO: 127-132, SEQ ID NO: 150-222, and SEQ ID NO: 234-244, and complementary sequences thereof.

In certain aspects the invention provides nucleic acids from Li or Om, including the nucleic acids set out above, that are about 80% or less identical to the honey bee ortholog of said nucleic acid.

In certain aspects the invention provides vectors that include nucleic acids from Li or Om, or reverse compliments of such sequences, operably linked to an expression control sequence.

In certain aspects the invention provides host cells transformed with and/or harboring vectors that include nucleic acids from Li or Om, or reverse compliments of such sequences, operably linked to an expression control sequence.

In certain aspects the invention provides plant tissues, for example, leaf tissue and seeds, transformed with and/or harboring vectors that include nucleic acids from Li or Om operably linked to an expression control sequence.

In certain aspects the invention provides isolated small inhibitory ribonucleic acid (siRNA) molecules that inhibit expression of Li or Om nucleic acids.

In certain aspects the invention provides isolated double stranded ribonucleic acid (dsRNA) molecules that include a first strand of nucleotides that is substantially identical to at least 17 contiguous nucleotides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26, SEQ ID NO: 45-123, SEQ ID NO: 127-132, SEQ ID NO: 150-222, and SEQ ID NO: 234-244, and a second strand of nucleotides that is substantially complementary to the first strand of nucleotides.

In certain aspects the invention provides double stranded ribonucleic acid (dsRNA) molecules with a high level of homology (greater than 80%) to mRNA from Li or Om (Li or Om targeting dsRNAs), including the dsRNA molecules set out above, that are about 80% or less identical to the honey bee ortholog of the dsRNA.

In certain aspects the invention provides vectors that include an expression control sequence operatively linked to a nucleotide sequence that is a template for one or both strands of a dsRNA from Li or Om.

In certain aspects the invention provides host cells transformed with and/or harboring vectors that include an expression control sequence operatively linked to a nucleotide sequence that is a template for one or both strands of a dsRNA from Li or Om.

In certain aspects the invention provides plant tissue transformed with and/or harboring vectors that include an expression control sequence operatively linked to a nucleotide sequence that is a template for one or both strands of a dsRNA from Li or Om.

In certain aspects the invention provides isolated small inhibitory ribonucleic acid (siRNA) molecules that inhibit expression of an essential gene of Li or Om.

In certain aspects the invention provides methods of producing a pest resistant plant by expressing a Li or Om dsRNA in the plant or in propagative or reproductive material of the plant.

In certain aspects the invention provides methods of producing pest resistant *eucalyptus* by expressing a Li or Om dsRNA in the *eucalyptus* or in propagative or reproductive material of the *eucalyptus*.

In certain aspects the invention provides methods of producing *eucalyptus* resistant to gall wasp infection and/or infestation by expressing a Li or Om targeting dsRNA in the *eucalyptus* or in propagative or reproductive material of the *eucalyptus*.

In certain aspects the invention provides methods of producing a plant resistant to a plant pathogenic pest by transforming a plant cell with a recombinant DNA construct or combination of constructs that express a dsRNA; regenerating a plant from the transformed plant cell; and growing the transformed plant cell under conditions suitable for the expression of the recombinant DNA construct.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts certain, non-limiting nucleic acids according to the invention.

FIG. 2 depicts certain, non-limiting nucleic acids according to the invention.

FIG. 3 depicts certain, non-limiting nucleic acids according to the invention.

Like reference symbols in the various drawings indicate like elements.

DETAILED DESCRIPTION

Figures 1A, 1B:
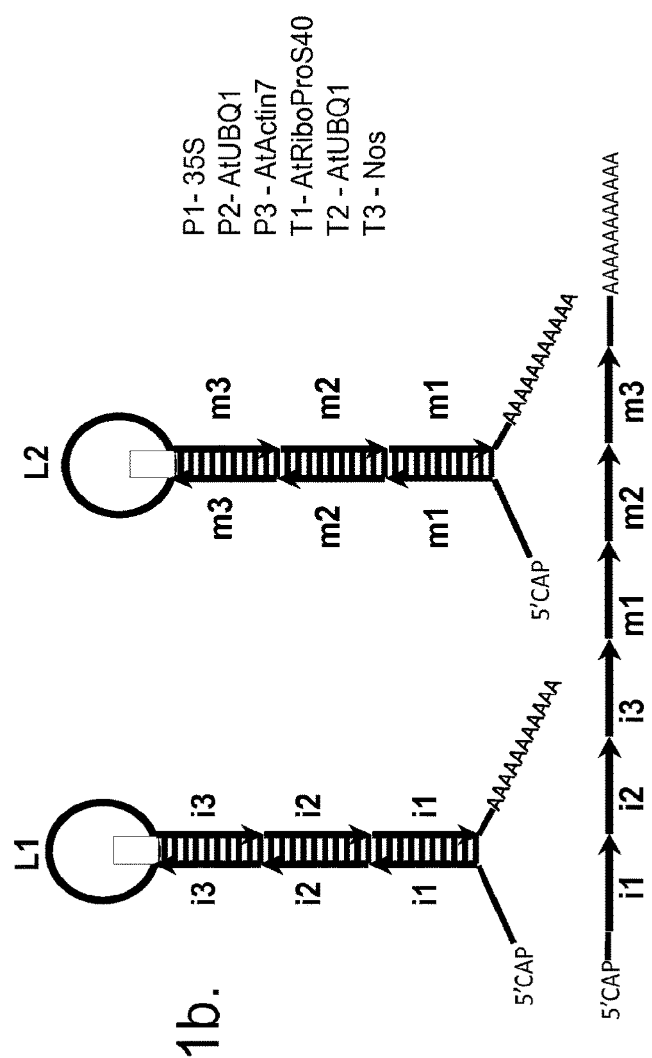
FIG. 1(A) Schematic of nucleic construct #1 (SEQ ID NO: 37) constructed with three transgenes. Transgene P1 to T1 encodes a hairpin RNA (hpRNA) for silencing Li Coatomer subunit alpha-like (Alpha COP), chromodomain-helicase DNA-binding protein Mi-2 homolog (Cdh3), and venom carboxylesterase-6 isoform 1(VCE-F2) genes. Transgene P2 to T2 encodes a hpRNA for silencing Om Alpha COP, Cdh3, and VCE-F2 genes. Transgene P3 to T3 encodes a mRNA with sense sequences of Li Alpha COP, Cdh3, and VCE-F2 genes and Om Alpha COP, Cdh3, and VCE-F2 genes. mRNA transcribed from transgene P3 to T3 is the template for cytoplasmic enhancement of the silencing signal.
FIG. 1(B) hpRNA molecules produced by transcription of nucleic acid construct #1 (Left-Li RNAi 1, SEQ ID NO: 137; Right-Om RNAi 1, SEQ ID NO: 138). Definitions: P1-CaMV 35S Promoter (SEQ ID NO: 27); P2-AtUBQ1 Promoter (SEQ ID NO: 28); P3-AtActin7 Promoter (SEQ ID NO: 29); T1-AtRiboProS40 Terminator (SEQ ID NO: 32); T2-AtUBQ1 Terminator (SEQ ID NO: 33); T3-NOS Terminator (SEQ ID NO: 34); i1-100 bp of Li Alpha COP gene (SEQ ID NO: 1); i2-100 bp of Li VCE-F2 gene (SEQ ID NO: 2); i3-100 bp of Li Cdh3gene (SEQ ID NO: 3); m1-100 bp of Om Alpha COP gene with A93C change to eliminate a predicted polyadenylation site (SEQ ID NO: 7); m1*(m1 between P3 and T3)-100 bp of Om Alpha COP gene (SEQ ID NO: 234); m2-100 bp of Om Cdh3 gene (SEQ ID NO: 8); m3-100 bp of Om VCE-F2 gene (SEQ ID NO: 9); L1-loop #1 with XhoI site (SEQ ID NO: 13); L2-loop #2 with AscI site (SEQ ID NO: 14). Poly A tail disclosed as SEQ ID NO: 245.

The present invention relates to using double stranded RNA (dsRNA)-mediated techniques to control insect infection and infestation of plants. The inventors have conducted transcriptome sequencing of the natural *eucalyptus* pests, *Leptocybe invasa* (Li) and *Ophelimus maskelli* (Om) and mined the respective transcriptomes to identify open reading frames of Li and Om genes that correspond to Li and Om mRNAs. The identification of Li and Om RNAs allows for the design of siRNA and dsRNA that mediate downregulation (silencing) of Li and Om genes. Such siRNA and dsRNAs are thus useful as biological control agents to kill or inhibit the development of Li and Om and inhibit infection of plants by Li and Om.

Accordingly, the present invention describes a nucleic acid based approach for the control of gall wasp pests. The active ingredient is a nucleic acid, for example a double-stranded RNA (dsRNA) or a nucleic acid that can promote or lead to production of a dsRNA, which can be used as an insecticidal formulation. dsRNA can be expressed in a host plant, plant part, plant cell or seed to protect the plant against gall wasps. The sequence of the dsRNA corresponds to part or whole of an essential gall wasp gene and causes down-regulation of the insect target gene via RNA interference (RNAi). As a result of the downregulation of mRNA, the dsRNA prevents expression of the target insect protein and causes death, growth arrest or sterility of the insect.

The methods of the invention find practical application in any area of technology where it is desirable to inhibit viability, growth, development or reproduction of gall wasps, or to decrease pathogenicity or infectivity of the insect. The methods of the invention further find practical application where it is desirable to specifically down-regulate expression of one or more target genes in a gall wasp insect. Particularly useful practical applications include, but are not limited to, protecting plants against gall wasp pest infestation.

siRNA control of insect growth, for preventing insect infestation of a cell or a plant susceptible to insect infection, is effected by contacting insects with a dsRNA produced by annealed complementary strands, one of which has a nucleotide sequence which is complementary to at least part of the nucleotide sequence of an insect target gene. dsRNA is expressed in plant tissue that is ingested by the insect and then taken up by the insect through the gut, and thereby controls growth or prevents infestation. See Huvenne et al., 2010, *J Insect Physiol* 56: 227-35.

Gall wasp target genes for siRNA-mediated intervention include are preferably non-redundant, vital genes. Vital target genes may be any gene that when inhibited interferes with growth or survival or pathogenicity or infectivity of the insect. Such vital target genes are essential for viability, growth, development or reproduction of the insect, or any gene that is involved with pathogenicity or infectivity of the insect, such that specific inhibition of the target gene leads to a lethal phenotype or decreases or stops insect infestation. Down regulation of such vital target genes, whose activity cannot be complemented by other related genes, results in significant damage to the pest larvae and provides an efficient pest control system for sessile gall wasp pests. The target gene may be any of the target genes herein described, for instance a target gene that is essential for the viability, growth, development or reproduction of the pest. Examples of target genes include, for example, genes that are involved in protein synthesis and/or metabolism and/or RNA synthesis and metabolism and/or cellular processes. A slight knockdown of these target genes will have an effect on many other genes and processes ultimately leading to a lethal effect on the target pest. Such a down-regulated target gene will result in the death of the insect, or the reproduction or growth of the insect being stopped or delayed. Such target genes are vital for the viability of the insect and are referred to as vital genes.

Potential target genes may be identified based on homologies to genes in other insect species. Published genome-wide RNAi mediated gene interference libraries (15, 16) may be used to identify genes that are lethal to other organisms when RNAi based on these genes is expressed and incorporated into target pest organisms by ingestion or any other means. Thus genes identified as being RNAi-lethal in *Drosophila* may be used to screen for orthologs in hymenoptera species. Such hymenoptera orthologs may further be used to screen gall wasp species for potential targets.

Li and Om are sessile pests. Accordingly, Li and Om vital target genes cannot be predicted solely on the basis of genes that were shown to be vital genes in a non-sessile pest. Sessile pests, for example, cannot migrate to an alternative feed source. In the case of Li and Om, developing pests are confined to the gall and during an 80-120 day period feed on the same source. This mode of development results in the possibility that slow but continuous uptake of dsRNA can have a cumulative effect that would not be effective in a non-sessile pest. A putative target gene that was not described as being a viable, target gene in a worm, for example, may thus nonetheless be a viable, target gene in a gall wasp.

Examples of target genes include, without limitation alpha COP, the alpha subunit of COPI vesicle coatomer complex; chromodomain-helicase-DNA-binding protein 3 (Cdh3); chitin synthase, venom carboxylesterase-6 isoform 1; juvenile hormone epoxide hydrolase; and ferritin. Nucleotide sequences of gall wasp target genes include, for example, the sequences set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26, SEQ ID NO: 45-123, SEQ ID NO: 127-132, SEQ ID NO: 150-222, and SEQ ID NO: 234-244, the complements of such sequences, and sequences that selectively hybridize to such sequences and complements under high stringency hybridization conditions.

Nucleotide sequences useful for dsRNA-mediated down-regulation of gall wasp target genes include, for example, (i) a sequences set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26, SEQ ID NO: 45-123, SEQ ID NO: 127-132, SEQ ID NO: 150-222, and SEQ ID NO: 234-244, and the complements of such sequences; (ii) sequences which are at least 70%, 75%, 80%, 85%, 90%, 95%, 96%, 97%, 98%, 99% or 99.9% identical to a sequence set out in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26, SEQ ID NO: 45-123, SEQ ID NO: 127-132, SEQ ID NO: 150-222, and SEQ ID NO: 234-244, and the complements of such sequences; (iii) sequences comprising at least 17 contiguous nucleotides of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 or SEQ ID NO: 26, SEQ ID NO: 45-123, SEQ ID NO: 127-132, SEQ ID NO: 150-222, and SEQ ID NO: 234-244, and the complements of such sequences; and (iv) sequences that selectively hybridize to such sequences and complements under high stringency hybridization conditions.

An "isolated" nucleic acid as used herein is a nucleic that has been identified and separated and/or recovered from a component of its natural environment.

"Controlling pests" as used herein means killing pests, or preventing pests to develop, or to grow or preventing pests to infect or infest. Controlling pests as used herein also encompasses controlling pest progeny (development of eggs). Controlling pests as used herein also encompasses inhibiting viability, growth, development or reproduction of the pest, or to decrease pathogenicity or infectivity of the pest. The compounds and/or compositions described herein, may be used to keep an organism healthy and may be used curatively, preventively or systematically to control pests or to avoid pest growth or development or infection or infestation.

Particular pests envisaged for control by methods described herein are plant pathogenic insect pests. "Controlling insects" as used herein thus encompasses controlling insect progeny (such as development of eggs). Controlling insects as used herein also encompasses inhibiting viability, growth, development or reproduction of the insect, or decreasing pathogenicity or infectivity of the insect. As used herein, controlling insects may refer to inhibiting a biological activity in an insect, resulting in one or more of the following attributes: reduction in feeding by the insect, reduction in viability of the insect, death of the insect, inhibition of differentiation and development of the insect, absence of or reduced capacity for sexual reproduction by the insect.

The compounds and/or compositions described herein, may be used to keep an organism healthy and may be used curatively, preventively or systematically to control an insect or to avoid insect growth or development or infection or infestation. Thus, the invention may allow previously susceptible organisms to develop resistance against infestation by the insect organism.

The term "complementary to at least part of" refers to a nucleotide sequence that is fully complementary to the nucleotide sequence of the target over more than ten nucleotides, for instance over at least 15, 16, 17, 18, 19, 20, 21, 22, 23, 24 or more contiguous nucleotides. Notwithstanding the above, "complementary to at least part" of may also include complementary sequences that are greater than 80% complementary to a nucleotide sequence of a target sequence over a length of more than 20 nucleotides, for instance over at least 20, 21, 22, 23, 24 or more contiguous nucleotides [13, 14].

In certain aspects, the invention provides a method for down-regulating expression of a target gene in an insect, comprising contacting the insect with a dsRNA, wherein the dsRNA comprises annealed complementary strands, one of which has a nucleotide sequence that is complementary to at least part of the nucleotide sequence of the insect target gene to be down-regulated, whereby the dsRNA is taken up into the insect and thereby down-regulates expression of the insect target gene.

The term "insect" encompasses insects of all types and at all stages of development, including egg, larval or nymphal, pupal and adult stages.

As used herein, the term "plant" encompasses any plant material that it is desired to treat to prevent or reduce insect growth and/or insect infestation. This includes, inter alia, whole plants, seedlings, propagation or reproductive material such as seeds, cuttings, grafts, explants, etc., and also plant cell and tissue cultures. The plant material should express, or have the capability to express, the RNA molecule comprising at least one nucleotide sequence that is the RNA complement of or that represents the RNA equivalent of at least part of the nucleotide sequence of the sense strand of at least one target gene of the pest organism, such that the RNA molecule is taken up by a pest upon plant-pest interaction, said RNA molecule being capable of inhibiting the target gene or down-regulating expression of the target gene by RNA interference.

The terms "down-regulation of gene expression" and "inhibition of gene expression" are used interchangeably and refer to a measurable or observable reduction in gene expression or a complete abolition of detectable gene expression, at the level of protein product and/or mRNA product from the target gene. The down-regulation effect of the dsRNA on gene expression may be calculated as being at least 30%, 40%, 50%, 60%, preferably 70%, 80% or even more preferably 90% or 95% when compared with normal gene expression. Depending on the nature of the target gene, down-regulation or inhibition of gene expression in cells of an insect can be confirmed by phenotypic analysis of the cell or the whole insect or by measurement of mRNA or protein expression using molecular techniques such as RNA solution hybridization, PCR, nuclease protection, Northern hybridization, reverse transcription, gene expression monitoring with a microarray, antibody binding, enzyme-linked immunosorbent assay (ELISA), Western blotting, radioimmunoassay (RIA), other immunoassays, or fluorescence-activated cell analysis (FACS).

Down-regulation of an essential gene leads to growth inhibition. Depending on the assay used, the growth inhibition can be quantified as being greater than about 5%, 10%, more preferably about 20%, 25%, 33%, 50%, 60%, 75%, 80%, most preferably about 90%, 95%, or about 99% as compared to a pest organism that has been treated with control dsRNA.

The "target gene" may be essentially any gene that is desirable to be inhibited because it interferes with growth or pathogenicity or infectivity of the insect. For instance, if the method of the invention is to be used to prevent insect growth and/or infestation then it is preferred to select a target gene which is essential for viability, growth, development or reproduction of the insect, or any gene that is involved with pathogenicity or infectivity of the insect, such that specific inhibition of the target gene leads to a lethal phenotype or decreases or stops insect infestation.

According to one non-limiting embodiment, the target gene is such that when its expression is down-regulated or inhibited using the method of the invention, the insect is killed, or the reproduction or growth of the insect is stopped or retarded. This type of target gene is considered to be essential for the viability of the insect and is referred to as essential genes. Therefore, the present invention encompasses a method as described herein, wherein the target gene is an essential gene.

Without being bound by theory, the target gene is such that when it is down-regulated the infestation or infection by the insect, the damage caused by the insect, and/or the ability of the insect to infest or infect host organisms and/or cause such damage, is reduced. The terms "infest" and "infect" or "infestation" and "infection" are generally used interchangeably throughout. This type of target genes is considered to be involved in the pathogenicity or infectivity of the insect. Therefore, the present invention extends to methods as described herein, wherein the target gene is involved in the pathogenicity or infectivity of the insect. The advantage of choosing the latter type of target gene is that the insect is blocked to infect further plants or plant parts and is inhibited to form further generations.

In dsRNA-mediated methods of controlling growth or infestation of a specific insect in or on a host cell or host organism, it is preferred that the dsRNA does not share any significant homology with any host gene, or at least not with any essential gene of the host. In this context, it is preferred that the dsRNA shows less than 30%, more preferably less that 20%, more preferably less than 10%, and even more preferably less than 5% nucleic acid sequence identity with any gene of the host cell. Percent sequence identity should be calculated across the full length of the dsRNA region. If genomic sequence data is available for the host organism one may cross-check sequence identity with the dsRNA using standard bioinformatics tools. In one embodiment, there is no sequence identity between the dsRNA and a host sequences over 21 contiguous nucleotides, meaning that in this context, it is preferred that 21 contiguous base pairs of the dsRNA do not occur in the coding sequences (CDS) of the host organism. In another embodiment, there is less than about 10% or less than about 12.5% sequence identity over 24 contiguous nucleotides of the dsRNA with any nucleotide sequence from a host species.

dsRNA comprises annealed complementary strands, one of which has a nucleotide sequence which corresponds to a target nucleotide sequence of the target gene to be down-regulated. The other strand of the dsRNA is able to base-pair with the first strand.

The expression "target region" or "target nucleotide sequence" of the target insect gene may be any suitable region or nucleotide sequence of the gene. The target region should comprise at least 17, at least 18 or at least 19 consecutive nucleotides of the target gene, more preferably at least 20 or at least 21 nucleotide and still more preferably at least 22, 23 or 24 nucleotides of the target gene.

It is preferred that (at least part of) the dsRNA will share 100% sequence identity with the target region of the insect target gene. However, it will be appreciated that 100% sequence identity over the whole length of the double stranded region is not essential for functional RNA inhibition. RNA sequences with insertions, deletions, and single point mutations relative to the target sequence have also been found to be effective for RNA inhibition.

The terms "corresponding to" or "complementary to" are used herein interchangeably, and when these terms are used to refer to sequence correspondence between the dsRNA and the target region of the target gene, they are to be interpreted accordingly, i.e., as not absolutely requiring 100% sequence identity. However, the percent sequence identity between the dsRNA and the target region will generally be at least 80% or 85% identical, preferably at least 90%, 95%, 96%, or more preferably at least 97%, 98% and still more preferably at least 99%. Two nucleic acid strands are "substantially complementary" when at least 85% of their bases pair.

The term "complementary" as used herein relates to all of DNA-DNA complementarity, RNA-RNA complementarity and to DNA-RNA complementarity. In analogy herewith, the term "RNA equivalent" substantially means that in the DNA sequence(s), the base "T" may be replaced by the corresponding base "U" normally present in ribonucleic acids.

Although dsRNA contains a sequence which corresponds to the target region of the target gene, it is not essential for the whole of the dsRNA to correspond to the sequence of the target region. For example, the dsRNA may contain short non-target regions flanking the target-specific sequence, provided that such sequences do not affect performance of the dsRNA in RNA inhibition to a material extent.

The dsRNA may contain one or more substitute bases in order to optimize performance in RNAi. It will be apparent to one of ordinary skill in the art how to vary each of the bases of the dsRNA in turn and test the activity of the resulting dsRNAs (e.g., in a suitable in vitro test system) in order to optimize the performance of a given dsRNA.

The dsRNA may further contain DNA bases, non-natural bases or non-natural backbone linkages or modifications of the sugar-phosphate backbone, for example to enhance stability during storage or enhance resistance to degradation by nucleases.

Interfering RNAs (siRNAs) of about 21 bp are useful for effective gene silencing. Increasing the length of dsRNA preferably to at least about 80-100 bp may increase the efficiency by which dsRNA is taken up by pest organisms. Such longer fragments may be more effective in gene silencing, possibly due to a more efficient uptake of these long dsRNA by the invertebrate.

RNA duplexes consisting of either 27-mer blunt or short hairpin (sh) RNAs with 29 bp stems and 2-nt 3' overhangs may also be used as siRNAs. Thus, molecules based upon the targets identified above and being either 27-mer blunt or short hairpin (sh) RNA's with 29-bp stems and 2-nt 3'-overhangs are also included within the scope of the invention.

Therefore, in one embodiment, the dsRNA fragment (or region) will itself preferably be at least 17 bp in length, preferably 18 or 19 bp in length, more preferably at least 20 bp, more preferably at least 21 bp, or at least 22 bp, or at least 23 bp, or at least 24 bp, 25 bp, 26 bp or at least 27 bp in length. The expressions "double-stranded RNA fragment"

or "double-stranded RNA region" refer to a small entity of the dsRNA corresponding with (part of) the target gene.

More generally, the double stranded RNA is preferably between about 17-1500 bp, even more preferably between about 80-1000 bp and most preferably between about 17-27 bp or between about 80-250 bp; such as double stranded RNA regions of about 17 bp, 18 bp, 19 bp, 20 bp, 21 bp, 22 bp, 23 bp, 24 bp, 25 bp, 27 bp, 50 bp, 80 bp, 100 bp, 150 bp, 200 bp, 250 bp, 300 bp, 350 bp, 400 bp, 450 bp, 500 bp, 550 bp, 600 bp, 650 bp, 700 bp, 900 bp, 100 bp, 1100 bp, 1200 bp, 1300 bp, 1400 bp or 1500 bp.

The upper limit on the length of the dsRNA may be dependent on i) the requirement for the dsRNA to be taken up by the insect and ii) the requirement for the dsRNA to be processed within the cell into fragments that direct RNAi. The chosen length may also be influenced by the method of synthesis of the RNA and the mode of delivery of the RNA to the cell. Preferably the dsRNA to be used in the methods of the invention will be less than 10,000 bp in length, more preferably 1000 bp or less, more preferably 500 bp or less, more preferably 300 bp or less, more preferably 100 bp or less. For any given target gene and insect, the optimum length of the dsRNA for effective inhibition may be determined by experiment.

The dsRNA may be fully or partially double-stranded. Partially dsRNAs may include short single-stranded overhangs at one or both ends of the double-stranded portion, provided that the RNA is still capable of being taken up by insects and directing RNAi. The dsRNA may also contain internal non-complementary regions.

The methods of the invention encompass the simultaneous or sequential provision of two or more different dsRNAs or RNA constructs to the same insect, so as to achieve down-regulation or inhibition of multiple target genes or to achieve a more potent inhibition of a single target gene.

Alternatively, multiple targets are hit by the provision of one dsRNA that hits multiple target sequences, and a single target is more efficiently inhibited by the presence of more than one copy of the double stranded RNA fragment corresponding to the target gene. Thus, in certain aspects, a dsRNA construct comprises multiple dsRNA regions, at least one strand of each dsRNA region comprising a nucleotide sequence that is complementary to at least part of a target nucleotide sequence of an insect target gene. The dsRNA regions in the RNA construct may be complementary to the same or to different target genes and/or the dsRNA regions may be complementary to targets from the same or from different insect species.

The terms "hit", "hits" and "hitting" are alternative wordings to indicate that at least one of the strands of the dsRNA is complementary to, and as such may bind to, the target gene or nucleotide sequence.

In one embodiment, the double stranded RNA region comprises multiple copies of the nucleotide sequence that is complementary to the target gene. Alternatively, the dsRNA hits more than one target sequence of the same target gene. The invention thus encompasses isolated double stranded RNA constructs comprising at least two copies of said nucleotide sequence complementary to at least part of a nucleotide sequence of an insect target.

The term "multiple" as used herein means at least two, at least three, at least four, at least five, at least six, etc.

The expressions "a further target gene" or "at least one other target gene" mean for instance a second, a third or a fourth, etc. target gene.

dsRNA that hits more than one of the above-mentioned targets, or a combination of different dsRNA against different of the above mentioned targets are developed and used in the methods of the present invention.

dsRNA regions (or fragments) in the double stranded RNA may be combined as follows: a) when multiple dsRNA regions targeting a single target gene are combined, they may be combined in the original order (i.e., the order in which the regions appear in the target gene) in the RNA construct; b) alternatively, the original order of the fragments may be ignored so that they are scrambled and combined randomly or deliberately in any order into the double stranded RNA construct; c) alternatively, one single fragment may be repeated several times, for example from 1 to 10 times, e.g., 1, 2, 3, 4, 5, 6, 7, 8, 9 or 10 times, in the ds RNA construct, or d) the dsRNA regions (targeting a single or different target genes) may be combined in the sense or antisense orientation.

Multiple dsRNA regions targeting a single or different weak gene(s) may be combined to obtain a stronger RNAi effect. "Insect specific" genes or sequences, e.g., gall wasp specific, particularly Li or Om specific genes and sequences, encompass genes that have no substantial homologous counterpart in non-insect organisms as can be determined by bioinformatics homology searches, for example by BLAST searches. The choice of a specific target gene results in a species specific RNAi effect, with no effect or no substantial (adverse) effect in non-target organisms. "Conserved genes" encompass genes that are conserved (at the amino acid level) between the target organism and non-target organism(s). To reduce possible effects on non-target species, such effective but conserved genes are analyzed and target sequences from the variable regions of these conserved genes are chosen to be targeted by the dsRNA regions in the RNA construct. Conservation is assessed at the level of the nucleic acid sequence. Such variable regions thus encompass the least conserved sections, at the level of the nucleic acid sequence, of the conserved target gene(s). The RNA constructs according to the present invention target multiple genes from different biological pathways, resulting in a broad cellular RNAi effect and more efficient insect control. In certain embodiments dsRNAs are constructed from sequences, e.g., Li and Om transcriptome sequences, that are equal to or less than 80% identical to the sequence of a honey bee ortholog, for example and without limitation, the honey bee orthologs of the Li and Om sequences disclosed herein are set out in SEQ ID NO: 39-44 and SEQ ID NO: 134-136.

In certain aspects, dsRNA constructs are constructed with gene sequences that affect different classes of cellular functions. Examples of such classes of cellular function include, without limitation, (i) protein synthesis and metabolism, (ii) RNA synthesis and metabolism, and (iii) cellular processes. In certain embodiments, dsRNA constructs comprise sequences from each of the aforementioned claims, i.e., three classes. In certain embodiments, dsRNA constructs comprise sequences from two of the aforementioned classes, e.g., protein synthesis and metabolism and RNA synthesis and metabolism; protein synthesis and cellular processes; or RNA synthesis and metabolism and cellular processes.

dsRNA regions comprise at least one strand that is complementary to at least part or a portion of the nucleotide sequence of any of the target genes herein described. However, provided one of the double stranded RNA regions comprises at least one strand that is complementary to a portion of the nucleotide sequence of any one of the target genes herein described, the other double stranded RNA regions may comprise at least one strand that is complementary to a portion of any other insect target gene (including known target genes).

In some constructs, dsRNAs may comprise additional sequences and optionally a linker. Additional sequences may include, for example, (i) a sequence facilitating large-scale production of the dsRNA construct; (ii) a sequence effecting an increase or decrease in the stability of the dsRNA; (iii) a sequence allowing the binding of proteins or other molecules to facilitate uptake of the RNA construct by insects; (iv) a sequence which is an aptamer that binds to a receptor or to a molecule on the surface or in the cytoplasm of an insect to facilitate uptake, endocytosis and/or transcytosis by the insect; or (v) additional sequences to catalyze processing of dsRNA regions. In one embodiment, the linker is a conditionally self-cleaving RNA sequence, preferably a pH sensitive linker or a hydrophobic sensitive linker.

Multiple dsRNA regions of the dsRNA construct may be connected directly or by one or more linkers. A linker may be present at a site in the RNA construct, separating dsRNA regions from another region of interest. Multiple dsRNA regions of dsRNA constructs may be connected without linkers.

When present, linkers may be used to disconnect smaller dsRNA regions in the pest organism. Advantageously, in this situation the linker sequence may promote division of a long dsRNA into smaller dsRNA regions under particular circumstances, resulting in the release of separate dsRNA regions under these circumstances and leading to more efficient gene silencing by these smaller dsRNA regions. Examples of suitable conditionally self-cleaving linkers are RNA sequences that are self-cleaving at high pH conditions. Suitable examples of such RNA sequences are described by Borda et al. (Nucleic Acids Res. 2003 May 15; 31(10):2595-600), which document is incorporated herein by reference. This sequence originates from the catalytic core of the hammerhead ribozyme HH16.

Linkers may also be located at a site in the dsRNA construct, separating the dsRNA regions from another, e.g., an additional, sequence of interest, which preferably provides some additional function to the RNA construct.

dsRNA constructs may include aptamers to facilitate uptake of the dsRNA by the insect. The aptamer is designed to bind a substance which is taken up by the insect. Such substances may be from an insect or plant origin. One specific example of an aptamer, is an aptamer that binds to a transmembrane protein, for example a transmembrane protein of an insect. Alternatively, the aptamer may bind a (plant) metabolite or nutrient which is taken up by the insect.

Linkers may undergo self-cleaving in the endosome. This may be advantageous when the constructs of the present invention are taken up by the insect via endocytosis or transcytosis, and are therefore compartmentalized in the endosomes of the insect species. The endosomes may have a low pH environment, leading to cleavage of the linker.

Linkers that are self-cleaving in hydrophobic conditions are particularly useful in dsRNA constructs when used to be transferred from one cell to another via the transit in a cell wall, for example when crossing the cell wall of an insect pest organism.

An intron may be used as a linker. An "intron" as used herein may be any non-coding RNA sequence of a messenger RNA.

A non-complementary RNA sequence, ranging from about 1 base pair to about 10,000 base pairs, may also be used as a linker.

Without wishing to be bound by any particular theory or mechanism, it is thought that long dsRNAs are taken up by the insect from their immediate environment. dsRNAs taken up into the gut and transferred to the gut epithelial cells are then processed within the cell into short dsRNAs, called small interfering RNAs (siRNAs), by the action of an endogenous endonuclease. The resulting siRNAs then mediate RNAi via formation of a multi-component RNase complex termed the RISC or RNA interfering silencing complex.

In order to achieve down-regulation of a target gene within an insect cell the dsRNA added to the exterior of the cell wall may be any dsRNA or dsRNA construct that can be taken up into the cell and then processed within the cell into siRNAs, which then mediate RNAi, or the RNA added to the exterior of the cell could itself be an siRNA that can be taken up into the cell and thereby direct RNAi.

siRNAs are generally short dsRNAs having a length in the range of from 19 to 25 base pairs, or from 20 to 24 base pairs. In preferred embodiments siRNAs having 19, 20, 21, 22, 23, 24 or 25 base pairs, and in particular 21 or 22 base pairs, corresponding to the target gene to be down-regulated may be used. However, the invention is not intended to be limited to the use of such siRNAs.

siRNAs may include single-stranded overhangs at one or both ends, flanking the double-stranded portion. The siRNA may contain 3' overhanging nucleotides, preferably two 3' overhanging thymidines (dTdT) or uridines (UU). 3' TT or UU overhangs may be included in the siRNA if the sequence of the target gene immediately upstream of the sequence included in double-stranded part of the dsRNA is AA. This allows the TT or UU overhang in the siRNA to hybridize to the target gene. Although a 3' TT or UU overhang may also be included at the other end of the siRNA it is not essential for the target sequence downstream of the sequence included in double-stranded part of the siRNA to have AA. In this context, siRNAs which are RNA/DNA chimeras are also contemplated. These chimeras include, for example, the siRNAs comprising a dsRNA with 3' overhangs of DNA bases (e.g., dTdT), as discussed above, and also dsRNAs which are polynucleotides in which one or more of the RNA bases or ribonucleotides, or even all of the ribonucleotides on an entire strand, are replaced with DNA bases or deoxyribonucleotides.

dsRNA may be formed from two separate (sense and antisense) RNA strands that are annealed together by (non-covalent) base pairing. Alternatively, the dsRNA may have a foldback stem-loop or hairpin structure, wherein the two annealed strands of the dsRNA are covalently linked. In this embodiment the sense and antisense stands of the dsRNA are formed from different regions of single polynucleotide molecule that is partially self-complementary. RNAs having this structure are convenient if the dsRNA is to be synthesized by expression in vivo, for example in a host cell or organism, or by in vitro transcription. The precise nature and sequence of the "loop" linking the two RNA strands is generally not material to the invention, except that it should not impair the ability of the double-stranded part of the molecule to mediate RNAi. The features of "hairpin" or "stem-loop" RNAs for use in RNAi are generally known in the art (see for example WO 99/53050, the contents of which are incorporated herein by reference). In other embodiments of the invention, the loop structure may comprise linker sequences or additional sequences as described above.

In certain aspects, the Li and Om sequences disclosed herein and the complements of such sequences may also be used to inhibit expression of Li or Om nucleic acids via expression of antisense RNA or overexpression of sense RNA, using methods well known in the art. See, e.g., Frizzi et al., Plant Biotech J, (2010) 8:655-677; Brodersen et al., Trends in Genetics, (2008) 22:268-280; and U.S. Pat. No. 5,759,829. Using expression elements, vectors and methods described herein, antisense RNAs or sense RNAs for Li and Om target genes are expressed in *eucalyptus* plants. Upon ingestion by Om or Li pests, the antisense or sense RNAs inhibit expression of the target genes to control pest infestation.

Target nucleotide sequences for design the dsRNA constructs are preferably at least 17, preferably at least 18, 19, 20 or 21, more preferably at least 22, 23 or 24 nucleotides in length. Non-limiting examples of preferred target nucleotide sequences are given in the examples.

Target sequences may include sequences that are homologous to sequences disclosed herein. Homologues of target genes can be found using methods well known to those of ordinary skill in the art. Preferred homologues are genes comprising a sequence which is at least about 85% or 87.5%, still more preferably about 90%, still more preferably at least about 95% and most preferably at least about 99% or 99.9% identical to a sequence disclosed herein, or the complement thereof. Methods for determining sequence identity are routine in the art and include use of the Blast software and EMBOSS software (The European Molecular Biology Open Software Suite (2000), Rice, P. Longden, I. and Bleasby, A. Trends in Genetics 16, (6) pp 276-277). The term "identity" as used herein refers to the relationship between sequences at the nucleotide level. The expression "% identical" is determined by comparing optimally aligned sequences, e.g., two or more, over a comparison window wherein the portion of the sequence in the comparison window may comprise insertions or deletions as compared to the reference sequence for optimal alignment of the sequences. The reference sequence does not comprise insertions or deletions. The reference window is chosen from between at least 10 contiguous nucleotides to about 50, about 100 or to about 150 nucleotides, preferably between about 50 and 150 nucleotides. "percent identity" is then calculated by determining the number of nucleotides that are identical between the sequences in the window, dividing the number of identical nucleotides by the number of nucleotides in the window and multiplying by 100.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C. and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) Anal. Biochem., 138:267-84: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$, is reduced by about 1° C. for each 1% of mismatching; thus, $T_m$, hybridization and/or wash conditions can be adjusted to hybridize to sequences of the desired identity. For example, if sequences with >90% identity are sought, the $T_m$, can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, Laboratory Techniques in Biochemistry and Molecular Biology—Hybridization with Nucleic Acid Probes, part I, chapter 2, "Overview of principles of hybridization and the strategy of nucleic acid probe assays," Elsevier, N.Y. (1993); and Current Protocols in Molecular Biology, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C. and a wash in 0.1×SSC, 0.1% SDS at 65° C.

dsRNA may be expressed by (e.g., transcribed within) a host cell or host organism. The host cell or organism may or may not be a host cell or organism susceptible or vulnerable to infestation by an insect. If the host cell or organism is a host cell or organism susceptible or vulnerable to infestation by an insect, RNAi-mediated gene silencing of one or more target genes in the insect may be used as a mechanism to control growth of the insect in or on the host organism and/or to prevent or reduce insect infestation of the host organism. Expression of the dsRNA within cells of the host organism may thus confer resistance to a particular insect or to a class of insects. In case the dsRNA hits more than one insect target gene, expression of the dsRNA within cells of the host organism may confer resistance to more than one insect or more than one class of insects.

In a preferred embodiment the host organism is a plant and the insect is a plant pathogenic insect. In this embodiment the insect is contacted with the dsRNA by expressing the dsRNA in a plant, plant tissue or plant cell that is infested with or susceptible to infestation with, or ingestion by, the plant pathogenic insect. A preferred plant host organism is *eucalyptus*. Examples of *eucalyptus* include, without limitation, the following species: *E. botryoides, E. bridgesiana, E. camaldulensis, E. cinerea, E. globule, E. grandis, E. gunii, E. nicholii, E. pulverulenta, E. robusta, E. rudis, E. saligna, E. Tereticornis, E. Urophilla, E. viminalis* and a cross hybrids of any of the preceding species especially *Eucalyptus grandis* and *Eucalyptus urophylla*. A preferred plant pathogenic insect is a gall wasp, e.g., Li or Om.

The term "plant" encompasses any plant material that it is desired to treat to prevent or reduce insect growth and/or insect infestation. This includes, inter alia, whole plants, seedlings, propagation or reproductive material such as seeds, cuttings, grafts, explants, etc. and also plant cell and tissue cultures. The plant material should express, or have the capability to express, dsRNA corresponding to one or more target genes of the insect.

In certain aspects the invention provides a plant, preferably a transgenic plant, or propagation or reproductive material for a (transgenic) plant, or a plant cell culture expressing or capable of expressing at least one dsRNA, wherein the dsRNA comprises annealed complementary strands, one of which has a nucleotide sequence which is complementary to at least part of a target nucleotide sequence of a target gene of an insect, such that the dsRNA is taken up by an insect upon plant-insect interaction, said double stranded RNA being capable of inhibiting the target gene or down-regulating expression of the target gene by RNA interference. The target gene may be any of the target genes herein described, for instance a target gene that is essential for the viability, growth, development or reproduction of the insect.

A plant may be provided in a form that is actively expressing (transcribing) a dsRNA in one or more cells, cell types or tissues. Alternatively, a plant may be "capable of expressing", meaning that it is transformed with a transgene which encodes the desired dsRNA but that the transgene is not active in the plant when (and in the form in which) the plant is supplied. A recombinant DNA construct comprising a nucleotide sequence encoding a dsRNA or dsRNA construct may be thus be operably linked to at least one regulatory sequence. Preferably, the regulatory sequence is selected from the group comprising constitutive promoters or tissue specific promoters as described below.

A target gene may be any target gene herein described. Preferably a regulatory element is a regulatory element that is active in a plant cell. More preferably, the regulatory element is originating from a plant. The term "regulatory sequence" is to be taken in a broad context and refers to a regulatory nucleic acid capable of effecting expression of the sequences to which it is operably linked.

Encompassed by the aforementioned term are promoters and nucleic acids or synthetic fusion molecules or derivatives thereof which activate or enhance transcription of a nucleic acid, so called activators or enhancers. The term "operably linked" as used herein refers to a functional linkage between the promoter sequence and the gene of interest, such that the promoter sequence is able to initiate transcription of the gene of interest.

By way of example, the transgene nucleotide sequence encoding the dsRNA could be placed under the control of an inducible or growth or developmental stage-specific promoter which permits transcription of the dsRNA to be turned on, by the addition of the inducer for an inducible promoter or when the particular stage of growth or development is reached.

Alternatively, the transgene encoding the dsRNA is placed under the control of a strong constitutive promoter such as any selected from the group comprising the CaMV35S promoter, doubled CaMV35S promoter, ubiquitin promoter, actin promoter, rubisco promoter, GOS2 promoter, Figwort mosaic virus (FMV) 34S promoter, cassaya vein mosaic virus (CsVMV) promoter (Verdaguer B. et al, Plant Mol. Biol. 1998 37(6):1055-67).

Alternatively, the transgene encoding the dsRNA is placed under the control of a tissue specific promoter such as any selected from the group comprising root specific promoters of genes encoding PsMTA Class III chitinase, photosynthetic tissue-specific promoters such as promoters of cab1 and cab2, rbcS, gapA, gapB and ST-LS1 proteins, JAS promoters, chalcone synthase promoter and promoter of RJ39 from strawberry.

A transgene encoding the dsRNA may also be placed under the control of an insect-induced promoter, for instance the potato proteinase inhibitor II (PinII) promoter (Duan X et al, Nat. Biotechnol. 1996, 14(4):494-8)); or a wounding-induced promoter, for instance the jasmonates and ethylene induced promoters, PDF1.2 promoter (Manners J Metal., Plant Mol. Biol. 1998, 38(6):1071-80); or under a defense related promoter, for instance the salicylic acid induced promoters and plant-pathogenesis related protein (PR protein) promoters (PR1 promoter (Cornelissen B J et al., Nucleic Acids Res. 1987, 15(17):6799-811; COMT promoter (Toquin V et al, Plant Mol. Biol. 2003, 52(3):495-509).

When using the methods described herein for developing transgenic plants resistant against insects, it may be beneficial to place the nucleic acid encoding the dsRNA under the control of a tissue-specific promoter. In order to improve the transfer of the dsRNA from the plant cell to the pest, the plants could preferably express the dsRNA in a plant part that is first accessed or damaged by the plant pest. In case of plant pathogenic insects, preferred tissues to express the dsRNA are the leaves, stems, roots, and seeds. Therefore, in the methods disclosed herein, a plant tissue-preferred promoter may be used, such as a leaf-specific promoter, a stem-specific promoter, a phloem-specific promoter, a xylem-specific promoter, a root-specific promoter, or a seed-specific promoter (sucrose transporter gene AtSUC promoter (Baud S et al., Plant J. 2005, 43(6):824-36), wheat high molecular weight glutenin gene promoter (Robert L S et al., Plant Cell. 1989, 1(6):569-78.)).

Suitable examples of a root specific promoter are PsMTA (Fordam-Skelton, A. P., et al., 1997 Plant Molecular Biology 34: 659-668.) and the Class III Chitinase promoter. Examples of leaf- and stem-specific or photosynthetic tissue-specific promoters that are also photoactivated are promoters of two chlorophyll binding proteins (cab1 and cab2) from sugar beet (Stahl D. J., et al., 2004 BMC Biotechnology 2004 4:31), ribulose-bisphosphate carboxylase (Rubisco), encoded by rbcS (Nomura M. et al., 2000 Plant Mol. Biol. 44: 99-106), A (gapA) and B (gapB) subunits of chloroplast glyceraldehyde-3-phosphate dehydrogenase (Conley T. R. et al. 1994 Mol. Cell. Biol. 19: 2525-33; Kwon H. B. et al. 1994 Plant Physiol. 105: 357-67), promoter of the *Solanum tuberosum* gene encoding the leaf and stem specific (ST-LS1) protein (Zaidi M. A. et al., 2005 Transgenic Res. 14:289-98), stem-regulated, defense-inducible genes, such as JAS promoters (patent publication no. 20050034192/US-A1). An example of a flower-specific promoter is for instance, the chalcone synthase promoter (Faktor O. et al. 1996 Plant Mol. Biol. 32: 849) and an example of a fruit-specific promoter is for instance RJ39 from strawberry (WO 98 31812).

Other promoters useful for the expression of dsRNA are used and include, but are not limited to, promoters from an RNA PolI, an RNA PolI, an RNA PolIII, T7 RNA polymerase or SP6 RNA polymerase. These promoters are typically used for in vitro-production of dsRNA, which dsRNA is then included in an anti-insecticidal agent, for example, in an anti-insecticidal liquid, spray or powder.

The dsRNA or RNA constructs described herein may be generated by the steps of (i) contacting an isolated nucleic acid or a recombinant DNA construct with cell-free components; or (ii) introducing (e.g., by transformation, transfection or injection) an isolated nucleic acid or a recombinant DNA construct into a cell, under conditions that allow transcription of the nucleic acid or recombinant DNA construct to produce the dsRNA or RNA construct.

Optionally, one or more transcription termination sequences may also be incorporated in the recombinant construct. The term "transcription termination sequence" encompasses a control sequence at the end of a transcriptional unit, which signals 3' processing and poly-adenylation of a primary transcript and termination of transcription. Additional regulatory elements, such as transcriptional or translational enhancers, may be incorporated in the expression construct.

Recombinant constructs may further include an origin of replication which is required for maintenance and/or replication in a specific cell type. One example is when an expression construct is required to be maintained in a bacterial cell as an episomal genetic element (e.g., plasmid or cosmid molecule) in a cell. Preferred origins of replication include, but are not limited to, f1-ori and colE1 ori.

Recombinant construct may optionally include a selectable marker gene. As used herein, the term "selectable marker gene" includes any gene, which confers a phenotype on a cell in which it is expressed to facilitate the identification and/or selection of cells, which are transfected or transformed, with an expression construct of the invention. Examples of suitable selectable markers include resistance genes against ampicillin ($Amp^r$), tetracycline ($Tc^r$), kanamycin ($Kan^r$), phosphinothricin, and chloramphenicol (CAT) gene. Other suitable marker genes provide a metabolic trait, for example manA. Visual marker genes may also be used and include for example beta-glucuronidase (GUS), luciferase and Green Fluorescent Protein (GFP).

Plants that have been stably transformed with a transgene encoding the dsRNA may be supplied as seed, reproductive material, propagation material or cell culture material which does not actively express the dsRNA but has the capability to do so. The plant may be provided in a form wherein it is actively expressing (transcribing) the RNA molecule in one or more cells, cell types or tissues. Alternatively, the plant may be "capable of expressing", meaning that it is transformed with a transgene which encodes the desired RNA molecule but that the transgene is not active in the plant when (and in the form in which) the plant is supplied. Many vectors are available for this purpose, and selection of the appropriate vector will depend mainly on the size of the nucleic acid to be inserted into the vector and the particular host cell to be transformed with the vector.

General techniques for expression of exogenous dsRNA in plants for the purposes of RNAi are known in the art (see Baulcombe D, 2004, Nature. 431(7006):356-63. RNA silencing in plants, the contents of which are incorporated herein by reference). More particularly, methods for expression of dsRNA in plants for the purposes of down-regulating gene expression in plant pests such as nematodes or insects are also known in the art. Similar methods can be applied in an analogous manner in order to express dsRNA in plants for the purposes of down-regulating expression of a target gene in a plant pathogenic insect. In order to achieve this effect it is necessary only for the plant to express (transcribe) the dsRNA in a part of the plant which will come into direct contact with the insect, such that the dsRNA can be taken up by the insect. Depending on the nature of the insect and its relationship with the host plant, expression of the dsRNA could occur within a cell or tissue of a plant within which the insect is also present during its life cycle, or the RNA may be secreted into a space between cells, such as the apoplast, that is occupied by the insect during its life cycle. Furthermore, the dsRNA may be located in the plant cell, for example in the cytosol, or in the plant cell organelles such as a chloroplast, mitochondrion, vacuole or endoplastic reticulum.

During development, gall wasp larvae are exposed to the extracellular environment and to intracellular contents, due to ingestion (e.g., ingestion of apoplasts) or cell lysis. Accordingly, gall wasp larvae may be exposed to dsRNA that is either present in cells in the gall or that is secreted by cells in or around the gall.

Alternatively, the dsRNA may be secreted by the plant cell and by the plant to the exterior of the plant. As such, the dsRNA may form a protective layer on the surface of the plant.

In a further aspect, the invention also provides combinations of methods and compositions for preventing or protecting plants from pest infestation. For instance, one means provides using the plant transgenic approach combining methods using expression of dsRNA molecules and methods using expression of such Bt insecticidal proteins.

In a further embodiment, the invention relates to a composition for controlling insect growth and/or preventing or reducing insect infestation, comprising at least a plant part, plant cell, plant tissue or seed comprising at least one dsRNA, wherein said dsRNA comprises annealed complementary strands, one of which has a nucleotide sequence which is complementary to at least part of a nucleotide sequence of an insect target gene. Optionally, the composition further comprises at least one suitable carrier, excipient or diluent. The target gene may be any target gene described herein. Preferably the insect target gene is essential for the viability, growth, development or reproduction of the insect.

Whenever the term "a" is used within the context of "a target gene", this means "at least one" target gene. The same applies for "a" target organism meaning "at least one" target organism, and "a" RNA molecule or host cell meaning "at least one" RNA molecule or host cell.

According to one embodiment, the methods of the invention rely on uptake by the insect of dsRNA present outside of the insect (e.g., by feeding) and does not require expression of dsRNA within cells of the insect. In addition, the present invention also encompasses methods as described above wherein the insect is contacted with a composition comprising the dsRNA. Gall wasp larvae typically do not feed outside the gall and it is thus preferable that gall wasp larvae are exposed to dsRNA via transgenic plant material.

The invention further provides a method for down-regulating expression of at least one target gene in a target organism (which is capable of ingesting a plant, plant part, plant cell or seeds) comprising feeding a plant, plant part, plant cell or seed to the target organism which plant, plant part, plant cell or seed expresses dsRNA.

In a more preferred aspect, the invention provides a method for down-regulating expression of at least one target gene in a target organism (which is capable of ingesting a host cell, or extracts thereof) comprising feeding a host plant, plant part, plant cell or seed to the target organism which host plant, plant part, plant cell or seed expresses a dsRNA molecule comprising a nucleotide sequence complementary to or representing the RNA equivalent of at least part of the nucleotide sequence of the at least one target gene, whereby the ingestion of the host cell, host plant, plant part, plant cell or seed by the target organism causes and/or leads to down-regulation of expression of the at least one target gene.

The invention provides for use of a plant, plant part, plant cell or seed as defined herein for down regulation of expression of an insect target gene. In more detailed terms, the invention provides for use of a host cell as defined herein and/or an RNA molecule comprising a nucleotide sequence that is the RNA complement of or that represents the RNA equivalent of at least part of the nucleotide sequence of a target gene from a target organism, as produced by transcription of a nucleic acid molecule in a plant, plant part, plant cell or seed, for instance in the manufacture of a commodity product, for down regulation of expression of a target gene.

According to one embodiment, the methods of the invention rely on a genetically modified organism (GMO) approach wherein the dsRNA is expressed by a cell or an organism infested with or susceptible to infestation by insects. Preferably, said cell is a plant cell or said organism is a plant.

For siRNA mediated downregulation of insect genes, dsRNA is introduced and/or expressed in an insect cell, either directly or indirectly. dsRNA can be added to an insect diet artificially or produced by a transgenic source of food such as bacteria and plants [2,8]. Transgenic plants transcribing inverted repeat RNAs comprised of insect gene specific sequences, can process it to dsRNA and later into siRNA (small interfering RNA that are the first product in the silencing pathway).

Insects digesting such transgenic plants are affected by the plant synthesized dsRNA and siRNA [5]. This insect control method can be utilized to protect plants efficiently against specific pests [2,8]. It is not required, however, that dsRNA be processed to siRNA in plant material. dsRNA may be ingested by the insect pest and processed to siRNA for the first time within the insect cell.

Numerous methods for introducing foreign genes into plants are known and can be used to insert an NT polynucleotide into a plant host, including biological and physical plant transformation protocols. See, e.g., Miki et al., "Procedure for Introducing Foreign DNA into Plants," in Methods in Plant Molecular Biology and Biotechnology, Glick and Thompson, eds., CRC Press, Inc., Boca Raton, pp. 67-88 (1993). The methods chosen vary with the host plant, and include chemical transfection methods such as calcium phosphate, microorganism-mediated gene transfer such as *Agrobacterium* (Horsch et al., Science 227:1229-31 (1985)), electroporation, micro-injection, and biolistic bombardment.

Expression cassettes and vectors and in vitro culture methods for plant cell or tissue transformation and regeneration of plants are known and available. See, e.g., Gruber et al., "Vectors for Plant Transformation," in Methods in Plant Molecular Biology and Biotechnology, supra, pp. 89-119.

The isolated polynucleotides or polypeptides may be introduced into the plant by one or more techniques typically used for direct delivery into cells. Such protocols may vary depending on the type of organism, cell, plant or plant cell, i.e., monocot or dicot, targeted for gene modification. Suitable methods of transforming plant cells include microinjection (Crossway, et al., (1986) Biotechniques 4:320-334; and U.S. Pat. No. 6,300,543), electroporation (Riggs, et al., (1986) Proc. Natl. Acad. Sci. USA 83:5602-5606, direct gene transfer (Paszkowski et al., (1984) EMBO J. 3:2717-2722), and ballistic particle acceleration (see, for example, Sanford, et al., U.S. Pat. No. 4,945,050; WO 91/10725; and McCabe, et al., (1988) Biotechnology 6:923-926). Also see, Tomes, et al., "Direct DNA Transfer into Intact Plant Cells Via Microprojectile Bombardment". pp. 197-213 in Plant Cell, Tissue and Organ Culture, Fundamental Methods. eds. O. L. Gamborg & G. C. Phillips. Springer-Verlag Berlin Heidelberg N.Y., 1995; U.S. Pat. No. 5,736,369 (meristem); Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); WO 91/10725 (maize); Klein, et al., (1988) Plant Physiol. 91:440-444 (maize); Fromm, et al., (1990) Biotechnology 8:833-839; and Gordon-Kamm, et al., (1990) Plant Cell 2:603-618 (maize); Hooydaas-Van Slogteren & Hooykaas (1984) Nature (London) 311:763-764; Bytebierm, et al., (1987) Proc. Natl. Acad. Sci. USA 84:5345-5349 (Liliaceae); De Wet, et al., (1985) In The Experimental Manipulation of Ovule Tissues, ed. G P. Chapman, et al., pp. 197-209. Longman, N.Y. (pollen); Kaeppler, et al., (1990) Plant Cell Reports 9:415-418; and Kaeppler, et al., (1992) Theor. Appl. Genet. 84:560-566 (whisker-mediated transformation); U.S. Pat. No. 5,693,512 (sonication); D'Halluin, et al., (1992) Plant Cell 4:1495-1505 (electroporation); Li, et al., (1993) Plant Cell Reports 12:250-255; and Christou and Ford, (1995) Annals of Botany 75:407-413 (rice); Osjoda, et al., (1996) Nature Biotech. 14:745-750; *Agrobacterium* mediated maize transformation (U.S. Pat. No. 5,981,840); silicon carbide whisker methods (Frame, et al., (1994) Plant J. 6:941-948); laser methods (Guo, et al., (1995) Physiologia Plantarum 93:19-24); sonication methods (Bao, et al., (1997) Ultrasound in Medicine & Biology 23:953-959; Finer and Finer, (2000) Lett Appl Microbiol. 30:406-10; Amoah, et al., (2001) J Exp Bot 52:1135-42); polyethylene glycol methods (Krens, et al., (1982) Nature 296:72-77); protoplasts of monocot and dicot cells can be transformed using electroporation (Fromm, et al., (1985) Proc. Natl. Acad. Sci. USA 82:5824-5828) and microinjection (Crossway, et al., (1986) Mol. Gen. Genet. 202:179-185); all of which are herein incorporated by reference.

The most widely utilized method for introducing an expression vector into plants is based on the natural transformation system of *Agrobacterium. A. tumefaciens* and *A. rhizogenes* are plant pathogenic soil bacteria, which genetically transform plant cells. The Ti and Ri plasmids of *A. tumefaciens* and *A. rhizogenes*, respectively, carry genes responsible for genetic transformation of plants. See, e.g., Kado, (1991) Crit. Rev. Plant Sci. 10:1. Descriptions of the *Agrobacterium* vector systems and methods for *Agrobacterium*-mediated gene transfer are provided in Gruber, et al., supra; Miki, et al., supra; and Moloney, et al., (1989) Plant Cell Reports 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey and Chua, (1989) Science 244:174-81. Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. patent application Ser. No. 913,914, filed Oct. 1, 1986, as referenced in U.S. Pat. No. 5,262,306, issued Nov. 16, 1993; and Simpson, et al., (1986) Plant Mol. Biol. 6:403-15m all incorporated by reference in their entirety.

Once constructed, these plasmids can be placed into *A. rhizogenes* or *A. tumefaciens* and these vectors used to transform cells of plant species, which are ordinarily susceptible to *Fusarium* or *Alternaria* infection. The selection of either *A. tumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g., certain members of the Liliales and Arales) are susceptible to infection with *A. tumefaciens. A. rhizogenes* also has a wide host range, embracing most dicots and some gymnosperms, which includes members of the Leguminosae, Compositae, and Chenopodiaceae. Monocot plants can now be transformed with some success. European Patent Application No. 604 662 A1 discloses a method for transforming monocots using *Agrobacterium*. European Application No. 672 752 A 1 discloses a method for transforming monocots with *Agrobacterium* using the scutellum of immature embryos. Ishida, et al., discuss a method for transforming maize by exposing immature embryos to *A. tumefaciens* (Nature Biotechnology 14:745-50 (1996)).

Once transformed, these cells can be used to regenerate transgenic plants. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenes* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, (1985) Theor. Appl. Genet. 69:235-40; U.S. Pat. No. 4,658,082; Simpson, et al., supra; and U.S. patent application Nos. 913,913 and 913,914, both filed Oct. 1, 1986, as referenced in U.S. Pat. No. 5,262,306, issued Nov. 16, 1993, the entire disclosures therein incorporated herein by reference.

Several methods of plant transformation, collectively referred to as direct gene transfer, have been developed as an alternative to *Agrobacterium*-mediated transformation.

A generally applicable method of plant transformation is microprojectile-mediated transformation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes (Sanford, et al., (1987) Part. Sci. Technol. 5:27; Sanford, (1988) Trends Biotech 6:299; Sanford, (1990) Physiol. Plant 79:206; and Klein, et al., (1992) Biotechnology 10:268).

Another method for physical delivery of DNA to plants is sonication of target cells as described in Zang, et al., (1991) BioTechnology 9:996. Alternatively, liposome or spheroplast fusions have been used to introduce expression vectors into plants. See, e.g., Deshayes, et al., (1985) EMBO J. 4:2731; and Christou, et al., (1987) Proc. Natl. Acad. Sci. USA 84:3962. Direct uptake of DNA into protoplasts using $CaCl_2$ precipitation, polyvinyl alcohol, or poly-L-ornithine has also been reported. See, e.g., Hain, et al., (1985) Mol. Gen. Genet. 199:161; and Draper, et al., (1982) Plant Cell Physiol. 23:451.

Electroporation of protoplasts and whole cells and tissues has also been described. See, e.g., Donn, et al., (1990) Abstracts of the VIIth Int'l. Congress on Plant Cell and Tissue Culture IAPTC, A2-38, p. 53; D'Halluin, et al., (1992) Plant Cell 4:1495-505; and Spencer, et al., (1994) Plant Mol. Biol. 24:51-61.

Following stable transformation, plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant.

Transformed plant may be regenerated by micropropagation which provides a rapid, consistent reproduction of the transformed plants. Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

In certain aspects the invention provides methods of producing a plant resistant to a plant pathogenic pest by transforming a plant cell with a recombinant DNA construct or combination of constructs that express a dsRNA; regenerating a plant from the transformed plant cell; and growing the transformed plant cell under conditions suitable for the expression said recombinant DNA construct.

The methods of the invention are applicable to gall wasp species, e.g., *Leptocybe invasa* (Li) and *Ophelimus maskelli* (Om) that are susceptible to gene silencing by RNA interference and that are capable of internalizing dsRNA from their immediate environment. The invention is applicable to the insect at any stage in its development. Because insects have a non-living exoskeleton, they cannot grow at a uniform rate and rather grow in stages by periodically shedding their exoskeleton. This process is referred to as molting or ecdysis. The stages between molts are referred to as "instars" and these stages may be targeted according to the invention.

Also, insect eggs or live young may also be targeted according to the present invention. All stages in the developmental cycle, which includes metamorphosis in the pterygotes, may be targeted according to the present invention. Thus, individual stages such as larvae, pupae, nymph etc. stages of development may all be targeted.

Li and Om are pests for *eucalyptus*. The nucleic acids, dsRNAs and methods described herein are thus useful for treating or inhibiting Li and Om infection and infestation of *eucalyptus*.

In a preferred aspect, the invention provides RNAi mediated pest control to generate transgenic *eucalyptus* resistant to Gall wasps. Two *eucalyptus* gall wasp invasive species *Leptocybe invasa* (Li) and *Ophelimus maskelli* (Om) have recently spread out of Australia into plantations worldwide [6, 9]. Females can reproduce sexually or parthenogenetically and a full life cycle takes about 130 days. Eggs laid by these pests under the surface of tree veins and leaves induce the formation of galls in the target tissues that serve as a host shelter and food stock for the developing larvae. The exact compounds or signals that induce gall formation have not been elucidated. Thus secretions of compounds from the egg and larva but not from the mother are associated with gall wasp formation. Meristematic or omnipotent cells in young leaves are induced by either chemical, mechanical, viral or DNA manipulations which trigger their proliferation. The gall development parallels larvae development, thus the size and age of the gall can be correlated with the larvae developmental stage. Stone et al., 2002, "The population biology of oak gall wasps (Hymenoptera: Cynipidae)". Annu. Rev. Entomol. 47:633-68. Larval maturation induces further development of the galls until pupal stage. When the adult gall wasps emerge they are able to fly away and lay hundreds of eggs, infecting both the same tree as well as close and remote trees during a period of 3-6 days before they die. Massive gall wasp attacks cause growth arrest, leaf defoliation and death resulting in potentially massive forest yield losses. The sessile developing larvae, which, feed on transgenic plant tissue producing RNAi active against vital genes in the larvae, are affected by a consistent and relatively long term uptake of the si/dsRNA molecules tailor designed to silent specific vital gall wasp genes. Ultimately the silencing effect leads to larval mortality in the early growth stage thus protecting the host and minimizing the size of the gall wasp population, protecting the host plant from the damage.

The larvae stage of gall wasps in non-transgenic trees can be as long as 130 days and thus the lethal effect of dsRNA can accumulate during the entire potential larvae growth phase. Once the larvae are dead, the development of the galls is arrested and the adult population is reduced, subsequently preventing infection on the same, neighboring or distal trees.

Transgenic resistant trees may be characterized by one or more of the following results on a "Gall Wasp Developmental Scale":

1. No galls are developed.
2. Small galls (indicator of low larval mass measurements) are developed as compared to WT [maximum length, diameter, area and/or volume are measured].
3. Low larval mass measurements compared to WT: total larval weight reduced compared to WT
4. More galls are hosting dead larvae compared to WT.
5. More galls are hosting dead pupas compared to WT.
6. No adults are emerging from the gall or galls compared to WT.
7. Developmentally impaired adults lacking the ability to reproduce or spread compared to the adults grown on wild type trees compared to WT.

EXAMPLES

Example 1

Gall Wasp Transcriptome Sequencing

Gall wasp infected leaves were collected from infected *E. camaldulensis* from Emek Izrael, Israel. Gall wasp larvae were removed from galls found on the leaves and or petioles of the trees by cutting and opening the galls using a sharp knife under a binocular microscope. A mixture of larval from various larval developmental stages were used. Batches of 100 larva was placed in a microtube on ice. The tube was then sealed and immediately frozen in liquid nitrogen and kept at −80° C. until further treatment. Total RNA was isolated using MasterPure RNA purification kit and protocol (MRC85102-Epicentere Biotechnologies). Total RNA volume was 50 μl. The total RNA was then treated with DNAse to remove any residual DNA remaining, followed by isolation of poly A mRNA (MicroPoly(A) Purist, Small scale mRNA Purification kit, AM1919 Ambion). mRNA final volume was 20 μl. The purified mRNA was kept at −80° C. until 454 Sequencing was performed. 454 Sequencing was carried out according to standard protocols to provide transcriptomes of the target pests.

Example 2

Identification of Li and Om Target Genes and Sequences

Unique, vital Li and Om genes essential either for cellular processes or proper developmental processes of a specific tissue or entire organism were chosen as targets for gene silencing. Initially, standard procedures using degenerate primers based on known homologous hymenopterans sequences were used to identify fragments of target genes. Thereafter, the respective transcriptomes of the Li and Om gall wasp larvae were sequenced using the 454 Sequencer deep sequencing platform. (454 Life Sciences; Branford, CT, USA; now Roche, Basel). Sequences were assembled and 20 results annotated on the basis of sequence alignment with known published hymenopteran transcriptomes using the Roche software package and annotated using the Blast2Go program.

Table 1 gives the SEQ ID NOs: for complete or partial gene sequences of identified genes 1-9 from Li and Om.

TABLE 1

| Li and Om genes | | | |
|---|---|---|---|
| | Gene | *Leptocybe invasa* | *Ophelimus maskelli* |
| 1 | Coatomer subunit alpha-like (Alpha COP) | SEQ ID NO: 15 | SEQ ID NO: 21 |
| 2 | chromodomain helicase DNA binding protein Mi-2 homolog (Cdh3) | SEQ ID NO: 16 | SEQ ID NO: 22 |
| 3 | venom carboxylesterase-6 isoform 1 (VCE-F2) | SEQ ID NO: 17 | SEQ ID NO: 23 |
| 4 | hypothetical protein LOC100118280 (Chitin_synth_C) | SEQ ID NO: 18 | SEQ ID NO: 24 |
| 5 | Ferritin precursor | SEQ ID NO: 19 | SEQ ID NO: 25 |
| 6 | juvenile hormone epoxide hydrolase 2-like (JHEH) | SEQ ID NO: 20 | SEQ ID NO: 26 |
| 7 | SWI/SNF complex subunit SMARCC2 (MOR) | SEQ ID NO: 104 | SEQ ID NO: 103 |
| 8 | Eukaryotic translation initiation factor 3 subunit I-like (TIF) | SEQ ID NO: 121 | SEQ ID NO: 120 |
| 9 | Protein phosphatase PP2A 55 kDa regulatory subunit-like isoform 1 | SEQ ID NO: 123 | SEQ ID NO: 122 |

Genes 1-9 were compared to the respective A. mellifera genes for Alpha COP sequence (XM_623195, coding region set out in SEQ ID NO: 39), Cdh3 sequence (XM_624411, coding region set out in SEQ ID NO: 40), venom carboxylesterase-6isoform 1 (VCE-F2) (XM_391943, coding region set out in SEQ ID NO: 44), chitin synthase (XP_395677, coding region set out in SEQ ID NO: 43), ferritin sequence (XM_624041, coding region set out in SEQ ID NO: 41), JHEH (XM_394922, coding region set out in SEQ ID NO: 42), SWI/SNF complex subunit SMARCC2 (MOR) (XM_393008, coding region set out in SEQ ID NO: 134), Eukaryotic translation initiation factor 3 subunit I-like (TIF) (XM_392780, coding region set out in SEQ ID NO: 135) and Protein phosphatase PP2A 55 kDa regulatory subunit-like isoform 1(XM_394082, coding region set out in SEQ ID NO: 136). Comparisons were made using a publicly available NCBI B12Seq analysis program to identify 100 bp sequences from each gene that share limited (i.e., less than 80%) identity to corresponding Li and Om genes (or, when not possible to identify a 100 bp sequence with less than 80% identity as for OM Protein phosphatase PP2A 55 kDa regulatory subunit-like isoform 1, identify a smaller fragment such as an 81 bp sequence). The regions identified all exhibited 33-76% identity to the respective honey bee sequences. The respective 100 bp sequences for each gene (81 bp for OM Protein phosphatase PP2A 55 kDa regulatory subunit-like isoform 1) with limited identity to the corresponding honey bee gene are identified in Table 2, with the percent identity to the corresponding honey bee sequence indicated for each fragment.

TABLE 2

| Li and Om 100 bp Gene Fragments With Limited Identity to honey bee (*Apis mellifera*) sequence.[1] | | | |
|---|---|---|---|
| Gene No. | Gene (*A. mellifera* accession no.) | *Leptocybe invasa* | *Ophelimus maskelli* |
| 1 | Coatomer subunit alpha-like (Alpha COP) (XM_623195) | SEQ ID NO: 1 (53) | SEQ ID NO: 7[4] (47) |
| 2 | chromodomain helicase DNA binding protein Mi-2 homolog (Cdh3) (XM_624411) | SEQ ID NO: 3 (33) | SEQ ID NO: 8 (34) |
| 3 | venom carboxylesterase-6 isoform 1(VCE-F2) (XM_391943) | SEQ ID NO: 2 (48) | SEQ ID NO: 9 (51) |
| 4 | hypothetical protein LOC100118280 (Chitin_synth_C) (XP_395677) | SEQ ID NO: 4 (50) | SEQ ID NO: 10 (65) |
| 5 | Ferritin precursor (XM_624041) | SEQ ID NO: 5 (39) | SEQ ID NO: 11 (40) |
| 6 | juvenile hormone epoxide hydrolase 2-like (JHEH) (XM_394922) | SEQ ID NO: 6 (36) | SEQ ID NO: 12 (45) |
| 7 | SWI/SNF complex subunit SMARCC2 (MOR) (XM_393008) | SEQ ID NO: 127 (72) | SEQ ID NO: 130 (75) |
| 8 | Eukaryotic translation initiation factor 3 subunit I-like (TIF) (XM_392780) | SEQ ID NO: 128 (70) | SEQ ID NO: 131[2] (61) |

TABLE 2-continued

| Li and Om 100 bp Gene Fragments With Limited Identity to honey bee (*Apis mellifera*) sequence.[1] | | | |
|---|---|---|---|
| Gene No. | Gene (*A. mellifera* accession no.) | *Leptocybe invasa* | *Ophelimus maskelli* |
| 9 | Protein phosphatase PP2A 55 kDa regulatory subunit-like isoform 1 (PPR) (XM_394082) | SEQ ID NO: 129 (69) | SEQ ID NO: 132[3] (76) |

[1]Percent identity to the corresponding honey bee sequence is indicated in parenthesis for each fragment
[2]C472G change to eliminate SacI site
[3]81 bp sequence of limited homology identified and T2C change to eliminate XbaI site
[4]A93C change to eliminate predicted polyadenylation site Additional Li and Om target sequences with <80% identity to the respective honey bee sequences are set out in Table 3, with the accession no. for the honey bee used as in the comparison and the percent identity to the corresponding honey bee sequence indicated for each fragment

TABLE 3

| Additional Li and Om 100 bp Gene Fragments With Limited Identity to honey bee (*Apis mellifera*) sequence.[1] | | |
|---|---|---|
| Gene (*A. mellifera* accession no.) | *Leptocybe invasa* | *Ophelimus maskelli* |
| blw (XM_392639) | SEQ ID NO: 150 (53) | SEQ ID NO: 191 (63) |
| CG10881 (XM_391934) | SEQ ID NO: 151 (57) | SEQ ID NO: 192 (65) |
| RagA (XM_001119898) | SEQ ID NO: 152 (73) | |
| CG2931 (XM_392161) | SEQ ID NO: 153 (60) | |
| CG31524 (XM_392392) | SEQ ID NO: 154 (52) | |
| fred (XM_396867) | SEQ ID NO: 155 (66) | SEQ ID NO: 193 (65) |
| CG3590 (XM_393961) | SEQ ID NO: 156 (64) | SEQ ID NO: 194 (62) |
| CG5451 (XM_393446) | SEQ ID NO: 157 (71) | SEQ ID NO: 195 (67) |
| wls (XM_003250465) | SEQ ID NO: 158 (67) | |
| CG6690 (XM_001121155) | SEQ ID NO: 159 (51) | SEQ ID NO: 196 (51) |
| Cic (XM_395004) | SEQ ID NO: 160 (51) | SEQ ID NO: 197 (68) |
| Crc (XM_394892) | SEQ ID NO: 161 (47) | SEQ ID NO: 198 (75) |
| D (XM_624095) | SEQ ID NO: 162 (44) | SEQ ID NO: 199 (69) |
| Dad (XM_396056) | SEQ ID NO: 163 (72) | SEQ ID NO: 200 (51) |
| Dhc64C (XM_003251584) | SEQ ID NO: 164 (63) | SEQ ID NO: 201 (65) |
| Dlg1 (XM_393395) | SEQ ID NO: 165 (44) | SEQ ID NO: 202 (51) |
| Dnc (XM_394762) | SEQ ID NO: 166 (60) | SEQ ID NO: 203 (67) |
| Ds (XM_393497) | SEQ ID NO: 167 (46) | |
| E[r] (XM_001119900) | SEQ ID NO: 168 (69) | |
| E(z) (XM_003249869) | SEQ ID NO: 169 (50) | |
| Ebi (XM_003251282) | SEQ ID NO: 170 (71) | SEQ ID NO: 204 (65) |
| EcR (NM_001159355) | SEQ ID NO: 171 (53) | |
| Ef1alpha48D (NM_001014993) | SEQ ID NO: 172 (70) | SEQ ID NO: 205 (75) |
| Ef1gamma (XM_623679) | SEQ ID NO: 173 (68) | SEQ ID NO: 206 (70) |
| eIF-2alpha (XM_001122232) | SEQ ID NO: 174 (46) | SEQ ID NO: 207 (68) |
| eIF3-S8 (XM_623577) | SEQ ID NO: 175 (52) | SEQ ID NO: 208 (46) |
| eIF5 (XM_392511) | SEQ ID NO: 176 (68) | SEQ ID NO: 209 (65) |
| Faf (XM_395447) | SEQ ID NO: 177 (59) | SEQ ID NO: 210 (70) |
| Hel25E (XM_624891) | SEQ ID NO: 178 (70) | SEQ ID NO: 211 (65) |
| HLH106 (XM_396866) | SEQ ID NO: 179 (44) | SEQ ID NO: 212 (50) |
| Hr38 (NM_001011634) | SEQ ID NO: 180 (51) | SEQ ID NO: 213 (56) |
| La (XM_395300) | SEQ ID NO: 181 (53) | SEQ ID NO: 214 (55) |
| Lin19 (XM_394044) | SEQ ID NO: 182 (72) | SEQ ID NO: 215 (64) |
| NAT1 (XM_394628) | SEQ ID NO: 183 (49) | SEQ ID NO: 216 (52) |
| Noi (XM_397399) | SEQ ID NO: 184 (66) | SEQ ID NO: 217 (68) |
| Pit (XM_397167) | | SEQ ID NO: 218 (42) |
| Psi (XM_624670 | SEQ ID NO: 185 (51) | SEQ ID NO: 219 (44) |
| Rb (XM_624443) | SEQ ID NO: 186 (54) | SEQ ID NO: 220 (74) |
| Sas (XR_120050) | SEQ ID NO: 187 (51) | |
| SCAR (XM_394398) | SEQ ID NO: 188 (45) | SEQ ID NO: 221 (55) |
| Shi (XM_394399) | SEQ ID NO: 189 (66) | |
| su(w[a]) (XM_392191) | SEQ ID NO: 190 (64) | SEQ ID NO: 222 (63) |

[1]Percent identity to the corresponding honey bee sequence is indicated in parenthesis for each fragment Example 3

Identification of Li and Om Target Genes and Sequences

BLAST (NCBI) comparisons using 141 genes identified as being lethal when expressed as RNAi in *Drosophila* (15, 16) were used to identify 127 orthologous sequences in *Nasonia vitiripines* (Nv). The identified Nv sequences were further used to screen Om and Li transcriptome libraries, prepared as in Example 1, for lethal genes. This screen identified 39 potential target sequences from the Om transcriptome library and 48 potential targets from the Li transcriptome, respectively, that included a continuous reading frame of at least 500 nucleotides and 1 potential target gene from Li that included a continuous open reading frame of 309 nucleotides (SEQ ID NO: 76) or were at least 50% of the respective predicted full length genes. In one example BLAST (NCBI) comparison using the *Drosophila melanogaster* gene ADV37321 (CG18740), which has been identified as being RNAi-lethal (15), was used to identify the Nv homolog gene XP_001605573. The Nv homolog gene XP_001605573 was used with BLAST to identify a Li homolog gene partial sequence, SEQ ID NO: 104 from the L±454 transcriptome library.

Three additional targets were identified by a PCR-based procedure, using degenerate primers to Nv genes. This procedure was used to identify potential targets set out in SEQ ID NO: 17, 23 and 24.

Li VCE-F2 (SEQ ID NO: 17) and Om VCE-F2 (SEQ ID NO: 23) were amplified using primer GATACCNTTYAGACCTGTWATTGARCC (SEQ ID NO: 143, based on nucleotides 1026-1052 of Nv gene XM_001599205) and primer GGATTTCCAGAWTTKGCRAARTTRTACC (SEQ ID NO: 144, based on nucleotides 1628-1655 of Nv gene XM_001599205). The fragments was sequenced and then re-amplified by nested specific primers in order to verify the sequence.

Om Chitin Synthase gene (SEQ ID NO: 24) was amplified using primer GGRAYCCACCGCCGAAGATCG (SEQ ID NO: 145, based on 158-178 of Nv gene XM_001602240.2) and primer GCGAATTTACCGAAKATGTACATG (SEQ ID NO: 146, based on nucleotides 1197-1220 of Nv gene XM_001602240.2). The fragment was sequenced and then re-amplified by nested specific primers in order to verify the sequence:

Prospective target sequences identified in Om and Li are set out respectively in SEQ ID SEQ ID NO: 15-26, 45-123 and 235-244.

The identified genes were divided into the following categories:

Proteins synthesis and metabolism: SEQ ID NO: 15, 21, 47, 48, 76, 80, 81, 82, 83, 84, 85, 86, 87, 88, 89, 90, 91, 92, 105, 106, 120, and 121.

Cellular processes: SEQ ID NO: 16-20, 22-26, 45, 46, 49, 51, 52, 53, 54, 55, 58, 59, 60, 65, 66, 67, 68, 69, 70, 71, 72, 73, 74, 75, 77, 78, 79, 97, 98, 101, 102, 112, 113, 114, 115, 116, 117, 122, 123, 235, 237, 238, 239, 240, 242, 243 and 244.

RNA synthesis and metabolism: SEQ ID NO: 50, 56, 57, 61, 62, 63, 64, 93, 94, 95, 96, 99, 100, 103, 104, 107, 108, 109, 110, 111, 118, 119, 236 and 241.

Example 4

Preparation of dsRNA Silencing Constructs

Alpha COP, Cdh3, VCE-F2 Silencing Construct (Construct #1)

The structure of construct 1 is shown in FIG. 1A. A 100 bp fragment of each of the Li Alpha COP, VCE-F2 and Cdh3genes (i.e., 100 bp of Li genes 1, 3 and 2; SEQ ID NO: 1, SEQ ID NO: 2, SEQ ID NO: 3) were fused and synthesized in inverted repeats separated by 106 bp of a first loop sequence (Loop 1; SEQ ID NO: 13) between 35S CaMV promoter (SEQ ID NO: 27) to AtRiboProS40 Terminator (SEQ ID NO: 32). A 100 bp fragment of each of the Om Alpha COP, Cdh3 and VCE-F2 genes (i.e., 100 bp of Om genes 1-3; SEQ ID NO: 7, SEQ ID NO: 8, SEQ ID NO: 9) were fused and synthesized in inverted repeat separated by 108 bp of a second loop sequence (Loop 2; SEQ ID NO: 14) between AtUBQ1 Promoter (SEQ ID NO: 28) to AtUBQ1 Terminator (SEQ ID NO: 33). The select 100 bp of Li genes 1, 3 and 2 (SEQ ID NO: 1, SEQ ID NO: 2, SEQ ID NO: 3) were fused to the select Om genes 1-3 (SEQ ID NO: 7, SEQ ID NO: 8, SEQ ID NO: 9) and synthesized in sense orientation between AtActin7 Promoter (SEQ ID NO: 29) to NOS Terminator (SEQ ID NO: 34).

Transcription of construct 1 would yield three mRNAs: (1) hairpin RNA (hpRNA) of 3×100 bp sequence of Li genes 1,3 and 2 to silence the corresponding genes of Li (see FIG. 1B); (2) hpRNA of 3×100 bp sequence of Om genes 1-3 to silence the corresponding genes of Om (see FIG. 1B); and (3) mRNA of 3×100 bp sense sequence of Li genes 1, 3 and 2 fused to 3×100 bp sense sequence of Om genes 1-3.

Chitin Synthase, Ferritin, JHEH Silencing Construct (Construct #2)

Figure 2A:
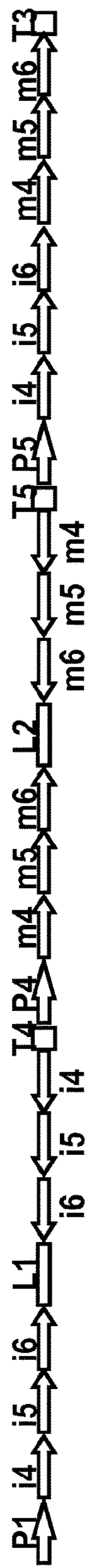
FIG. 2(A) Schematic of nucleic construct #2 (SEQ ID NO: 38) constructed with three transgenes. Transgene P1 to T4 encodes a hairpin RNA (hpRNA) for silencing Li chitin synthase, ferritin, and juvenile hormone epoxide hydrolase (JHEH) genes. Transgene P4 to T5 encodes a hpRNA for silencing Om chitin synthase, ferritin, and JHEH genes. Transgene P5 to T3 encodes a mRNA with sense sequences of Li chitin synthase, ferritin, and JHEH genes and Om chitin synthase, ferritin, and JHEH genes. mRNA transcribed from transgene P5 to T3 is the template for cytoplasmic enhancement of the silencing signal.

The structure of construct 2 is shown in FIG. 2A. A 100 bp fragment of each of the Li chitin synthase, ferritin and JHEH genes (i.e., 100 bp of Li genes 4-6; SEQ ID NO: 4, SEQ ID NO: 5, SEQ ID NO: 6) were fused and synthesized in inverted repeats separated by 106 bp of a first loop sequence (Loop 1; SEQ ID NO: 13) between 35S CaMV promoter (SEQ ID NO: 27) to AtDelta TIP Terminator (SEQ ID NO: 35). A 100 bp fragment of each of the Om chitin synthase, ferritin and JHEH genes (i.e., 100 bp of Om genes 4-6; SEQ ID NO: 10, SEQ ID NO: 11, SEQ ID NO: 12) were fused and synthesized in inverted repeat separated by 108 bp of a second loop sequence (Loop 2; SEQ ID NO: 14) between AtGammTI P2 Promoter (SEQ ID NO: 30) to AtGammTI P2 Terminator (SEQ ID NO: 36). The select 100 bp of Li genes 4-6 (SEQ ID NO: 4, SEQ ID NO: 5, SEQ ID NO: 6) were fused to the select Om genes 4-6 (SEQ ID NO: 10, SEQ ID NO: 11, SEQ ID NO: 12) and synthesized in sense orientation between sgFIMV Promoter (SEQ ID NO: 31) to NOS Terminator (SEQ ID NO: 34).

Transcription of Construct 2 would yield three mRNAs: (1) hairpin RNA (hpRNA) of 3×100 bp sequence of Li genes 4-6 to silence the corresponding genes of Li (see FIG. 2B); (2) hpRNA of 3×100 bp sequence of Om genes 4-6 to silence the corresponding genes of Om (see FIG. 2B); and (3) mRNA of 3×100 bp sense sequence of Li genes 4-6 fused to 3×100 bp sense sequence of Om genes 4-6.

The sense mRNAs produced from constructs 1 and 2 are used as templates for cytoplasmic enhancement of the silencing signal, producing secondary siRNA and longer dsRNA to be digested by the target larvae [10]. Plant cells use some siRNA to prime RNA dependent RNA polymerization using mRNA with identical sense sequences as templates.

Example 5

Additional Gall Wasp dsRNA Silencing Sequences

Li RNAi3

A Li dsRNA silencing construct is constructed by combining Li sequences from Li mor-SWI/SNF complex subunit SMARCC2 (MOR) (SEQ ID NO: 104), Li eukaryotic translation initiation factor 3 subunit I-like (TIF) (SEQ ID NO: 121) and Li protein phosphatase PP2A 55 kDa regulatory subunit-like isoform 1 (PPR) (SEQ ID NO: 123), respectively, each from different functional categories as described above and a Li chitin synthase intron to yield a construct comprising the sequence set out in SEQ ID NO: 133. The respective nucleotides of SEQ ID NO: 133 were obtained from the following Li gene sequences, respectively:

Nucleotides 1-100 (SEQ ID NO: 127) and 607-706 (reverse complement of SEQ ID NO: 127): nucleotides 493-592 of SEQ ID NO: 104

Nucleotides 101-200 (SEQ ID NO: 128) and 507-606 (reverse complement of SEQ ID NO: 128): nucleotides 840-939 of SEQ ID NO: 121

Nucleotides 201-300 (SEQ ID NO: 129) and 407-506 (reverse complement of SEQ ID NO: 129): nucleotides 682-781 of SEQ ID NO: 123

Nucleotides 301-406: Li Chitin Synthase intron (SEQ ID NO: 13)

Om RNAi 3

An Om dsRNA silencing construct is constructed by combining sequences from Om mor-SWI/SNF complex subunit SMARCC2 (MOR) (SEQ ID NO: 103), Om eukaryotic translation initiation factor 3 subunit I-like (TIF) (SEQ ID NO: 120) and Om protein phosphatase PP2A 55 kDa regulatory subunit-like isoform 1 (PPR) (SEQ ID NO: 122), and a Li chitin synthase intron to yield a construct comprising the sequence set out in SEQ ID NO: 147. The respective nucleotides of SEQ ID NO: 147 were obtained from the following Om gene and Li intron sequences, respectively:

Nucleotides 1-100 (SEQ ID NO: 130) and 571-670 (reverse complement of SEQ ID NO: 130): nucleotides 955-1054 of SEQ ID NO: 103

Nucleotides 101-200 (SEQ ID NO: 131) and 471-570 (reverse complement of SEQ ID NO: 131): nucleotides 375-474 of SEQ ID NO: 120 with a C472G mutation Nucleotides 201-281 (SEQ ID NO: 132) and 390-470 (reverse complement of SEQ ID NO: 132): nucleotides 1247-1327 of SEQ ID NO: 122 with a T1332C mutation Nucleotides 282-389: Li Chitin Synthase intron with Asc1 site (SEQ ID NO: 139)

Single-Gene Control Sequences

Single gene control sequences are generated using a combination of sequences comprising a first sequence of 100 bp sense-100 bp (approximate) loop-100 bp antisense, where "100 bp sense" and "100 bp antisense" refer to complementary sequences from a target gene, and a second 100-bp sense amplifying sequence.

Li Control Sequences

The following sequences, based on SEQ ID: 104, are used as Li control sequences:

```
Complementary-Loop Construct
(100 bp sense-106 bp loop-100 bp antisense):
                                        (SEQ ID NO: 233)
AGAGGCGACGGCAGCAAGAGCGATGAGCCCGAGGATAACGTGAC
CGAGCAGACTCATCACATTGTGATTCCGAGCTACTCGGCGTGGT
TTGACTACAACTGGCTCGAACGAGCCGACTAATTGTCTTTAAAC
GCGCGATATAAGCGCACAATGCTCGAGAAACGATAAACTCTATC
```

-continued

```
GCTCTGTCGCGTGCGTGGCATCTTCGCGCGAGTTGTAGTCAAAC
CACGCCGAGTAGCTCGGAATCACAATGTGATGAGTCTGCTCGGT
CACGTTATCCTCGGGCTCATCGCTCTTGCTGCCGTCGCCTCT

Amplifying sense 100 bp:
                                        (SEQ ID NO: 140)
AGAGGCGACGGCAGCAAGAGCGATGAGCCCGAGGATAACGTGAC
CGAGCAGACTCATCACATTGTGATTCCGAGCTACTCGGCGTGGT
TTGACTACAACT
```

Control Sequences for Om

The following sequences, based on SEQ ID: 103, are used as Om control sequences:

```
Complementary-Loop Construct
(100 bp sense-108 bp loop-100 bp antisense):
                                        (SEQ ID NO: 148)
ATCGACACTTATCGTTTGAACCCAACAGAGTACATCACGTCAAC
AGCGTGCAGGCGAAATTTGGCTGGTGATGTTTGTGCGATAATGC
GCGTACATGCTTGCGCGCGAAACAACGGTAATCAACCGGCAATT
ATTAATCGTACATGCGCGGCGCAGGCGCGCCTGCATTATCCCTC
GTCATCACCAAAGCGCCACATTATGCTTCTTCAAGCATGTACGC
GCATTATCGCACAAACATCACCAGCCAAATTTCGCCTGCACGCT
GTTGACGTGATGTACTCTGTTGGGTTCAAACGATAAGTGTCGAT

Amplifying sense 100 bp:
                                        (SEQ ID NO: 149)
ATCGACACTTATCGTTTGAACCCAACAGAGTACATCACGTCAAC
AGCGTGCAGGCGAAATTTGGCTGGTGATGTTTGTGCGATAATGC
GCGTACATGCTT
```

Example 6

Expression of RNAi Constructs in *Eucalyptus* dsRNA constructs #1 and #2 were transformed into *eucalyptus* using a protocol essentially described in Prakash et al., *In Vitro Cell Dev Biol.—Plant,* 2009, 45:429-434. Briefly, shoots of *Eucalyptus* were propagated in vitro on Murashige and Skoog (MS) basal salt medium consisting of 3% (w/v) sucrose and 0.8% (w/v) agar. All in vitro plant materials were incubated at 25±2° C. under a 16-h photoperiod with cool white fluorescent lamps with an intensity of 30 $\mu Em^{-2} s^{-1}$. *A. tumefaciens* strain LBA 4404 harboring a binary vector pBI121 containing nptII gene was used for transformation. Bacterial culture collected at late log phase were pelleted and resuspended in MS basal salt medium. Leaves from in vitro material were collected and used as explants for transformation experiments.

Explants were precultured on the MS regeneration medium supplemented with 0.5 mg/l BAP and 0.1 mg/l NAA for 2 d. Precultured leaf explants were gently shaken in the bacterial suspension for 10 min and blotted dry on a sterile filter paper. Explants were then cocultivated in medium under the preculture conditions for 2 d. Following cocultivation, explants were washed in MS liquid medium, blotted dry on a sterile filter paper, and transferred to MS regeneration medium containing 0.5 mg/l BAP and 0.1 mg/l NAA supplemented with 40 mg/l kanamycin and 300 mg/l cefotaxime. After 4-5 weeks of culture, regeneration was observed and explants were transferred to liquid elongation medium (MS medium supplemented with 0.5 mg/l BAP, 40 mg/l kanamycin, and 300 mg/l cefotaxime) on paper bridges. The elongated shoots (1.5-2 cm) were propagated on MS medium with 0.1 mg/l BAP. Leaf segments from regenerated and elongated shoots were analyzed by PCR and western blot. Positive shoots were multiplied to 10 copies on MS medium containing 0.04 mg/L BAP. A few leaves were excised from the shoots and analyzed by RT-PCR.

Expression of dsRNAs was measured using RT-PCR. Total RNA from 50 mg fresh transgenic plant tissue was purified using EPICENTRE MasterPure™ Plant RNA Purification Kit (Cat. #MPRO9010) following by DNAse treatment with Ambion TURBO DNA-free™ Dnase (Cat. #AM1907). 1 μl of total RNA from each sample was analyzed by RT PCR. RT PCR was performed using Invitrogen SuperScript III One-Step RT-PCR System with Platinum Taq DNA Polymerase kit (Cat. #12574-018). As a control, the Platinum Taq DNA Polymerase kit (Cat. #12574-018 and #10966-018) was used to recognize traces of DNA contaminations. No fragment amplification was expected for this control.

To detect expression of RNA from construct #1, RT-PCR was prepared with primer pairs CGAACGAGCCGACTAATTGTCTT (SEQ ID NO: 223) and CACGCGACAGAGCGATAGAGTTTA (SEQ ID NO: 224), to detect an 85 bp fragment from L1 present in hpRNA Li RNAi 1 (see FIG. 1B); CAAGAATCCCATCTCTTGCTTGC (SEQ ID NO: 225) and AGCAAGAATCTTCCGTAATCG (SEQ ID NO: 226), to detect a 91 bp fragment from the 3' UTR of terminator AtUBQ1 present in hpRNA Om RNAi 1 (see FIG. 2B); and, GAAGATGGTTCTGGGTGCCATAAG (SEQ ID NO: 227) and CTGGAGTAACTGGAACTGCTGAAC (SEQ ID NO: 228), to detect a 360 bp fragment from the linear RNA produced from expression of transgene P3 to T3 (see FIG. 1A).

Figure 2B:
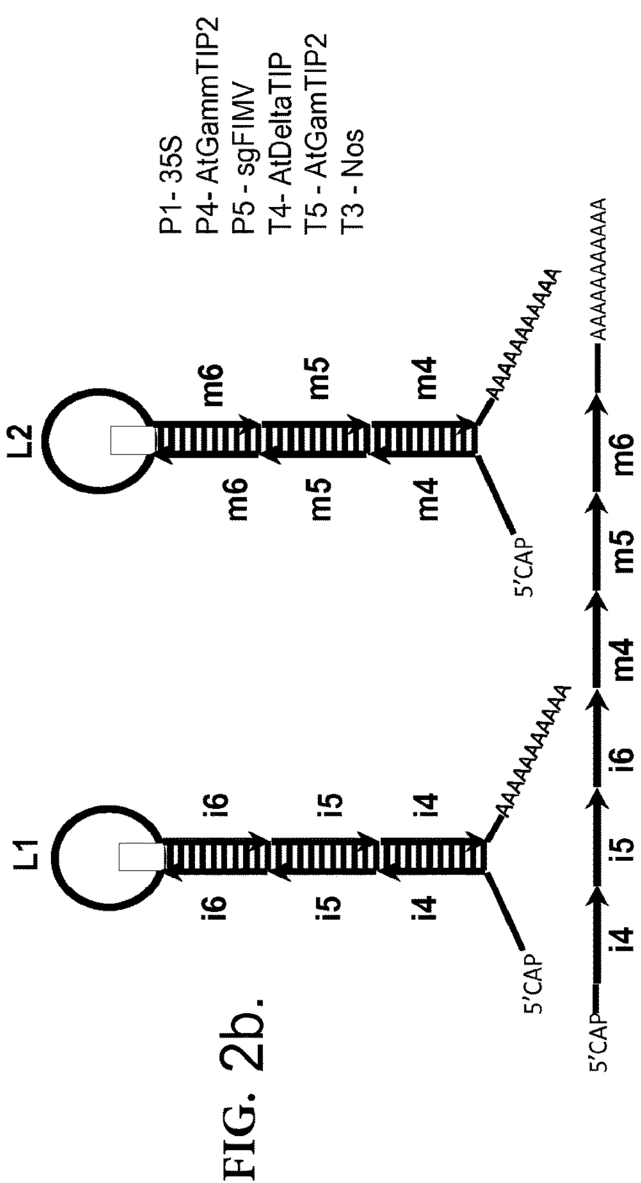
FIG. 2(B) hpRNA molecules produced by transcription of nucleic acid construct #2. (Left-Li RNAi 2, SEQ ID NO: 141; Right-Om RNAi 2, SEQ ID NO: 142) Definitions: P1-CaMV 35S Promoter (SEQ ID NO: 27); P4-AtGammTI P2 Promoter (SEQ ID NO: 30); P5-sgFIMV Promoter (SEQ ID NO: 31); T4-AtDelta TIP Terminator (SEQ ID NO: 35); T5-AtGammTI P2 Terminator (SEQ ID NO: 36); T3-NOS Terminator (SEQ ID NO: 34); i4-100 bp of Li Chitin synthase gene (SEQ ID NO: 4); i5-100 bp of Li Ferritin gene (SEQ ID NO: 5); i6-100 bp of Li JHEH gene (SEQ ID NO: 6); m4-100 bp of Om Chitin synthase gene (SEQ ID NO:10); m5-100 bp of Om Ferritin gene (SEQ ID NO: 11); m6-100 bp of Om JHEH gene (SEQ ID NO: 12); L1-loop #1 (SEQ ID NO: 13); L2-loop #2 (SEQ ID NO: 14). Poly-A tail disclosed as SEQ ID NO: 245.
Figures 3A, 3B:
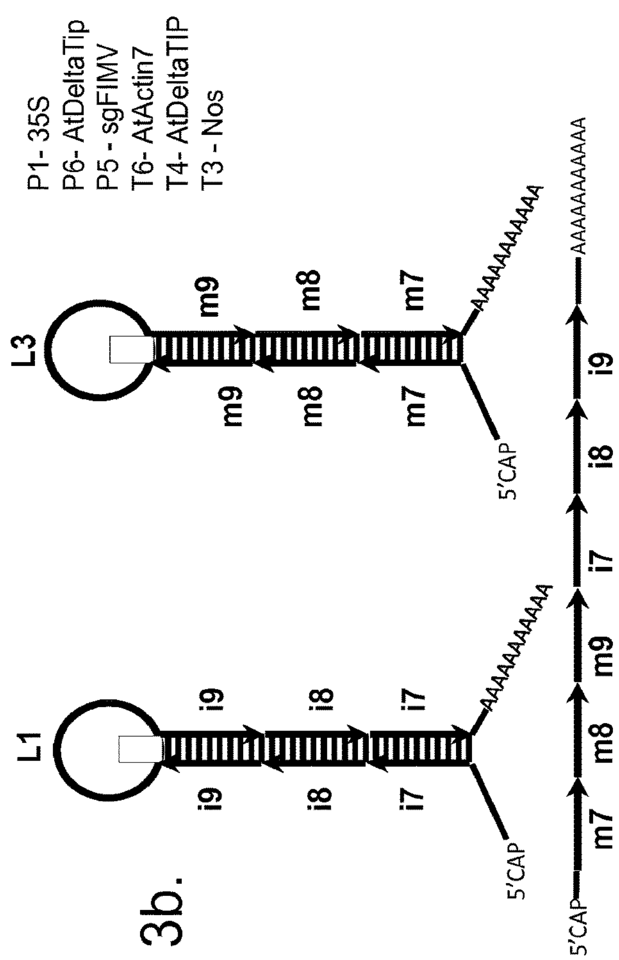
FIG. 3(A) Schematic of nucleic construct #3 (SEQ ID NO: 124) constructed with three transgenes. Transgene P1 to T6 encodes a hairpin RNA (hpRNA) for silencing Li mor-SWI/SNF complex subunit SMARCC2 (MOR), eukaryotic translation initiation factor 3 subunit I-like (TIF), and protein phosphatase PP2A 55 kDa regulatory subunit-like isoform 1(PPR) genes. Transgene P6 to T4 encodes a hpRNA for silencing Om MOR, TIF, and PPR genes. Transgene P5 to T3 encodes a mRNA with sense sequences of Om MOR, TIF, and PPR genes and Li MOR, TIF, and PPR genes. mRNA transcribed from transgene P5 to T3 encodes non-functional protein and is the template for cytoplasmic enhancement of the silencing signal.
FIG. 3(B) hpRNA molecules produced by transcription of nucleic acid construct #3. Definitions: P1-CaMV 35S Promoter (SEQ ID NO: 27); P6-AtDelta TIP Promoter (SEQ ID NO: 125); P5-sgFIMV Promoter (SEQ ID NO: 31); T6-AtActin7 Terminator (SEQ ID NO: 126); T4-AtDelta TIP Terminator (SEQ ID NO: 35); T3-NOS Terminator (SEQ ID NO: 34); i7-100 bp of Li MOR (SEQ ID NO: 127); i8-100 bp of Li TIF gene (SEQ ID NO: 128); i9-100 bp of Li PPR gene (SEQ ID NO: 129); m7-100 bp of Om MOR gene (SEQ ID NO: 130); m8-100 bp of Om TIF gene with C98G change to eliminate SacI site (SEQ ID NO: 131; equivalent to a C472G in target sequence); m9-81 bp of Om PPR gene with T2C change to eliminate XbaI site (SEQ ID NO: 132); L1-loop #1 (SEQ ID NO: 13); L3-loop #3 (SEQ ID NO: 139). Poly-A tail disclosed as SEQ ID NO: 245.

To detect expression of RNA from construct #2, RT-PCR was prepared with primer pairs CGAACGAGCCGACTAATTGTCTT (SEQ ID NO: 223) and CACGCGACAGAGCGATAGAGTTTA (SEQ ID NO: 224), to detect an 85 bp fragment from L1 present in hpRNA Li RNAi 2 (see FIG. 2B); GCGCGAAACAACGGTAATCAAC (SEQ ID NO: 229) and CGCTTTGGTGATGACGAGGGATAA (SEQ ID NO: 230), to detect a 97 bp fragment from L2 present in hpRNA Om RNAi 2 (see FIG. 2B); and, GATCTGTTCGAGATACTGCCCAAC (SEQ ID NO: 231) and CTAGATCGACGAGTACCAGCACAA (SEQ ID NO: 232), to detect a 348 bp fragment from the linear RNA produced from expression of transgene P5 to T3 (see FIG. 2A).

RT-PCR results showed that the predicted fragments from both construct #1 and construct #2 were detected after 40 amplification cycles, for three independent transgenic events for each construct. These results indicated that the respective hp RNAs and sense mRNA were being transcribed from each of construct #1 and construct #2 and that the silencing machinery was active.

Example 7

Bioassay of Li and Om dsRNA Constructs

To prepare a gall tissue homogenate, galls are opened and all larvae are removed. Larvae-free galls and surrounding leaf area are then homogenized in liquid nitrogen with mortar and pestle until a fine powder homogenate is achieved. An agar-based wasp larvae artificial feed is prepared by dissolving agar (50 mg) at 100° C. in buffer, cooling to 45° C. and adding 5 g of gall tissue homogenate and bringing total volume to 10 ml. Aliquots of artificial feed (10 μl) are placed in a sealable tube and allowed to cool to room temperature. Gall wasp larva are isolated from galls with live larvae from which adult gall wasps have not yet emerged, by cutting gall lids from plant tissue surface to expose the gall interior and collecting larvae using a sharp-tipped rod by gently contacting the larvae. Individual larvae are placed in each tube of artificial feed. Tubes are humidified by placing a drop of water in each tube, and tubes are sealed and incubated at 25° C.

Artificial feed is prepared from gall tissue prepared from *eucalyptus* plants that are transformed with construct 1 (SEQ ID NO: 37), construct 2 (SEQ ID NO: 38), construct 3 (SEQ ID NO: 124) or control plants (i.e., wt un-transformed plants or plants transformed with vector alone, without insertion of Li or Om nucleic acids or without nucleic acids that could form siRNAs). Effects of Li and Om dsRNA are determined by examining effects on development of gall wasp larvae grown on artificial feed prepared from transformed *eucalyptus* tissue, compared to larvae grown on artificial feed prepared from wt and control transformed *eucalyptus* tissue.

Example 8

Test of Protective Effect of Li and Om dsRNA Constructs

*Eucalyptus* plants are transformed with construct 1 (SEQ ID NO: 37), construct 2 (SEQ ID NO: 38) or construct 3 and transgenic lines are established. Controls lines are established by transforming plants with vector alone, without insertion of Li or Om nucleic acids or without nucleic acids that could form siRNAs.

Transgenic, wt, and control *eucalyptus* plants are grown in insect proof cages in the greenhouse together with adult gall wasps. The insect proof cages keep the inoculums in while preventing outside pests from entering the cage. Following wasp inoculation, the appearance of galls in the veins and in the leaves is evaluated. Plants are examined to determine number of galls, gall size (maximum length), number of vital larvae in galls and the number of emerging matured gall wasps. Five independent transformation events of transgenic *eucalyptus* plants transcribing dsRNA are tested. Ten lines of each transformation event are inoculated with adult gall wasps in 3 independent repeats. Number of galls, gall size, vital larvae per 10 galls and emerging adults (by the exit hole) are recorded 1, 2, 3 and 4 months after inoculation.

Exemplary prophetic result: Transgenic plants transcribing dsRNA targeting gall wasp genes exhibit fewer galls, and/or of smaller size, compared to controls and galls do not develop further. No vital larvae are detected in the small galls and no adult wasps emerge. Transgenic plants lines are resistant to gall wasp infection, compared to control and wt plants that are infected with fully developed galls.

A number of embodiments of the invention have been described. Nevertheless, it will be understood that various modifications may be made without departing from the spirit and scope of the invention. Accordingly, other embodiments are within the scope of the following claims.

All patents, patent publications and non-patent literature referenced in the specification are hereby incorporated herein by reference in their entireties.

Note on Sequence Listing: Certain sequences in the Sequence Listing set out below are believed to discontinuous fragments from a single gene, as follows:

SEQ ID NO: 60 and 235 are respective, discontinuous 5' and 3' fragments of a single gene;

SEQ ID NO: 64 and 236 are respective, discontinuous 5' and 3' fragments of a single gene;

SEQ ID NO: 69 and 237 are respective, discontinuous 5' and 3' fragments of a single gene;

SEQ ID NO: 73 and 238 are respective, discontinuous 5' and 3' fragments of a single gene;

SEQ ID NO: 75, 239, and 240 are respective, discontinuous 5', median, and 3' fragments of a single gene;

SEQ ID NO: 107 and 241 are respective, discontinuous 5' and 3' fragments of a single gene;

SEQ ID NO: 115, 242, and 243 are respective, discontinuous 5', median, and 3' fragments of a single gene; and SEQ ID NO: 117 and 244 are respective, discontinuous 5' and 3' fragments of a single gene.

REFERENCES

1. Baum J A, et al., Control of coleopteran insect pests through RNA interference, (2007), Nat Biotechnol. 25:1322-6.
2. Frizzi A, et al., Tapping RNA silencing pathways for plant biotechnology, (2010), Plant Biotechnol 8:655-77.
3. Gordon K H, et al., RNAi for insect-proof plants, (2007), Nat Biotechnol 25:1231-2.
4. Huvenne H, et al., Mechanisms of dsRNA uptake in insects and potential of RNAi for pest control: a review, (2010), J Insect Physiol 56:227-35.
5. Mao Y B, et al., Silencing a cotton bollworm P450 monooxygenase gene by plant-mediated RNAi impairs larval tolerance of gossypol, (2007), Nat Biotechnol 25:1307-13.
6. Mendel Z, et al., The taxonomy and natural history of *Leptocybe invasa* (Hymenoptera: Eulophidae) gen & sp. nov., an invasive gall inducer on *Eucalyptus*, (2004), Australian J Entomol, 43:101-13.
7. Nunes F M, et al., A non-invasive method for silencing gene transcription in honeybees maintained under natural conditions., (2009), Insect Biochem Mol Biol 39:157-60.
8. Price D R, et al., RNAi-mediated crop protection against insects, (2008), Trends Biotechnol 26:393-400.
9. Protasov A, et al., Biology, revised taxonomy and impact on host plants of *Ophelimus maskelli*, an invasive gall inducer on *Eucalyptus* spp. In the Mediterranean area, (2007), Phytoparasitica 35:50-76.
10. Tinoco M L, et al., In vivo trans-specific gene silencing in fungal cells by in planta expression of a double-stranded RNA, (2010), BMC Biol 8:27.
11. Hannon, G. J., RNA interference., (2002), Nature 418: 244-251
12. Baulcombe, D., RNA silencing in plants, (2004), Nature 431:356-363.
13. Pei Y, et al., On the art of identifying effective and specific siRNAs, (2006), Nature Methods 3(9):670-676.
14. Cullen, B R., Enhancing and confirming the specificity of RNAi experiments, (2006), Nature Methods 3(9):677-681.
15. Chen et. al, New Genes in *Drosophila* Quickly become essential, Science (2010), 330:1682-5.
16. Dietzl et. al., A Genome Wide Transgenic RNAi Library for Conditional Gene Inactivation in *Drosophila*. Nature (2007), 448:151-7.

What is claimed is:

1. A small inhibitory ribonucleic acid molecule (siRNA) as set forth in SEQ ID NO:1 that inhibits expression of an *Leptocybe invasa* nucleic acid molecule encoding coatomer subunit alpha (alpha COP).

2. A small inhibitory ribonucleic acid molecule (siRNA) as set forth in SEQ ID NO:345 that inhibits expression of an *Ophelimus maskelli* nucleic acid molecule encoding coatomer subunit alpha (alpha COP).

* * * * *

UNITED STATES PATENT AND TRADEMARK OFFICE

CERTIFICATE OF CORRECTION

PATENT NO. : 9,970,022 B2
APPLICATION NO. : 14/008914
DATED : May 15, 2018
INVENTOR(S) : Dror Avisar et al.

It is certified that error appears in the above-identified patent and that said Letters Patent is hereby corrected as shown below:

On the Title Page

Item (73), (Assignee): delete “Peta” and insert -- Petah -- therefor.

Signed and Sealed this
Fourth Day of June, 2019

Andrei Iancu
*Director of the United States Patent and Trademark Office*